United States Patent
Henriksen et al.

(10) Patent No.: US 12,318,481 B2
(45) Date of Patent: *Jun. 3, 2025

(54) IMMUNE STIMULATING MICELLE COMPOSITION

(71) Applicant: Danmarks Tekniske Universitet, Kgs. Lyngby (DK)

(72) Inventors: Jonas Rosager Henriksen, Allerød (DK); Thomas Lars Andresen, Vanløse (DK); Simon Skjøde Jensen, Brønshøj (DK); Ladan Parhamifar, Hillerød (DK); Rasmus Dithmar Münter, Birkerød (DK); Anders E. Hansen, Linhamn (SE); Camilla Stavnsbjerg, Copenhagen Ø (DK); Esben Christensen, Copenhagen NV (DK)

(73) Assignee: Danmarks Tekniske Universitet, Kongens Lyngby (DK)

( * ) Notice: Subject to any disclaimer, the term of this patent is extended or adjusted under 35 U.S.C. 154(b) by 505 days.

This patent is subject to a terminal disclaimer.

(21) Appl. No.: 17/760,885

(22) PCT Filed: Sep. 18, 2020

(86) PCT No.: PCT/EP2020/076136
§ 371 (c)(1),
(2) Date: Mar. 16, 2022

(87) PCT Pub. No.: WO2021/053163
PCT Pub. Date: Mar. 25, 2021

(65) Prior Publication Data
US 2022/0354789 A1    Nov. 10, 2022

(30) Foreign Application Priority Data

Sep. 19, 2019 (EP) .................... 19198424
Nov. 7, 2019 (EP) .................... 19207727
Apr. 3, 2020 (EP) .................... 20167952

(51) Int. Cl.
*A61K 47/00* (2006.01)
*A61K 8/02* (2006.01)
(Continued)

(52) U.S. Cl.
CPC .......... *A61K 9/1075* (2013.01); *A61K 31/683* (2013.01); *A61K 31/704* (2013.01);
(Continued)

(58) Field of Classification Search
None
See application file for complete search history.

(56) References Cited

U.S. PATENT DOCUMENTS 8,241,663 B2    8/2012  Isozaki et al.
8,357,374 B2    1/2013  Carson et al.
(Continued)

FOREIGN PATENT DOCUMENTS

EP    1731172 1 B    12/2006
EP    2125007 A2    12/2009
(Continued)

OTHER PUBLICATIONS

Hennessy et al. (Nature Reviews 2010;9:293-407) (Year: 2010).*
(Continued)

*Primary Examiner* — Ernst V Arnold
(74) *Attorney, Agent, or Firm* — Choate, Hall & Stewart LLP; Michael A. Shinall

(57) ABSTRACT

The present invention relates to immune stimulating micelle compositions, and their use in treatment of diseases and disorders, such as cancer. In particular, the present invention relates to micelle compositions comprising a TLR7 agonist, such as 1V270.

22 Claims, 75 Drawing Sheets

(51) Int. Cl.

| | |
|---|---|
| *A61K 9/107* | (2006.01) |
| *A61K 31/683* | (2006.01) |
| *A61K 31/704* | (2006.01) |
| *A61K 39/00* | (2006.01) |
| *A61K 39/395* | (2006.01) |
| *A61K 47/24* | (2006.01) |
| *A61P 35/00* | (2006.01) |
| *C07K 16/28* | (2006.01) |
| *C07K 16/32* | (2006.01) |

(52) U.S. Cl.
CPC ............... *A61K 39/00117* (2018.08); *A61K 39/001186* (2018.08); *A61K 39/00119* (2018.08); *A61K 39/001194* (2018.08); *A61K 39/3955* (2013.01); *A61K 39/39558* (2013.01); *A61K 47/24* (2013.01); *A61P 35/00* (2018.01); *C07K 16/2803* (2013.01); *C07K 16/2818* (2013.01); *C07K 16/2863* (2013.01); *C07K 16/2887* (2013.01); *C07K 16/2896* (2013.01); *C07K 16/32* (2013.01); *A61K 2039/505* (2013.01); *C07K 2317/21* (2013.01); *C07K 2317/24* (2013.01)

(56) References Cited

U.S. PATENT DOCUMENTS

| | | | |
|---|---|---|---|
| 8,507,507 | B2 | 8/2013 | Halcomb et al. |
| 8,747,869 | B2 | 6/2014 | Irvine et al. |
| 8,790,655 | B2 | 7/2014 | Carson et al. |
| 8,951,542 | B2 | 2/2015 | Irvine et al. |
| 8,962,652 | B2 | 2/2015 | Halcomb et al. |
| 9,050,376 | B2 | 6/2015 | Carson et al. |
| 9,149,432 | B2 | 10/2015 | Irvine et al. |
| 9,161,934 | B2 | 10/2015 | Halcomb et al. |
| 9,339,462 | B2 | 5/2016 | Irvine et al. |
| 9,445,994 | B2 | 9/2016 | Irvine et al. |
| 2013/0251783 | A1 | 9/2013 | Parmentier et al. |
| 2013/0336996 | A1 | 12/2013 | Vernejoul et al. |
| 2015/0079155 | A1 | 3/2015 | Jensen et al. |
| 2015/0246137 | A1 | 9/2015 | Guo et al. |
| 2015/0246888 | A1 | 9/2015 | Johnson et al. |
| 2015/0272886 | A1 | 10/2015 | Chen et al. |
| 2015/0366962 | A1 | 12/2015 | Carson et al. |
| 2016/0199499 | A1 | 7/2016 | Carson et al. |
| 2017/0035701 | A1* | 2/2017 | Sheu ............... A61K 31/337 |
| 2021/0008190 | A1 | 1/2021 | Wang |
| 2022/0364095 | A1 | 11/2022 | Mirkin et al. |

FOREIGN PATENT DOCUMENTS

| | | | |
|---|---|---|---|
| EP | 2491035 A1 | 8/2012 | |
| EP | 2510946 A1 | 10/2012 | |
| EP | 2547327 A2 | 1/2013 | |
| EP | 2674170 B1 | 11/2014 | |
| EP | 2825158 A1 | 1/2015 | |
| EP | 3033089 A2 | 6/2016 | |
| WO | 2008/115319 A2 | 9/2008 | |
| WO | WO2010/014117 A1 | 2/2010 | |
| WO | 2011/139348 A2 | 11/2011 | |
| WO | WO2013/066903 A1 | 5/2013 | |
| WO | 2015/023858 A2 | 2/2015 | |
| WO | WO-2015036044 A1 * | 3/2015 | ......... A61K 47/6911 |
| WO | WO2018147710 A1 | 8/2018 | |
| WO | 2019/012107 A1 | 1/2019 | |

OTHER PUBLICATIONS

MayoClinic [online] retrieved on Jan. 19, 2011 from: http://www.mayoclinic.com/health/huntingtonsdisease/DS00401/DSECTION=prevention; May 8, 2009:8 pages (Year: 2009).*
Jhaveri et al. (Frontiers in Phamacology 2014;5(&&): 26 pages) (Year: 2014).*
Remsburg et al. (Pharmaceutics 2013;5:81-93). (Year: 2013).*
Cabral et al. (Chemical Reviews 2018; 118:6844-6892). (Year: 2018).*
Cheng, C. et al., Advanced nanotechnology: An arsenal to enhance immunotherapy in fighting cancer, Clinica Chimica Acta, 492: 12-19, 2019.
Goff, P. et al., Synthetic Toll-Like Receptor 4 (TLR4) and TLR7 Ligands as Influenza Virus Vaccine Adjuvants Induce Rapid, Sustained, and Broadly Protective Responses, Journal of Virology, 89(6): 3221-3235, 2015.
Hosoya, T. et al., Induction of oligoclonal CD8 T cell responses against pulmonary metastatic cancer by a phospholipid-conjugated TLR7 agonist, PNAS, 115(29):E6836-E6844, 2018.
Jiménez-Sánchez, G. et al., Preparation and in Vitro Evaluation of Imiquimod Loaded Polylactide-based Micelles as Potential Vaccine Adjuvants, Pharmaceutical Research, 32(1):311-320, Sep. 24, 2014.
Koide, H. et al., Particle size-dependent triggering of accelerated blood clearance phenomenon, International Journal of Pharmaceutics, 362: 197-200, 2008.
Li, C. et al., Synthetic Polymeric Mixed Micelles Targeting Lymph Nodes Trigger Enhanced Cellular and Humoral Immune Responses, ACS Applied Materials & Interfaces, 10(3): 2874-2889, 2018.
Lynn, G. et al., Impact of Polymer-TLR-7/8 Agonist (Adjuvant) Morphology on the Potency and Mechanism of CD8 T-Cell Induction, Biomacromolecules, 20: 854-870, 2019.
Sevimli, S. et al., Fatty Acid-Mimetic Micelles for Dual Delivery of Antigens and Imidazoquinoline Adjuvants, ACS Biomaterials Science & Engineering, 3(2): 179-194, 2017.
Van Herck, S. et al., Lymph-Node-Targeted Immune Activation by Engineered Block Copolymer Amphiphiles—TLR7/8 Agonist Conjugates, J. Am. Chem. Soc., 140: 14300-14307, 2018.
Christensen, E., Preclinical Evaluation of Drug Delivery Systems for Immunotherapy, PhD Dissertation, Technical University of Denmark, Dec. 1, 2019, 135 pages.
Ashok et al., In Vitro Characterization of PEGylated Phospholipid Micelles for Improved Drug Solubilization: Effects of PEG Chain Length and PC Incorporation, Wiley InterScience, May 15, 2004, DOI 10.1002/jps.20150.
Dolor et al., Sterol-modified PEG lipids: Alteration of bilayer anchoring moiety has an unexpected effect on liposome circulation, www.rsc.org/, DOI: 10.1039/x0xx00000x, Jun. 2018.
Gleue et al., Stability of Alkyl Chain-Mediated Lipid Anchoring in Liposomal Membranes, Cells 2020, 9, 2213, 13 pages, doi:10.3390/cells9102213, Sep. 29, 2019.
Hattori et al., Effects of PEG anchors in PEGylated siRNA lipoplexes on in vitro gene silencing effects and siRNA biodistribution in mice, Molecular Medicine Reports, 22: 4183-4196, 2020.
Lipfert et al., Size and Shape of Detergent Micelles Determined by Small-Angle X-ray Scattering, J. Phys. Chem. B, 111: 12427-12438, Aug. 16, 2007.
Oliver et al., Dependence of Micelle Size and Shape on Detergent Alkyl Chain Length and Head Group, PLoS ONE 8 (5): e62488. doi: 10.1371/journal.pone.0062488, May 8, 2013.
Stavnsbjerg, C., et al., Accelerated blood clearance and hypersensitivity by PEGylated liposomes containing TLR agonists, J Control Release, 342:337-344 (2022).

* cited by examiner

| Name | Batch name | Composition | Molar ratio | Zeta (mV) | Size (nm) | PDI |
|---|---|---|---|---|---|---|
| Empty Micelle /MBS0/ Vehicle | RML212 | DSPE-PEG2000 | | N.D. | 10.9 | 0.972 |
| | RML225 | | | N.D. | 10.5 | 0.165 |
| | Empty Micelle | | | N.D. | 13.6 | 0.190 |
| | RML259 | | | -4.3 | 11.4 | 0.045 |
| | RML289 | | | -4.5 | 10.6 | 0.090 |
| MBS6 | RML20(50) RML20(200) | DSPE-PEG2000:1v270 | 80:20 | -7.3 -10.1 | 13.0 14.1 | 0.604 0.572 |
| | RML209 | | | N.D. | 13.1 | 0.316 |
| | RML222 | | | N.D. | 14.1 | 0.430 |
| | RML226 (40) RML226 (200) | | | -5.2 -6.1 | 13.3 10.6 | 0.384 0.256 |
| | RML20(50) RML20(100) RML20(200) | | | -5.1 | 14.7 13.6 11.5 | 0.565 0.154 0.120 |
| MBS7 | RML5(100) | DSPE-PEG2000:1v270 | 95:5 | -6.6 | 17.6 | 0.249 |
| | RML211 | | | N.D. | 10.6 | 0.346 |
| | RML224 | | | N.D. | 12.3 | 0.818 |
| | RML227 (40) RML227 (200) | | | -5.0 -4.1 | 12.2 14.1 | 0.311 0.191 |
| | RML5(50) RML5(100) | | | -9.6 | 12.5 11.3 | 0.574 0.565 |
| MBS8 | RML210 | DSPE-PEG2000:1v270 | 90:10 | N.D. | 11.5 | 0.585 |
| | RML223 | | | N.D. | 12.4 | 0.436 |
| | RML258 | | | -6.7 | 12.9 | 0.556 |
| | RML10(50) RML10(100) RML10(200) | | | -11.5 | 18.5 15.1 14.8 | 0.301 0.294 N.D. |
| | RML288 | | | -5.5 | 10.6 | 0.359 |

Fig. 1A

| Tumor model | Treatment groups (nr. mice) | TGI% | P value | CR | Rechallenge resistant |
|---|---|---|---|---|---|
| CT26, colon cancer, syngeneic | Vehicle | NA | NA | NA | NA |
| | a-PD-1 | 63.38 | <0.0001 | 0/10 | NA |
| | MBS8 | 97.16 | 0.0015 | 7/10 | NA |
| | a-PD-1 + MBS8 | 97.97 | <0.0001 | 8/10 | NA |
| H22, hepatoma syngeneic | Vehicle | NA | NA | NA | NA |
| | a-PD-1 | 72.93 | <0.0001 | 0/10 | NA |
| | MBS8 | 94.35 | <0.0001 | 5/10 | NA |
| | a-PD-1 + MBS8 | 94.47 | <0.0001 | 4/10 | NA |
| MC38, colon cancer, syngeneic | Vehicle | NA | NA | NA | NA |
| | a-PD-1 | 38,77 | 0.0089 | 0/10 | NA |
| | MBS8 | 86,14 | <0.0001 | 0/10 | NA |
| | a-PD-1 + MBS8 | 94,65 | <0.0001 | 0/10 | NA |
| Pan02, pancreatic cancer, syngeneic | Vehicle | NA | NA | NA | NA |
| | a-PD-1 | 5,11 | ns | 0/10 | NA |
| | MBS8 | 65,79 | 0.0001 | 1/10 | NA |
| | a-PD-1 + MBS8 | 86,37 | <0.0001 | 3/10 | NA |
| LL/2, lung cancer, syngeneic | Vehicle | NA | NA | NA | NA |
| | a-PD-1 | -15,48 | ns | 0/10 | NA |
| | MBS8 | 33,27 | 0.0355 | 0/10 | NA |
| | a-PD-1 + MBS8 | 57,20 | <0.0001 | 0/10 | NA |

Fig. 13A

| | | | | | |
|---|---|---|---|---|---|
| A20, B-cell lymphoma, syngeneic | Vehicle | NA | NA | NA | NA |
| | a-PD-1 | 11.02 | ns | 0/10 | NA |
| | MBS8 | 90.98 | <0.0001 | 4/10 | NA |
| | a-PD-1 + MBS8 | 87.79 | <0.0001 | 4/10 | NA |
| RM-1, prostate cancer, syngeneic | Vehicle | NA | NA | NA | NA |
| | a-PD-1 | 1,03 | ns | 0/10 | NA |
| | MBS8 | 45,14 | 0.0003 | 0/10 | NA |
| | a-PD-1 + MBS8 | 76,50 | <0.0001 | 0/10 | NA |
| Renca, kidney cancer, syngeneic | Vehicle | NA | NA | NA | NA |
| | a-PD-1 | 8,1 | ns | 0/10 | NA |
| | MBS8 | 61,2 | <0.0001 | 0/10 | NA |
| | a-PD-1 + MBS8 | 82,9 | 0.0001 | 0/10 | NA |
| Hepa 1-6, hepatoma, syngeneic | Vehicle | NA | NA | NA | NA |
| | a-PD-1 | 54,18 | 0.0007 | 0/10 | NA |
| | MBS8 | 80,14 | <0.0001 | 5/10 | NA |
| | a-PD-1 + MBS8 | 93,34 | <0.0001 | 8/10 | NA |
| B16F10, melanoma, syngeneic | Vehicle | NA | NA | NA | NA |
| | a-PD-1 | 16,77 | ns | 0/10 | NA |
| | MBS8 | 41,48 | 0.0029 | 0/10 | NA |
| | a-PD-1 + MBS8 | 48,31 | 0.0041 | 0/10 | NA |
| B16BL6, melanoma, syngeneic | Vehicle | NA | NA | NA | NA |
| | a-PD-1 | 6,02 | ns | 0/10 | NA |
| | MBS8 | 23,55 | 0.0089 | 0/10 | NA |
| | a-PD-1 + MBS8 | 28,81 | 0.0029 | 0/10 | NA |

Fig. 13A (continued)

| | | | | | |
|---|---|---|---|---|---|
| EMT-6, breast cancer, syngeneic | Vehicle | NA | NA | NA | NA |
| | a-PD-1 | 70,32 | <0.0001 | 2/10 | NA |
| | MBS8 | 94,95 | <0.0001 | 8/8* | 8/8 |
| | a-PD-1 + MBS8 | 95,11 | <0.0001 | 10/10 | 10/10 |
Fig. 13A (continued)
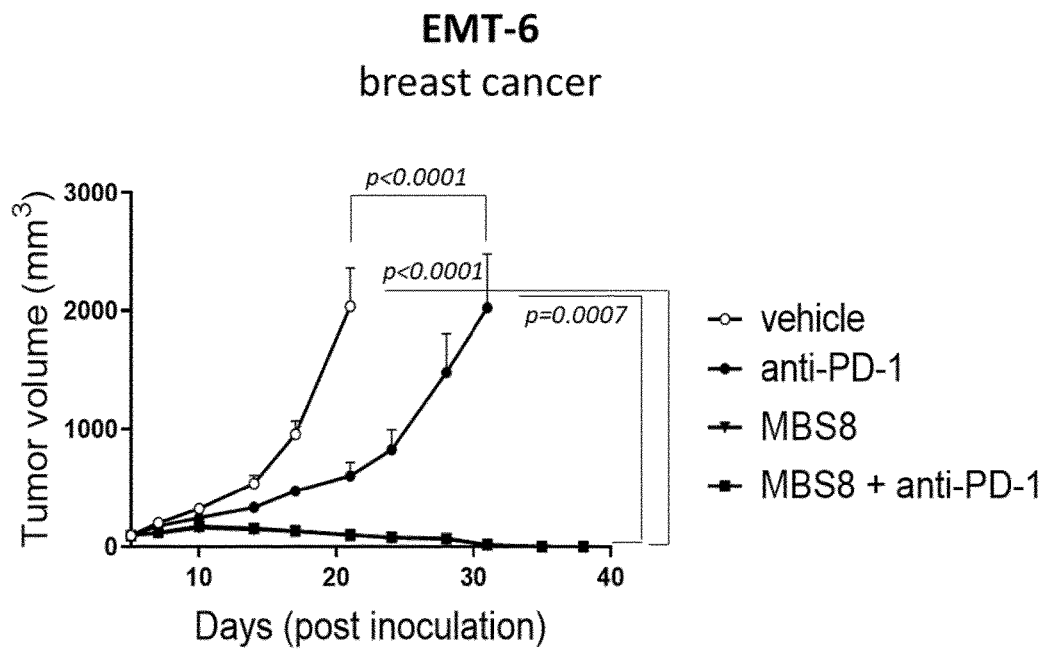
Fig. 13B
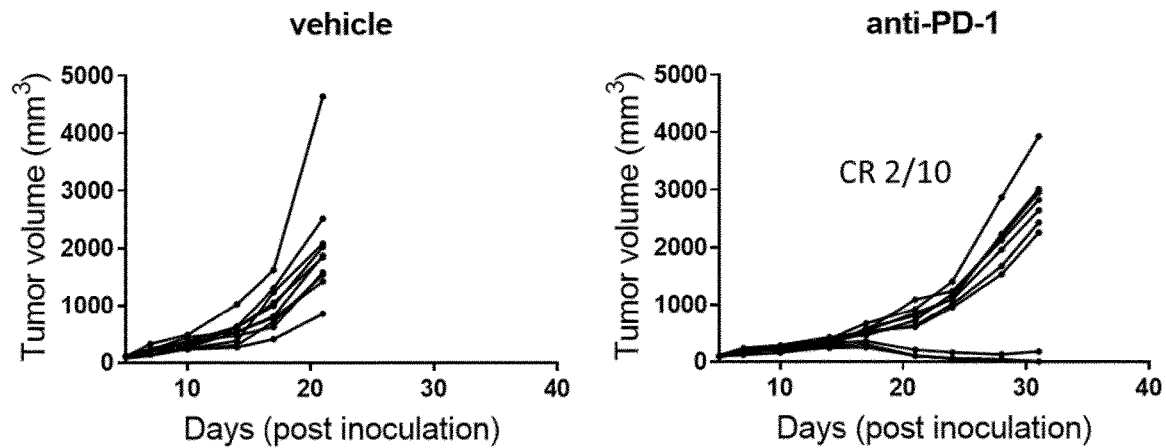
Fig. 13B (continued)

B.

IMMUNE STIMULATING MICELLE COMPOSITION

TECHNICAL FIELD

The present invention relates to immune stimulating micelle compositions, and their use in treatment of diseases and disorders, such as cancer. In particular, the present invention relates to micelle compositions comprising a TLR7 agonist, such as 1V270.

BACKGROUND

Toll-like receptors (TLRs) are a class of receptors expressed on various cell types and play a key role in the innate immune system. Upon activation, TLRs activate signal transduction pathway involved in immune activation. Several mammalian TLRs and a number of their agonists have been identified. For example, guanine and uridine rich single-stranded RNA has been identified as a natural ligand for TLR7. In addition, several low molecular weight activators of TLR7 have been identified, including imidazoquinolines, and purine-like molecules. While TLR stimulation initiates a common signaling cascade (involving the adaptor protein MyD88, the transcription factor NFκB, and proinflammatory and effector cytokines), different TLRs are expressed by different cell types, however, TLR7 is mainly expressed in monocytes, plasmacytoid dendritic cells, myeloid dendritic cells and B-cells and are localized to the endosome membrane.

TLR7 has been shown to play a significant role in the pathogenesis of autoimmune disorders such as Systemic Lupus Erythematosus (SLE) as well as in the regulation of antiviral immunity. A TLR7 agonist, Aldara (Imiquimod), an imidazoquinoline, has been approved for topical use in treating warts caused by papillomavirus, for basal cell carcinoma and actinic keratoses. Due to their ability to induce robust production of anti-cancer cytokines such as interleukin-12, TLR7 agonists have also been investigated for cancer immunotherapy. Recent examples include TMX-202 delivery via liposomal formulation, as well as the delivery of resiquimod via nanoparticles formed from beta-cyclodextrin.

However, repeated injections of therapeutic nanoparticle compositions have been shown to trigger an accelerated blood clearance (ABC) phenomenon by antibodies, in particular for PEG-based liposomes, which tampers the utility of therapeutic nanoparticle delivery systems. Hence, there is an impetus in the art for the development of more effective therapeutic nanoparticle compositions.

SUMMARY

The present inventors have surprisingly discovered that micelle compositions comprising a TLR7 agonist show very potent anti-cancer activity and are devoid of previously recognized undesired pharmacokinetic behaviour.

In a first aspect, the present disclosure provides a micelle composition comprising: a toll-like receptor 7 (TLR7) agonist of formula (I), formula (II), formula (III) or formula (IV);

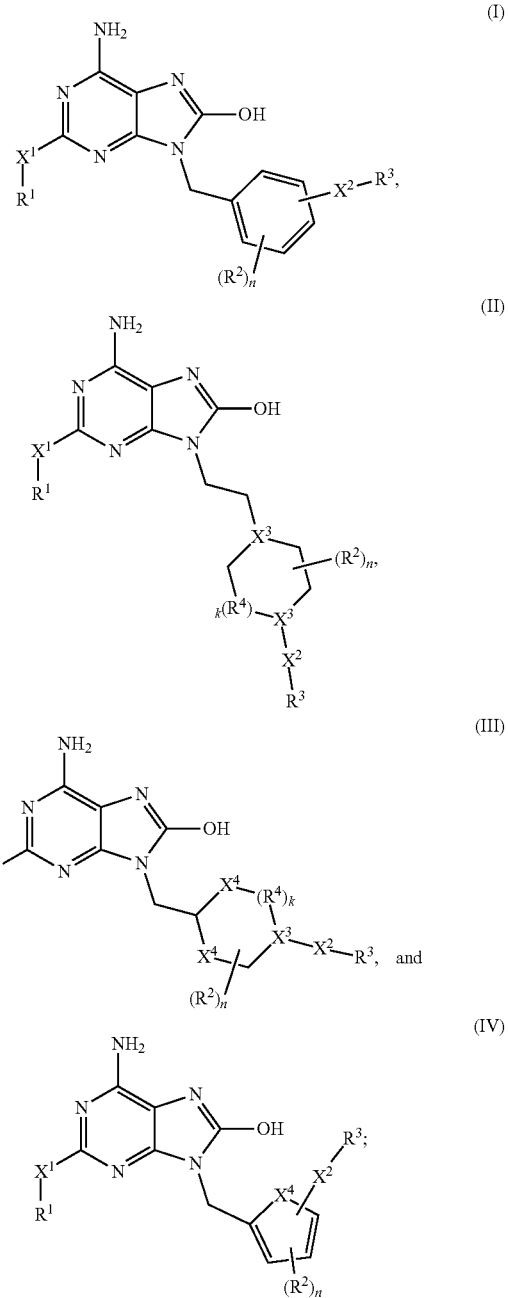

wherein X is —O—, —S—, or —$NR^C$;

$R^1$ is hydrogen, ($C_1$-$C_{10}$)alkyl, substituted ($C_1$-$C_{10}$)alkyl, $C_{6-10}$aryl, or substituted $C_{6-10}$aryl, $C_{5-9}$heterocyclic, substituted $C_{5-9}$heterocyclic;

$R^1$ is hydrogen, $C_{1-10}$alkyl, or substituted $C_{1-10}$alkyl; or $R^C$ and $R^1$ taken together with the nitrogen to which they are attached form a heterocyclic ring or a substituted heterocyclic ring;

each $R^2$ is independently —OH, ($C_1$-$C_6$)alkyl, substituted ($C_1$-$C_6$)alkyl, ($C_1$-$C_6$)alkoxy, substituted ($C_1$-$C_6$) alkoxy, —C(O)—($C_1$-$C_6$)alkyl (alkanoyl), substituted —C(O)—($C_1$-$C_6$)alkyl, —C(O)—($C_6$-$C_{10}$)aryl (aroyl), substituted —C(O)—($C_6$-$C_{10}$)aryl, —C(O)OH (carboxyl), —C(O)O($C_1$-$C_6$)alkyl (alkoxycarbonyl), substituted —C(O)O(C$_1$-C$_6$)alkyl, —NR$^a$R$^b$, —C(O)NR$^a$R$^b$ (carbamoyl), halo, nitro, or cyano, or R$^2$ is absent;

each R$^a$ and R$^b$ is independently hydrogen, (C$_1$-C$_6$)alkyl, substituted (C$_1$-C$_6$)alkyl, (C$_3$-C$_8$)cycloalkyl, substituted (C$_3$-C$_3$)cycloalkyl, (C$_1$-C$_6$)alkoxy, substituted (C$_1$-C$_6$)alkoxy, (C$_1$-C$_6$)alkanoyl, substituted (C$_1$-C$_6$) alkanoyl, aryl, aryl(C$_1$-C$_6$)alkyl, Het, Het (C$_1$-C$_6$)alkyl, or (C$_1$-C$_6$)alkoxycarbonyl;

wherein the substituents on any alkyl, aryl or heterocyclic groups are hydroxy, C$_{1-6}$alkyl, hydroxyC$_{1-6}$alkylene, C$_{1-6}$alkoxy, C$_{3-6}$cycloalkyl, C$_{1-6}$alkoxy C$_{1-6}$alkylene, amino, cyano, halo, or aryl;

n is 0, 1, 2, 3 or 4;

X$^2$ is a bond or a linking group; and

R$^3$ is a lipid;

X$^3$ is —N— or —CH—;

R$^4$ is —CH$_2$— or —CH(R$^2$)—; and k is 0 or 1;

X$^4$ is —O—, —S—, —NH—, —N(R$^d$)—, —CH$_2$—, or —CH(R$^2$)—;

each R$^d$ is independently —OH, (C$_1$-C$_6$)alkyl, substituted (C$_1$-C$_6$)alkyl, (C$_1$-C$_6$)alkoxy, substituted (C$_1$-C$_6$) alkoxy, —C(O)—(C$_1$-C$_6$)alkyl (alkanoyl), substituted —C(O)—(C$_1$-C$_6$)alkyl, —C(O)—(C$_6$-C$_{10}$)aryl (aroyl), substituted —C(O)—(C$_6$-C$_{10}$)aryl, —C(O)O(C$_1$-C$_6$) alkyl (alkoxycarbonyl), substituted —C(O)O(C$_1$-C$_6$) alkyl, —C(O)NR$^a$R$^b$ (carbamoyl);

or a tautomer thereof;

or a pharmaceutically acceptable salt or solvate thereof, and wherein the ring system of formula (II) is a piperidine ring with one heteroatom being an N atom and with the N-atom of the piperidine ring adjacent to X$^2$, and wherein the purine group in any of Formula (I), (II), (III), or (IV) is subject to tautomeric rearrangements;

and an amphiphilic micelle-forming agent.

In a second aspect, a micelle composition or pharmaceutical composition as defined herein is provided for use in the prevention, treatment or amelioration of a disease or disorder.

In a third aspect, a method for in vivo activation of immune cells in a subject is provided, comprising administering the micelle composition or pharmaceutical composition as defined herein to said subject in an amount sufficient to activate said immune cells.

In a fourth aspect, a method for enhancing or potentiating a treatment comprising radiotherapy and/or administration of a chemotherapeutic agent or an immune checkpoint inhibitor is provided, the method comprising administering the micelle composition or pharmaceutical composition as defined herein to said subject in combination with radiotherapy, administration of a chemotherapeutic agent and/or administration of an immune checkpoint inhibitor.

DESCRIPTION OF DRAWINGS

FIG. 1: FIG. 1A: Overview of micelles used, micelle name, composition, molar ratio, surface charge (Zeta), size and Polydispersity Index (PDI). Micelles were composed of 1,2-dioleoyl-sn-glycero-3-phosphoethanolamine-N-[methoxy(polyethylene glycol)-2000] (DOPE-PEG2000 or PEG) and TLR7 agonist 1v270 (2-(4-((6-amino-2-(2-methoxyethoxy)-8-oxo-7H-purin-9(8H)-yl)methyl)benzamido)ethyl 2,3-bis(oleoyloxy)propyl phosphate) (1v270). Composition and molar ratio of each component in the micelles is shown. Micelle surface charge expressed in mV. Micelle size measured in nanometer (nm). Error is expressed as SEM. Micelle names are used in the figures to clarify exact composition.

FIG. 3.

FIG. 4.

FIG. 5.

FIG. 6: Tumor growth and survival of mice bearing subcutaneous CT26 tumors and treated with 50, 100, or 200 nmol micelles in combination with radiotherapy (RT). Mice were treated on day 12 post inoculation and treated on 5 consecutive days with 2 Gy RT (day 12, 13, 14, 15, 16) and every fourth day for a total of 5 treatments with micelles (day 12, 16, 20, 24, 28). Groups contain 8-10 mice. Tumor growth curves are displayed as mean±SEM. Statistical significance on survival was determined using Mantel-Cox test.

FIG. 10: Tumor growth of mice bearing subcutaneous CT26 tumors treated with radiotherapy (RT) in combination with 100 nmol MBS8 intratumorally or 200 nmol MBS8 intravenously. When indicated, mice were treated with lipid matched vehicle instead of MBS8. Mice were treated on day 12 post inoculation and treated on 5 consecutive days with 2 Gy RT and every fourth day for a total of 5 treatments with micelles. Groups contain 8 mice. Tumor growth curves are displayed as mean±SEM.

FIG. 11: Tumor growth and survival of mice bearing subcutaneous EL4 or MC38 tumors treated with radiotherapy (RT) in combination with 200 nmol MBS8 or vehicle. Tumor growth curves are displayed as mean±SEM. EL4 bearing mice started treatment on day 7 after inoculation and were treated with 2 Gy RT on 3 consecutive days and MBS8 or vehicle every fourth day for a total of 5 treatments. Groups contain 9-10 mice.

MC38 bearing mice started treatment on day 10 after inoculation and were treated with 2 Gy RT on 5 consecutive days and MBS8 or vehicle every second (q2d), fourth (q4d), seventh day (q7d) for a total of 5 treatments. Groups contain 9 mice.

DETAILED DESCRIPTION

Definitions

Figure 1B:
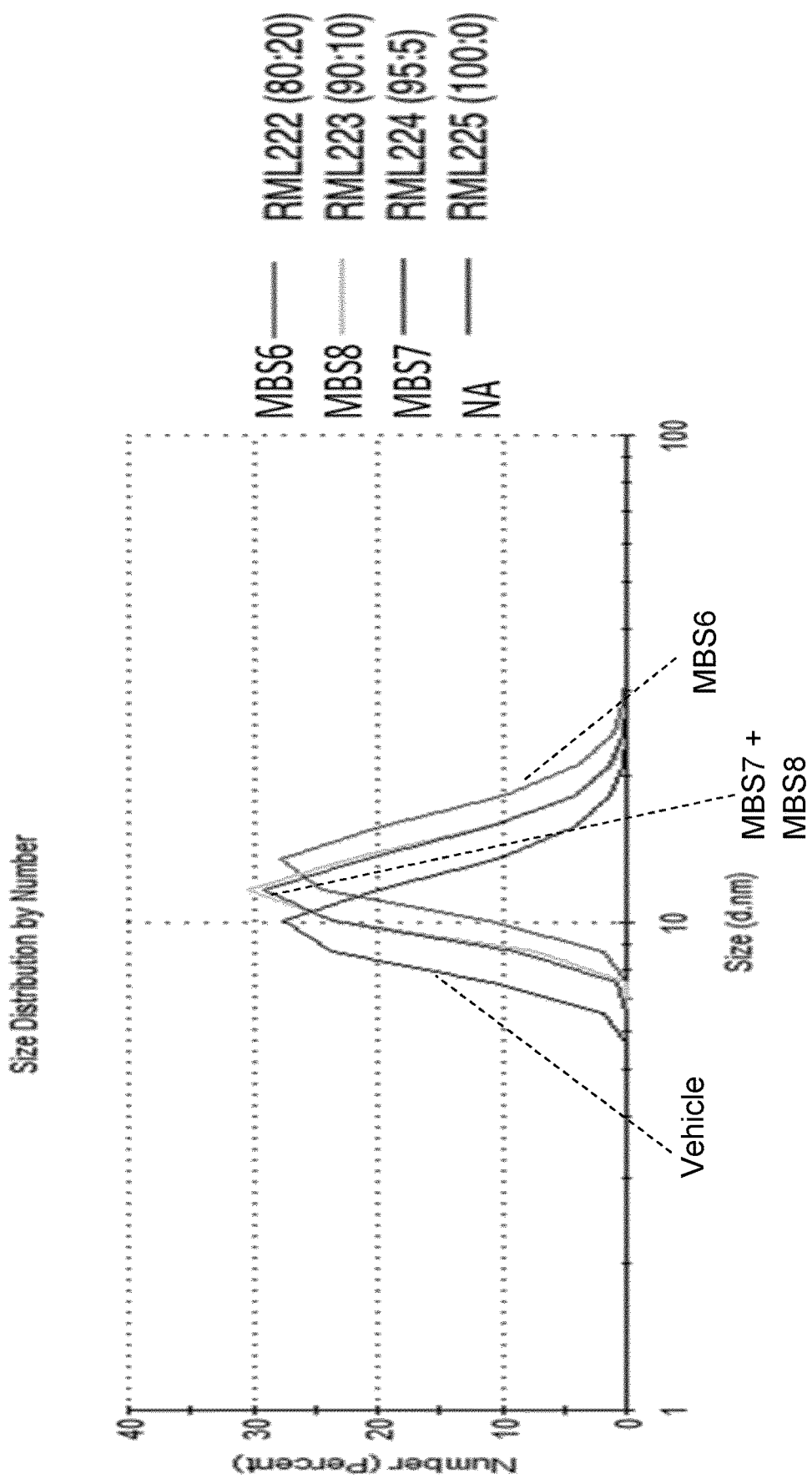
FIG. 1B: Micelle size by number distribution for the four micelles tested. Micelle size increases when 1v207 is added to the formulation.

A "lipid" as disclosed herein refers to a group of substances comprising at least one hydrophobic part, which by itself would be insoluble in water. Exemplary groups of lipids may without limitation be fatty acids, glycerolipids, glycerophospholipids, sphingolipids, sterol lipids, prenol lipids, saccharolipids, and polyketides.

The term "prophylaxis", as used herein, refers to prevention of a disease or prevention of spreading of a disease.

The term "treatment", as used herein, refers to the combating of a disease or disorder. "Treatment" or "treating," as used herein, includes any desirable effect on the symptoms or pathology of a disease or condition as described herein, and may include even minimal changes or improvements in one or more measurable markers of the disease or condition being treated. "Treatment" or "treating" does not necessarily indicate complete eradication or cure of the disease or condition, or associated symptoms thereof.

The term "PEG" as used herein, refers to polyethylene glycol.

The term "amphiphilic micelle-forming agent" as used herein refers to an agent which is both "amphiphilic" i.e. possessing both hydrophilic (water-loving, polar) and lipophilic (fat-loving) properties while also being capable of forming micelles. The amphiphilic micelle-forming agent disclosed herein are capable of forming micelles in a mixture with other compounds in solution.

The term "linking group" as used herein refers to a grouping of bonded atoms, such as a functional group, which covalently connects at least two parts of a molecule. In one example, a linking group is a carbonyl group, i.e. "—C(O)—" that may on one end bind e.g. an amine "H2N-alkyl(1)" and on the other end bind an alkyl(2) thereby forming an amide "alkyl(2)-C(O)—NH-alkyl(1)".

The terms "anti-PD-1", "α-PD-1, and "a-PD-1" are used interchangeably herein to refer to the group of immune check point inhibitors, anti-PD-1.

The terms "anti-PD-L1", "α-PD-L1, and "a-PD-L1" are used interchangeably herein to refer to the group of immune check point inhibitors, anti-PD-L1.

The term "MBS6" as used herein, refers to a micelle composition of DSPE-PEG2000:1V270 in a molar ratio of 80:20.

The term "MBS7" as used herein, refers to a micelle composition of DSPE-PEG2000:1V270 in a molar ratio of 95:5.

The term "MBS8" as used herein, refers to a micelle composition of DSPE-PEG2000:1V270 in a molar ratio of 90:10.

Micelles

A micelle is an aggregate particle of amphiphilic molecules dispersed in a liquid colloid. Most micelles in aqueous solution form an aggregate particle with the hydrophilic head group in contact with the surrounding hydrophilic solvent, sequestering the hydrophobic tail regions in the micelle centre.

Among the micelle-forming compounds, micelles made of polyethylene glycol-phosphatidylethanolamine (PEG-PE) have particularly attractive properties such as good stability, longevity, and ability to accumulate in the areas with an abnormal vasculature via the enhanced permeability and retention effect (into the areas with leaky vasculature, such as tumors). Additionally, these micelles can be made "targeted" by attaching specific targeting ligand molecules to the micelle surface or can be comprised of stimuli-responsive amphiphilic block copolymers. Addition of second component such as surfactant or another hydrophobic material to the main micelle forming material further improves the solubilizing capacity of micelles without compromising their stability. Micelles are more simple to prepare compared to other nanoparticles e.g. liposomes, and may be produced by lipid mixture and sonication The size of a micelle can be determined by various techniques known to a person of skill in the art. Dynamic light scattering (DLS) experiments may be performed using e.g. a Malvern Zetasizer Nano ZS instrument, suitable for measuring the size and size distribution of micelles formed in aqueous solution. The diameter measured in DLS is a value that refers to how a particle diffuses within a fluid and is referred to as a hydrodynamic diameter.

The diameter of the micelles disclosed herein is expressed as a numerical average.

In one embodiment, the diameter of the micelle disclosed herein is between 5 nm and 50 nm, such as between 6 and 46 nm, such as between 7 and 42 nm, such as between 8 and 38 nm, such as between 9 and 34 nm, such as between 10 and 34 nm, such as between 11 nm and 30 nm, such as between 12 nm and 26 nm.

In one embodiment, the diameter of the micelle is from 5 nm to 39 nm, such as from 5 nm to 20 nm, such as from 20 nm to 30 nm, such as from 30 nm to 35 nm, such as from 35 nm to 39 nm.

In one embodiment, the diameter of the micelle is from 5 nm to 39 nm, such as from 5 nm to 38 nm, such as from 5 nm to 37 nm, such as from 5 nm to 36 nm, such as from 5 nm to 35 nm, such as from 5 nm to 34 nm, such as from 5 nm to 33 nm, such as from 5 nm to 32 nm, such as from 5 nm to 31 nm.

In one embodiment, the diameter of the micelle is between 5 nm and 25 nm, such as between 6 nm and 24 nm, such as between 7 nm and 23 nm, such as between 8 nm and 22 nm, such as between 9 nm and 21 nm, such as between 10 nm and 20 nm, such as between 11 nm and 19 nm, such as between 12 nm and 18 nm, such as between 13 nm and 17 nm, such as between 14 nm and 16 nm, such as 15 nm.

An "amphiphilic micelle-forming agent" of the present disclosure may in some embodiments comprise a phospholipid. The structure of the phospholipid generally comprises two hydrophobic fatty acid "tails" and a hydrophilic "head" group comprising of a phosphate group. The two components are joined together by a glycerol molecule. The phosphate groups can be modified with simple organic molecules, such as choline, ethanolamine or serine. In some embodiments, the simple organic molecule acts as a linking group to a polymer, such as PEG.

In one embodiment, the amphiphilic micelle-forming agent is selected from the group consisting of: a poloxamer, a poloxamine, a PEG-polyester, a PEG-polyanhydride, a PEG-poly-amino acid, a phospholipid, a polysorbate, and a polyoxyethylene alkyl ether.

In one embodiment, the PEG-polyester is selected from the group consisting of: a PEG-poly(lactic acid) (PEG-PLA), a PEG-poly(lactic-co-glycolic acid) (PLGA), and a PEG-poly(ε-caprolactone) (PCL).

In one embodiment, the PEG-polyanhydride is a PEG-polysebacic anhydride (PSA).

In one embodiment, a micelle composition is provided comprising a PEG-poly-amino acid, wherein the PEG-poly-amino acid is selected from the group consisting of: a PEG-poly(L-histidine), a PEG-poly(L-aspartic acid), a PEG-poly(L-asparagine), a PEG-poly(L-glutamic acid), a PEG-poly(L-glutamine), and a PEG-poly(L-lysine).

In one embodiment, the amphiphilic micelle-forming agent is a phospholipid conjugated to polyethylene glycol (PEG). In one embodiment, the phospholipid conjugated to PEG is conjugated via a carbonyl group.

An example of a preferred amphiphilic micelle-forming agent is DSPE-PEG2000, exemplified below as an ammonium salt:

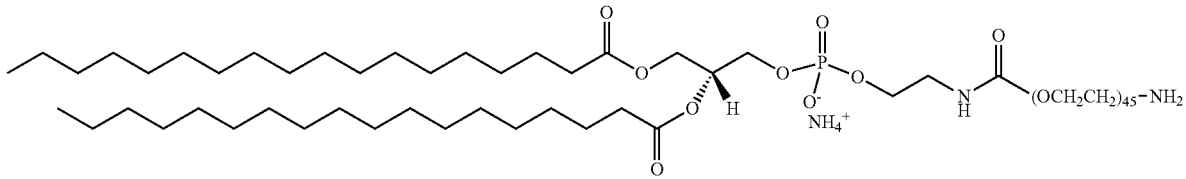

(DSPE-PEG2000)

DSPE-PEG2000 comprises phosphatidylethanolamine, which is bound to PEG via a carbonyl group. Phosphatidylethanolamine comprises glycerol esterified with two fatty acids and phosphoric acid. Whereas the phosphate group is combined with choline in phosphatidylcholine, it is combined with the ethanolamine in phosphatidylethanolamine. The two fatty acids may be the same, or different, and are usually in the 1,2 positions, but can also be in the 1,3 positions. The terminal end of PEG is in some embodiments aminated i.e. bound to $NH_2$.

Polyethylene Glycol (PEG)

In one embodiment, the micelles of the present disclosure comprise PEG. In one embodiment, the PEG is in the form of PEG conjugated to a phospholipid. The size of the PEG is between PEG350 to PEG30.000.

In one embodiment, the size of PEG is between PEG350 and PEG5000, for example between PEG550 and PEG4000, for example between PEG750 and PEG3000, such as between PEG1000 and PEG3000, preferably the size of the PEG is PEG2000.

Phospholipids of the Disclosure

The phospholipids disclosed herein may be part of the TLR7 agonist or the amphiphilic micelle-forming agent. Examples of phospholipids disclosed in the context of the amphiphilic micelle-forming agent may also be used as part of the TLR7 agonist, and vice versa.

In one embodiment, the micelle composition according to the present disclosure is provided, comprising a phospholipid, wherein the phospholipid comprises one or more alkyl chains that are C8-C24 alkyl(s), such as C10-C22, such as C12-C20, preferably C14-C18, most preferred C16-C18 saturated alkyl chains or unsaturated alkyl chains.

In one embodiment, the micelle composition according to the present disclosure is provided, comprising a phospholipid, wherein the phospholipid comprises a phosphatidylethanolamine (PE), a phosphatidylcholine (PC), a phosphatidylserine (PS), a phosphatidylglycerol (PG), a phosphatidylinositol (PI), a phosphatidic acid (PA), a bisphosphatidyl glycerol (DPG), or a phosphatidyl alcohol.

In one embodiment, the phosphatidylethanolamine is selected from the group consisting of 1,2-dioleoyl-phosphatidylethanolamine, 1,2-dipalmitoyl-phosphatidylethanolamine, 1,2-dimyristoyl-phosphatidylethanolamine, 1,2-distearoyl-phosphatidylethanolamine, 1-oleoyl-2-palmitoyl-phosphatidylethanolamine, 1-oleoyl-2-stearoyl-phosphatidylethanolamine, 1-palmitoyl-2-oleoyl-phosphatidylethanolamine, and 1-stearoyl-2-oleoyl-phosphatidylethanolamine.

In one embodiment, the phospholipid conjugated to PEG is selected from the group consisting of: 1,2-dioleoyl-sn-glycero-3-phosphoethanolamine (DOPE)-PEG, 1,2-distearoyl-sn-glycero-3-phosphoethanolamine (DSPE)-PEG, 1,2-dimyristoyl-sn-glycero-3-phosphoethanolamine (DMPE)-PEG, and 1,2-dipalmitoyl-sn-glycero-3-phosphoethanolamine (DPPE)-PEG.

In one embodiment, a micelle composition is provided comprising a phospholipid conjugated to PEG, wherein the phospholipid is: 1,2-distearoyl-sn-glycero-3-phosphoethanolamine (DSPE)-PEG.

In one embodiment, the amphiphilic micelle-forming agent is DSPE-PEG2000.

Pharmaceutical Compositions

The micelles of the present disclosure are useful as constituents of a pharmaceutical formulation. Thus, in one embodiment, the micelle compositions of the present disclosure are pharmaceutical compositions. In one embodiment, a pharmaceutical composition comprising the micelle composition as defined herein is provided.

Any form of such formulation which is suitable for administration to a mammal is contemplated.

The pharmaceutical formulation according to the present disclosure is preferably in the form of a solution, dispersion, suspension, lyophilisate, or frozen form.

In one embodiment, the administration route may be intravenous, intratumoral, oral, subcutaneous, intradermal, intramuscular, nasal, intraperitoneal, pulmonary or renal administration.

In one embodiment, the micelle composition according to the present disclosure comprises the amphiphilic micelle-forming agent and the TLR7 agonist, wherein the molar ratio between the amphiphilic micelle-forming agent and the TLR7 agonist is from 50:50 to 99.5:0.5, such as from 60:40 to 99:1, such as from 70:30 to 98:2, such as from 80:20 to 95:5, for example 95:5, 90:10, or 80:20.

In one embodiment, the micelle composition as disclosed herein is provided, wherein the composition comprises between 1% and 25% molar concentration of TLR7 agonist, such as 1%, such as 2%, such as 3%, such as 4%, such as 5%, such as 6%, such as 7%, such as 8%, such as 9%, such as 10%, such as 11%, such as 12%, such as 13%, such as 14%, such as 15%, such as 16%, such as 17%, such as 18%, such as 19%, such as 20%, such as 21%, such as 22%, such as 23%, such as 24%, such as 25%.

A micelle composition or pharmaceutical composition as defined herein is further provided, for use in the prevention, treatment or amelioration of a disease or disorder.

Therapeutic Uses and Methods

The micelle composition of the present disclosure may be used in prophylaxis, treatment or amelioration of cancer, an infectious disease, an inflammatory condition or disease, an autoimmune disease or allergy. In one embodiment, the micelle composition of the present disclosure is used in treatment of cancer.

The micelle composition or pharmaceutical composition may thus be used for treatment of a cancer; an infectious disease; an inflammatory condition or disease; an autoimmune disease; or an allergy.

In one embodiment, the disease or disorder is cancer, such as colon cancer. In one embodiment, the disease or disorder is cancer, such as a solid tumor.

Infectious Diseases

Another aspect of the disclosure is to provide a prevention or treatment for infectious diseases, by administration of the micelle composition disclosed herein to a subject. In a preferred embodiment, the micelle composition used to prevent or treat the infectious diseases is MBS8. Prevention or treatment of infectious diseases in both humans and livestock may be facilitated by the micelle composition disclosed herein. In one embodiment, the infectious disease is a viral infection or a bacterial infection. In a preferred embodiment, the treatment of infectious diseases is preventive. Thus in one embodiment, a method of preventing infectious disease is provided by administration of the micelle composition, such as MBS8, to a subject in need thereof. Suitable subjects for preventive treatment may be, without limitation, healthcare professionals and/or other humans working in close contact with infected subjects. These suitable subjects are at increased risk of getting infected, thus, preventive treatment by the micelle composition disclosed herein is advantageous.

Combination Therapy

In one embodiment, the treatment of cancer is enhanced by combination of existing treatments like monoclonal antibodies (Trastuzumab, Rituximab, Cetuximab), radiotherapy, chemotherapy or immune checkpoint inhibitors like Pembrolizumab, Ipilimumab. Hence, in one embodiment, the treatment of cancer is a combination treatment further comprising administering a monoclonal antibody to the subject suffering from cancer.

As demonstrated in examples 11, 13, 14, 15, 16, 18 and 24 an enhancing or synergistic effect may be obtained when the micelle composition or pharmaceutical composition as disclosed herein is administered in combination with radiotherapy, chemotherapeutic agents or immune checkpoint inhibitors. Thus, in one embodiment, the treatment of cancer is a combination treatment further comprising radiotherapy.

Certain types of chemotherapy are especially relevant for combination with TLR7 assets; these are chemotherapy compounds that induce what is called "immunogenic cell death" (ICD). As shown in example 14 and 24, micelle compositions comprising 1V270 significantly potentiate efficacy of doxorubicin and doxil and leads to effective treatment. In one embodiment, the treatment of cancer is a combination treatment further comprising administering a chemotherapeutic agent, such as doxorubicin or doxil. In one embodiment, the chemotherapeutic agent is selected from the group consisting of Doxorubicin, Doxil, Epirubicin, Cyclophosphamide, Bortezomib, and Oxaliplatin. In one embodiment, the treatment of cancer is a combination treatment further comprising administering immune checkpoint inhibitors, such as monoclonal antibodies targeting PD-1, PD-L1 or CTLA-4, such as α-PD-1, α-PD-L1 or α-CTLA-4, for example Atezolizumab, Avelumab, Durvalumab, Nivolumab, Tislelizumab, Pembrolizumab, or Ipilimumab. Preferably the immune checkpoint inhibitor is an α-PD-1, such as Nivolumab or Pembrolizumab. In a preferred embodiment, the micelle composition is MBS8 and the immune checkpoint inhibitor is Nivolumab or Pembrolizumab.

As demonstrated in example 18, the micelle composition is extremely effective in treating various cancers. This effect is demonstrated both as monotherapy and in combination with α-PD-1, even in treatment of cancers that do not respond to α-PD-1 monotherapy. In one embodiment, the combination treatment comprises administering the micelle composition and α-PD-1 for treatment of a cancer, in particular a cancer selected from the group consisting of: hepatoma, pancreatic, lymphoma, breast and colon cancer. In one embodiment, the combination treatment comprises administering the micelle composition and α-PD-1 for treatment of a cancer selected from the group consisting of: prostate cancer and kidney cancer. In particular the combination of the micelle composition and α-PD-1 is effective in treating cancers that do not respond to α-PD-1 monotherapy.

In one embodiment, the micelle composition used in combination treatment is MBS8. A preferred combination treatment is MBS8 and α-PD-1. In particular, this preferred combination treatment is effective in treating cancers that do not respond to anti-PD-1 monotherapy.

As shown in example 13, micelle compositions comprising 1V270 are very potent in combination with α-PD-1 leading to complete remission of at least 90% of treated mice carrying the CT26 tumor model. In one embodiment, MBS8 is administered in combination with a therapeutic antibody targeting the PD-1/PD-L1 pathway to a cancer patient in need of treatment. In one embodiment, the therapeutic antibody targeting the PD-1/PD-L1 pathway is selected from the group consisting of: Atezolizumab, Avelumab, Durvalumab, Nivolumab, Pembrolizumab, Spartalizumab/PDR001, Tislelizumab, BCD-100, TSR-042, Camrelizumab, IB1308, KN035, and CS1001.

Figure 16:
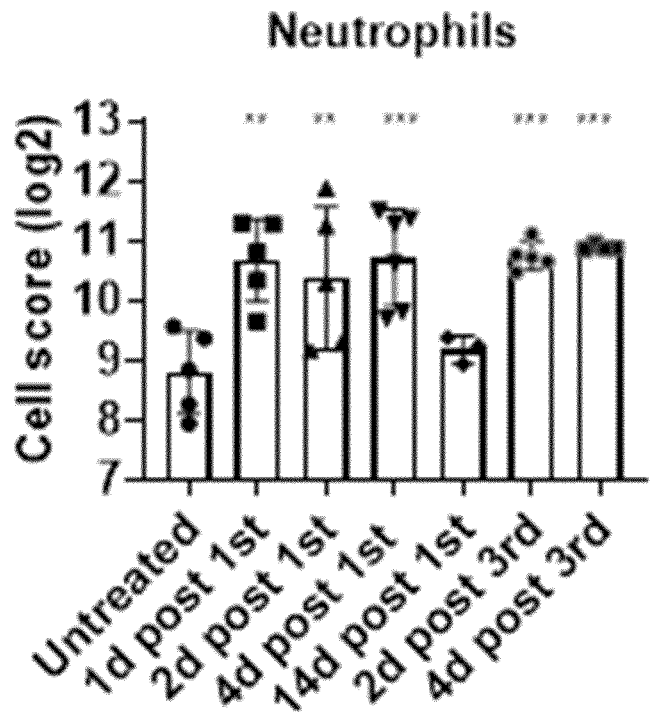
FIG. 16: Cell types in tumors from mice treated with MBS8 monotherapy based on gene expression analysis. Mice were treated with 200 nmol MBS8 in a q4d schedule for a total of 1 or 3 injections. Tumors were collected on day 0 (Untreated), 1 day post 1$^{st}$ injection, 2 days post 1$^{st}$ injection, 4 days post 1$^{st}$ injection, 14 days post 1$^{st}$ injection, 2 days post 3$^{rd}$ injection, 4 days post 3$^{rd}$ injection, n=3-6 for all groups. Gene expression analysis was performed on extracted RNA and cell type analysis was performed from the data with the Nanostring advanced software module. Two-way ANOVA with multiple comparison correction was performed to compare the different time points to untreated. * indicates p<0.05;  indicates p<0.01; * indicates p<0.001 and **** indicates p<0.0001
Figure 16:
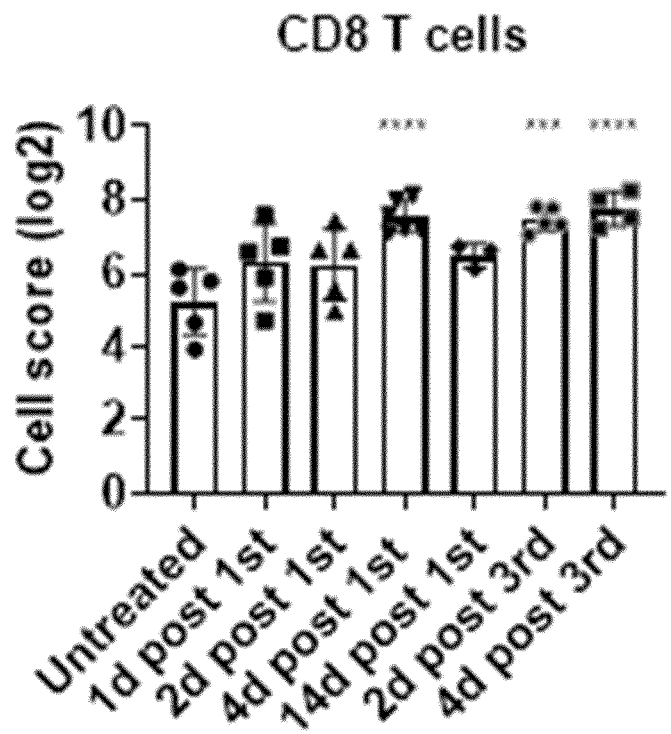
Figure 16:
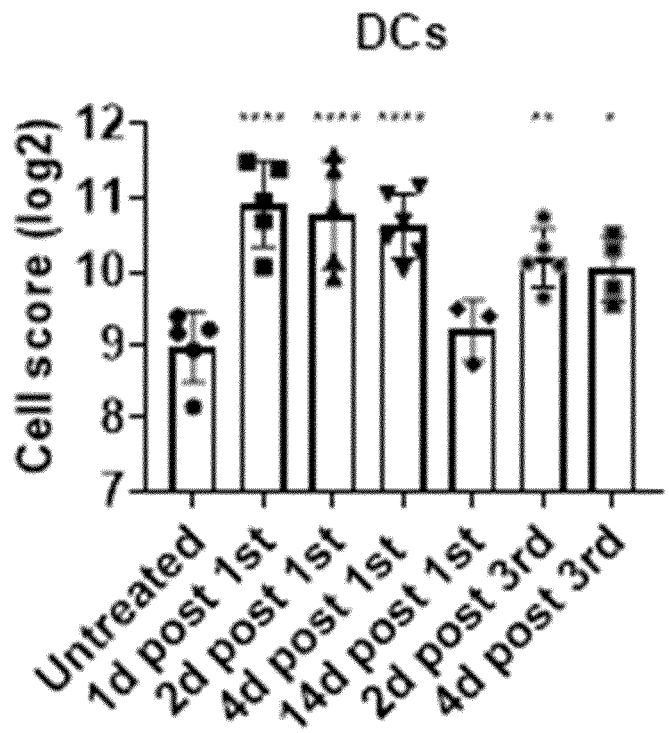
Figure 16:
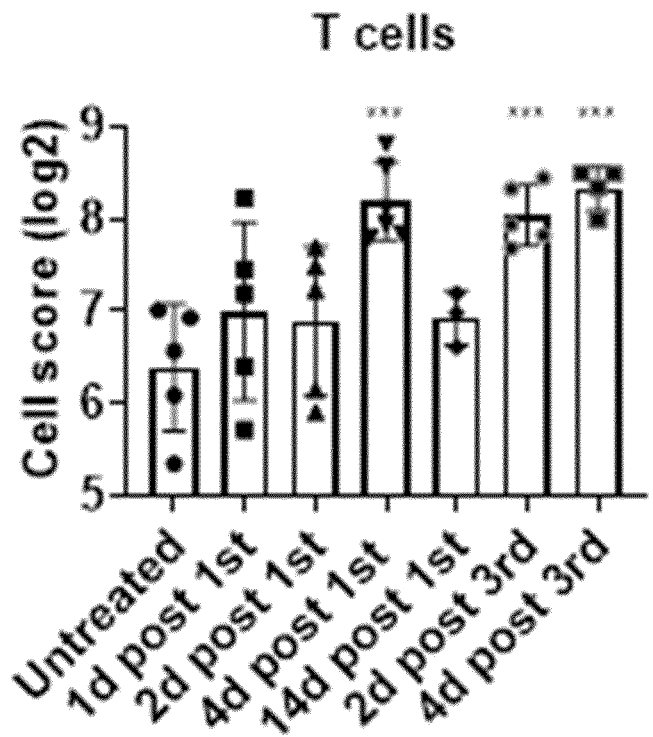
Figure 16:
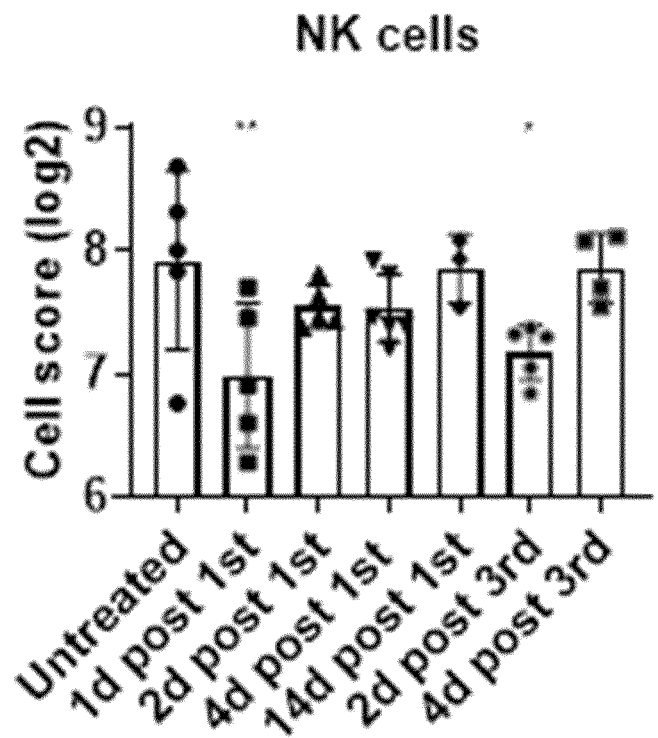
Figure 16:
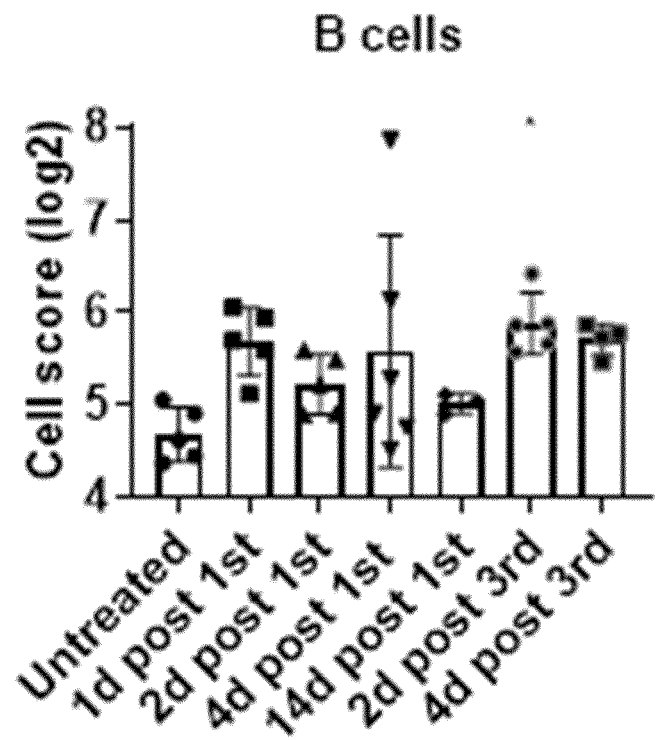
Figure 16:
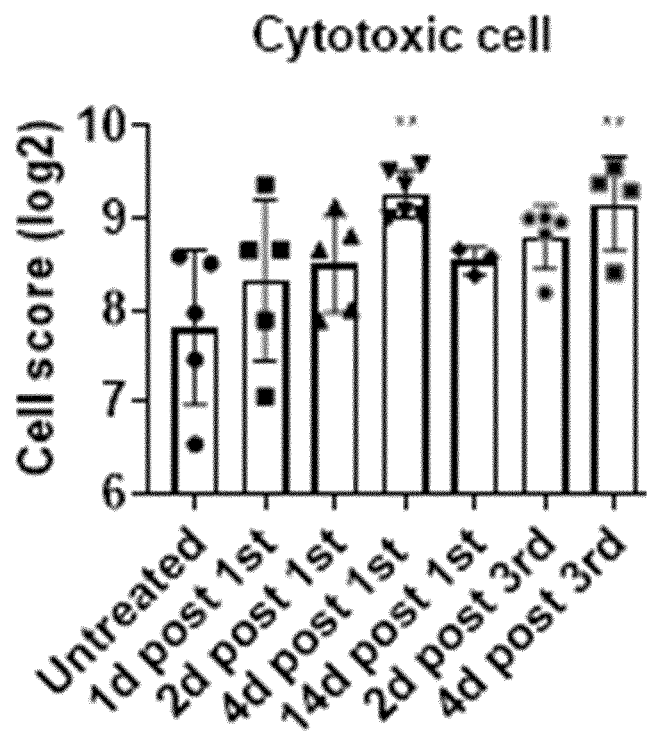
Figure 16:
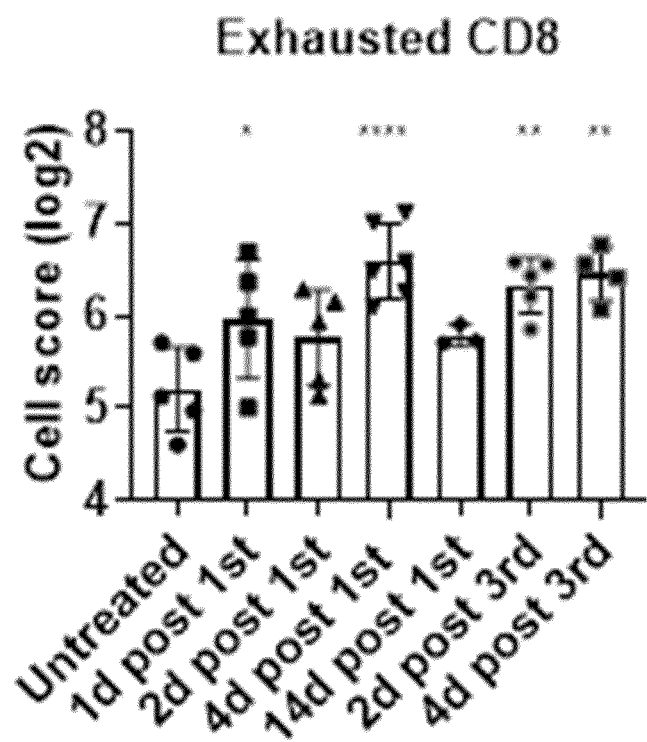
Figure 16:
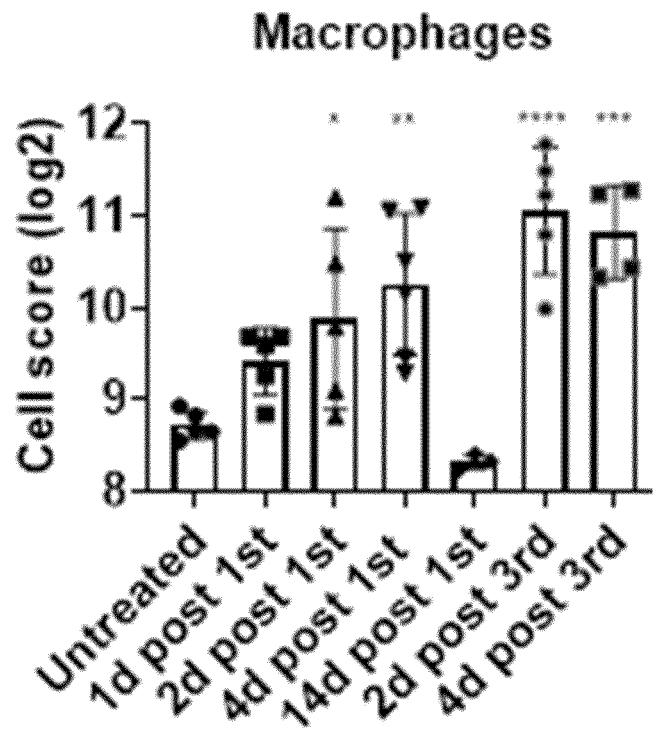

Monoclonal antibodies are beneficial in combination with TLR7 agonists through the activation of the complement-dependent cytotoxicity (CDC), antibody-dependent cellular cytotoxicity (ADCC), and antibody-dependent cellular phagocytosis (ADCP). This is relevant for antibodies against e.g. CD20, EGFR, CD38 and HER2. The ADCC, ADCP and CDC mediated tumor cell killing is dependent on activated NK-cells, macrophages and neutrophils which are activated by the micelle composition of the present disclosure (FIG. 16), in particular MBS8.

In one embodiment, MBS8 is administered to a cancer patient in combination with a monoclonal antibody targeting CD20.

In one embodiment, MBS8 is administered to a cancer patient in combination with a monoclonal antibody targeting the epidermal growth factor receptor (EGFR).

In one embodiment, MBS8 is administered to a cancer patient in combination with a monoclonal antibody targeting the Human Epidermal Growth Factor Receptor 2 (HER2).

In one embodiment, MBS8 is administered to a cancer patient in combination with a monoclonal antibody targeting CD38. In a particular embodiment, the monoclonal antibody targeting CD38 is selected from Daratumumab and Isatuximab.

In one embodiment, MBS8 is administered to a cancer patient in combination with a monoclonal antibody selected from the group consisting of: Ublituximab, Obinutuzumab, Ofatumumab, Ibritumomab tiuxetan, Rituximab, Tositumomab, Depatuxizumab mafodotin, Necitumumab, Panitumumab, Cetuximab, Trastuzumab, Trastuzumab-dkst, Trastuzumab emtansine, BAT8001, Pertuzumab, Margetuximab, Trastuzumab deruxtecan, Trastuzumab duocarmazine, Daratumumab, and Isatuximab.

In one embodiment, MBS8 is administered in combination with an antibody targeting CD47, such as Magrolimab.

In one embodiment, the treatment of cancer is performed as monotherapy, comprising administration of the micelle composition or pharmaceutical composition as disclosed herein.

The term "prophylaxis", as used herein, refers to prevention of a disease or prevention of spreading of a disease.

The term "treatment", as used herein, refers to the combating of a disease or disorder. "Treatment" or "treating," as used herein, includes any desirable effect on the symptoms or pathology of a disease or condition as described herein, and may include even minimal changes or improvements in one or more measurable markers of the disease or condition being treated. "Treatment" or "treating" does not necessarily indicate complete eradication or cure of the disease or condition, or associated symptoms thereof.

The term "amelioration", as used herein, refers to moderation in the severity of the symptoms of a disease or condition. Improvement in a patient's condition, or the activity of making an effort to correct, or at least make more acceptable, conditions that are difficult to endure related to patient's conditions is considered "ameliorative" treatment.

In one embodiment, the micelle composition is used in prophylaxis, treatment or amelioration of cancer.

In one embodiment, the micelle composition is used in prophylaxis, treatment or amelioration of an infectious disease.

In one embodiment, a method for in vivo activation of immune cells in a subject is provided, comprising administering the micelle composition or pharmaceutical composition as defined herein to said subject in an amount sufficient to activate said immune cells. A preferred subject is a human being, such as human being suffering from cancer.

TLR7 Agonists

Toll-like receptor 7, also known as TLR7, is a protein that in humans is encoded by the TLR7 gene. It is a member of the toll-like receptor (TLR) family and plays an important role in pathogen recognition and activation of innate immunity. Due to their ability to induce robust production of anti-cancer cytokines such as interleukin-12, TLR7 agonists have been investigated for cancer immunotherapy.

The micelle compositions of the present disclosure comprises a toll-like receptor 7 (TLR7) agonist of formula (I), formula (II), formula (III) or formula (IV);

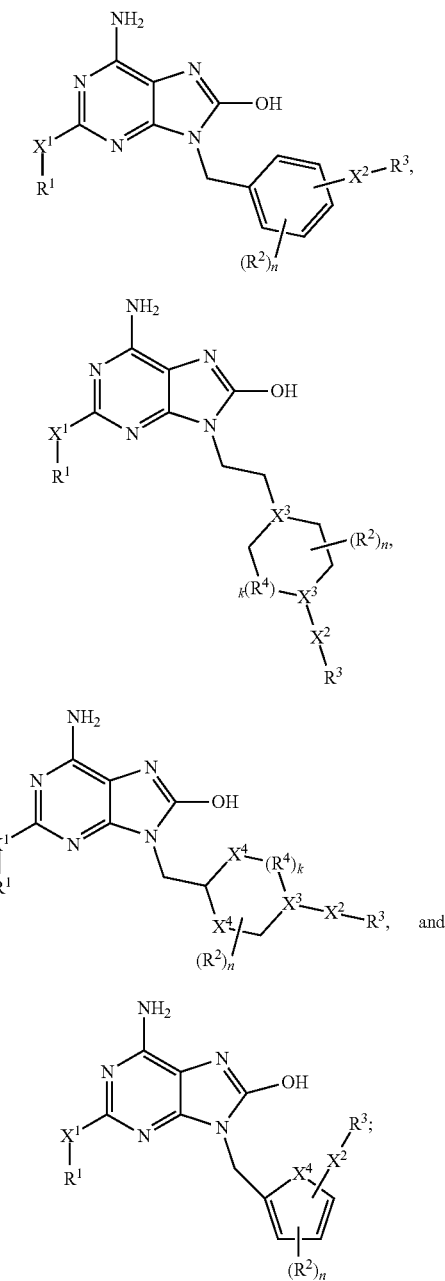

wherein $X^1$ is —O—, —S—, or —NR$^C$;

$R^1$ is hydrogen, $(C_1-C_{10})$alkyl, substituted $(C_1-C_{10})$alkyl, $C_{6-10}$aryl, or substituted $C_{6-10}$aryl, $C_{5-9}$heterocyclic, substituted $C_{5-9}$heterocyclic;

$R^C$ is hydrogen, $C_{1-10}$alkyl, or substituted $C_{1-10}$alkyl; or $R^C$ and $R^1$ taken together with the nitrogen to which they are attached form a heterocyclic ring or a substituted heterocyclic ring;

each $R^2$ is independently —OH, $(C_1-C_6)$alkyl, substituted $(C_1-C_6)$alkyl, $(C_1-C_6)$alkoxy, substituted $(C_1-C_6)$alkoxy, —C(O)—$(C_1-C_6)$alkyl (alkanoyl), substituted —C(O)—$(C_1-C_6)$alkyl, —C(O)—$(C_6-C_{10})$aryl (aroyl), substituted —C(O)—$(C_6-C_{10})$aryl, —C(O)OH (carboxyl), —C(O)O$(C_1-C_6)$alkyl (alkoxycarbonyl), substituted —C(O)O$(C_1-C_6)$alkyl, —NR$^a$R$^b$, —C(O)NR$^a$R$^b$ (carbamoyl), halo, nitro, or cyano, or $R^2$ is absent;

each R$^a$ and R$^b$ is independently hydrogen, $(C_1-C_6)$alkyl, substituted $(C_1-C_6)$alkyl, $(C_3-C_8)$cycloalkyl, substituted $(C_3-C_3)$cycloalkyl, $(C_1-C_6)$alkoxy, substituted $(C_1-C_6)$alkoxy, $(C_1-C_6)$alkanoyl, substituted $(C_1-C_6)$alkanoyl, aryl, aryl$(C_1-C_6)$alkyl, Het, Het $(C_1-C_6)$alkyl, or $(C_1-C_6)$alkoxycarbonyl;

wherein the substituents on any alkyl, aryl or heterocyclic groups are hydroxy, $C_{1-6}$alkyl, hydroxy$C_{1-6}$alkylene, $C_{1-6}$alkoxy, $C_{3-6}$cycloalkyl, $C_{1-6}$alkoxy $C_{1-6}$alkylene, amino, cyano, halo, or aryl;

n is 0, 1, 2, 3 or 4;

$X^2$ is a bond or a linking group; and $R^3$ is a lipid;

$X^3$ is —N— or —CH—;

$R^4$ is —CH$_2$— or —CH(R$^2$)—; and k is 0 or 1;

$X^4$ is —O—, —S—, —NH—, —N(R$^d$)—, —CH$_2$—, or —CH(R$^2$)—;

each R$^d$ is independently —OH, $(C_1-C_6)$alkyl, substituted $(C_1-C_6)$alkyl, $(C_1-C_6)$alkoxy, substituted $(C_1-C_6)$alkoxy, —C(O)—$(C_1-C_6)$alkyl (alkanoyl), substituted —C(O)—$(C_1-C_6)$alkyl, —C(O)—$(C_5-C_{10})$aryl (aroyl), substituted —C(O)—$(C_5-C_{10})$aryl, —C(O)O$(C_1-C_6)$alkyl (alkoxycarbonyl), substituted —C(O)O$(C_1-C_6)$alkyl, —C(O)NR$^a$R$^b$ (carbamoyl);

or a tautomer thereof;

or a pharmaceutically acceptable salt or solvate thereof, and wherein the ring system of formula (II) is a piperidine ring with one heteroatom being an N atom and with the N-atom of the piperidine ring adjacent to $X^2$, and wherein the purine group in any of Formula (I), (II), (III), or (IV) is subject to tautomeric rearrangements;

and an amphiphilic micelle-forming agent.

It is to be understood that the purine group in any of Formula (I), (II), (III), or (IV) is subject to tautomeric rearrangements.

In one embodiment, the micelle composition according to the present disclosure is provided, wherein the TLR7 agonist is of formula (I):

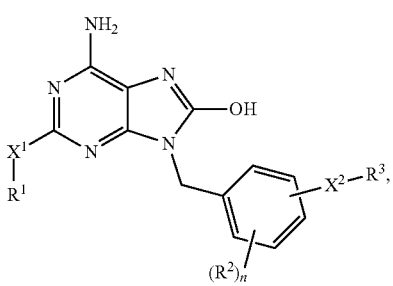

wherein $X^1$ is —O—, —S—, or —NR$^C$;

$R^1$ is hydrogen, $(C_1-C_{10})$alkyl, substituted $(C_1-C_{10})$alkyl, $C_{6-10}$aryl, or substituted $C_{6-10}$aryl, $C_{5-9}$heterocyclic, substituted $C_{5-9}$heterocyclic; $R^C$ is hydrogen, $C_{1-10}$alkyl, or substituted $C_{1-10}$alkyl; or $R^C$ and $R^1$ taken together with the nitrogen to which they are attached form a heterocyclic ring or a substituted heterocyclic ring;

each R² is independently —OH, (C₁-C₆)alkyl, substituted (C₁-C₆)alkyl, (C₁-C₆)alkoxy, substituted (C₁-C₆)alkoxy, —C(O)—(C₁-C₆)alkyl (alkanoyl), substituted —C(O)—(C₁-C₆)alkyl, —C(O)—(C₆-C₁₀)aryl (aroyl), substituted —C(O)—(C₆-C₁₀)aryl, —C(O)OH (carboxyl), —C(O)O(C₁-C₆)alkyl (alkoxycarbonyl), substituted —C(O)O(C₁-C₆)alkyl, —NRᵃRᵇ, —C(O)NRᵃRᵇ (carbamoyl), halo, nitro, or cyano, or R² is absent;

each Rᵃ and Rᵇ is independently hydrogen, (C₁-C₆)alkyl, substituted (C₁-C₆)alkyl, (C₃-C₈)cycloalkyl, substituted (C₃-C₃)cycloalkyl, (C₁-C₆)alkoxy, substituted (C₁-C₆)alkoxy, (C₁-C₆)alkanoyl, substituted (C₁-C₆)alkanoyl, aryl, aryl(C₁-C₆)alkyl, Het, Het (C₁-C₅)alkyl, or (C₁-C₆)alkoxycarbonyl;

wherein the substituents on any alkyl, aryl or heterocyclic groups are hydroxy, C₁₋₆alkyl, hydroxyC₁₋₆alkylene, C₁₋₆alkoxy, C₃₋₆cycloalkyl, C₁₋₆alkoxy C₁₋₆alkylene, amino, cyano, halo, or aryl;

n is 0, 1, or 2;

X² is a bond or a linking group; and

R³ is a lipid;

or a tautomer thereof;

or a pharmaceutically acceptable salt or solvate thereof, and wherein the purine group is subject to tautomeric rearrangements.

In one embodiment, the micelle composition according to the present disclosure is provided, wherein the TLR7 agonist is of formula (I):

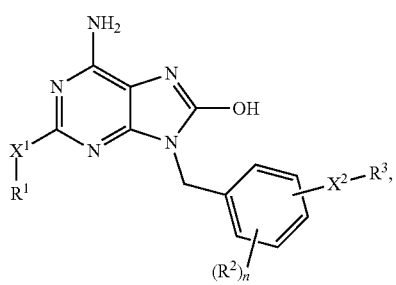

(I)

wherein X¹ is —O—, —S—, or —NRᶜ;

R¹ is hydrogen, (C₁-C₁₀)alkyl, substituted (C₁-C₁₀)alkyl, C₆₋₁₀aryl, or substituted C₆₋₁₀aryl, C₅₋₉heterocyclic, substituted C₅₋₉heterocyclic;

Rᶜ is hydrogen, C₁₋₁₀alkyl, or substituted C₁₋₁₀alkyl; or Rᶜ and R¹ taken together with the nitrogen to which they are attached form a heterocyclic ring or a substituted heterocyclic ring;

R² is absent;

n is 0;

X² is a bond or a linking group; and

R³ is a lipid;

or a tautomer thereof;

or a pharmaceutically acceptable salt or solvate thereof, and wherein the purine group is subject to tautomeric rearrangements. It is understood by a person of skill in the art that when R² is absent, n must be 0 i.e. not present.

In one embodiment, the micelle composition according to the present disclosure is provided, wherein the TLR7 agonist is of formula (I):

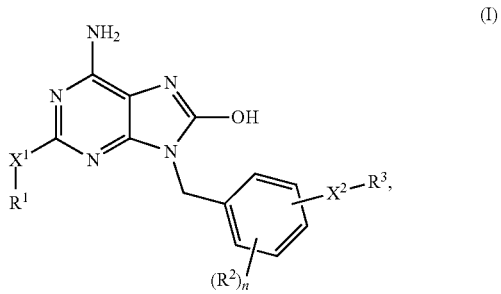

(I)

wherein X¹ is —O—;

R¹ is hydrogen, (C₁-C₁₀)alkyl, substituted (C₁-C₁₀)alkyl, C₆₋₁₀aryl, or substituted C₆₋₁₀aryl, C₅₋₉heterocyclic, substituted C₅₋₉heterocyclic;

R² is absent;

n is 0;

X² is a bond or a linking group; and

R³ is a lipid;

or a tautomer thereof;

or a pharmaceutically acceptable salt or solvate thereof, and wherein the purine group is subject to tautomeric rearrangements.

In one embodiment, the micelle composition according to the present disclosure is provided, wherein the TLR7 agonist is of formula (V):

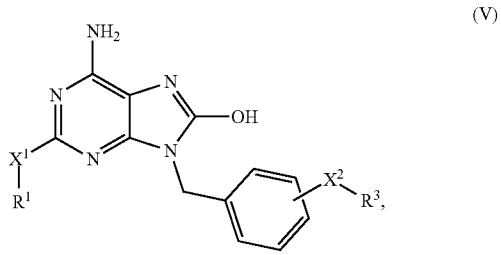

(V)

wherein X¹ is —O—;

R¹ is hydrogen, (C₁-C₆)alkyl, substituted (C₁-C₆)alkyl, C₆aryl, or substituted C₆aryl, C₅₋₆ heterocyclic, substituted C₅₋₆heterocyclic;

X² is a bond or a linking group; and

R³ is a lipid;

or a tautomer thereof;

or a pharmaceutically acceptable salt or solvate thereof, and wherein the purine group is subject to tautomeric rearrangements.

In one embodiment, the micelle composition according to the present disclosure is provided, wherein the TLR7 agonist is of formula (VI):

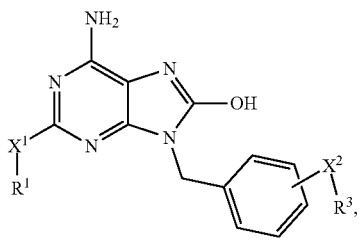

(VI)

wherein $X^1$ is —O—;

$R^1$ is hydrogen, $(C_1\text{-}C_6)$alkyl, substituted $(C_1\text{-}C_6)$alkyl, $C_6$aryl, or substituted $C_6$aryl, $C_{5\text{-}6}$ heterocyclic, substituted $C_{5\text{-}6}$heterocyclic;

$X^2$ is a bond or a linking group; and $R^3$ is a lipid;

or a tautomer thereof;

or a pharmaceutically acceptable salt or solvate thereof, and wherein the purine group is subject to tautomeric rearrangements.

In one embodiment, the micelle composition according to the present disclosure is provided, wherein the TLR7 agonist is of formula (VII):

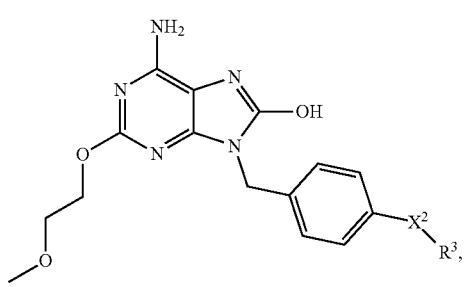

(VII)

wherein $X^2$ is a bond or a linking group; and $R^3$ is a lipid;

or a tautomer thereof;

or a pharmaceutically acceptable salt or solvate thereof, and wherein the purine group is subject to tautomeric rearrangements.

In one embodiment, the micelle composition according to the present disclosure is provided, wherein the TLR7 agonist is of formula (VIII):

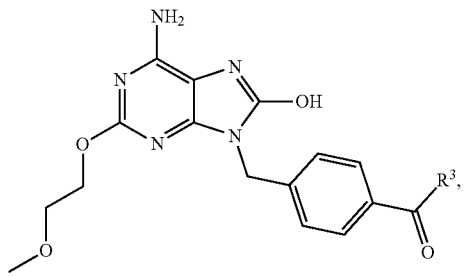

(VIII)

wherein $R^3$ is a lipid;

or a tautomer thereof;

or a pharmaceutically acceptable salt or solvate thereof, and wherein the purine group is subject to tautomeric rearrangements.

In one embodiment, $X^2$ is selected from the group consisting of: a bond, —O—, —C(O)-(carbonyl), $(C_1\text{-}C_6)$alkyl, substituted $(C_1\text{-}C_6)$alkyl, $(C_1\text{-}C_6)$alkoxy, substituted $(C_1\text{-}C_6)$ alkoxy, —C(O)—$(C_1\text{-}C_6)$alkyl (alkanoyl), substituted —C(O)—$(C_1\text{-}C_6)$alkyl, —C(O)—$(C_6\text{-}C_{10})$aryl (aroyl), substituted —C(O)—$(C_6\text{-}C_{10})$aryl, —C(O)OH (carboxyl), —C(O)O$(C_1\text{-}C_6)$alkyl (alkoxycarbonyl), substituted —C(O)O$(C_1\text{-}C_6)$alkyl, —NR$^a$R$^b$, —C(O)NR$^a$R$^b$ (carbamoyl); and each R$^a$ and R$^b$ is independently hydrogen, $(C_1\text{-}C_6)$alkyl, substituted $(C_1\text{-}C_6)$alkyl, $(C_3\text{-}C_8)$cycloalkyl, substituted $(C_3\text{-}C_3)$cycloalkyl, $(C_1\text{-}C_6)$alkoxy, substituted $(C_1\text{-}C_6)$alkoxy, $(C_1\text{-}C_6)$alkanoyl, substituted $(C_1\text{-}C_6)$ alkanoyl, aryl, aryl$(C_1\text{-}C_6)$alkyl, Het, Het $(C_1\text{-}C_6)$alkyl, or $(C_1\text{-}C_6)$alkoxycarbonyl;

and wherein $X^1$ is —O—, —S—, or —NR$^C$;

$R^1$ is hydrogen, $(C_1\text{-}C_6)$alkyl, or substituted $(C_1\text{-}C_6)$alkyl;

$R^C$ is hydrogen, $C_{1\text{-}6}$alkyl, or substituted $C_{1\text{-}6}$alkyl; or R$^C$ and $R^1$ taken together with the nitrogen to which they are attached form a heterocyclic ring or a substituted heterocyclic ring.

In a preferred embodiment, $X^2$ is —C(O)— (carbonyl). In a preferred embodiment, $X^2$ is —C(O)— (carbonyl) and $R^3$ is 1,2-dioleoyl-phosphatidylethanolamine according to the formulas disclosed herein.

In one embodiment, $R^3$ is a lipid selected from the group consisting of: a phospholipid comprising one or two carboxylic esters, a gonane, such as cholesterol, a saccharolipid, and a glyceride. In one embodiment, $R^3$ is a phospholipid comprising one or two carboxylic esters.

A "lipid" as disclosed herein refers to a group of substances comprising at least one hydrophobic part, which by itself would be insoluble in water. Exemplary groups of lipids may without limitation be fatty acids, glycerolipids, glycerophospholipids, sphingolipids, sterol lipids, prenol lipids, saccharolipids, and polyketides.

In a particularly preferred embodiment, the TLR7 agonist according to Formula (I) has a structure according to Formula (IA),
wherein the definitions of Formula (I) are as follows:
$X^1$ is —O—;
$R^1$ is 2-methoxy-1-ethyl
$R^2$ is absent;
$X^2$ is carbonyl; and
$R^3$ is 1,2-dioleoyl-sn-glycero-3-phosphoethanolamine (DOPE);
or a pharmaceutically acceptable salt or solvate thereof;

Aryl refers to a C6-10 monocyclic or fused cyclic aryl group, such as phenyl, indenyl, or naphthyl, and the like.

Heterocyclic or heterocycle (Het) refers to monocyclic saturated heterocyclic groups, or unsaturated monocyclic or fused heterocyclic group containing at least one heteroatom, e.g., 0-3 nitrogen atoms, 0-1 oxygen atom (—O—), and 0-1 sulfur atom (—S—). Non-limiting examples of saturated monocyclic heterocyclic group includes 5 or 6 membered saturated heterocyclic group, such as tetrahydrofuranyl, pyrrolidinyl, morpholinyl, piperidyl, piperazinyl or pyrazolidinyl. Non-limiting examples of unsaturated monocyclic het- (IA)

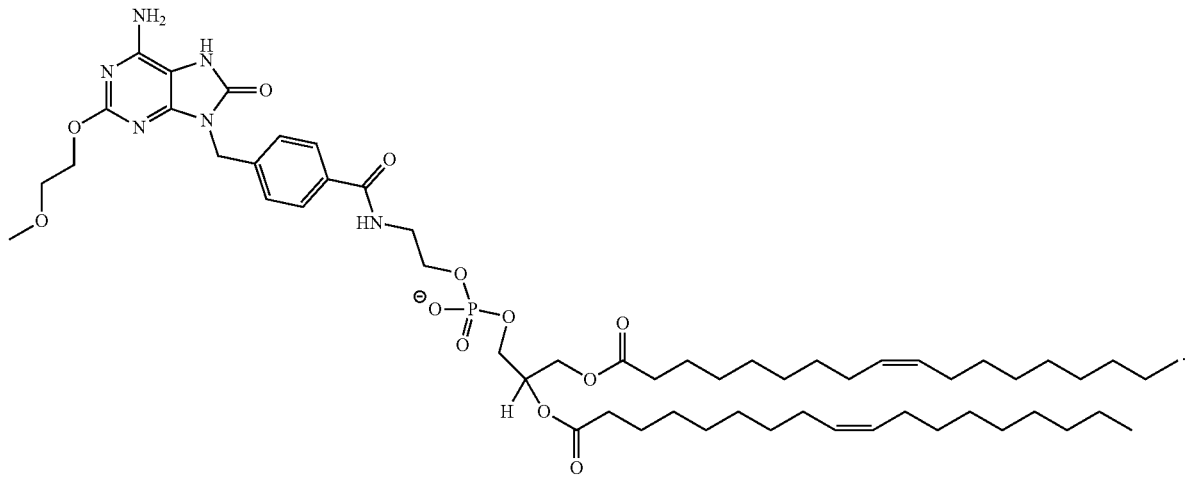

The compound according to Formula (IA) is also known in the literature as 1V270 from e.g. U.S. Pat. No. 8,357,374.

Thus, in a preferred embodiment, the micelle composition is provided, wherein the TLR7 agonist has a structure according to formula (IA):

erocyclic group includes 5 or 6 membered unsaturated heterocyclic group, such as furyl, pyrrolyl, pyrazolyl, imidazolyl, thiazolyl, thienyl, pyridyl or pyrimidinyl. Non-limiting examples of unsaturated fused heterocyclic groups includes unsaturated bicyclic heterocyclic group, such as (IA)

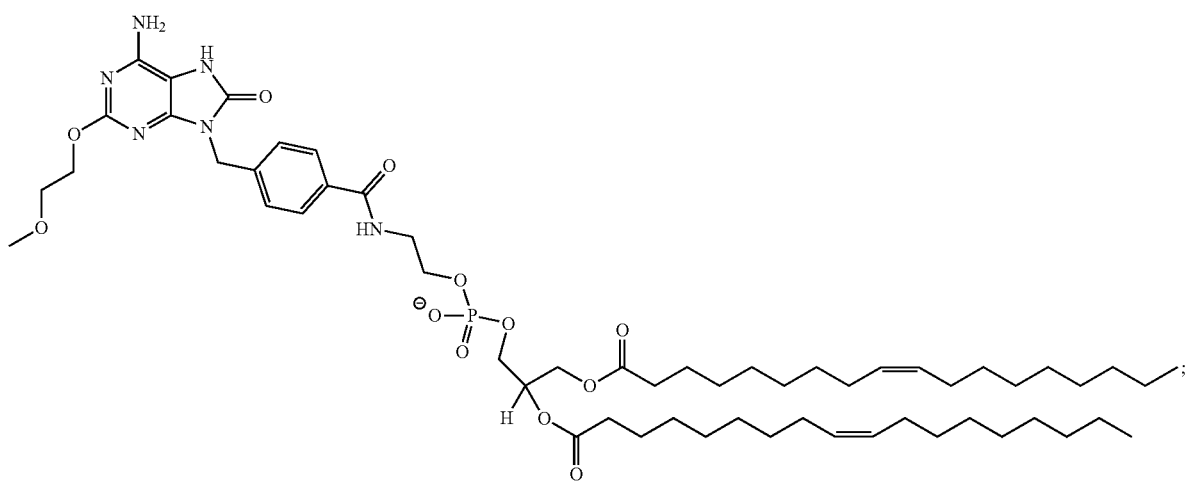

or a tautomer thereof;

A halogen atom as referred to herein refers to a fluorine atom, chlorine atom, bromine atom or iodine atom.

indolyl, isoindolyl, quinolyl, benzothizolyl, chromanyl, benzofliranyl, and the like. A Het group can be a saturated heterocyclic group or an unsaturated heterocyclic group, such as a heteroaryl group.

Non-limiting examples of heterocyclic rings include 5 or 6 membered saturated heterocyclic rings, such as 1-pyrrolidinyl, 4-morpholinyl, 1-piperidyl, 1-piperazinyl or 1-pyrazolidinyl, 5 or 6 membered unsaturated heterocyclic rings such as 1-imidazolyl, and the like.

The alkyl, aryl, heterocyclic groups of $R^1$ can be optionally substituted with one or more substituents, wherein the substituents are the same or different, and include lower alkyl; cycloalkyl, hydroxyl; hydroxy C1-6 alkylene, such as hydroxymethyl, 2-hydroxyethyl or 3-hydroxypropyl; lower alkoxy; C1-6 alkoxy C1-6 alkyl, such as 2-methoxyethyl, 2-ethoxyethyl or 3-methoxypropyl; amino; alkylamino; dialkyl amino; cyano; nitro; acyl; carboxyl; lower alkoxycarbonyl; halogen; mercapto; C1-6 alkylthio, such as, methylthio, ethylthio, propylthio or butylthio; substituted C1-6 alkylthio, such as methoxyethylthio, methylthioethylthio, hydroxyethylthio or chloroethylthio; aryl; substituted C6-10 monocyclic or fused-cyclic aryl, such as 4-hydroxyphenyl, 4-methoxyphenyl, 4-fluorophenyl, 4-chlorophenyl or 3,4-dichlorophenyl; 5-6 membered unsaturated heterocyclic, such as furyl, pyrrolyl, pyrazolyl, imidazolyl, thiazolyl, thienyl, pyridyl or pyrimidinyl; and bicyclic unsaturated heterocyclic, such as indolyl, isoindolyl, quinolyl, benzothiazolyl, chromanyl, benzofuranyl or phthalimino. In certain embodiments, one or more of the above groups can be expressly excluded as a substituent of various other groups of the formulas. In some embodiments, the five-membered ring of the formula is a thiazole ring.

The alkyl, aryl, heterocyclic groups of $R^2$ can be optionally substituted with one or more substituents, wherein the substituents are the same or different, and include hydroxyl; C1-6 alkoxy, such as methoxy, ethoxy or propoxy; carboxyl; C2-7 alkoxycarbonyl, such as methoxycarbonyl, ethoxycarbonyl or propoxycarbonyl) and halogen. The alkyl, aryl, heterocyclic groups of $R^c$ can be optionally substituted with one or more substituents, wherein the substituents are the same or different, and include C3-6 cycloalkyl; hydroxyl; C1-6 alkoxy; amino; cyano; aryl; substituted aryl, such as 4-hydroxyphenyl, 4-methoxyphenyl, 4-chlorophenyl or 3,4-dichlorophenyl; nitro and halogen.

The heterocyclic ring formed together with $R^c$ and $R^1$ and the nitrogen atom to which they are attached can be optionally substituted with one or more substituents, wherein the substituents are the same or different, and include C1-6 alkyl; hydroxy C1-6 alkylene; C1-6 alkoxy C1-6 alkylene; hydroxyl; C1-6 alkoxy; and cyano.

In one embodiment, the micelle composition as defined herein is provided, wherein: the TLR7 agonist is of formula (IA);
  the amphiphilic micelle-forming agent is DSPE-PEG2000; and
  the ratio between the TLR7 agonist and amphiphilic micelle-forming agent is 95:5, 90:10, or 80:20.

In a preferred embodiment, the micelle composition as defined herein is provided, wherein: the TLR7 agonist is of formula (IA);
  the amphiphilic micelle-forming agent is DSPE-PEG2000; and
  the molar ratio between the amphiphilic micelle-forming agent and the TLR7 agonist is 95:5, 90:10, or 80:20.

Further Active Agents

In one embodiment, the micelle composition as defined herein is provided, further comprising at least one further active ingredient. In one embodiment, the micelle composition further comprises at least one antigen.

Items

I-1. A micelle composition comprising:
  a toll-like receptor 7 (TLR7) agonist of formula (I), formula (II), formula (III) or formula (IV);

(I)

(II)

(III)

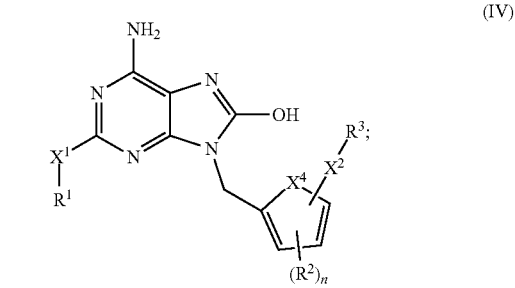
(IV)

wherein $X^1$ is —O—, —S—, or —$NR^C$;
$R^1$ is hydrogen, $(C_1$-$C_{10})$alkyl, substituted $(C_1$-$C_{10})$alkyl, $C_{6-10}$aryl, or substituted $C_{6-10}$aryl, $C_{5-9}$heterocyclic, substituted $C_{5-9}$heterocyclic;
$R^C$ is hydrogen, $C_{1-10}$alkyl, or substituted $C_{1-10}$alkyl; or $R^C$ and $R^1$ taken together with the nitrogen to which they are attached form a heterocyclic ring or a substituted heterocyclic ring;
each $R^2$ is independently —OH, $(C_1$-$C_6)$alkyl, substituted $(C_1$-$C_6)$alkyl, $(C_1$-$C_6)$alkoxy, substituted $(C_1$-$C_6)$alkoxy, —C(O)—$(C_1$-$C_6)$alkyl (alkanoyl), substituted —C(O)—($C_1$-$C_6$)alkyl, —C(O)—($C_6$-$C_{10}$) aryl (aroyl), substituted —C(O)—($C_6$-$C_{10}$)aryl, —C(O)OH (carboxyl), —C(O)O($C_1$-$C_6$)alkyl (alkoxycarbonyl), substituted —C(O)O($C_1$-$C_6$)alkyl, —NR$^a$R$^b$, —C(O)NR$^a$R$^b$ (carbamoyl), halo, nitro, or cyano, or R$^2$ is absent;

each R$^a$ and R$^b$ is independently hydrogen, ($C_1$-$C_6$) alkyl, substituted ($C_1$-$C_6$)alkyl, ($C_3$-$C_3$)cycloalkyl, substituted ($C_3$-$C_3$)cycloalkyl, ($C_1$-$C_6$)alkoxy, substituted ($C_1$-$C_6$)alkoxy, ($C_1$-$C_6$)alkanoyl, substituted ($C_1$-$C_6$)alkanoyl, aryl, aryl($C_1$-$C_6$)alkyl, Het, Het ($C_1$-$C_6$)alkyl, or ($C_1$-$C_6$)alkoxycarbonyl;

wherein the substituents on any alkyl, aryl or heterocyclic groups are hydroxy, $C_{1-6}$alkyl, hydroxy $C_{1-6}$alkylene, $C_{1-6}$alkoxy, $C_{3-6}$cycloalkyl, $C_{1-6}$alkoxy $C_{1-6}$alkylene, amino, cyano, halo, or aryl;

n is 0, 1, 2, 3 or 4;

X$^2$ is a bond or a linking group; and

R$^3$ is a lipid;

X$^3$ is —N— or —CH—;

R$^4$ is —CH$_2$— or —CH(R$^2$)—; and k is 0 or 1;

X$^4$ is —O—, —S—, —NH—, —N(R$^d$)—, —CH$_2$—, or —CH(R$^2$);

each R$^d$ is independently —OH, ($C_1$-$C_6$)alkyl, substituted ($C_1$-$C_6$)alkyl, ($C_1$-$C_6$)alkoxy, substituted ($C_1$-$C_6$)alkoxy, —C(O)—($C_1$-$C_6$)alkyl (alkanoyl), substituted —C(O)—($C_1$-$C_6$)alkyl, —C(O)—($C_6$-$C_{10}$) aryl (aroyl), substituted —C(O)—($C_6$-$C_{10}$)aryl, —C(O)O($C_1$-$C_6$)alkyl (alkoxycarbonyl), substituted —C(O)O($C_1$-$C_6$)alkyl, —C(O)NR$^a$R$^b$ (carbamoyl);

or a tautomer thereof;

or a pharmaceutically acceptable salt or solvate thereof, and wherein the ring system of formula (II) is a piperidine ring with one heteroatom being an N atom and with the N-atom of the piperidine ring adjacent to X$^2$, and wherein the purine group in any of Formula (I), (II), (III), or (IV) is subject to tautomeric rearrangements;

and an amphiphilic micelle-forming agent.

I-2. The micelle composition according to any one of the preceding items, wherein the TLR7 agonist is of formula (I):

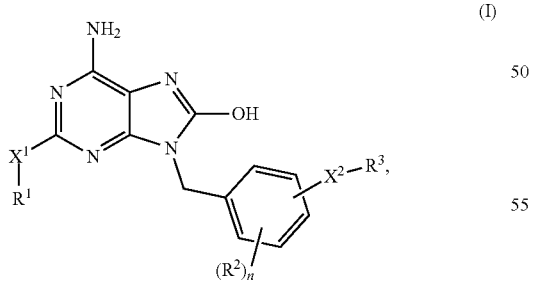

(I)

wherein X$^1$ is —O—, —S—, or —NR$^C$;

R$^1$ is hydrogen, ($C_1$-$C_{10}$)alkyl, substituted ($C_1$-$C_{10}$) alkyl, $C_{6-10}$aryl, or substituted $C_{6-10}$aryl, $C_{5-9}$heterocyclic, substituted $C_{5-9}$heterocyclic;

R$^C$ is hydrogen, $C_{1-10}$alkyl, or substituted $C_{1-10}$alkyl; or R$^C$ and R$^1$ taken together with the nitrogen to which they are attached form a heterocyclic ring or a substituted heterocyclic ring;

each R$^2$ is independently —OH, ($C_1$-$C_6$)alkyl, substituted ($C_1$-$C_6$)alkyl, ($C_1$-$C_6$)alkoxy, substituted ($C_1$-$C_6$)alkoxy, —C(O)—($C_1$-$C_6$)alkyl (alkanoyl), substituted —C(O)—($C_1$-$C_6$)alkyl, —C(O)—($C_6$-$C_{10}$) aryl (aroyl), substituted —C(O)—($C_6$-$C_{10}$)aryl, —C(O)OH (carboxyl), —C(O)O($C_1$-$C_6$)alkyl (alkoxycarbonyl), substituted —C(O)O($C_1$-$C_6$)alkyl, —NR$^a$R$^b$, —C(O)NR$^a$R$^b$ (carbamoyl), halo, nitro, or cyano, or R$^2$ is absent;

each R$^a$ and R$^b$ is independently hydrogen, ($C_1$-$C_6$) alkyl, substituted ($C_1$-$C_6$)alkyl, ($C_3$-$C_3$)cycloalkyl, substituted ($C_3$-$C_3$)cycloalkyl, ($C_1$-$C_6$)alkoxy, substituted ($C_1$-$C_6$)alkoxy, ($C_1$-$C_6$)alkanoyl, substituted ($C_1$-$C_6$)alkanoyl, aryl, aryl($C_1$-$C_6$)alkyl, Het, Het ($C_1$-$C_6$)alkyl, or ($C_1$-$C_6$)alkoxycarbonyl;

wherein the substituents on any alkyl, aryl or heterocyclic groups are hydroxy, $C_{1-6}$alkyl, hydroxy$C_{1-6}$alkylene, $C_{1-6}$alkoxy, $C_{3-6}$cycloalkyl, $C_{1-6}$alkoxy $C_{1-6}$alkylene, amino, cyano, halo, or aryl;

n is 0, 1, or 2;

X$^2$ is a bond or a linking group; and

R$^3$ is a lipid;

or a tautomer thereof;

or a pharmaceutically acceptable salt or solvate thereof, and wherein the purine group is subject to tautomeric rearrangements.

I-3. The micelle composition according to any one of the preceding items, wherein the TLR7 agonist is of formula (I):

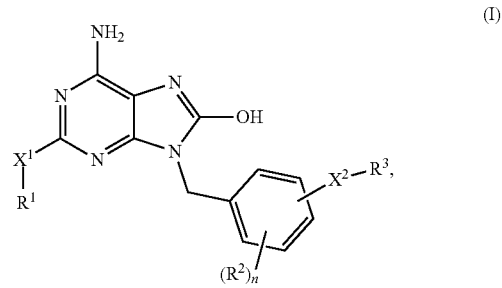

(I)

wherein X$^1$ is —O—, —S—, or —NR$^C$;

R$^1$ is hydrogen, ($C_1$-$C_{10}$)alkyl, substituted ($C_1$-$C_{10}$) alkyl, $C_{6-10}$aryl, or substituted $C_{6-10}$aryl, $C_{5-9}$heterocyclic, substituted $C_{5-9}$heterocyclic;

R$^C$ is hydrogen, $C_{1-10}$alkyl, or substituted $C_{1-10}$alkyl; or R$^C$ and R$^1$ taken together with the nitrogen to which they are attached form a heterocyclic ring or a substituted heterocyclic ring;

R$^2$ is absent;

n is 0;

X$^2$ is a bond or a linking group; and

R$^3$ is a lipid;

or a tautomer thereof;

or a pharmaceutically acceptable salt or solvate thereof, and wherein the purine group is subject to tautomeric rearrangements.

I-4. The micelle composition according to any one of the preceding items, wherein X$^2$ is selected from the group consisting of: a bond, —O—, —C(O)— (carbonyl), ($C_1$-$C_6$)alkyl, substituted ($C_1$-$C_6$)alkyl, ($C_1$-$C_6$)alkoxy, substituted ($C_1$-$C_6$)alkoxy, —C(O)—($C_1$-$C_6$)alkyl (alkanoyl), substituted —C(O)—(C$_1$-C$_6$)alkyl, —C(O)—(C$_6$-C$_{10}$)aryl (aroyl), substituted —C(O)—(C$_6$-C$_{10}$)aryl, —C(O)OH (carboxyl), —C(O)O(C$_1$-C$_6$)alkyl (alkoxycarbonyl), substituted —C(O)O(C$_1$-C$_6$)alkyl, —NR$^a$R$^b$, —C(O)NR$^a$R$^b$ (carbamoyl); and each R$^a$ and R$^b$ is independently hydrogen, (C$_1$-C$_6$) alkyl, substituted (C$_1$-C$_6$)alkyl, (C$_3$-C$_3$)cycloalkyl, substituted (C$_3$-C$_3$)cycloalkyl, (C$_1$-C$_6$)alkoxy, substituted (C$_1$-C$_6$)alkoxy, (C$_1$-C$_6$)alkanoyl, substituted (C$_1$-C$_6$)alkanoyl, aryl, aryl(C$_1$-C$_6$)alkyl, Het, Het (C$_1$-C$_6$)alkyl, or (C$_1$-C$_6$)alkoxycarbonyl;

and wherein

X$^1$ is —O—, —S—, or —NR$^C$;

R$^1$ is hydrogen, (C$_1$-C$_6$)alkyl, or substituted (C$_1$-C$_6$) alkyl;

R$^C$ is hydrogen, C$_{1-6}$alkyl, or substituted C$_{1-6}$alkyl; or R$^C$ and R$^1$ taken together with the nitrogen to which they are attached form a heterocyclic ring or a substituted heterocyclic ring.

I-5. The micelle composition according to any one of the preceding items, wherein R$^3$ is a lipid selected from the group consisting of: a phospholipid comprising one or two carboxylic esters; a gonane, such as cholesterol; a saccharolipid; and a glyceride.

I-6. The micelle composition according to any one of the preceding items, wherein R$^3$ is a phospholipid comprising one or two carboxylic esters.

I-7. The micelle composition according to any one of the preceding items, wherein the diameter of the micelle is between 5 nm and 50 nm, such as between 6 and 46 nm, such as between 7 and 42 nm, such as between 8 and 38 nm, such as between 9 and 34 nm, such as between 10 and 34 nm, such as between 11 nm and 30 nm, such as between 12 nm and 26 nm.

I-8. The micelle composition according to any one of the preceding items, wherein the diameter of the micelle is between 5 nm and 25 nm, such as between 6 nm and 24 nm, such as between 7 nm and 23 nm, such as between 8 nm and 22 nm, such as between 9 nm and 21 nm, such as between 10 nm and 20 nm, such as between 11 nm and 19 nm, such as between 12 nm and 18 nm, such as between 13 nm and 17 nm, such as between 14 nm and 16 nm, such as 15 nm.

I-9. The micelle composition according to any one of the preceding items, wherein the amphiphilic micelle-forming agent is selected from the group consisting of: a poloxamer, a poloxamine, a PEG-polyester, a PEG-polyanhydride, a PEG-poly-amino acid, a phospholipid, a polysorbate, and a polyoxyethylene alkyl ether.

I-10. The micelle composition according to any one of the preceding items, wherein the PEG-polyester is selected from the group consisting of: a PEG-poly(lactic acid) (PEG-PLA), a PEG-poly(lactic-co-glycolic acid) (PLGA), and a PEG-poly(ε-caprolactone) (PCL).

I-11. The micelle composition according to any one of the preceding items, wherein the PEG-polyanhydride is a PEG-polysebacic anhydride (PSA).

I-12. The micelle composition according to any one of the preceding items, wherein the PEG-poly-amino acid is selected from the group consisting of: a PEG-poly(L-histidine), a PEG-poly(L-aspartic acid), a PEG-poly(L-asparagine), a PEG-poly(L-glutamic acid), a PEG-poly(L-glutamine), and a PEG-poly(L-lysine).

I-13. The micelle composition according to any one of the preceding items, wherein the amphiphilic micelle-forming agent is a phospholipid conjugated to polyethylene glycol (PEG).

I-14. The micelle composition according to any one of the preceding items, wherein the phospholipid conjugated to PEG is conjugated via a carbonyl group.

I-15. The micelle composition according to any one of the preceding items, wherein the size of PEG is between PEG350 and PEG5000, for example between PEG550 and PEG4000, for example between PEG750 and PEG3000, such as between PEG1000 and PEG3000, preferably the size of the PEG is PEG2000.

I-16. The micelle composition according to any one of the preceding items, wherein the phospholipid comprises one or more alkyl chains that are C8-C24 alkyl(s), such as C10-C22, such as C12-C20, preferably C14-C18, most preferred C16-C18 saturated alkyl chains or unsaturated alkyl chains.

I-17. The micelle composition according to any one of the preceding items, wherein the phospholipid comprises a phosphatidylethanolamine (PE), a phosphatidylcholine (PC), a phosphatidylserine (PS), a phosphatidylglycerol (PG), a phosphatidylinositol (PI), a phosphatidic acid (PA), a bisphosphatidyl glycerol (DPG), or a phosphatidyl alcohol.

I-18. The micelle composition according to any one of the preceding items, wherein the phosphatidylethanolamine is selected from the group consisting of 1,2-dioleoyl-phosphatidylethanolamine, 1,2-dipalmitoyl-phosphatidylethanolamine, 1,2-dimyristoyl-phosphatidylethanolamine, 1,2-distearoyl-phosphatidylethanolamine, 1-oleoyl-2-palmitoyl-phosphatidylethanolamine, 1-oleoyl-2-stearoyl-phosphatidylethanolamine, 1-palmitoyl-2-oleoyl-phosphatidylethanolamine, and 1-stearoyl-2-oleoyl-phosphatidylethanolamine.

I-19. The micelle composition according to any one of the preceding items, wherein the phospholipid conjugated to PEG is selected from the group consisting of: 1,2-dioleoyl-sn-glycero-3-phosphoethanolamine (DOPE)-PEG, 1,2-distearoyl-sn-glycero-3-phosphoethanolamine (DSPE)-PEG, 1,2-dimyristoyl-sn-glycero-3-phosphoethanolamine (DMPE)-PEG, and 1,2-dipalmitoyl-sn-glycero-3-phosphoethanolamine (DPPE)-PEG.

I-20. The micelle composition according to any one of the preceding items, wherein the phospholipid conjugated to PEG is: 1,2-distearoyl-sn-glycero-3-phosphoethanolamine (DSPE)-PEG.

I-21. The micelle composition according to any one of the preceding items, wherein the amphiphilic micelle-forming agent is DSPE-PEG2000.

I-22. The micelle composition according to any one of the preceding items, wherein the molar ratio between the amphiphilic micelle-forming agent and the TLR7 agonist is from 50:50 to 99.5:0.5, such as from 60:40 to 99:1, such as from 70:30 to 98:2, such as from 80:20 to 95:5, for example 95:5, 90:10, or 80:20.

I-23. The micelle composition according to any one of the preceding items, wherein the composition comprises between 1% and 25% molar concentration of TLR7 agonist, such as 1%, such as 2%, such as 3%, such as 4%, such as 5%, such as 6%, such as 7%, such as 8%, such as 9%, such as 10%, such as 11%, such as 12%, such as 13%, such as 14%, such as 15%, such as 16%, such as 17%, such as 18%, such as 19%, such as 20%, such as 21%, such as 22%, such as 23%, such as 24%, such as 25%.

I-24. The micelle composition according to any one of the preceding items, wherein the TLR7 agonist has a structure according to formula (IA):

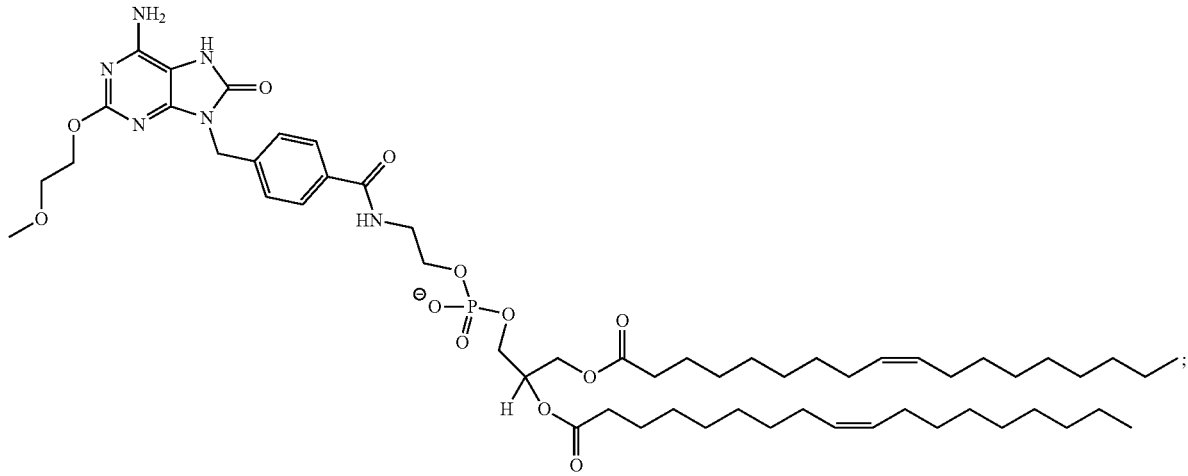

or
a tautomer thereof;
or a pharmaceutically acceptable salt or solvate thereof.

I-25. The micelle composition according to any one of the preceding items, wherein:
the TLR7 agonist is of formula (IA);
the amphiphilic micelle-forming agent is DSPE-PEG2000; and
the ratio between the TLR7 agonist and amphiphilic micelle-forming agent is 95:5, 90:10, or 80:20.

I-26. The micelle composition according to any one of the preceding items, wherein the molar ratio between DSPE-PEG2000 and the TLR7 agonist of formula (IA) is 90:10 (MBS8).

I-27. The micelle composition according to any one of the preceding items, further comprising at least one further active ingredient.

I-28. The micelle composition according to any one of the preceding items, further comprising at least one antigen.

I-29. A pharmaceutical composition comprising the micelle composition according to any one of the preceding items.

I-30. A micelle composition or pharmaceutical composition according to any one of the preceding items, for use in the prevention, treatment or amelioration of a disease or disorder.

I-31. The micelle composition or pharmaceutical composition for use according to any one of the preceding items, wherein the disease or disorder is selected from the group consisting of: a cancer, an infectious disease, an inflammatory condition or disease, an autoimmune disease, and an allergy.

I-32. The micelle composition or pharmaceutical composition for use according to any one of the preceding items, wherein the disease or disorder is cancer, such as colon cancer.

I-33. A method for in vivo activation of immune cells in a subject, comprising administering the micelle composition or pharmaceutical composition according to any one of the preceding items to said subject in an amount sufficient to activate said immune cells.

I-34. A method for treatment of cancer in a patient in need of treatment, comprising administering the micelle composition as defined in any one of the preceding items to the patient.

I-35. The method according to any one of the preceding items, further comprising administering a chemotherapeutic agent to the patient.

I-36. The method according to any one of the preceding items, wherein the chemotherapeutic agent is selected from the group consisting of Doxorubicin, Doxil, Epirubicin, Cyclophosphamide, Bortezomib, and Oxaliplatin.

I-37. The method according to any one of the preceding items, further comprising administering an immune check point inhibitor to the patient.

I-38. The method according to any one of the preceding items, wherein the immune check point inhibitor is selected from the group consisting of: Atezolizumab, Avelumab, Durvalumab, Nivolumab, Tislelizumab, Pembrolizumab, and Ipilimumab.

I-39. The method according to any one of the preceding items, wherein the micelle composition is MBS8 and the immune check point inhibitor is selected from the group consisting of: Nivolumab and Pembrolizumab.

I-40. The method according to any one of the preceding items, further comprising administering a monoclonal antibody targeting CD20 to the patient.

I-41. The method according to any one of the preceding items, comprising administering MBS8 and a monoclonal antibody targeting CD20.

I-42. The method according to any one of the preceding items, further comprising administering a monoclonal antibody targeting the epidermal growth factor receptor (EGFR) to the patient.

I-43. The method according to any one of the preceding items, comprising administering MBS8 and a monoclonal antibody targeting the epidermal growth factor receptor (EGFR).

I-44. The method according to any one of the preceding items, further comprising administering a monoclonal antibody targeting the Human Epidermal Growth Factor Receptor 2 (HER2) to the patient.

I-45. The method according to any one of the preceding items, comprising administering MBS8 and a monoclonal antibody targeting the Human Epidermal Growth Factor Receptor 2 (HER2).

I-46. The method according to any one of the preceding items, further comprising administering a monoclonal antibody targeting CD38, such as Daratumumab or Isatuximab, to the patient.

I-47. The method according to any one of the preceding items, comprising administering MBS8 and a monoclonal antibody targeting CD38, such as Daratumumab or Isatuximab.

I-48. The method according to any one of the preceding items, further comprising administering a monoclonal antibody targeting CD47, such as Magrolimab, to the patient.

I-49. The method according to any one of the preceding items, comprising administering MBS8 and a monoclonal antibody targeting CD47, such as Magrolimab.

I-50. The method according to any one of the preceding items, further comprising radiotherapy.

EXAMPLES

Example 1: Micelle and Liposome Preparation

Micelles were made from 1,2-distearyl-sn-glycero-3-phosphoethanolamine-N-[methoxy(polyethylene glycol)-2000] (DSPE-PEG2000) obtained from Lipoid GmbH. Briefly, the lipid was dissolved in tert-butanol:water (9:1 ratio by volume) to a final concentration of 5-10 mM in glass vials, and put under magnet stirring and heating to 50 degrees Celsius until completely dissolved. The solvent was removed by freezing the vials in liquid nitrogen followed by overnight lyophilization. Micelles were prepared by dispersing the dried lipids in a buffer solution containing: 150 mM NaCl, 10 mM Phosphate (pH=7.4), exposing the vial to gentle vortexing to establish initial contact between lipids and solvent before exposing to ultrasonication for 30 minutes to ensure formation of micellar structures. The dispersion was vortexed once again, before exposing the dispersion to 30 min of further ultrasonication. The micelles were stored at 4 degrees Celsius before use and/or characterization.

Unilamellar fully hydrated liposomes were made from mixtures of 1-palmitoyl-2-oleoyl-sn-glycero-3-phosphocholine (POPC), 1-palmitoyl-2-oleoyl-sn-glycero-3-phosphoglycerol (POPG), 1,2-dioleoyl-3-trimethylammonium-propane (DOTAP), Cholesterol (Chol) and 1,2-dioleoyl-sn-glycero-3-phosphoethanolamine-N-[methoxy(polyethylene glycol)-2000] (DOPE-PEG2000) and 1v270 (C57H93N6O12P, Mw=1085.4, (2-(4-((6-amino-2-(2-methoxyethoxy)-8-oxo-7H-purin-9(8H)-yl)methyl)benzamido)ethyl 2,3-bis(oleoyloxy)propyl phosphate). The molar ratios of each lipid in the liposomes were MBS1: POPC:Chol:DOTAP:1V270:DOPE-mPEG2k (44.25:30:20: 0.75:5), and MBS2: POPC:Chol:POPG:1V270:DSPE-PEG2k (44.25:30:20:0.75:5). All lipids were obtained from Avanti Polar lipids or Lipoid. Briefly, appropriate weighed amounts of POPC, POPG, Chol, DOTAP, 1V270 and DOPE-PEG2000 were dissolved in chloroform. The solvent was removed by a gentle stream of $N_2$ and the lipid films were dried overnight under low pressure to remove trace amounts of solvent. Multilamellar vesicles were prepared by dispersing the dried lipids in a buffer solution containing: 150 mM KCL, 10 mM HEPES (pH=7.5), 1 mM NaN$_3$, 30 μM CaCl$_2$ and 10 μM EDTA. The multilamellar vesicles were extruded ten times through two stacked 100 nm pore size polycarbonate filters as described by Mayer et al., Biochim. Biophys. Acta, 858, 161-168.

Example 2: Micelle Preparation with Incorporation of a Toll-Like Receptor 7 (TLR7) Agonist Micelles were made from 1,2-distearyl-sn-glycero-3-phosphoethanolamine-N-[methoxy(polyethylene glycol)-2000] (DSPE-PEG2000) obtained from Lipoid GmbH and the TLR7 agonist, 1v270 (C57H93N6O12P, Mw=1085.4, (2-(4-((6-amino-2-(2-methoxyethoxy)-8-oxo-7H-purin-9 (8H)-yl)methyl)benzamido)ethyl 2,3-bis(oleoyloxy)propyl phosphate). The chemical structure of 1v270 is outlined in FIG. 2 Briefly, the lipid was dissolved in tert-butanol:water (9:1 ratio by volume) to a final concentration of 5-10 mM (DSPE-PEG2000) or 1-3 mM (1v270) in glass vials, and put under magnet stirring and heating to 50 degrees Celsius until completely dissolved. The two lipid dispersions were then mixed to the desired ratio (95:5 to 80:20 DSPE-PEG2000: 1v270 molar ratio). The solvent was removed by freezing the vials in liquid nitrogen followed by overnight lyophilization. Micelles were prepared by dispersing the dried lipids in a buffer solution containing: 150 mM NaCl, 10 mM Phosphate (pH=7.4), exposing the vial to gentle vortexing to establish initial contact between lipids and solvent before exposing to ultrasonication for 30 minutes to ensure formation of micellar structures. The dispersion was vortexed once again, before exposing the dispersion to 30 min of further ultrasonication. The micelles were stored at 4 degrees Celsius before use and/or characterization. The batch names, molar ratios, lipid composition, zeta potentials (mV), size (nm) and polydispersity index (PDI) are outlined in FIG. 1.

Figure 1C:
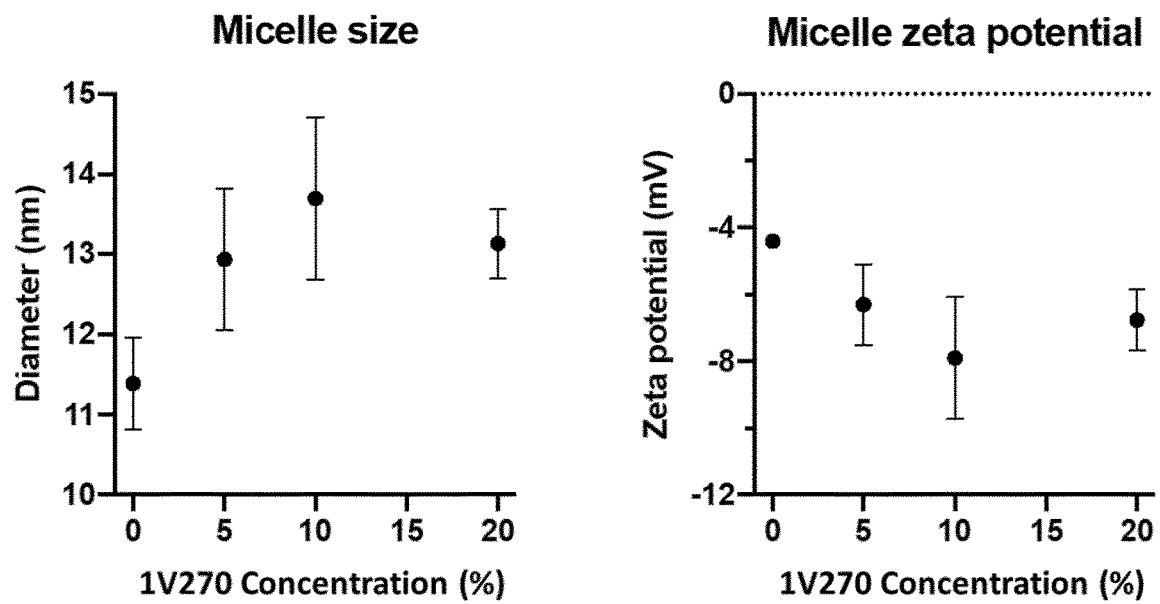
FIG. 1C: Micelle size by number distribution and zeta potential for the four micelles tested. Micelle size increase from 11.5 nm to 13-14 nm when 1v207 is added to the formulation. Zeta potential of the micelles decreases from −4 mV to −8 mV when 1v207 is added to the formulation.
Figure 2:
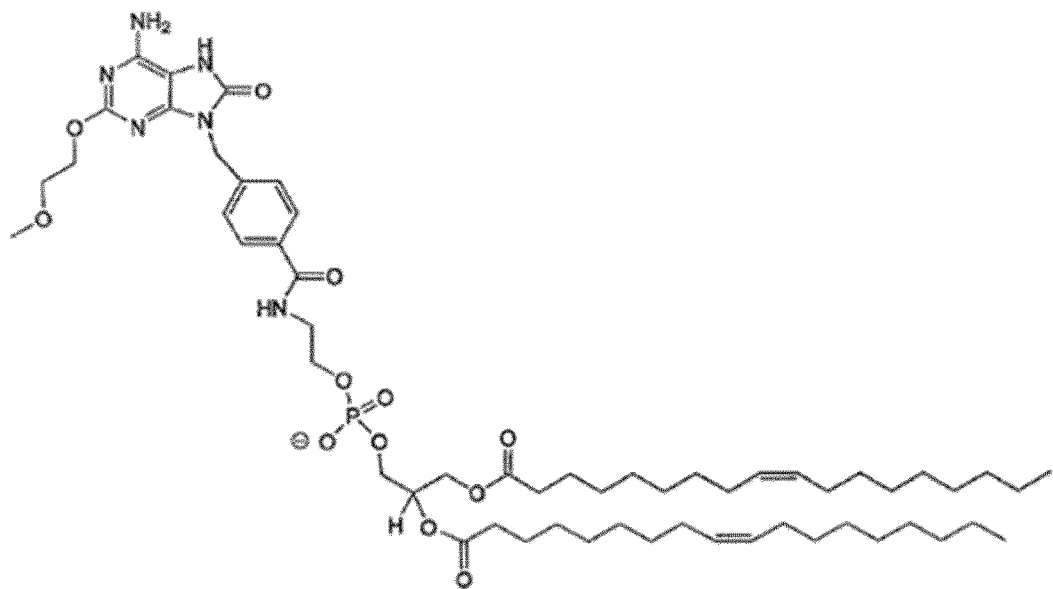
FIG. 2: Structure of the formulated TLR7 agonist 1v270 (also termed TMX-201) used for micelle preparations (Mw=1085.4, Name: 2-(4-((6-amino-2-(2-methoxyethoxy)-8-oxo-7H-purin-9(8H)-yl)methyl)benzamido) ethyl 2,3-bis (oleoyloxy)propyl phosphate).

Example 3: Characterization of Micelle Size and Surface Charge Dependent on Composition Micelles as outlined in FIG. 1 were prepared with the attempt to make a stable formulation of the TLR7 agonist 1v207 in aqueous solvents, thus allowing for injections in saline buffer. The micelles were prepared as described in examples 1+2, and their size (diameter) measured in nanometer (nm) by dynamic light scattering in a buffer consisting of 5% (w/w) glucose, 10 mM HEPES, 1 mM CaCl$_2$ in MilliQ water, pH 7.4. The micelles without 1V207 had a mean size of 11.5 nm (according to particle distribution by number), while micelles containing 1V270 had mean sizes ranging from 11.5 nm to 13-14 nm (according to distribution by particle number) when increasing 1V270 content from 5% to 20% (FIGS. 1B and 1C). The zeta potential of the empty micelles was measured in glucose buffer w. CaCl$_2$ to be around −4 mV, but becoming more negative when incorporating the anionic 1V270 compound into the micelles, thus decreasing to −8 mV for micelles with 10% 1V207 (FIG. 1C). Both size and zeta potential were measured on a Zetasizer from Malvern Instruments.

Figure 3A:
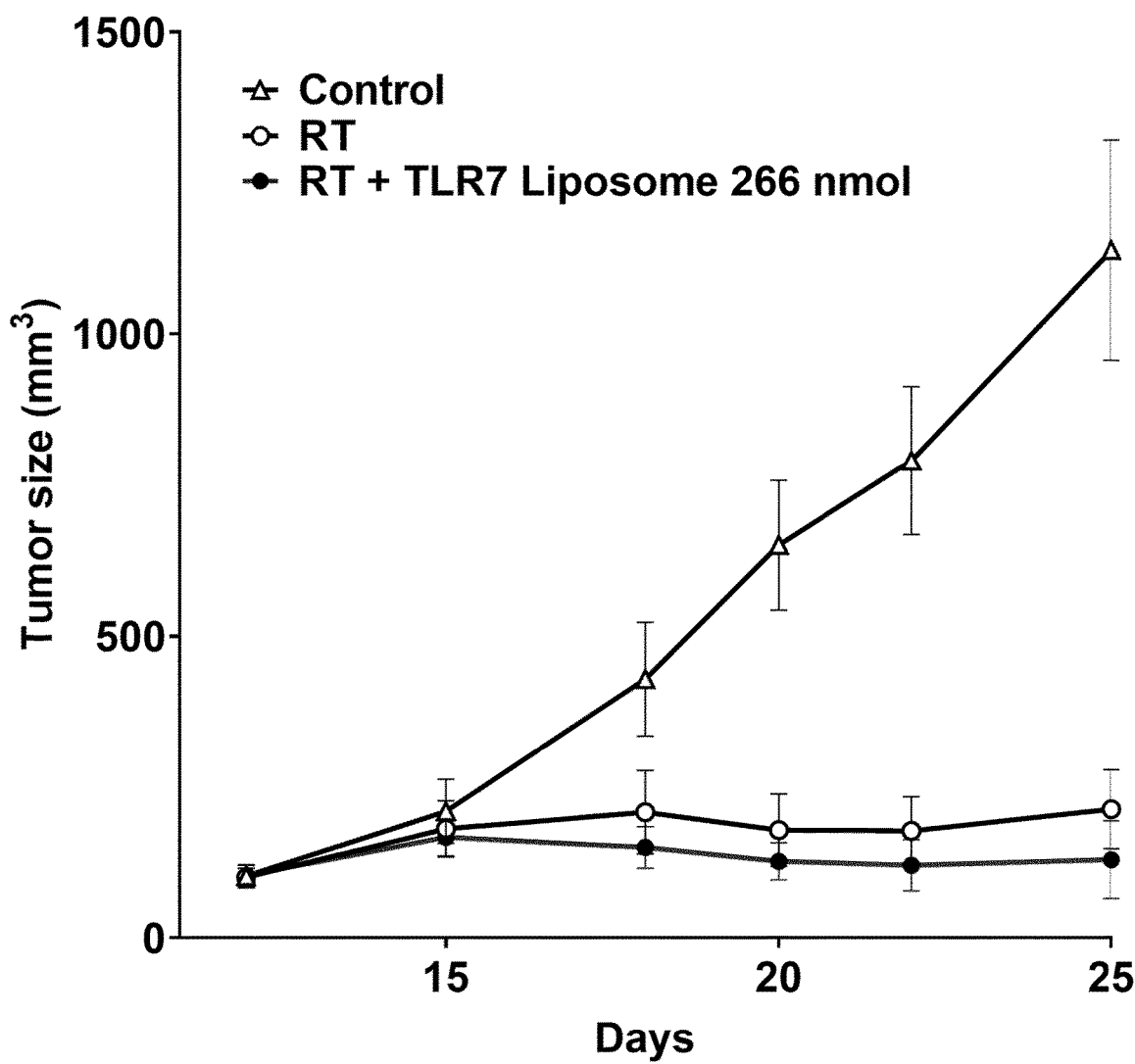
FIG. 3A-B compares antitumor studies between micelle containing 1V270 and liposome containing 1V270.
Figure 3B:
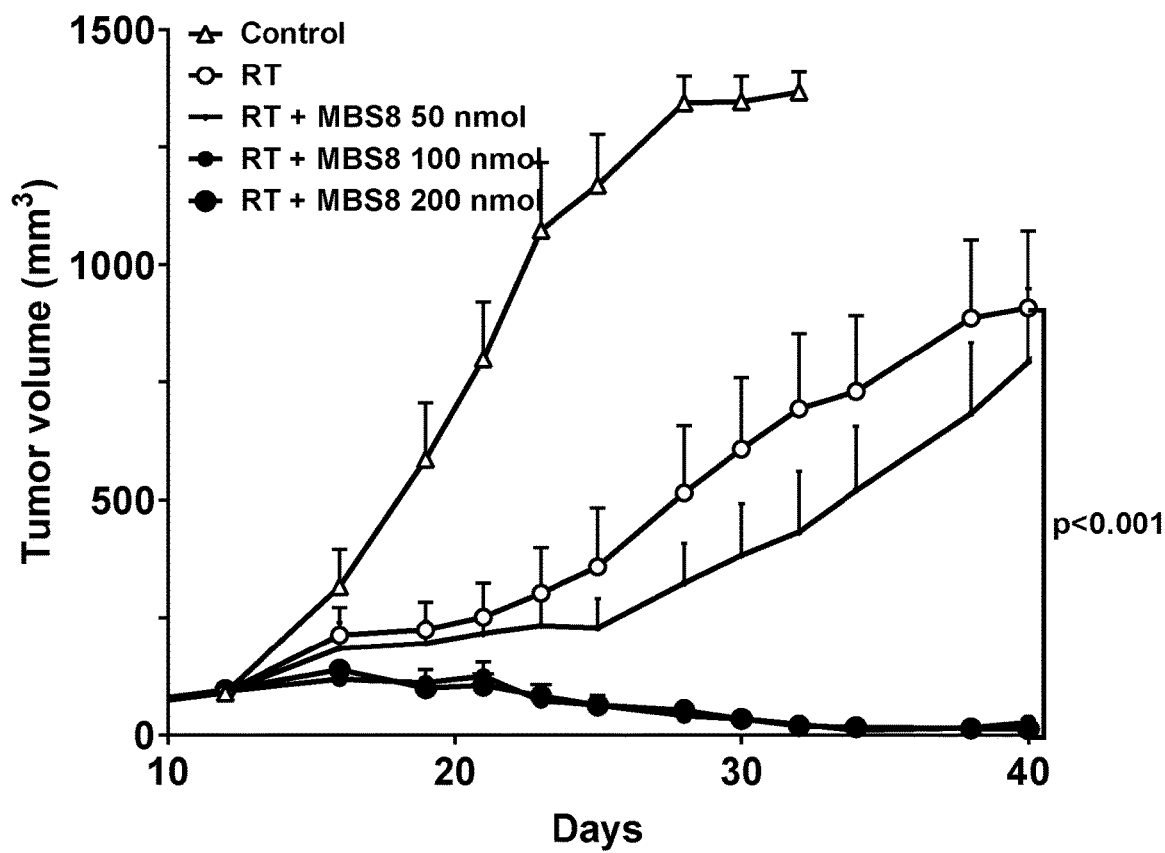
Figure 3C:
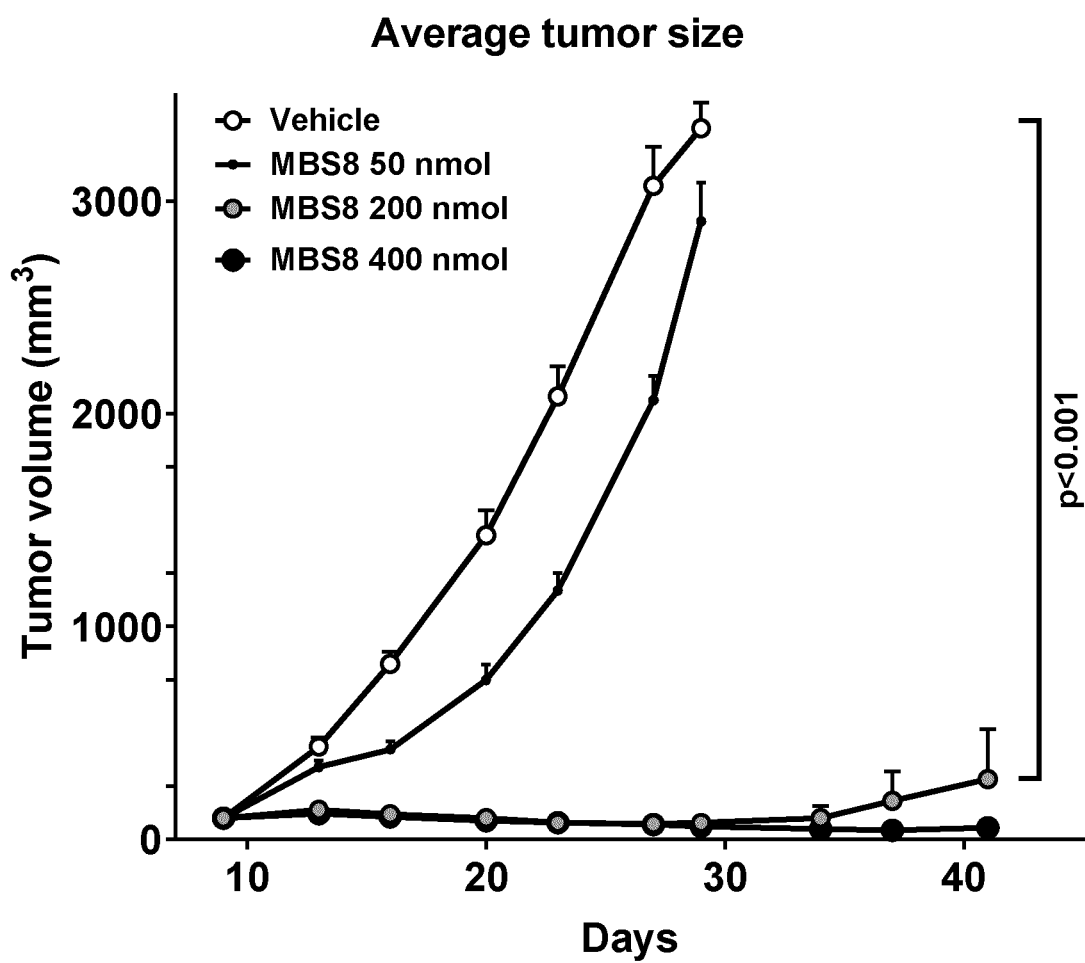
FIG. 3C shows antitumor activity of the micelle formulation MBS8 at three doses of 50, 200 and 400 nmol injected per mouse with first injection day 9, and then 4 more doses with 4 days interval.
Figure 3D:
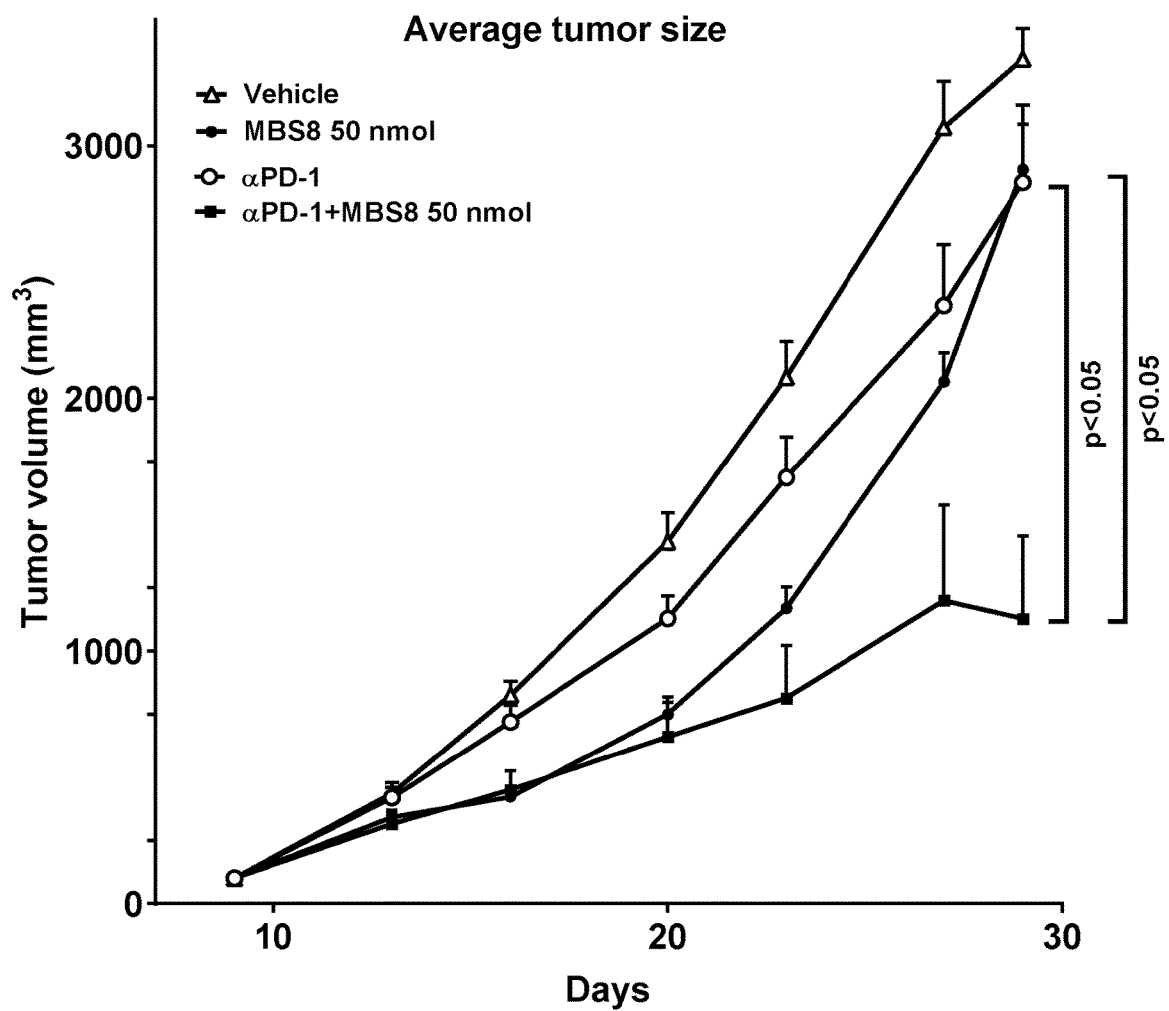
FIG. 3D shows a benefit of combination with a low dose MBS8 micelle at 50 nmol/mouse and optimal PD-1 treatment.

Example 4: Antitumor Activity of Micelles and Liposomes Containing 1V270 in the CT26 Model Tumor studies were conducted in the CT26 model (Adlard et al., Int J Cancer, 135, 820-829, 2014): Briefly the CT26 model is a colon cancer model established as a subcutaneous model in Balb/C mice which is frequently used as an immunocompetent tumor model to test cancer drugs and immunotherapeutic drugs. We used this model with control groups, radiotherapy treatment group from day 10 and daily for 5 days with 2 Gy. Liposomes or micelles containing 1V270 were injected IV at first day of radiotherapy and every four days after for five doses (FIGS. 3A and 3B). Liposomes containing 5% 1V270 were injected to reach a total dose of 266 nmol 1V270 per mouse (FIG. 3A). Micelles were injected at three doses of 50, 100 and 200 nmol 1V270 per mouse, and showed a significant tumor growth inhibition compared to radiotherapy treatment alone. Moreover, the lowest dose at 50 nmol showed 2/10 mice in complete remission, the 100 nmol dose showed 4/9 mice in complete remission, and the 200 nmol dose showed 8/8 mice in complete remission. In addition, nearly all mice in complete remission were able to resist a re-challenge with the same tumor cells after 100 days without tumor regrowth, demonstrating mice had generated an anti-tumor immune memory response. In monotherapy the MBS8 micelles were also very potent in showing anti-. tumor activity (FIG. 3C), where doses of MBS8 at 50, 200 and 400 nmol were injected intravenously in mice at day 9 and for additionally 4 times with 4 days interval. The two highest doses showed tumor growth suppression for all 10 mice in the groups lasting until 2 weeks after last dose (day 34). At day 41 there were three mice in complete remission in both high dose groups. The MBS8 micelles at 50 nmol/mouse/dose showed a synergy when combined with anti-PD1-treatment. This combo treatment showed a significantly better anti-tumor activity (p<0.05) than both anti-PD1 alone and MBS8 alone (FIG. 3D). anti-PD1 was dosed for 6 times IP at days 11, 15, 19, 23 and 27.

Figure 3E:
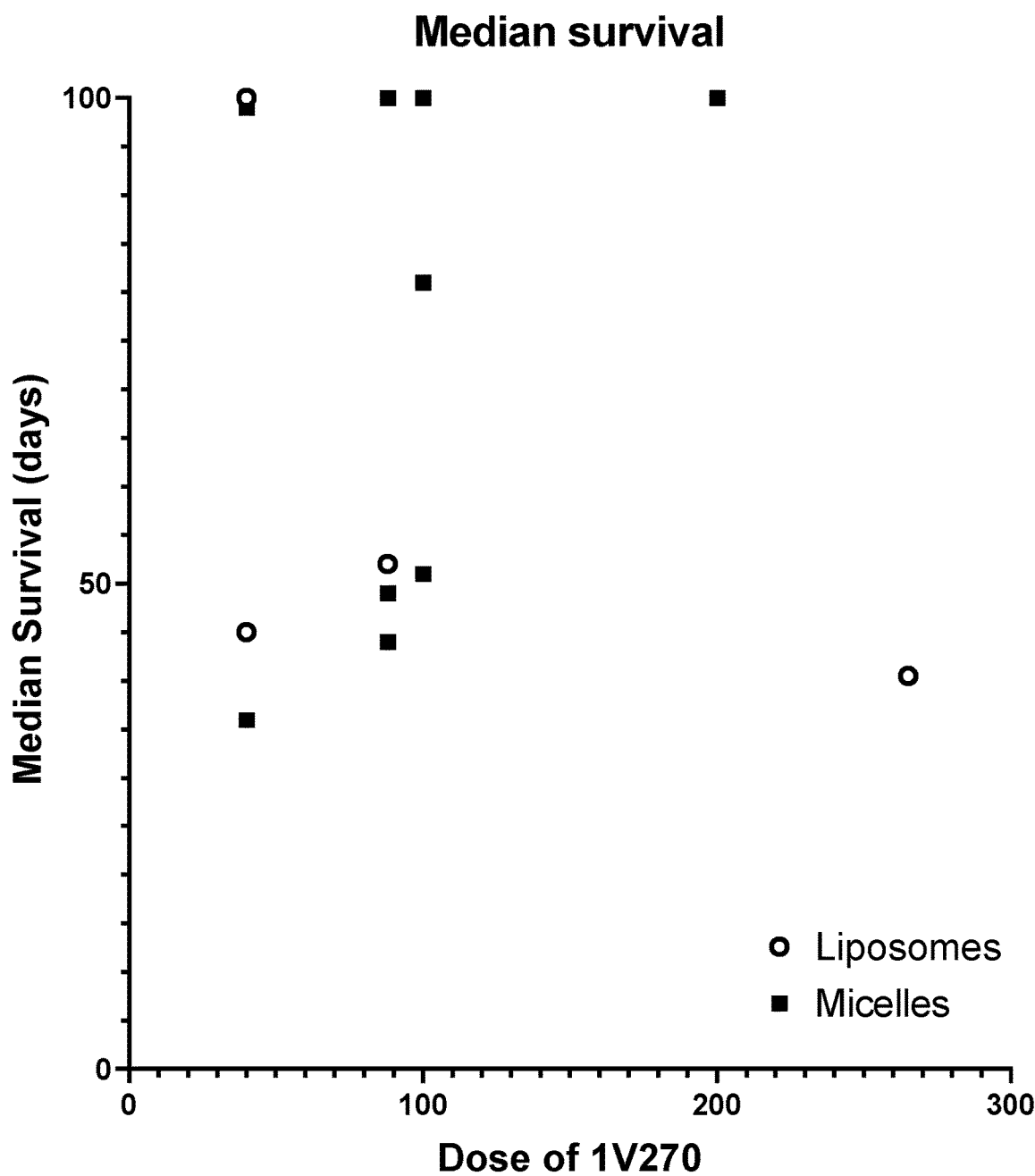
FIG. 3E shows median survival in groups of mice treated with radiotherapy in combination with liposomes and micelles containing 1V270.
Figure 3F:
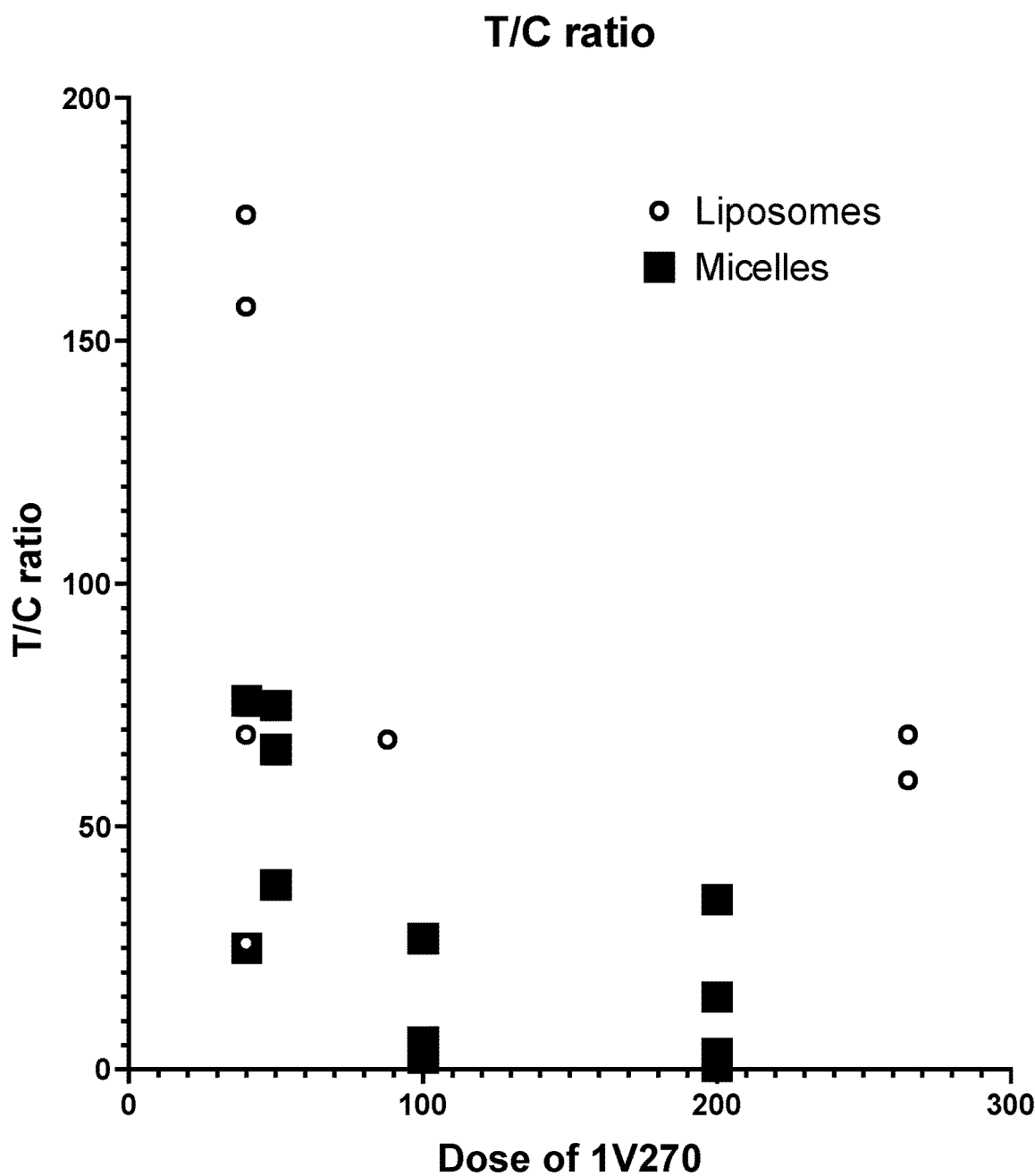
FIG. 3F shows tumor to control ratio (average tumor size of groups of mice treated with micelles or liposomes with 1V270 in combination with radiotherapy (Tumor=T), compared to average tumor size of control radiotherapy treated groups (Control=C)). Calculations are made by T/C×100. Micelles showed a significantly better anti-tumor activity than liposomes (p<0.01).
Figure 3G:
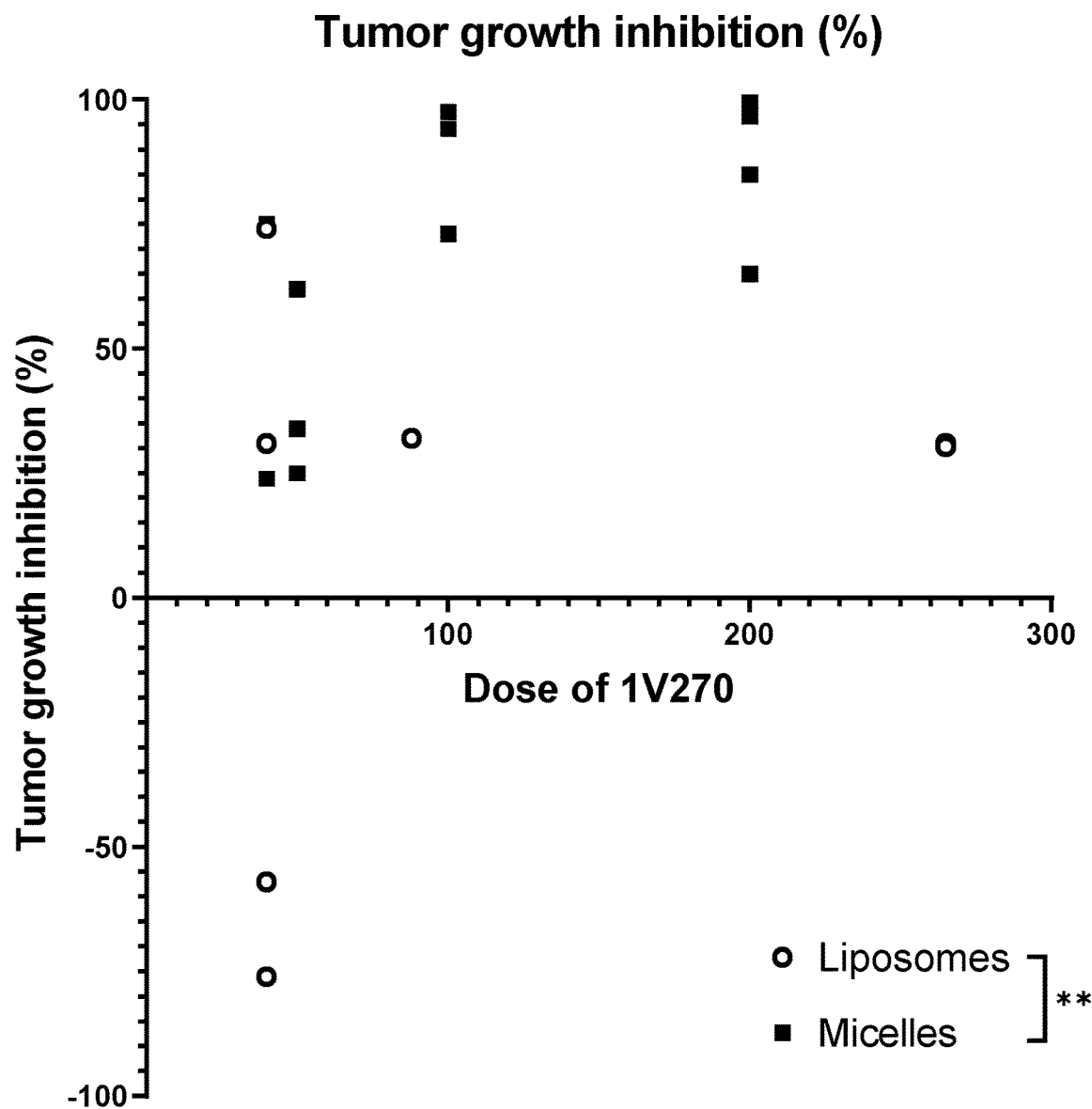
FIG. 3G shows tumor growth inhibition calculated by subtracting 100−T/C ratio. Micelles showed a significantly better tumor growth inhibition than liposomes (p<0.01).

Example 5: Antitumor Activity of Micelles Compared to Liposomes Containing a TLR7 Agonist in Combination with Radiotherapy in the CT26 Model Multiple tumor studies were conducted with groups of mice treated with radiotherapy and 7 groups of liposome treated mice in the range from 40 to 266 nmol 1V270 injected per mouse, and 13 groups of mice treated with micelles from 50-200 nmol 1V270 injected per mouse in combination with radiotherapy. The number of mice per group was 7-9, and median tumor size was compared between groups treated with radiotherapy alone, and radiotherapy with either liposomes or micelles. The median survival time for each group of micelle or liposome treated mice is seen in FIG. 3E. 4 micelle treated groups showing a median survival above 100 days, indicating that more than half of the mice showed a complete tumor remission (the survival of the median observed mouse showed complete tumor remission) This was not observed for any liposome+ RT treated groups. Tumor growth for liposome+RT and micelle+RT treated groups compared to groups treated with RT alone, (Termed T/C ratio) and calculated at the time when the RT alone treated group were sacrificed, showed a T/C ratio below 50% in 10 groups out 13 groups for micelles, whereas only 1 out of 7 liposome treated groups showed a T/C ratio below 50%. Using a Wilcoxon rank sum test the difference was significant at p<0.01 level (FIG. 3F). The T/C value can be translated into % tumor growth inhibition by 100% subtracted by the T/C-value (FIG. 3G), where values approaching 100% means a very strong inhibition of tumor growth. 10 out of 13 micelle treated groups showed a tumor growth inhibition above 60%, whereas only 1 of 7 liposome treated groups showed a tumor growth inhibition above 50%.

Conclusion

In conclusion, micelles comprising 1V270 showed a significantly better tumor growth inhibition than the corresponding liposomes comprising 1V270 (p<0.01, Wilcoxon rank sum test).

Example 6: Micelles Show Safer Cytokine Profile with Reduced Risk of Cytokine Release Syndrome (CRS)

The micelles MBS6, MBS7 and MBS8 containing the TLR7 agonist, 1V270 were compared to empty micelles (MBS0=vehicle), PBS and two different liposomes containing 1V270 by injection IV in Balb/C mice at a dose of 100 nmol 1V270 for all samples except PBS and vehicle. Plasma samples were taken at 2 and 6 h post injection and cytokines relevant for anti-tumor immune response and toxicity measured by multiplex or ELISA analyses.

Figure 4A:
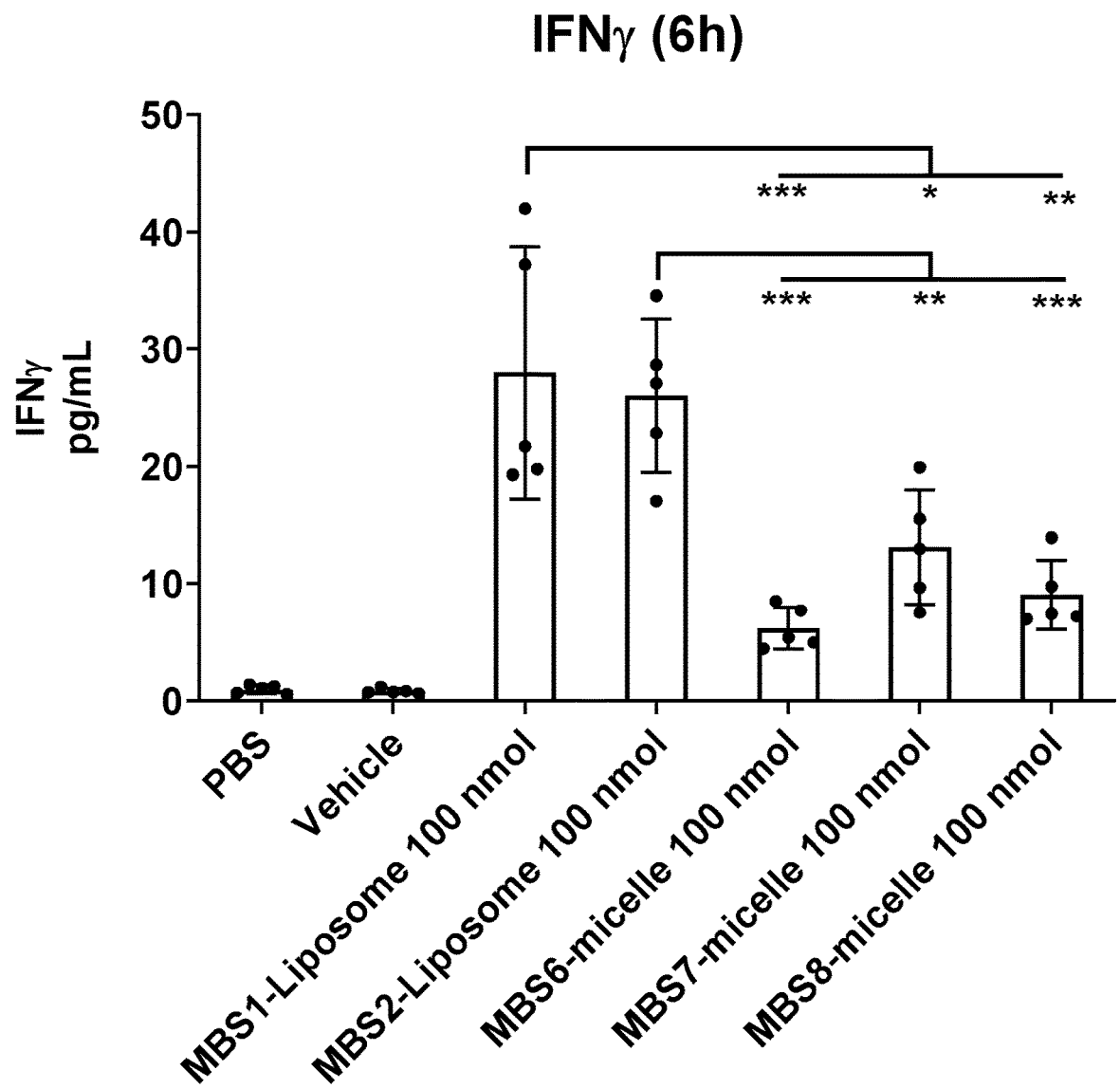
FIG. 4A-G show cytokine secretion in plasma from mice treated with micelles or liposomes at equal doses. In general liposome MBS1 showed higher cytokine secretion than micelles for all cytokines measured, and MBS2 liposomes showed higher cytokine secretion than micelles for most cytokines tested. This indicates that micelles have a reduced risk of Cytokine Related Syndrome (CRS) compared to liposomes containing 1V270.
Figure 4B:
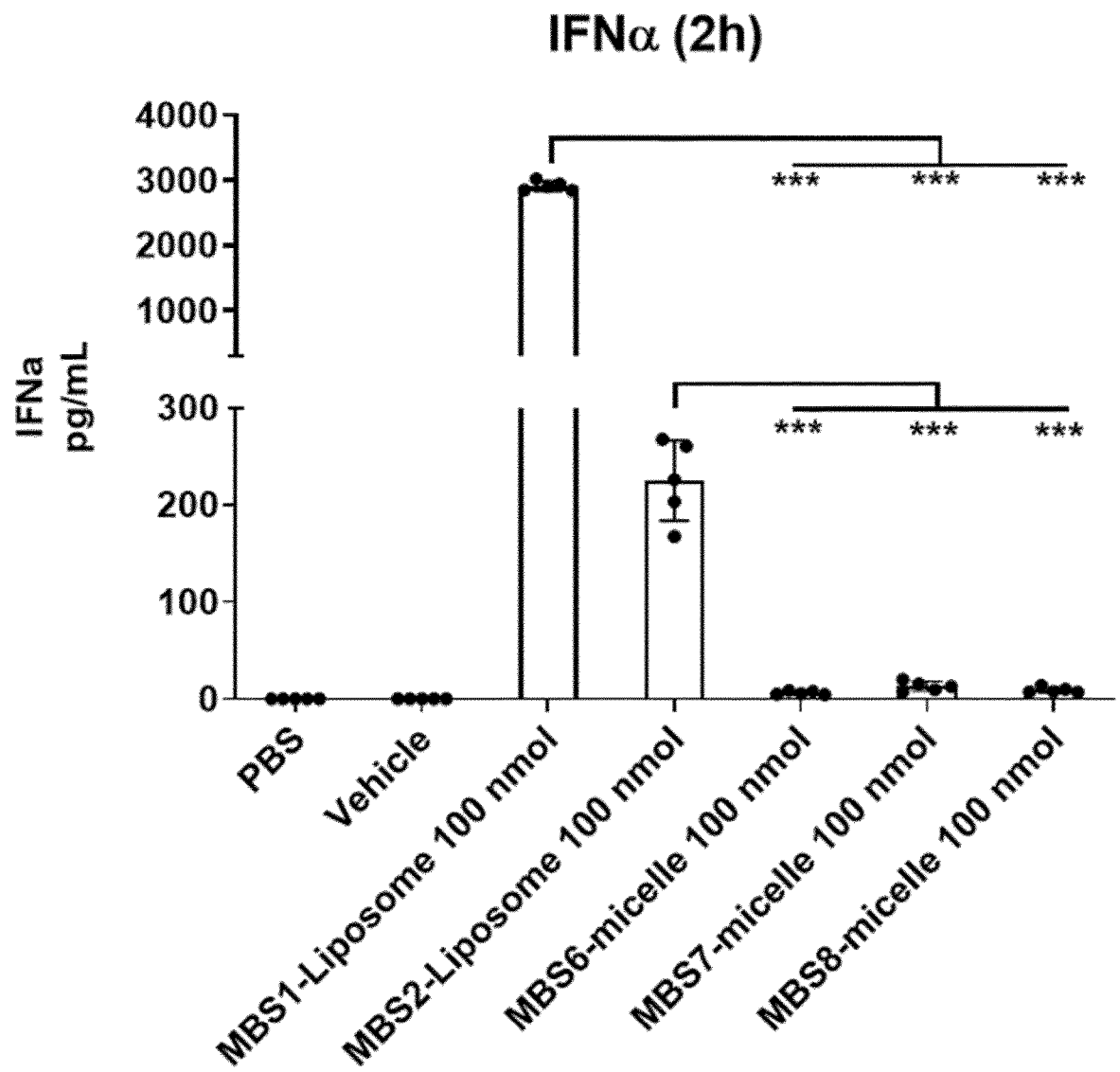
Figure 4C:
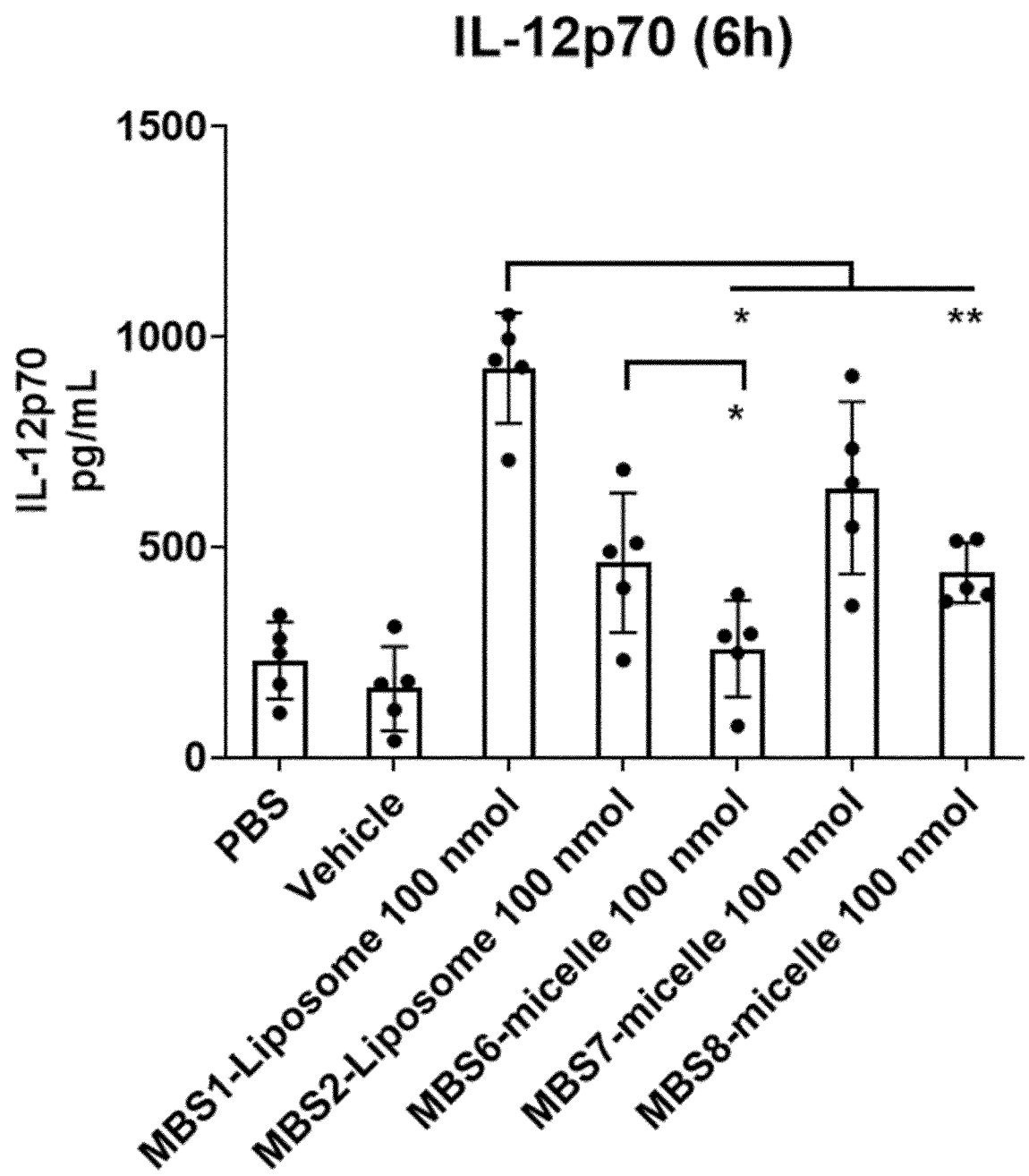
Figure 4D:
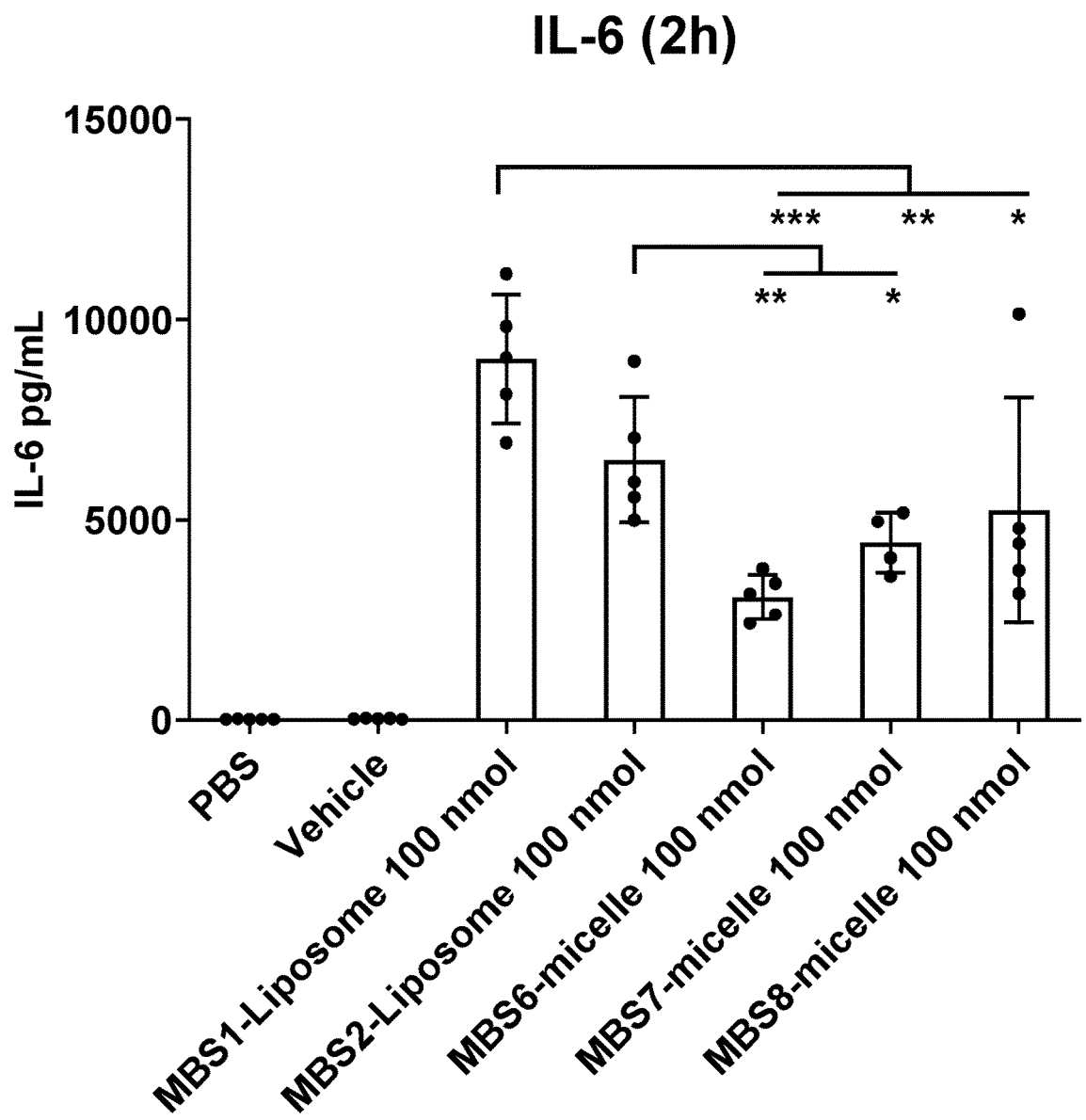
Figure 4E:
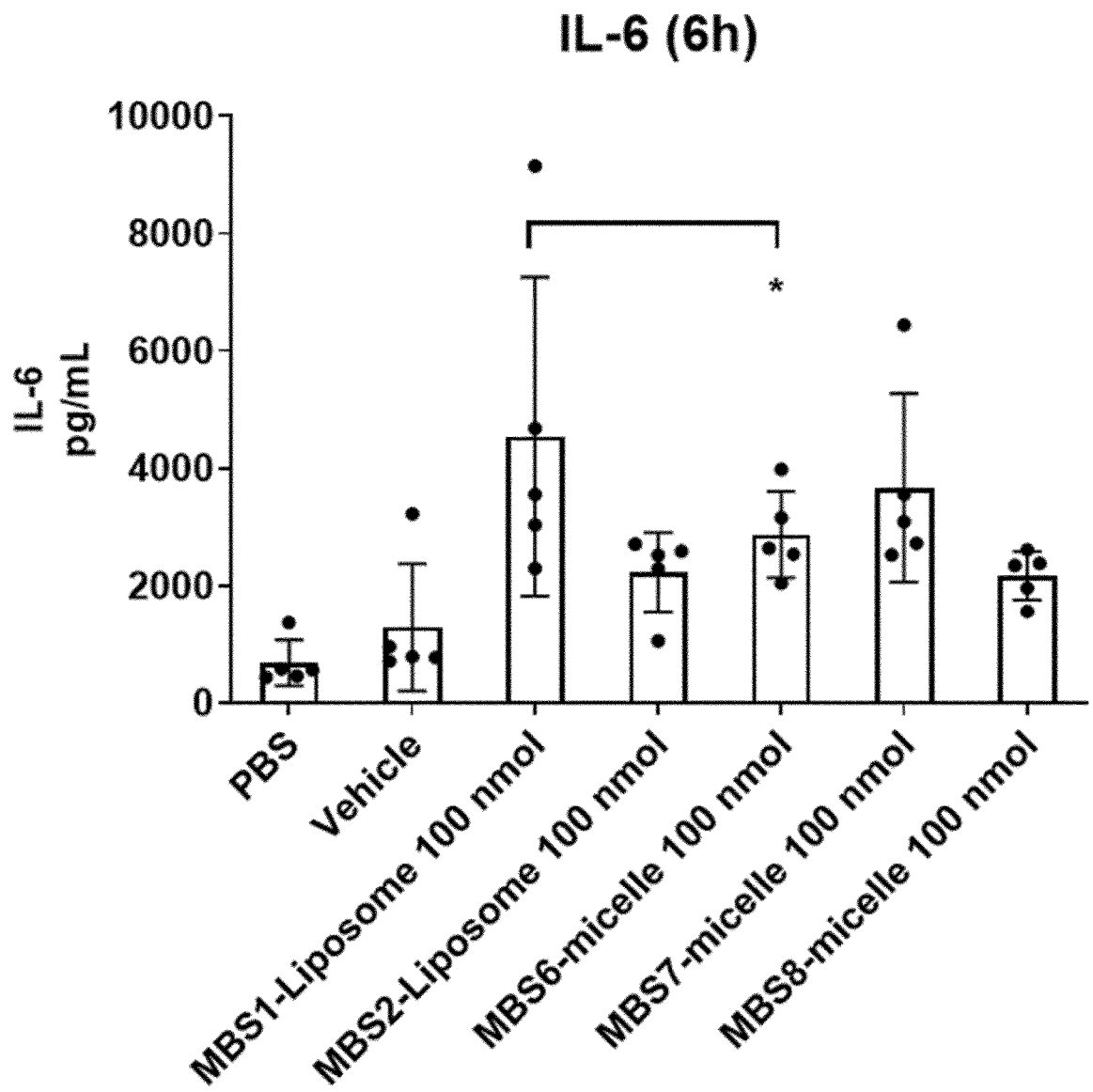
Figure 4F:
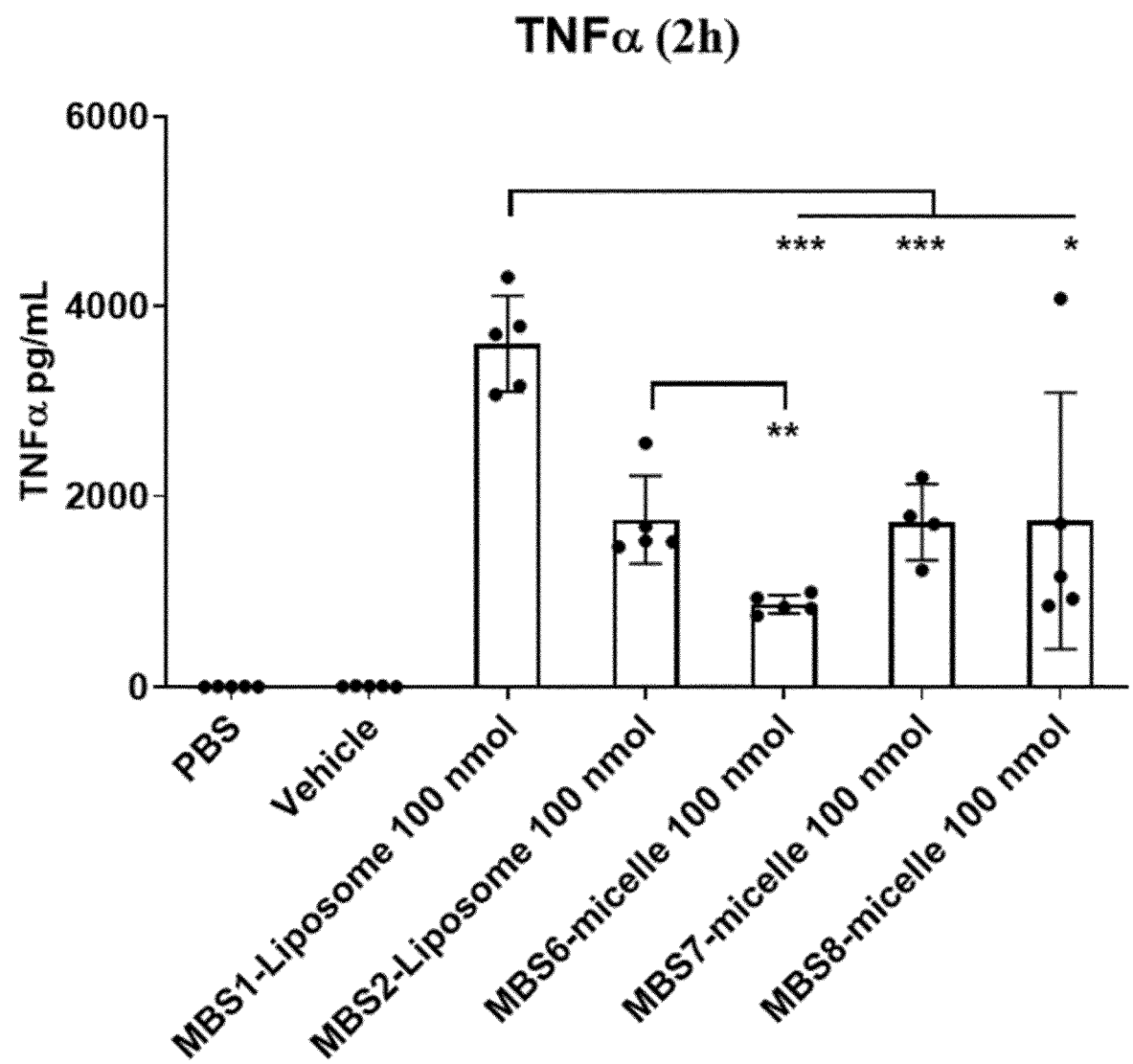
Figure 4G:
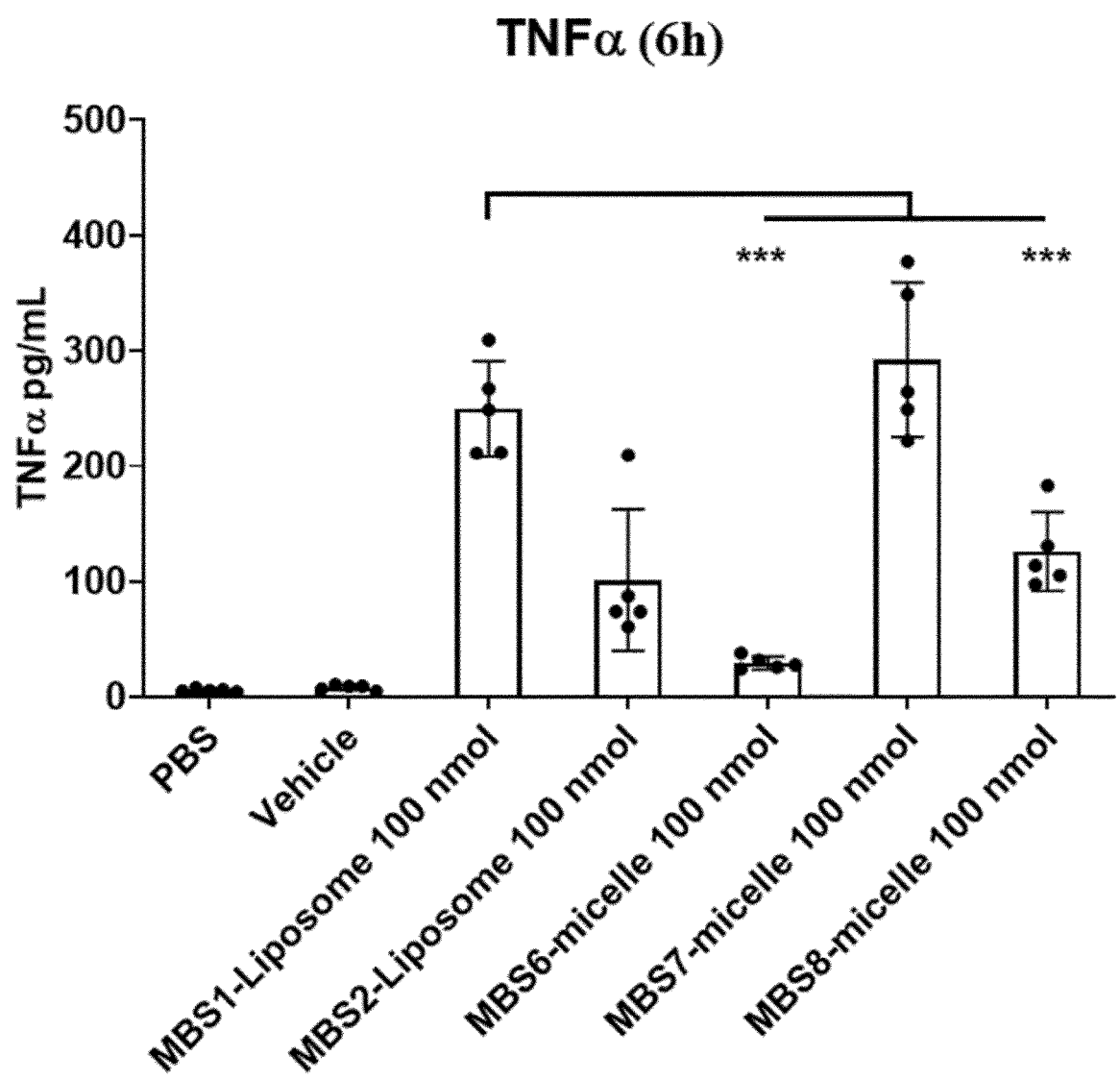

Both interferon gamma (FIG. 4A) and interferon alfa (FIG. 4B) were reduced for all three micelle formulations, MBS6-8, compared to the two liposome formulations at either 2 or 6 h post treatment, supporting a reduced risk of cytokine storm for the micelle formulations. IL-12p70 which is important for eliciting a type 1 cytotoxic T-cell response showed a slight but significant reduction for MBS6 and MBS8 treatment compared to MBS1 liposomes, but still a cytokine level expected to elicit an anti-tumor response (FIG. 4C). IL-6 which is a critical cytokine for initiation of CRS show reduced IL-6 level in plasma from mice treated with MBS6-8, compared to liposomes MBS1 and MBS2 at the 2 h time point. After 6 h, all mice showed lower IL-6 levels than after 2 h, with similar to or slightly lower IL-6 levels than the liposomes, demonstrating that the micelles show an overall reduction in IL-6 levels and not only a delay. TNF alpha which is also related to initiation of the CRS syndrome was also measured, and showed an overall cytokine reduction for micelles in particular compared to MBS1, and most pronounced for MBS6 and MBS8. Cytokines IL-1b and chemokine GRO were measured, but without showing significantly different cytokine levels.

Conclusion

In conclusion, administration of micelles MBS6-8 in mice resulted in a safer cytokine profile with reduced risk of Cytokine Release Syndrome (CRS) compared to the corresponding liposomes MBS1 and MBS2 comprising 1V270.

Example 7: Micelles Shows a Better Toxicology Profile Compared to Liposomes Containing 1V270

Multiple studies with liposomes of different charge and content of 1V270 ranging from 0.75-5% content of 1V270 and at doses of 13-266 nmol/mouse/dose were injected per mouse in groups of 7-9 mice/group. At the first two injections at day 0 and 4, the mice tolerated the liposomes well without any signs of adverse events or toxicity. However, at the third injection at day 8, mice showed adverse events and toxicity in 81% of the studies conducted. The toxicity was associated with lack of movement, piloerection, weight drop loss and general poor well-being for a transient period starting 10-15 minutes after dosing, and prolonged for 30-40 minutes. This observation was seen in of 37 studies with Liposomes across all dose ranges.

In contrast, micelles did not show this toxicity in any studies, currently in 30 of 30 studies, indicating that micelle formulations of 1V270 show a better toxicity profile than liposome formulations of 1V270.
Conclusion In conclusion, administration of micelles MBS6-8 in mice resulted in better toxicology profile compared to the corresponding liposomes comprising 1V270.

Figure 5A:
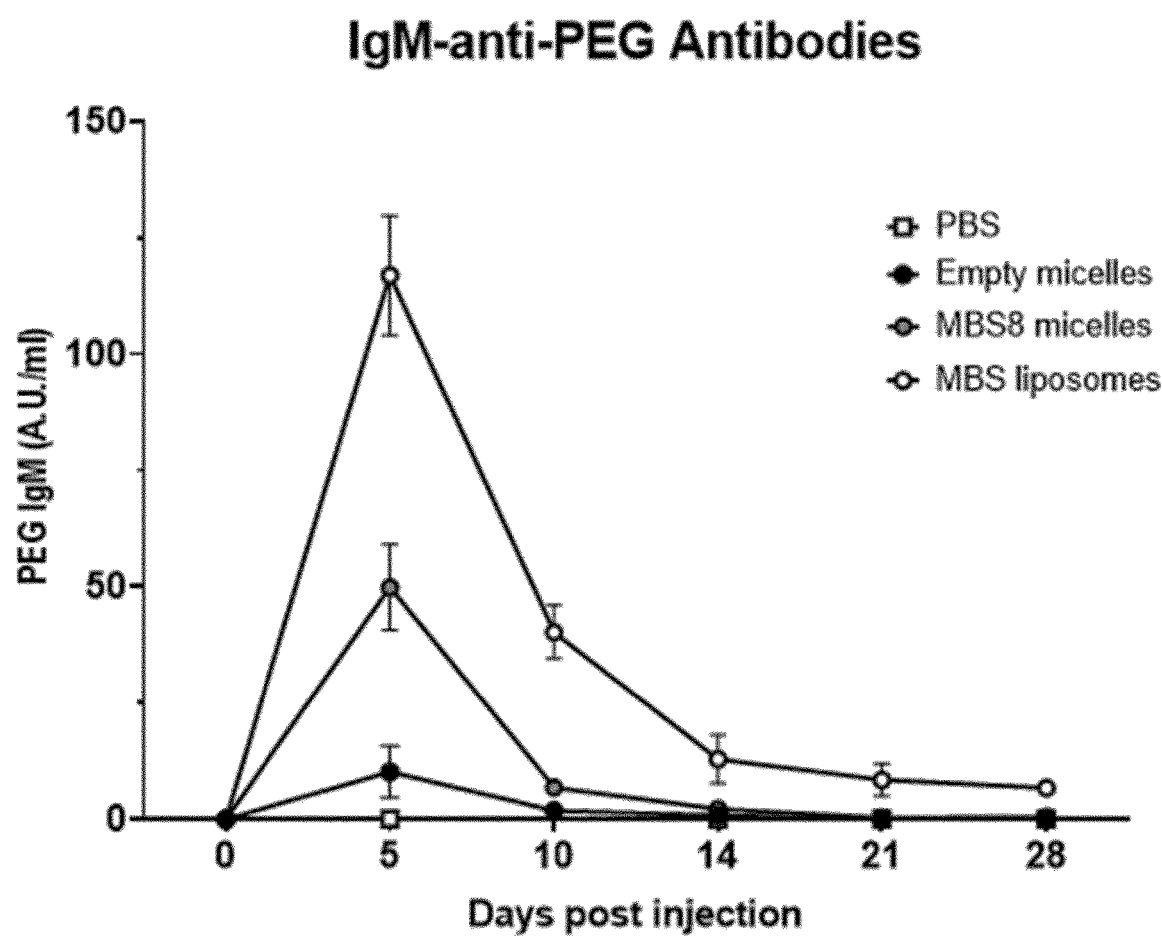
FIG. 5A-B show induction of anti PEG IgM and IgG molecules in plasma of mice treated once with IV injection of micelles or liposomes containing 1V270. The anti PEG IgM and IgG molecules are measured by ELISA designed for this purpose.
Figure 5B:
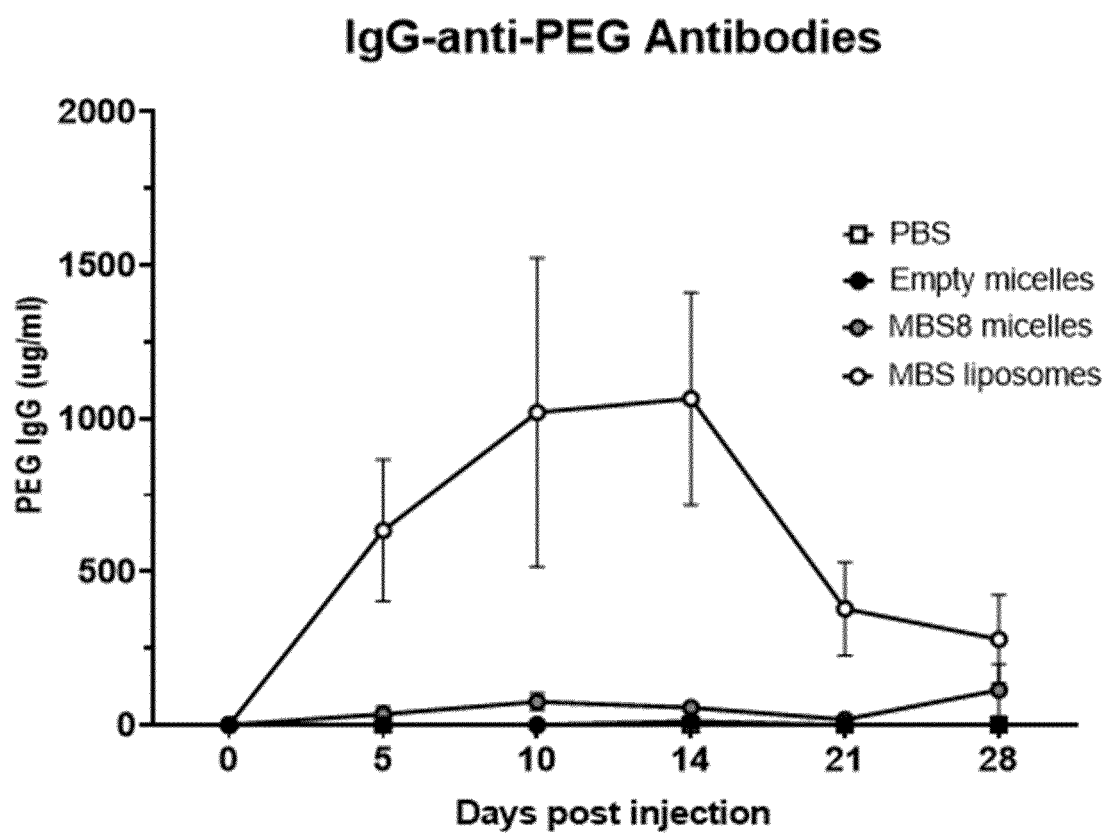

Example 8: Micelles Induce Lower IgM and IgG Anti-PEG Antibodies when Injected into Mice To explore the toxicity associated with liposomes containing 1V270 but not micelles containing 1V270, liposomes and micelles containing 1V270 were injected once by IV injection into mice, and blood samples drawn during a 28-day period. Micelles without 1V270 induced low levels of anti-PEG IgM antibodies in the mouse plasma when measured by an ELISA kit against anti-PEG IgM antibodies (FIG. 5A, empty micelles). MBS8 micelles induced anti PEG IgM molecules in plasma at day 5, but at levels lower than half of the amounts induced by liposomes containing 1V270 (FIG. 5A, MBS8 vs MBS liposomes). For anti PEG IgG antibodies which are normally more specific and present for longer times in mammals when induced, the induction was very high for liposomes 1-2 weeks after dosing and then dropped but was still present throughout the study (FIG. 5B). MBS8 micelles induced much lower IgG anti PEG antibodies (FIG. 5B, approximately 17 fold lower), than liposomes containing 1V270. This observation indicates that micelles induce lower levels of IgM and IgG anti PEG responses and thus reduce immune related toxicities in mice and potentially in other mammals, which is important in order to reduce toxicities in patients treated with micelles and liposomes with immune potentiating reagents.

Figure 5C:
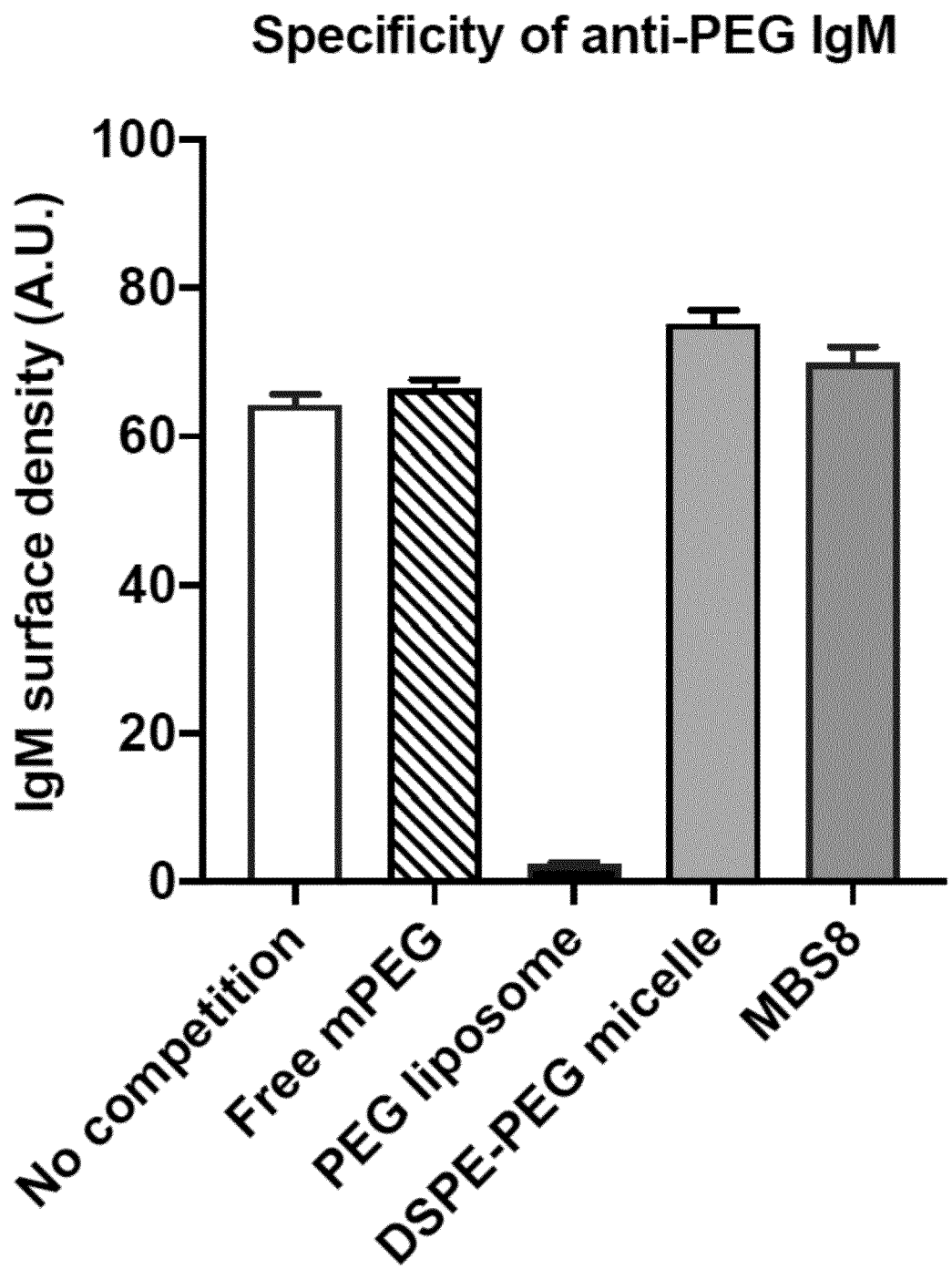
FIG. 5C show specificity of anti-PEG IgM determined with a competition assay. Only PEGylated liposomes are recognized by the generated IgM, whereas free PEG chains, DSPE-PEG micelles and MBS8 micelles are not recognized by the anti-PEG IgM molecules.

FIG. 5C show specificity of anti-PEG antibodies generated against MBS8.

Healthy mice were treated with a single dose of MBS8 micelles at a total dose of 200 nmol 1V270. Blood was drawn at day 5 post injection, and plasma acquired. Next, the plasma was incubated with either PBS, PEGylated liposomes, free mPEG2000 chains, DSPE-PEG micelles without 1V270 or MBS8 micelles. The PEG concentration was 1 µM in all pre-incubations. The plasma was then added to microscopy wells containing immobilized fluorescently labeled PEGylated liposomes and incubated for 10 minutes. The microscopy well was washed, and fluorescent secondary antibodies against murine IgM added. The liposomes were imaged with confocal microscopy to determine surface density of IgM on the single liposomes.

When plasma had been pre-incubated with PBS (no competition) the surface density was approx. 60 A.U. Similar IgM binding was measured when plasma had been pre-incubated with free mPEG, DSPE-PEG micelles or MBS8 micelles, and showed a high IgM surface density (AU in the 60-70 range) indicating no competition for binding the anti-PEG IgM present in plasma. When plasma was pre-incubated with PEG-liposomes (positive control for competition), the anti-PEG IgM binding to immobilized PEG-liposomes was almost completely abolished, indicating strong competition for the binding. Thus, the anti-PEG IgM detected with ELISA in FIG. 5A induced by the MBS8 micelles are only able to recognize PEG chains attached to planar or liposomal surfaces, but not the PEG micelles (MBS8 included) or free PEG chains.
Conclusion The anti-PEG IgM generated against MBS8 micelles after injection into mice is not able to recognize and bind to MBS8 micelles or DSPE-PEG micelles in general, supporting that a potential generation of anti-PEG IgM antibodies in patients is unlikely to bind to MBS8 upon multiple injections.

Example 9: Treatment of a Mammal with Cancer Using Immunostimulatory 1v270 Micelles (Non-Antigen Specific)

To obtain an immune stimulatory micelle suitable for cancer treatment, a micelle can be generated by mixing 1v270:DOPE-PEG2k (10:90=MBS8). The compounds are mixed in organic solvent and dried to a lipid film. This film is hydrated in a buffer suitable for intravenous administration, e.g. containing saline. The micelles are administered intravenously to a cancer patient suffering from e.g. lung cancer, breast cancer, prostate cancer, HNC, leukemia, lymphoma or melanoma with e.g. a one-two week interval. Combinations with clinically approved treatments is likely enhancing the anti-tumor effect. In particular in combination with immune checkpoint inhibitors, radiotherapy to boost the abscopal effect in e.g. lung cancer patients, to combine with mAb therapy like Rituximab and Trastuzumab to boost the Antibody Dependent Cell Cytotoxicity (ADCC), to enhance responses towards immunogenic cell death induced by certain chemotherapy like doxorubicin, oxaliplatin, cyclophosphamide and mitoxantrone.

Example 10: Treatment of a Mammal with Cancer Using Immune Stimulatory 1v270 Micelles (Antigen Specific)

To obtain an antigen specific immune response micelles are prepared as in example 9, but with addition of an antigen peptide comprising whole or parts of the antigen of interest linked to a lipid anchor like e.g. DOPE. The peptide antigen associated with a lipid anchor ensures sufficient micelle association as seen for a 25 amino acid peptide sequence from the MUC1 tumor antigen, where a palmitoylated lysine residue ensures sufficient liposome association of the antigen (Sangha and Butts, Clin Cancer Res 2007; 13, 15 supp, 2007, 4652-54s). The antigen may be e.g. a MAGE antigen for treatment of melanoma, PSA for treatment of prostate cancer, a neoantigen or a third antigen or a combination of antigens. The antigen together with 1v270 are administered to a cancer patient expected to express the loaded antigen in their tumors. The micelles are administered to the same patient for a number of times to boost an antigen specific response, preferably with 1-2 weeks interval.

Example 11: Antitumor Activity of MBS8 Micelles in Combination with Radiotherapy Mice bearing CT26 subcutaneous tumors were treated with radiotherapy (RT) and micelles containing 50, 100, or 200 nmol 1V270. Micelles were given intravenously every fourth day for a total of 5 treatments starting from day 12 after tumor inoculation. 2 Gy RT to the tumor-bearing flank was given every day for 5 consecutive days starting from day 12 after tumor inoculation. The number of mice per group was 8-10 and mice were rechallenged with CT26 on the opposite flank on day 101 after primary inoculation. Data on tumor growth curves are mean tumor size±SEM.

Figure 6A:
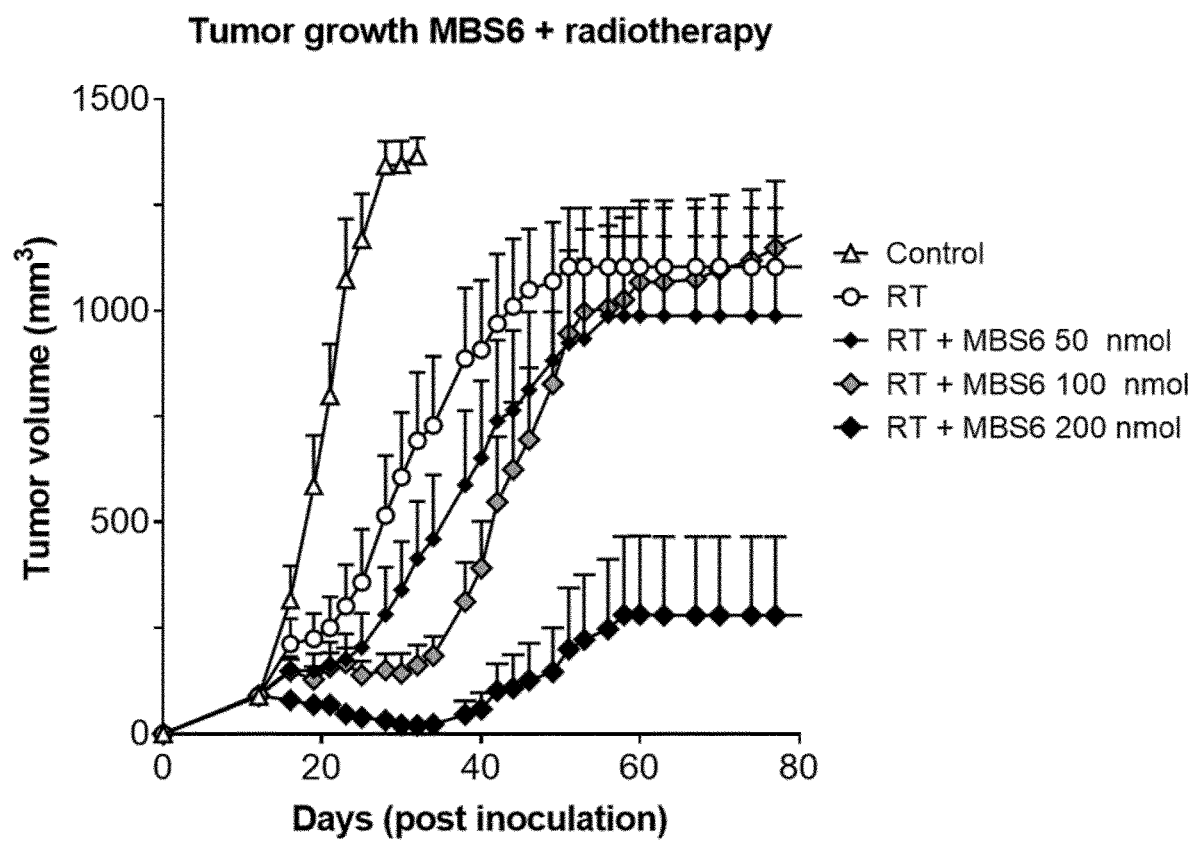
FIG. 6A: Tumor growth of mice treated with MBS6 in combination with radiotherapy.
Figure 6B:
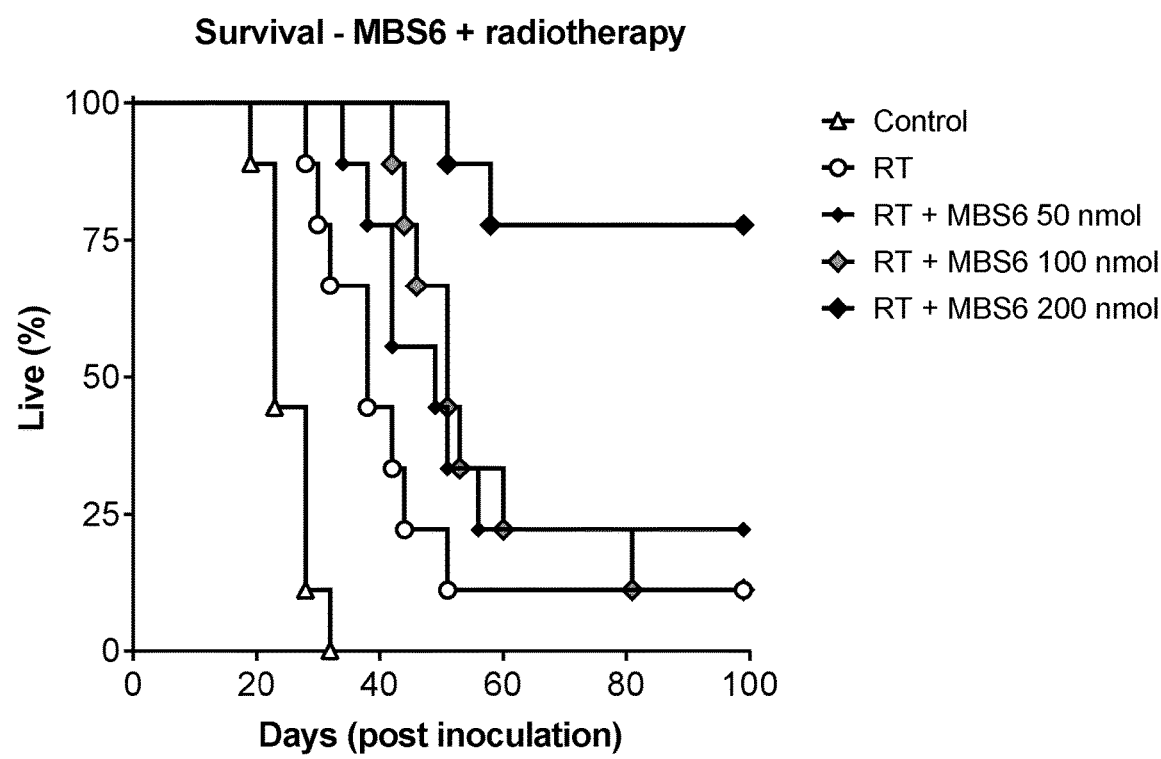
FIG. 6B: Survival of mice treated with MBS6 in combination with radiotherapy.

Combining 50 or 100 nmol MBS6 with RT provided only modest tumor control while 200 nmol MBS6 in combination with RT provided good tumor control (FIG. 6A). For RT alone, 1/9 mice were complete responders and 1/1 mice rejected rechallenge. For 50 nmol MBS6 combined with RT, 2/9 mice were complete responders and 2/2 rejected rechallenge. For 200 nmol MBS6 in combination with RT, 7/9 mice were complete responders and 7/9 rejected rechallenge (FIG. 6A-B).

Figure 6C:
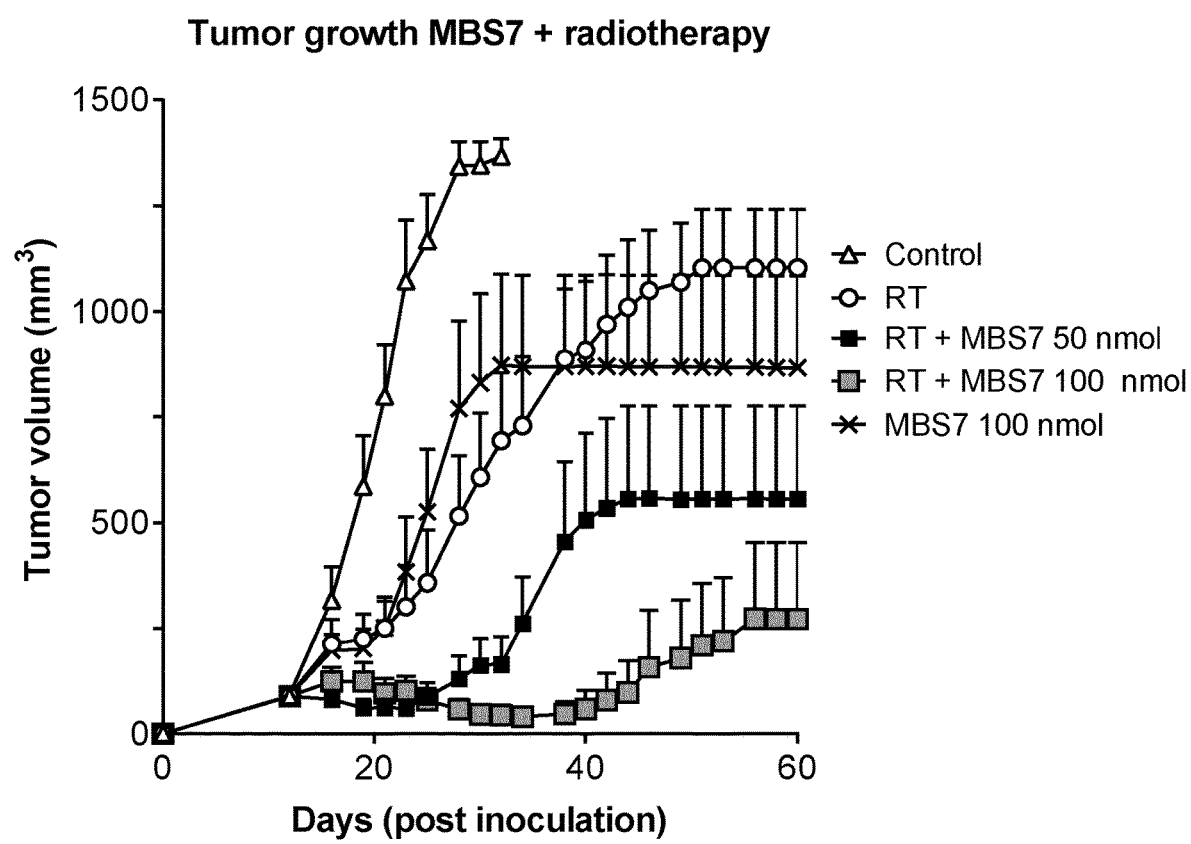
FIG. 6C: Tumor growth of mice treated with MBS7 in combination with radiotherapy.
Figure 6D:
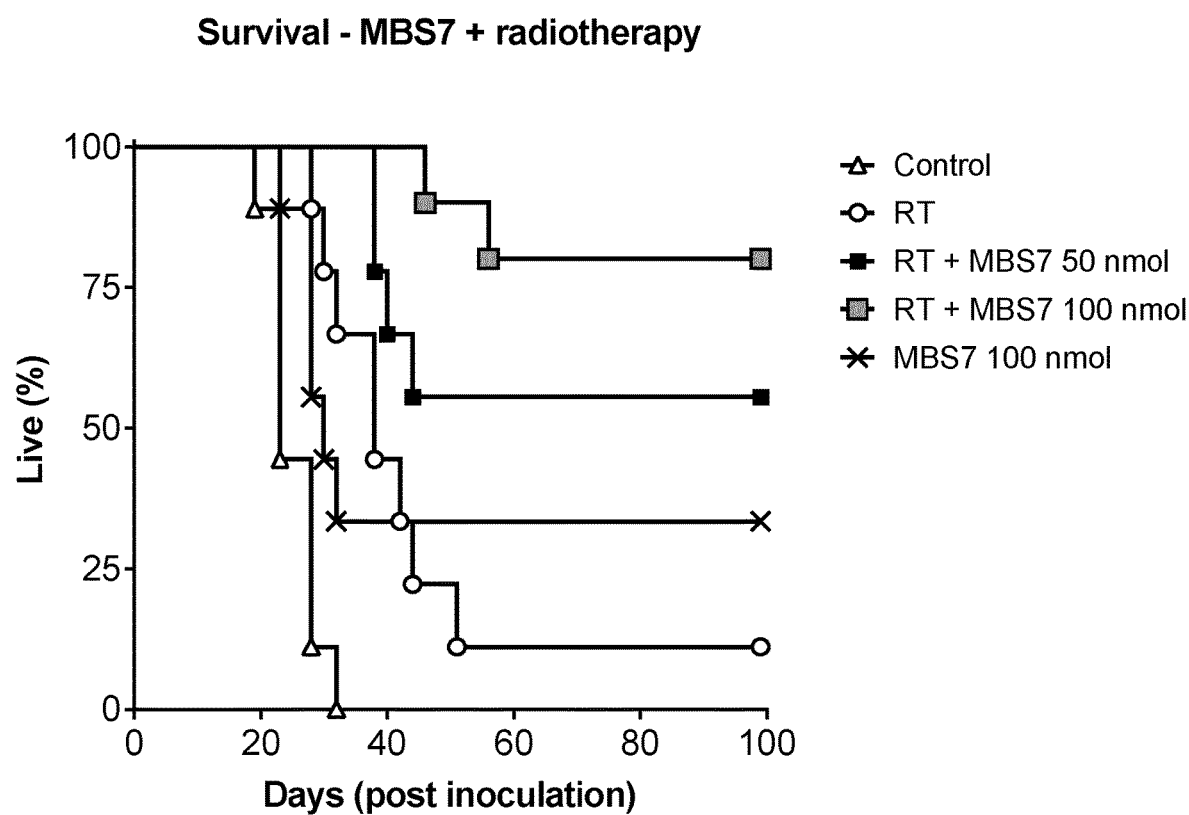
FIG. 6D: Survival of mice treated with MBS7 in combination with radiotherapy.

Combining MBS7 with RT showed synergistic effect. For 50 nmol MBS7 combined with RT, 5/9 mice were complete responders and 5/5 rejected rechallenge. For 100 nmol MBS7 as monotherapy, 3/9 mice were complete responders and 3/3 rejected rechallenge. Combining 100 nmol MBS7 with RT provided 8/10 complete responders and 3/3 mice rejected rechallenge and provided significantly improved survival compared to monotherapy (p=0.02, Mantel-Cox test; FIG. 6C-D).

Combining 50 nmol MBS8 with RT provided 2/10 complete responders and 2/2 mice rejected rechallenge. For 100 nmol MBS8 in combination with RT, 4/9 mice were complete responders and 4/4 rejected rechallenge. For 200 nmol MBS8 in combination with RT, 8/8 mice were complete responders and 7/8 rejected rechallenge.

Figure 6E:
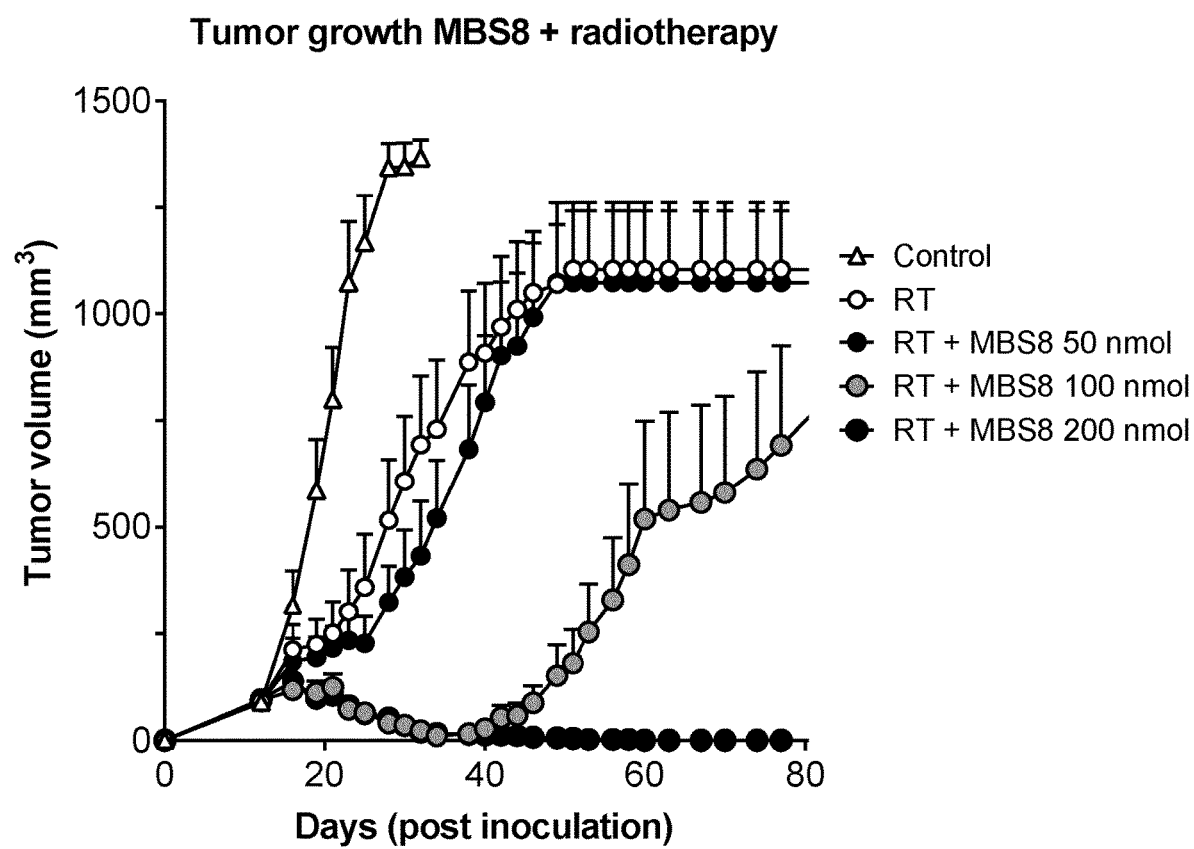
FIG. 6E: Tumor growth of mice treated with MBS8 in combination with radiotherapy.
Figure 6F:
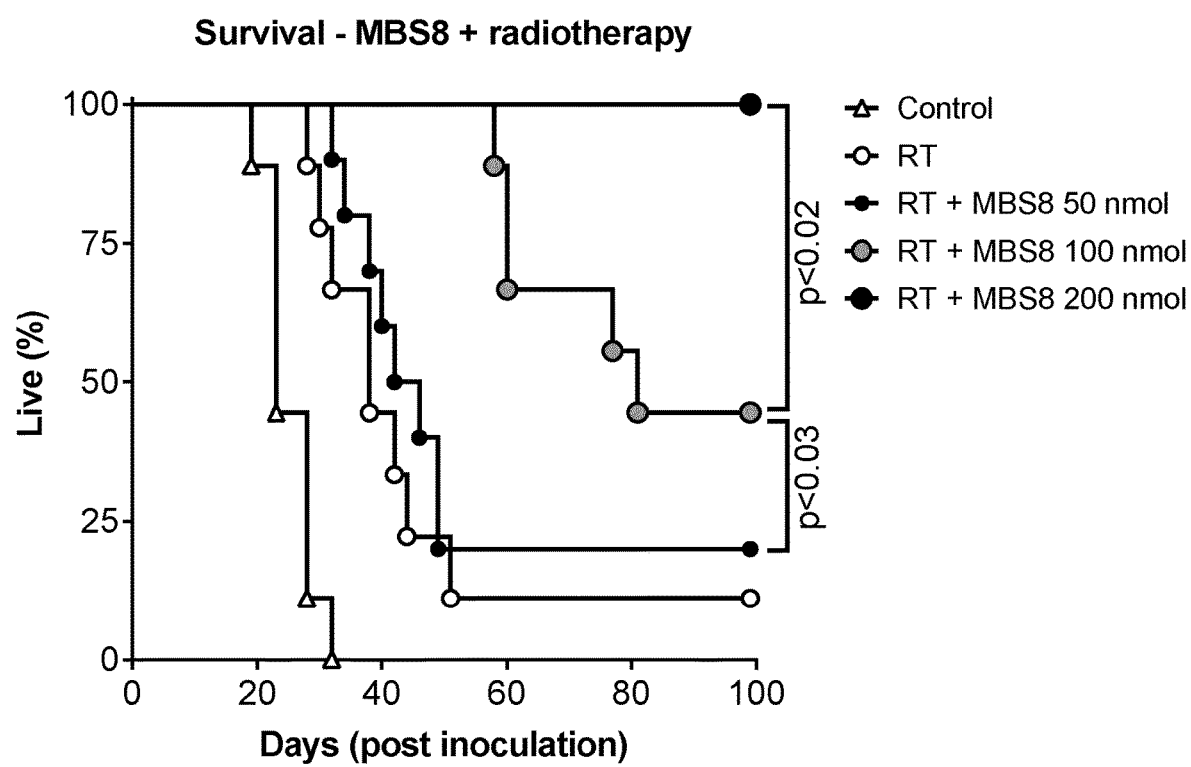
FIG. 6F: Survival of mice treated with MBS8 in combination with radiotherapy.

Furthermore, dose dependency could be observed for MBS8 in combination with RT (p<0.3, Mantel-Cox test; FIG. 6E-F).

Conclusion

Micelles containing 1V270 in molar ratios of 80:20, 90:10 and 95:5 all show strong antitumor activity both in monotherapy and in combination with radiotherapy.

Example 12: Antitumor Activity of MBS8 Micelles in Monotherapy

Figure 7A:
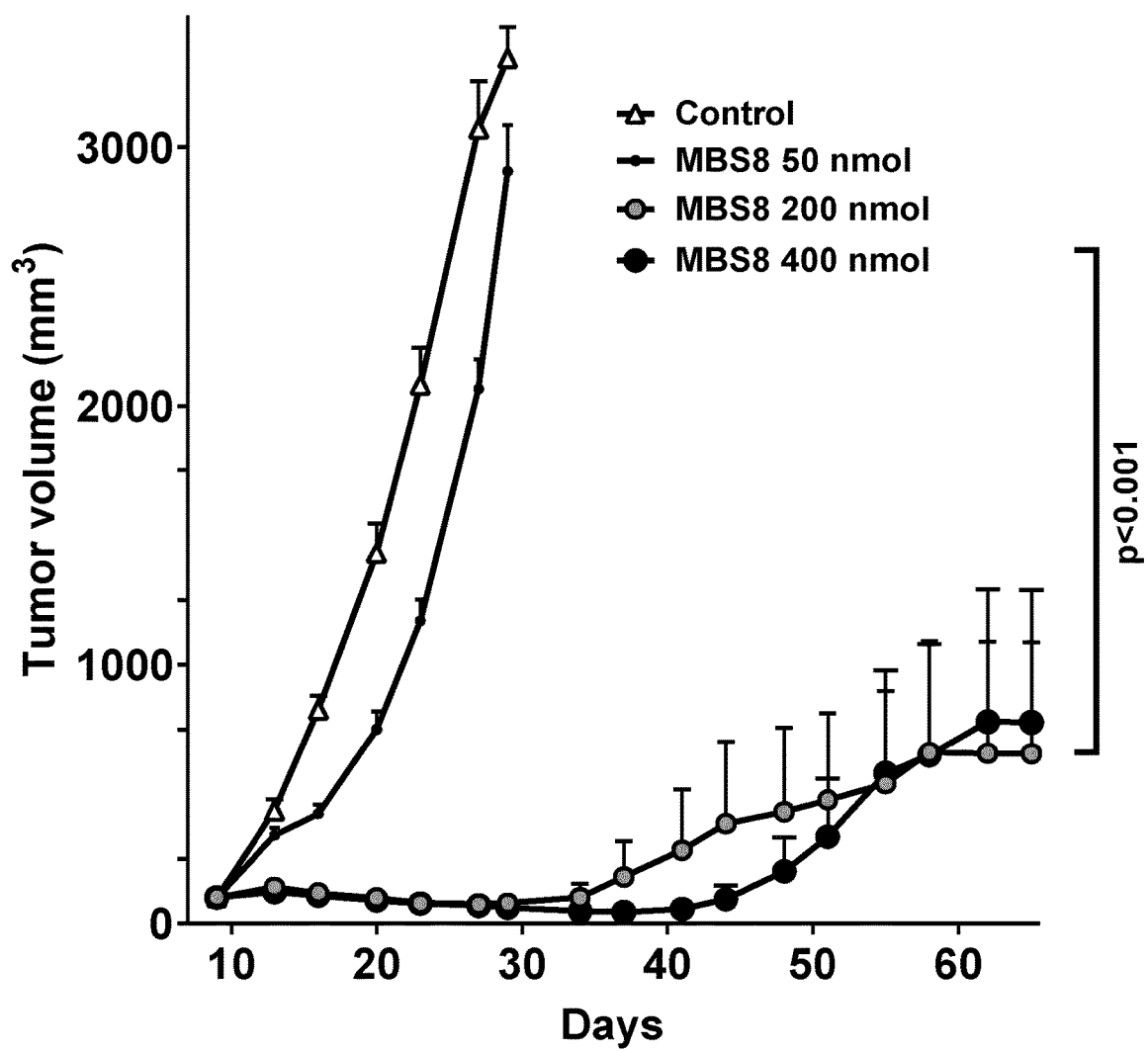
FIG. 7: Compares antitumor activity between MBS8 micelles containing DOPE-PEG2000 and TLR7 agonist 1v270 in a 90:10 molar ratio and dosed at three levels in the CT26 model. MBS8 was dosed at three doses of 50 (small black circle), 200 (grey circle) and 400 (large black circle) nmol injected IV per mouse. The two high doses at 200 and 400 nmol were significantly different from the control treated group ($p<0.001$). Individual growth of each tumor is shown in FIG. 7B with 1) control treatment (PBS), 2) low dose MBS8 at 50 nmol/injection/mouse 3) mid dose MBS8 at 200 nmol/injection/mouse and 4) high dose MBS8 at 400 nmol/injection/mouse.
Figure 7B:
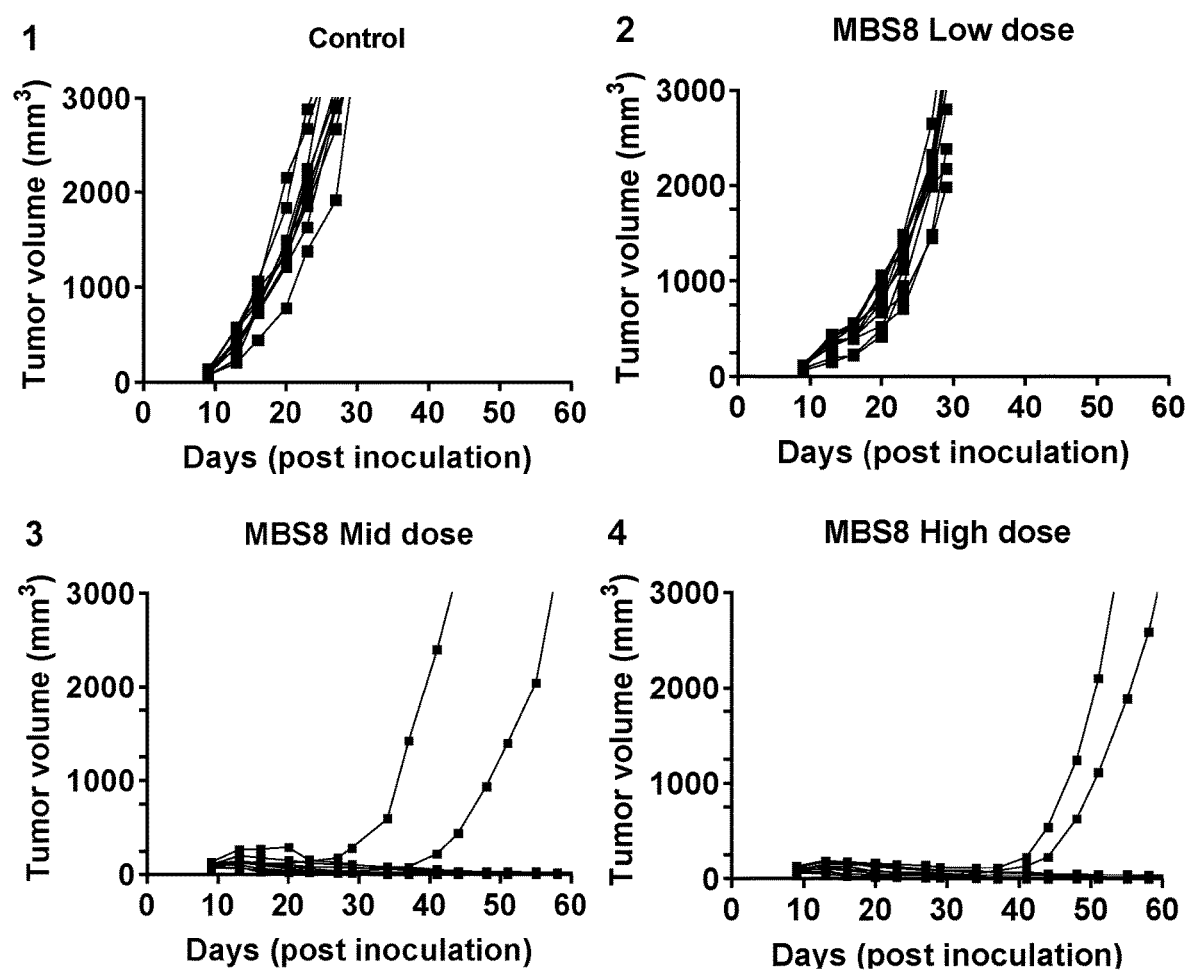

Efficacy of MBS8 micelles was studied in monotherapy in the CT26 syngenic subcutaneous colon cancer model. Randomisation of mice and treatment started when tumors reached an average volume of 100 mm$^3$ (Day 0). Groups of 10 mice each were treated with PBS as vehicle control or three doses of MBS8 at 50, 200 or 400 nmol/mouse/injection by intravenous bolus (FIG. 7A). MBS8 was given q4d, total of 5 injections starting on day 9 (day 9, 13, 17, 21 and 25). Growth of tumors was measured twice a week. Mean tumor volumes of treated mice are shown in FIG. 7A, while tumor volumes of individual animals are shown in FIG. 7B (1-4). Statistical analysis using a Wilcoxon rank sum test revealed a significant potentiation of the efficacy of MBS8 at the mid and high dose compared to control (p<0.01). 8 mice out of 10 showed complete remission in the mid and high dose MBS8 treatment groups.

Conclusion

MBS8 micelles comprising 1V270 in a 10 molar content show a significant antitumor activity at 200 and 400 nmol dose in the CT26 model, and are very potent in induction of complete remission.

Figure 8A:
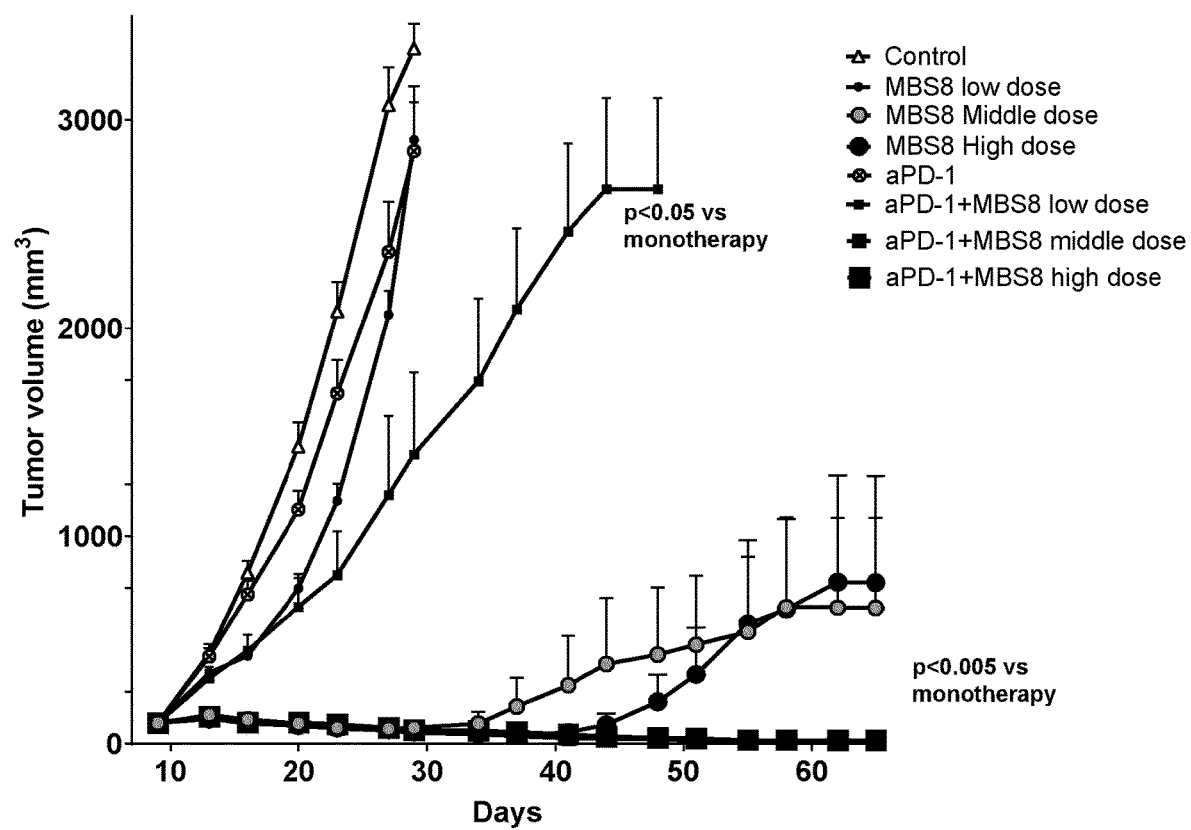
FIG. 8: MBS8 micelles at three different dose levels were combined with αPD-1 treatment (clone RMP1-14 with 10 mg/kg dosed IP) in the CT26 colon cancer syngenic mouse tumor model. MBS8 was dosed at three doses of 50, 200 and 400 nmol injected IV per mouse with first injection day 9, and then 4 more doses with 4 days interval at days 13, 17, 21 and 25. αPD-1 mAbs were injected IP starting day 11, twice weekly for three weeks. PD-1-MBS8 combination treatments were all significantly stronger than PD-1 monotherapy ($p<0.05$, $p<0.005$, Wilcoxon rank sum test) (FIG. 8A).
In FIG. 8B is shown individual tumor growth for all 10 mice per group with 1) control (PBS treated), 2) MBS8 at 50 nmol, 3) MBS8 at 200 nmol, 4) MBS8 at 400 nmol 5) PD1 treatment alone at 10 mg/kg injected IP 6) PD-1 and MBS8 at 50 nmol in combo therapy, 7) PD-1 and MBS8 at 200 nmol in combo therapy 8) PD-1 and MBS8 at 400 nmol in combo therapy.
Figure 8B:
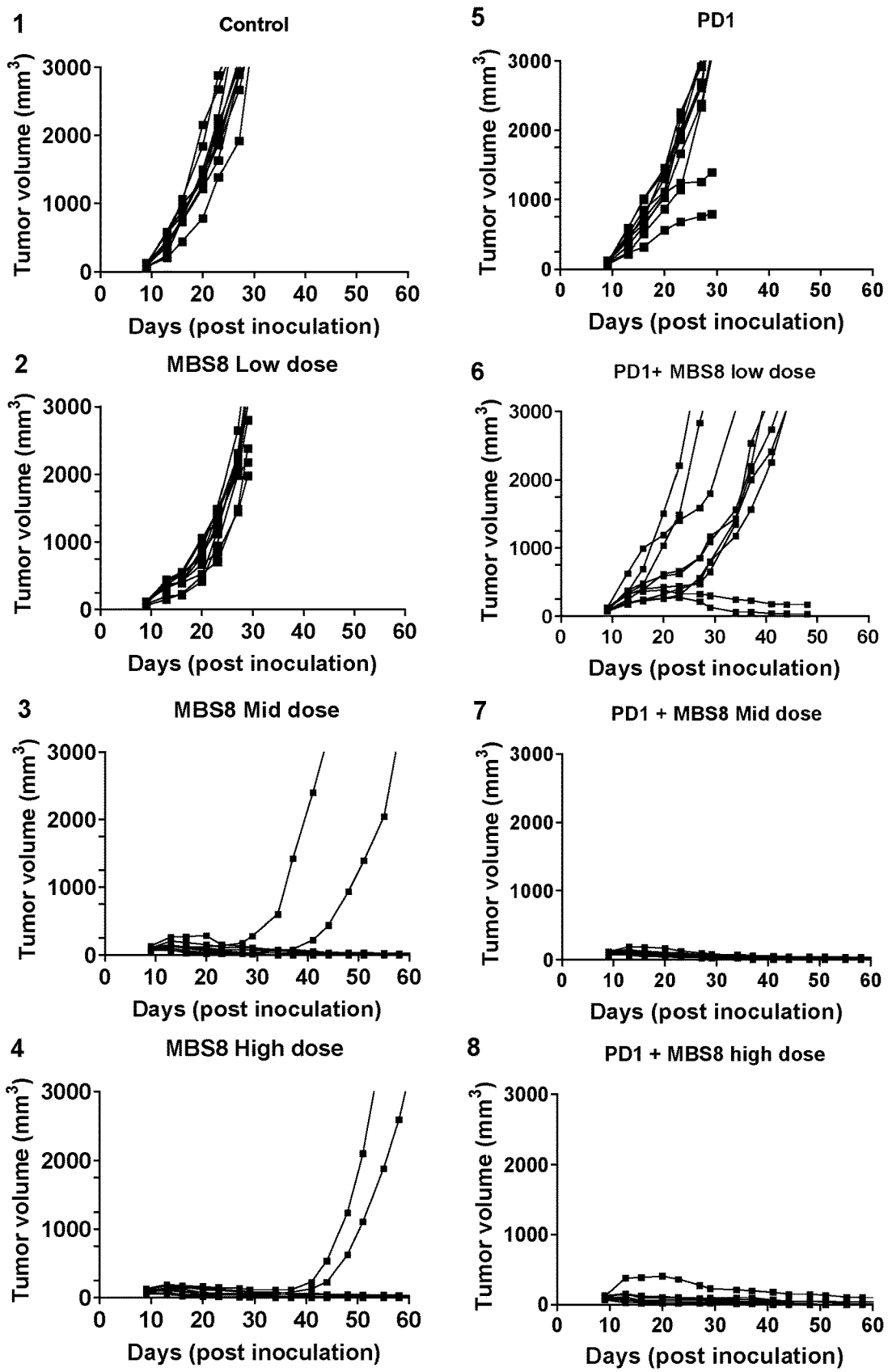

Example 13: Antitumor Activity of MBS8 Micelles in Combination with PD-1 Therapy Efficacy of MBS8 micelles in combination with αPD-1 therapy was studied with a fixed dose of αPD-1 at 10 mg/kg injected IP and increasing dose of MBS8 at 50, 200 and 400 nmol/mouse/injection. The CT26 model was carried out and MBS8 treatment performed as described in Example 12. MBS8 treatment started day 9, and αPD-1 started day 11 and then twice weekly for three weeks (FIG. 8A). Low dose MBS8 in combination with αPD-1 showed a significant tumor growth delay (p<0.05) versus MBS8 low dose alone and αPD-1 alone (FIGS. 8A and 8B, graph 1-4). At the mid and high dose MBS8 the combination therapy did not initially show any difference since all mice in each of the groups showed remission or very small tumors (FIG. 8A). However, at day 30-50 a few tumors started to grow in the MBS8 monotherapy groups with two escaping tumors (FIGS. 8A and 8B, graph 3-4). In the αPD-1 combo groups these escapers were not seen (FIG. 8B, graphs 7 and 8), and all tumors eventually disappeared or became very small (<30 mm3).

Conclusion

MBS8 micelles comprising 1V270 are very potent in combination with αPD-1 leading to complete remission of at least 90% of treated mice carrying the CT26 tumor model.

Figure 9A:
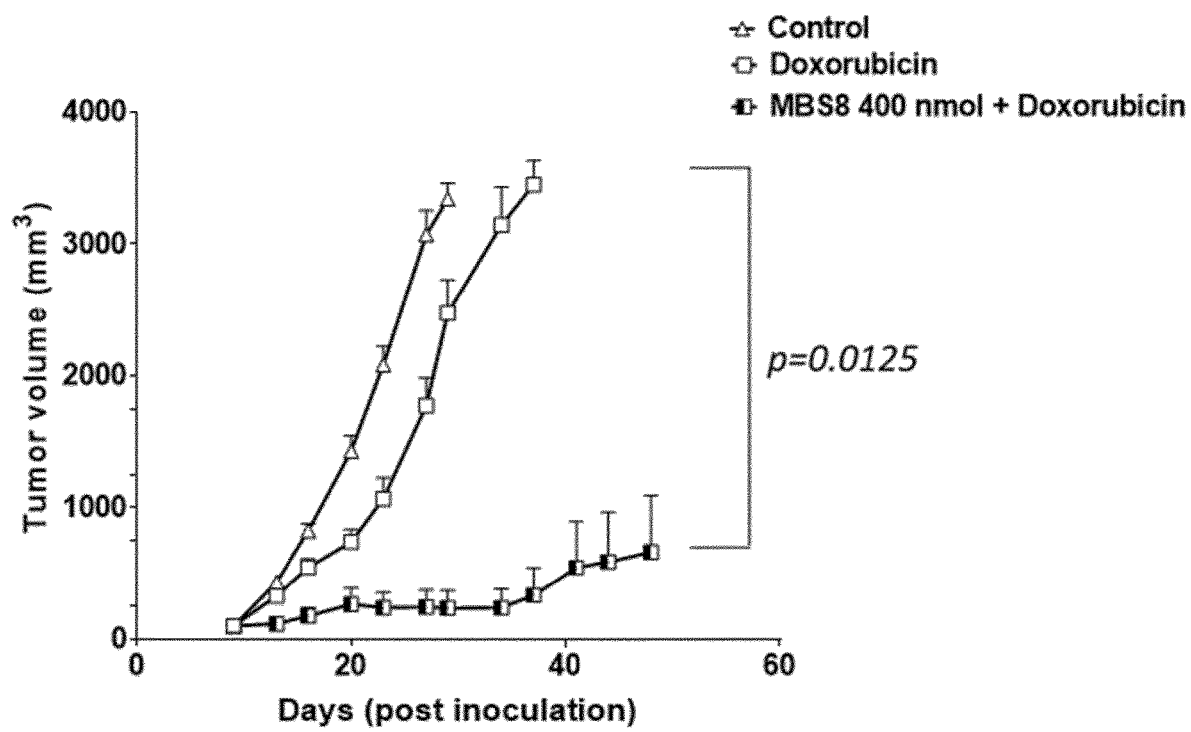
FIG. 9: MBS8 potentiates anti-tumor effect of doxorubicin (A-B) and doxil (C-D). Mean tumor volumes±SEM are shown, n=10 in (A) and (C). Wilcoxon rank sum test was used for statistical data treatment. Tumor volumes of individual animals are shown for the indicated groups in (B) and (D).
Figure 9B:
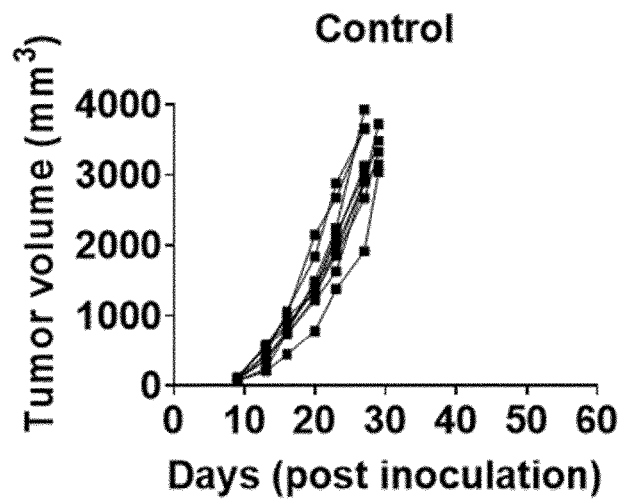
Figure 9B:
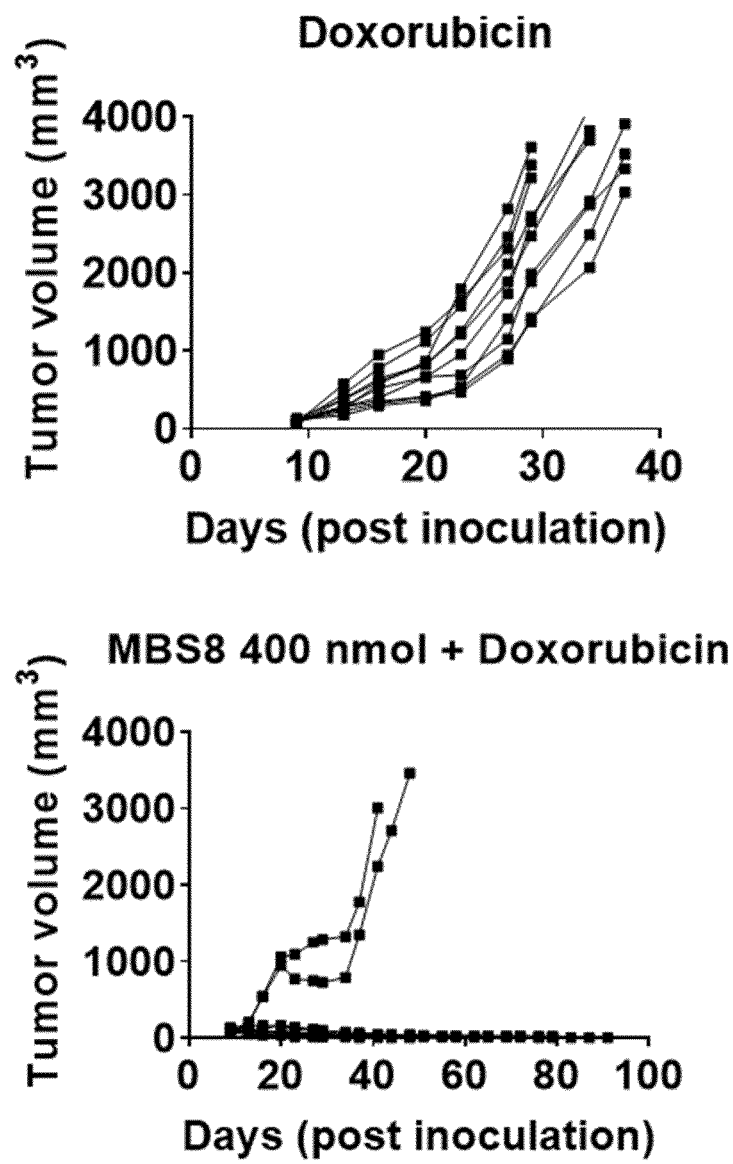
Figure 9C:
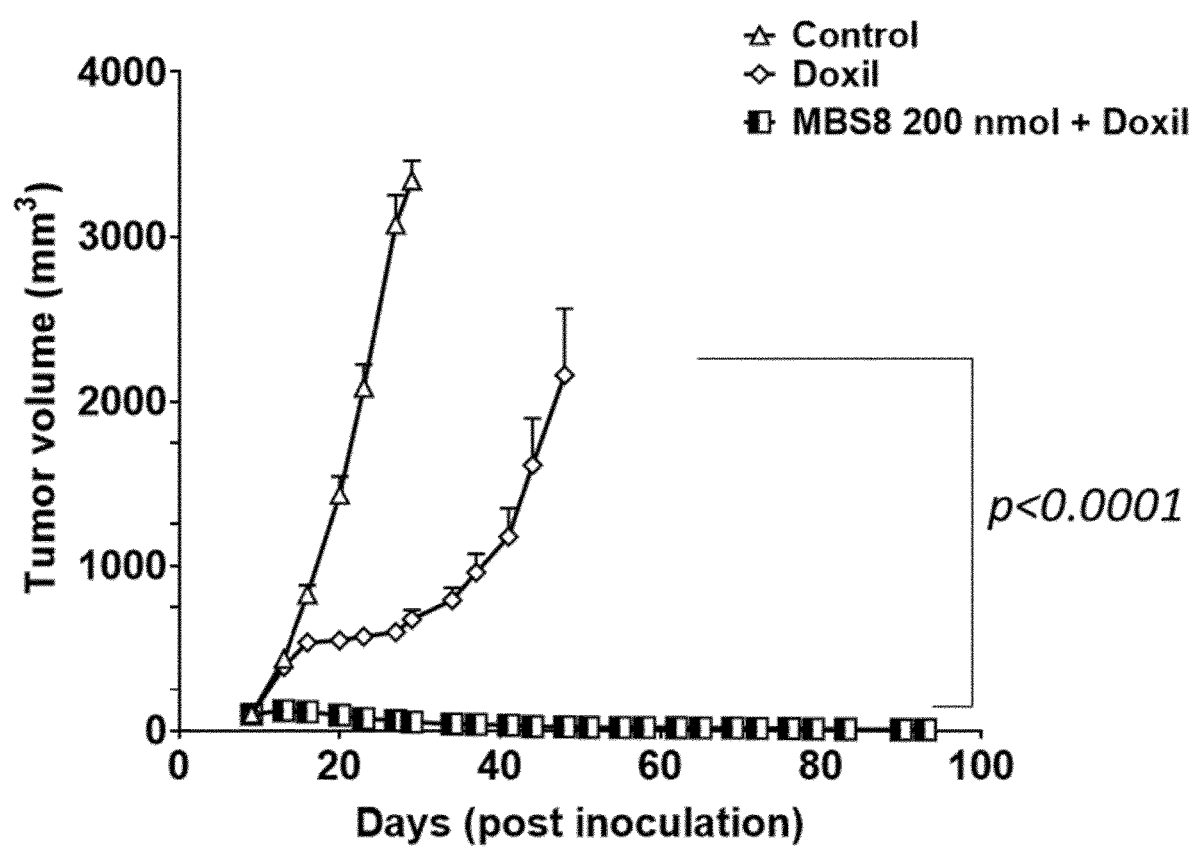
Figure 9D:
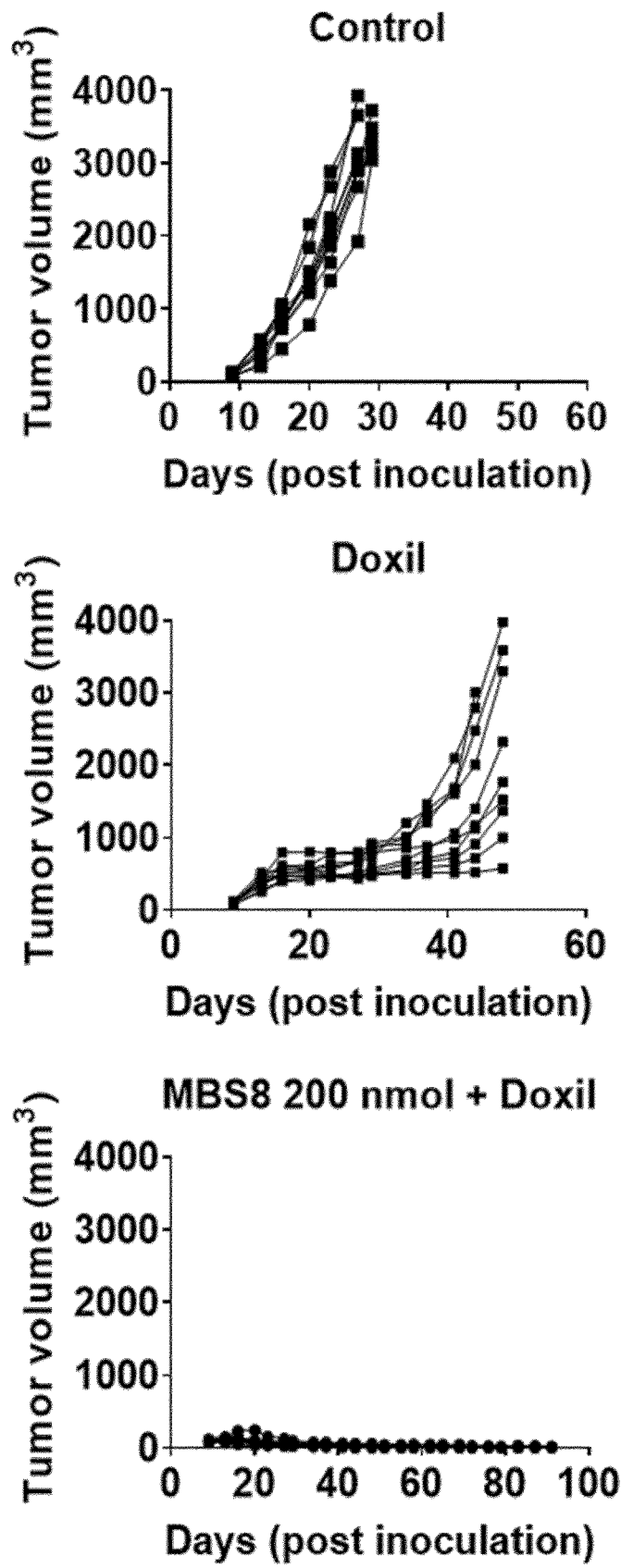

Example 14: Antitumor Activity of MBS8 Micelles in Combination with Chemotherapy (Doxorubicin and Doxil) in the CT26 Model Efficacy of MBS8 micelles was studied in combination with standard of care chemotherapy, including doxorubicin and doxil, and compared with the efficacy of the monotherapy with these chemotherapeutic drugs in the CT26 syngenic subcutaneous colon cancer model. Randomisation of mice and treatment started when tumors reached an average volume of 100 mm$^3$ (Day 0). Groups of 10 mice each were treated with PBS as vehicle control, doxorubicin (4 mg/kg) or combo of MBS8 (400 nmol/mouse) and doxorubicin (4 mg/kg) (FIG. 9A), or doxil (4 mg/kg) or combo of MBS8 (200 nmol/mouse) and doxil (4 mg/kg) (FIG. 9C). All drugs were administered by intravenous bolus. Doxorubicin or doxil were given q4d, total of 3 injections. MBS8 was given q4d, total of 5 injections. Doxorubicin or doxil were administered on Day 10, Day 14 and Day 18; MBS8 was administered on Day 10, 20, 24, 28 and 32. Growth of tumors was measured twice a week. Mean tumor volumes of doxorubicin and/or MBS8 treated animals are shown in FIG. 9A, while tumor volumes of individual animals are shown in FIG. 9B. Mean tumor volumes of doxil and/or MBS8 treated animals are shown in FIG. 9C, while tumor volumes of individual animals are shown in FIG. 9D. Statistical analysis using a Wilcoxon rank sum test revealed a significant potentiation of the efficacy of the chemotherapeutic drugs when combined with MBS8. All animals treated with MBS8/doxil combo showed a complete response and 8 out of 10 complete responders were in the group treated with MBS8/doxorubicin; no complete responders were found in the mono chemotherapy groups.

Conclusion

Micelles comprising 1V270 in a 10 molar content significantly potentiate efficacy of doxorubicin and doxil and leads to complete responders.

Figure 10A:
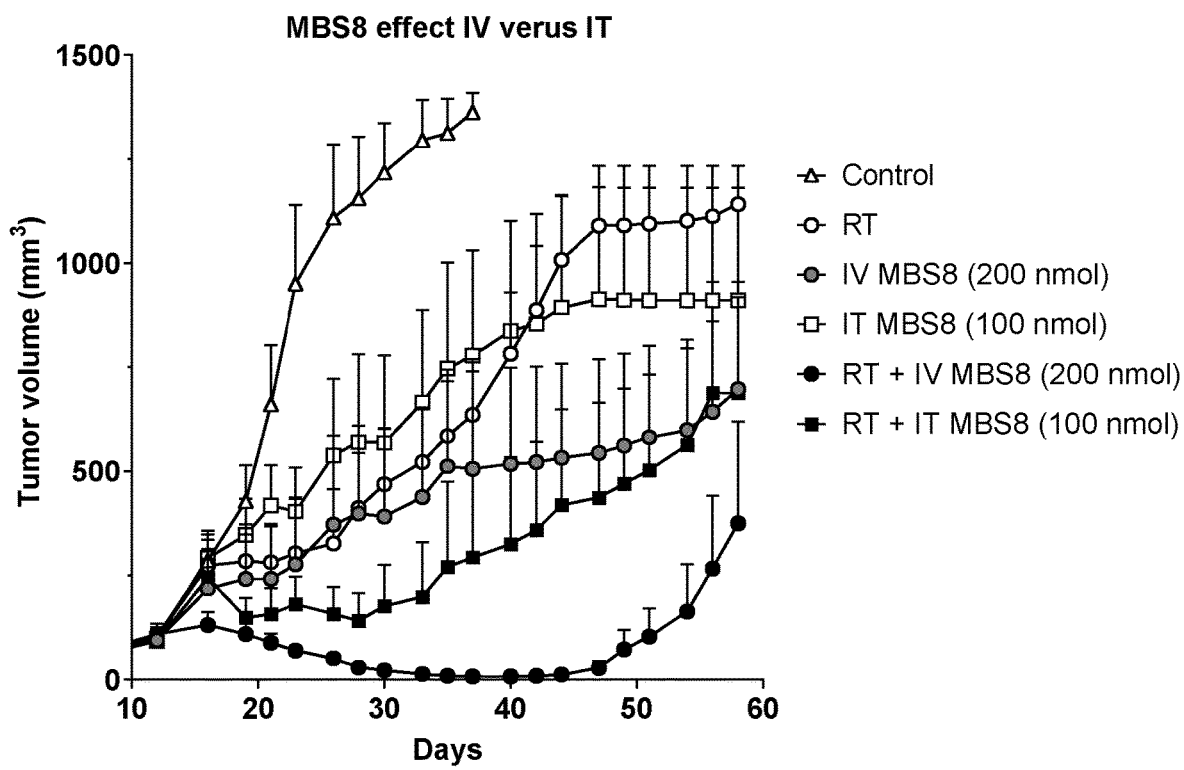
FIG. 10A: Tumor growth of mice treated with MBS8 intratumorally or intravenously in combination with radiotherapy.

Example 15: Antitumor Activity of MBS8 Micelles Using Intravenous Versus Intratumoral Administration Mice bearing CT26 subcutaneous tumors were treated with radiotherapy (RT) and injection of MBS8 intravenously or intratumorally. MBS8 or lipid matched micelle vehicle without TLR7 agonist 1V270 was given every fourth day for a total of 5 treatments starting from day 12 after tumor inoculation. 2 Gy RT to the tumor-bearing flank was given every day for 5 consecutive days starting from day 12 after tumor inoculation. Intratumoral MBS8 injections were given as 100 nmol 1V270 due to volume limitation and intravenous MBS8 injections were given as 200 nmol 1V270 (FIG. 10A). The number of mice per group was 8 and mice in complete remission were rechallenged with CT26 on the opposite flank on day 103 after primary challenge. Data on tumor growth curves are mean tumor size±SEM. MBS8 provided good tumor control as monotherapy and in combination with radiotherapy regardless of administration route, but with the IV route slightly more potent than IT administration (FIG. 10A). Intravenous injection of MBS8 alone resulting in 3/8 complete responders of which 3/3 rejected rechallenge. Intravenous injection of MBS8 in combination with RT resulted in 6/8 complete responders of which 5/6 rejected rechallenge. Intratumoral injection of MBS8 alone resulted in 3/8 complete responders of which 3/3 rejected rechallenge. Intratumoral injection of MBS8 in combination with radiotherapy resulted in 4/8 complete responders of which 4/4 rejected rechallenge.

Figure 10B:
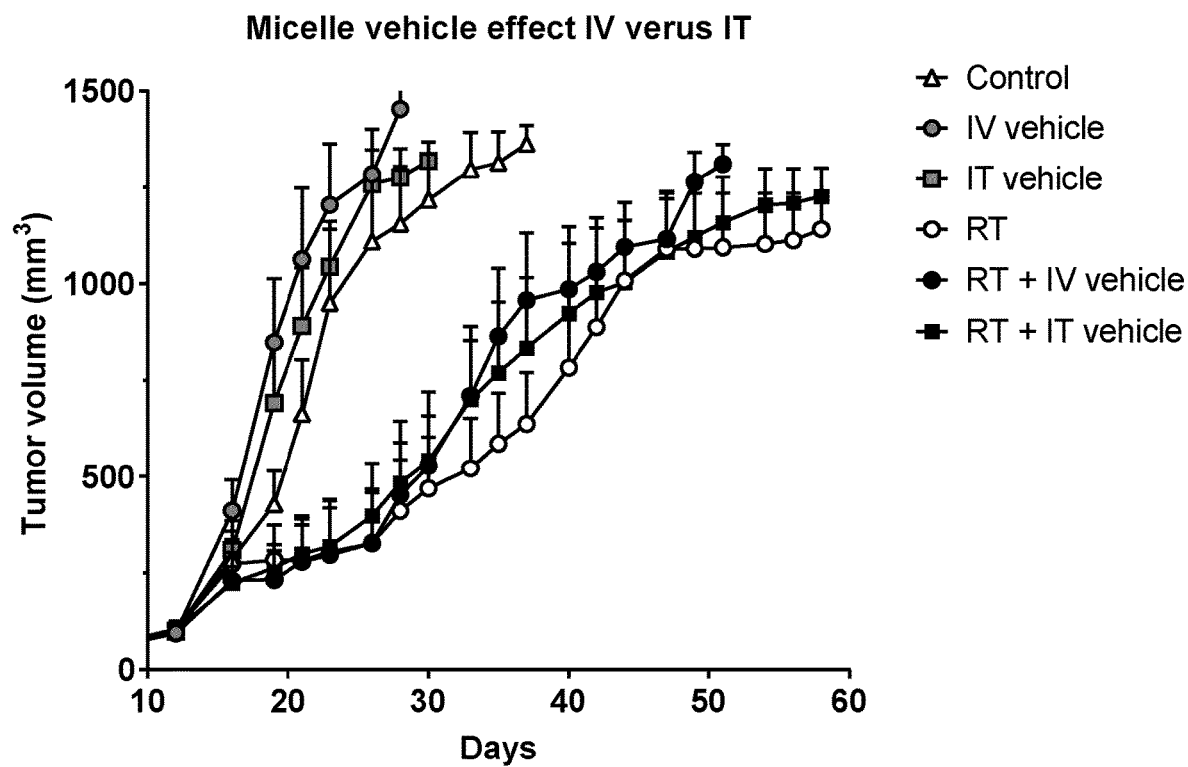
FIG. 10B: Tumor growth of mice treated with vehicle intratumorally or intravenously in combination with radiotherapy.
Figure 10C:
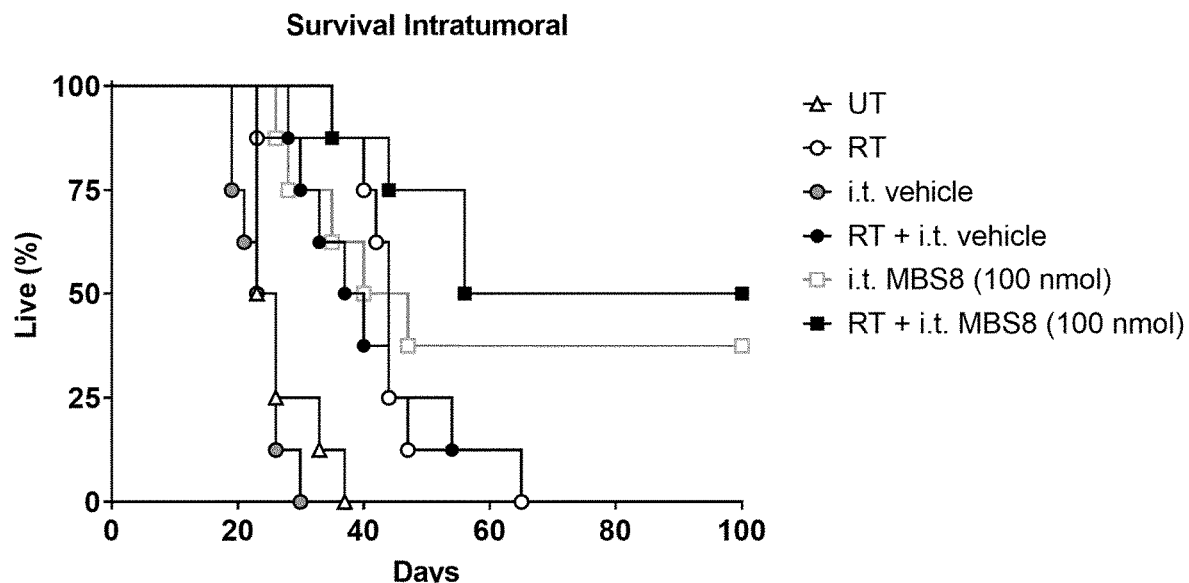
FIG. 10C: shows survival of mice treated treated with MBS8 by the intratumoral route either micelles without the TLR7 agonist (vehicle) or MBS8 with the TLR7 agonist 1V270. Groups are shown either with or without combination with radiotherapy.
Figure 10D:
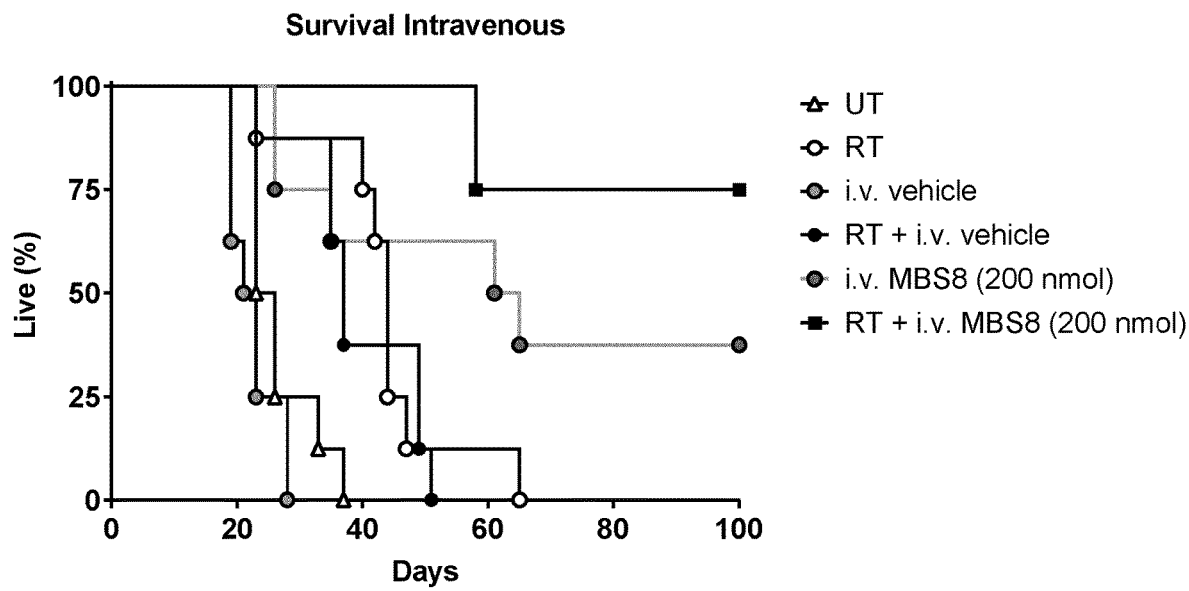
FIG. 10D: shows survival of mice treated treated with MBS8 by the intravenous route either micelles without the TLR7 agonist (vehicle) or MBS8 with the TLR7 agonist 1V270. Groups are shown either with or without combination with radiotherapy. The group treated with RT+ iv MBS8 showed significantly better anti-tumor activity than RT alone ($p=0.015$), whereas the group treated with RT+ it MBS8 did not show a significantly better anti-tumor activity than RT alone, n=8/group.

In contrast, vehicle injections did not improve tumor control (FIG. 10B). Radiotherapy alone or in combination with vehicle did not result in any complete responders. Survival of mice in the individual groups are shown for the intratumoral administration (FIG. 10C), and for the intravenous groups (FIG. 10D). Median survival days were for MBS8 treatment in monotherapy for IT administration 43.5 days versus 63 days for the IV administration. For MBS8 in combination with radiotherapy the median survival time was 56 days for the IT administration versus 100+ days for the IV administration, since 6 of 8 mice were in complete remission.

Conclusion

MBS8 micelles containing 1V270 provided good tumor control when injected either intravenously or intratumorally and showed synergistic effect with radiotherapy regardless of administration route.

Example 16: Antitumor Activity of MBS8 Micelles in Combination with Radiotherapy Mice bearing MC38, EL4, or B16-F10 tumors were treated with radiotherapy (RT) and MBS8 intravenously. 200 nmol MBS8 or lipid matched vehicle was given at q4d for a total of 5 treatments. For EL4 bearing mice, treatment was started on day 7 after inoculation, micelles were given as q4d, and radiotherapy was given as 2 Gy to the tumor-bearing flank on 3 consecutive days with 9-10 mice per group. For MC38 bearing mice, treatment was started on day 10 after inoculation and radiotherapy was given as 2 Gy to the tumor-bearing flank on 5 consecutive days with 9 mice per group. MC38 bearing complete responders were rechallenged with MC38 on the opposite flank on day 80 after primary challenge.

Figure 11A:
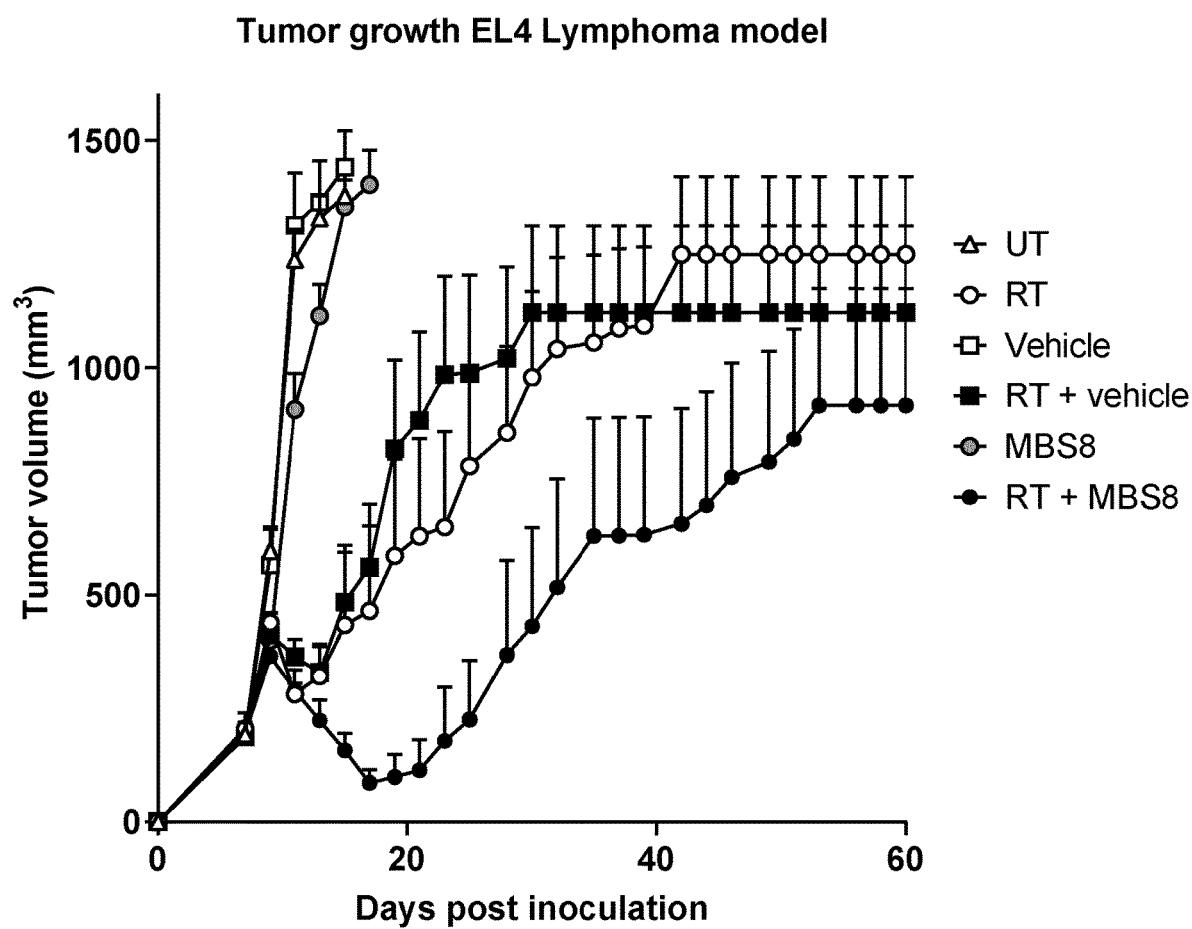
FIG. 11A: Tumor growth of treated EL4 bearing mice.
Figure 11B:
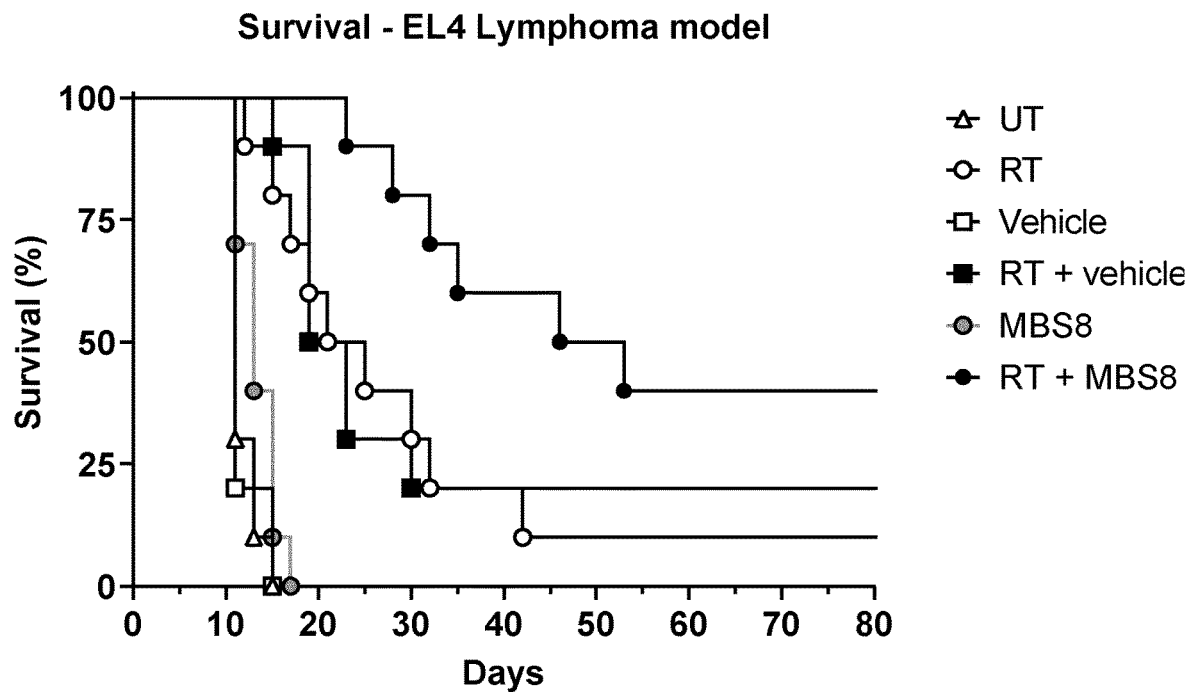
FIG. 11B: Survival of treated EL4 bearing mice.

MBS8 provided no tumor control in EL4 as monotherapy but in combination with RT resulted in 4/10 complete responders. RT alone only resulted in 1/9 complete responders and vehicle combined with RT resulted in 2/10 complete responders (FIG. 11A-B).

Figure 11C:
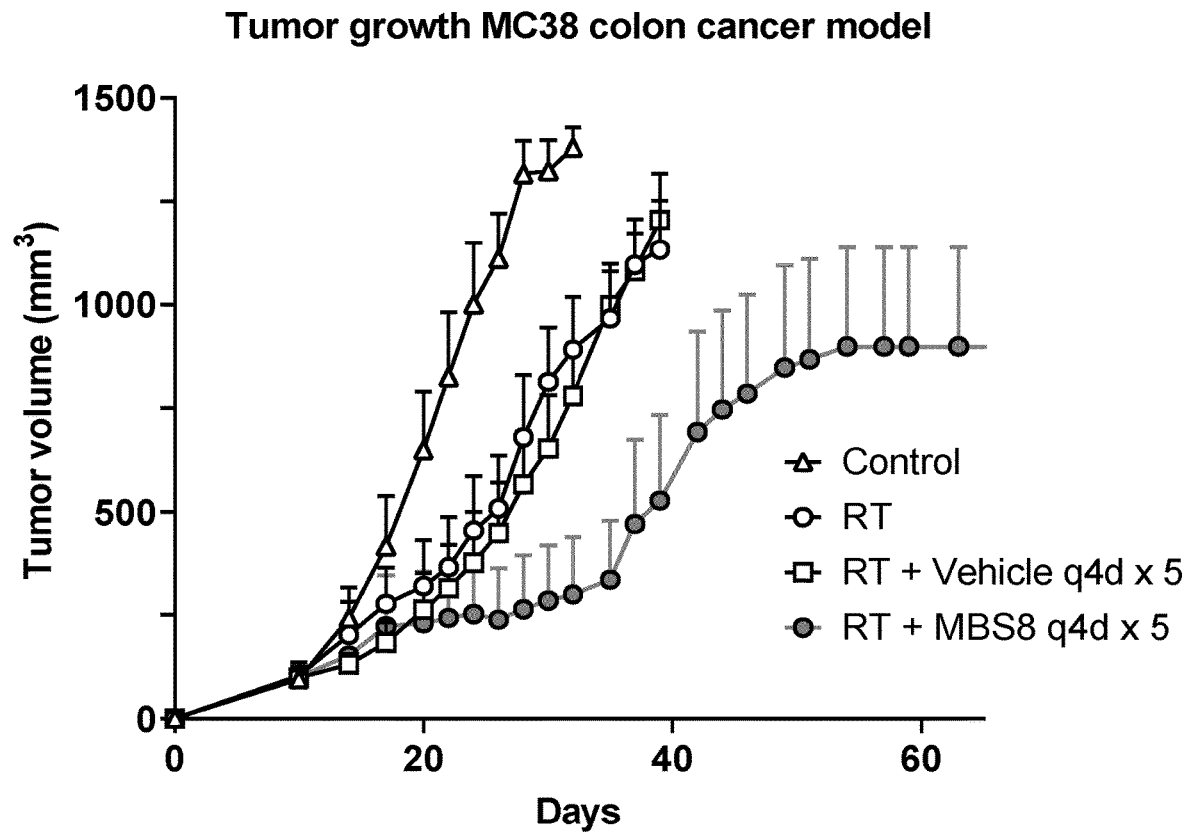
FIG. 11C: Tumor growth of treated MC38 bearing mice.
Figure 11D:
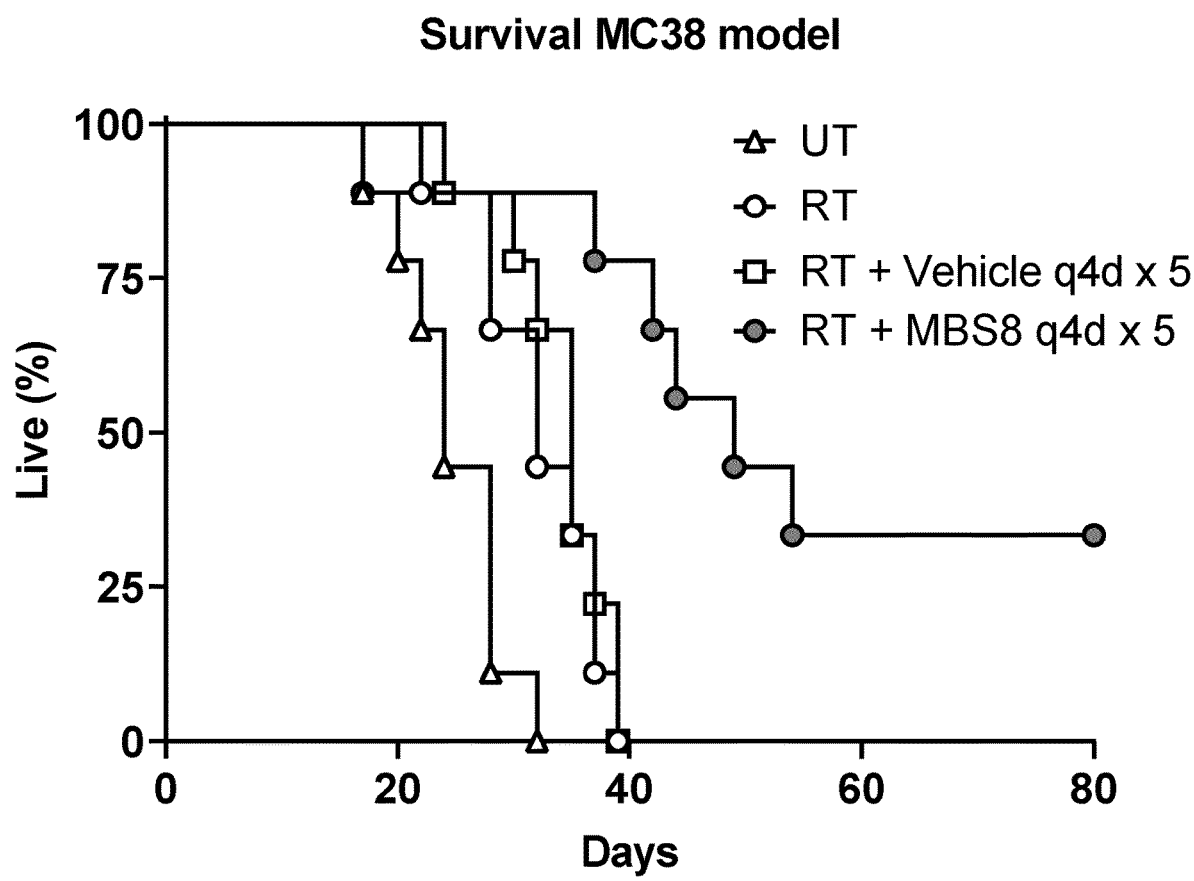
FIG. 11D: Survival of treated MC38 bearing mice.

MBS8 provided moderate tumor control in MC38 bearing mice when combined with radiotherapy. RT combined with MBS8 given q4d resulted in 3/9 complete responders of which 2/3 rejected rechallenge. (FIG. 11C-D).

Conclusion

In conclusion, MBS8 provides good tumor control in EL4 and MC38 when combined with RT.

Example 17: Tolerability of MBS8 Micelles in Monkeys

Tolerability of MBS8 micelles was assessed in cynomolgus monkeys (*Macaca fascicularis*). MBS8 was administered into three naive male monkeys, body weight ~3 kg, every 14 days with the following dose escalation scheme: 0.01 mg/kg→0.03 mg/kg→0.1 mg/kg→0.3 mg/kg→0.9 mg/kg→2.7 mg/kg. Administration of the drug was done by intravenous infusion of a total of 5 ml with the rate of 0.25 ml/min. During acclimation period, blood samples were taken at Day −14 and Day −7 as baseline controls and during treatment period at 2 h, 4 h, 8 h, 24 h, 72 h and Day 14. Hematology was analysed at 8 h, 24 h, 72 h and Day 14. Blood chemistry was analysed at Day 14 after each drug administration, i.e. immediately prior to the next dosing. C-reactive protein (CRP) was measured at 4 h, 8 h, 24 h, 72 h and Day 14 post-administration. Body temperature was monitored daily. Blood pressure was measured at 2 h, 4 h, 8 h after each drug administration and then daily until the next dose. Food consumption was checked daily and body weight—once a week.

Figure 12A:
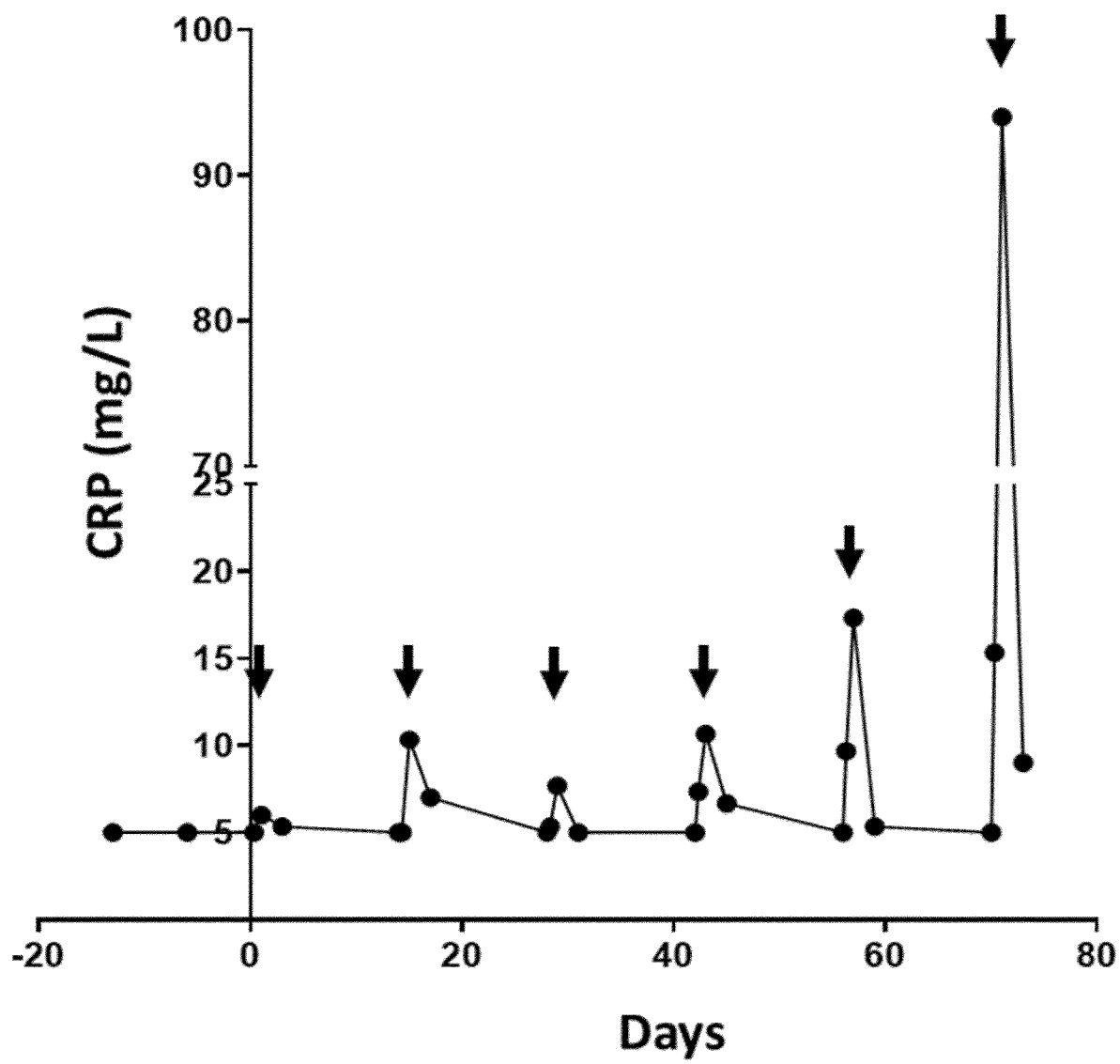
FIG. 12: MBS8 administration in cynomolgus monkeys. (A) C-reactive protein (CRP) was tested immediately before drug administration and at 8, 24 and 72 h post-infusion. Data represent mean values (n=3). The arrows indicate the peak of CRP at 24 h after each injection. Respective doses are as indicated in FIG. 12B. (B) Body temperature was monitored daily. Mean+SD values (n=3) are shown. Days of drug administration and respective doses are indicated. Dashed line indicates normal range based on the baseline measurements during acclimation period (Day −22-Day 0).
Figure 12B:
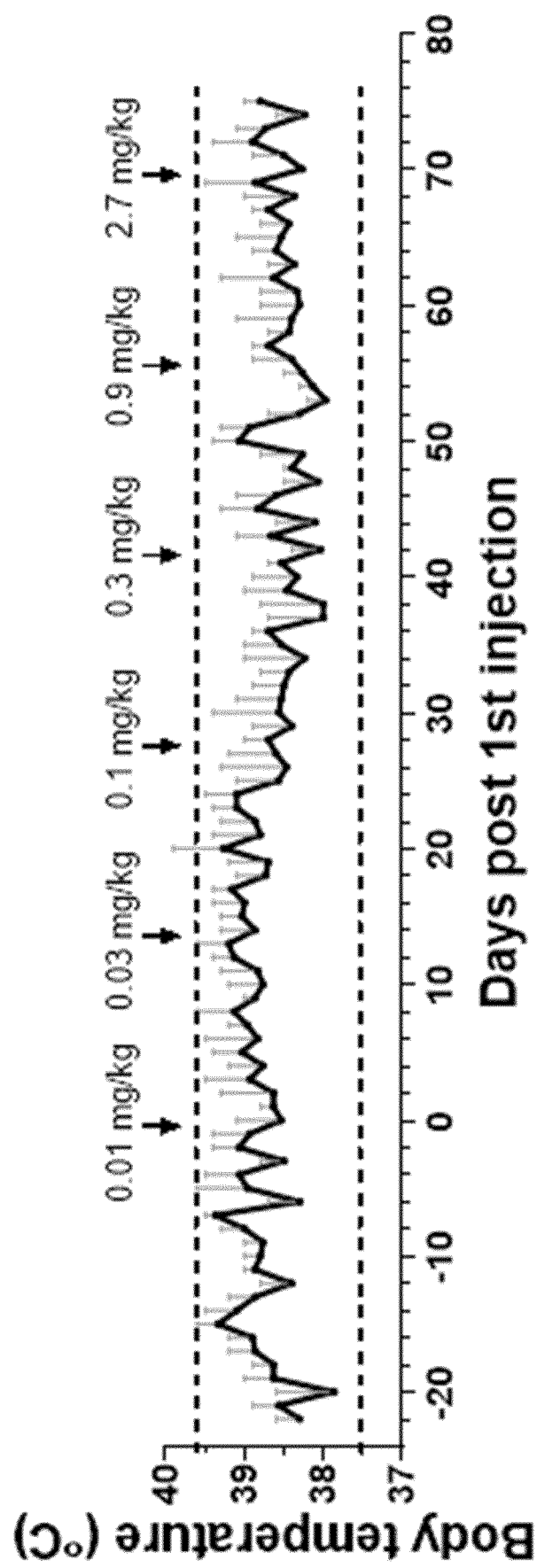

All doses were well tolerated. A transient dose-dependent increase in the CRP level was detected 24 h post-infusion, which returned to baseline level within 3 days (FIG. 12A). There were no significant changes in body temperature throughout the study (FIG. 12B). Based on the blood chemistry, there were no signs of liver toxicity or changes in electrolyte profile.

Conclusion

Intravenous infusion of MBS8 is well tolerated in cynomolgus monkey within the dose range of 0.01-2.7 mg/kg.

Example 18: Antitumor Activity of MBS8 Micelles and aPD-1 in Monotherapy and Combination Therapy in Multiple Syngeneic Tumor Models Efficacy of MBS8 as monotherapy or in combination with anti-PD1 monoclonal antibody (clone RMP1-14) was studies in a panel of 12 syngeneic mouse models (FIG. 13). Mice were inoculated s.c. with cancer cells; when average tumor size reached ~100 mm$^3$, the animals were randomised into 4 treatment groups of 10 animals each: Group 1, vehicle control (PBS); Group 2, anti-PD-1, 10 mg/kg; Group 3, MBS8, 300 microgram/mouse; Group 4, combination of MBS8 and anti-PD-1. Vehicle or MBS8 were administered by slow i.v. bolus, at a q4d schedule, 5 injections in total, starting at the day of randomization. Anti-PD-1 was administered i.p. starting two days after randomization, at a q4d schedule, 6 injections in total. Summary of results is shown in FIG. 13A. TGI %, tumor growth inhibition, was calculated as: TGI (%)=100×(1−T/C), where T and C are the mean tumor volumes of treated and control groups, respectively, on a day when the control group was terminated.

Figure 13B:
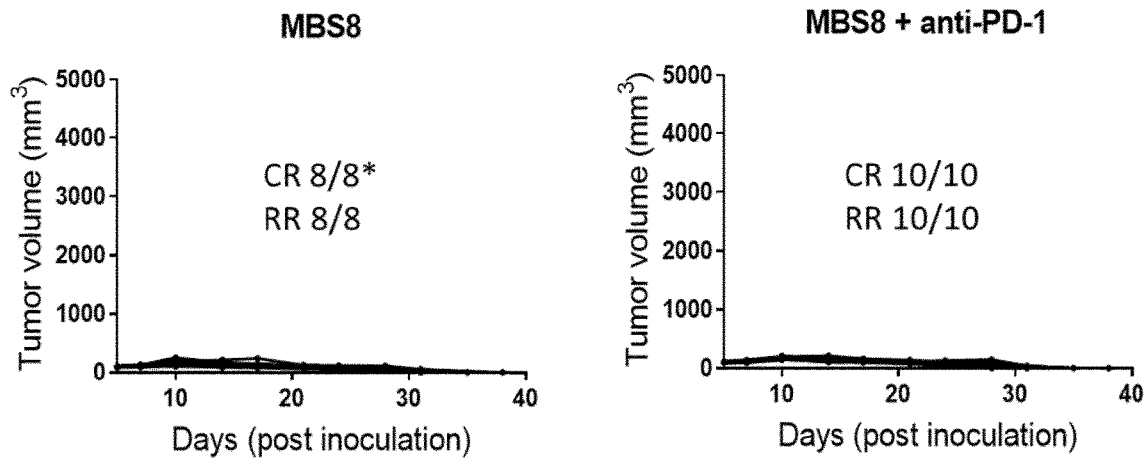
FIG. 13 In vivo efficacy studies using 12 syngeneic subcutaneous tumor models. (A) Table summarising results for all 12 models. Mice were randomized when average tumor size reached ~100 mm$^3$ and treated with the indicated remedies. αPD-1 (clone RMP1-14) was administered at 10 mg/kg i.p. six times at q4d, and MBS8 was dosed at 300 μg/mouse i.v., five times at q4d. The same dosing regimens were used for the combination studies. All groups included 10 mice/group. TGI, tumor growth inhibition; CR, complete responders; NA, not applicable. (B-D) Effect of MBS8 on the growth of subcutaneous tumors. Top panels: tumor growth curves in the indicated groups of animals. Mean tumor volumes+SEM are shown. Significant two-sided p-values are shown (Wilcoxon rank sum test). Middle and lower panels: tumor growth curves of individual animals in the indicated treatment groups are shown. (B) EMT-6, (C) Hepa 1-6 and (D) Pan02 are representative of three different response patterns found in the 12 tumor panel. CR, complete responders; RR, re-challenge resistant; *two animals died at the beginning of treatment and were excluded from statistical analysis. (E) Rejection of re-challenged EMT-6 tumors. Mice which showed CR to MBS8 (n=8) or MBS8+anti-PD-1 (n=10) treatment in the EMT-6 model and were tumor-free for at least three weeks were re-challenged on the contralateral flank with EMT-6 cells and were monitored for tumor growth 29 days. Naïve mice (n=5) innoculated with EMT-6 cells were used as untreated control. (F) Immune memory response in mice treated with MBS8 alone or in combination with a-PD-1. CR from the CT26 model were re-challenged and all demonstrated rejection of re-challenged tumors. In these animals, the presence of tumor specific T-cells was assessed using ELISPOT. Analysis was performed on splenocytes from untreated CT26 tumor bearing mice (control), mice previously treated with MBS8 and resistant to re-challenge (mono), mice treated with MBS8+a-PD-1 combo (combo) and naïve tumor-free mice (naïve) stimulated (+AH-1) or not with a CT26 tumor specific antigen AH-1 in vitro. Number of IFN-γ expressing cells per well was quantified. Means+SEM are shown; n=5 mice/group. Statistical analysis was performed using Wilcoxon rank sum test. Significant two-sided p-values are shown.
Figure 13C:
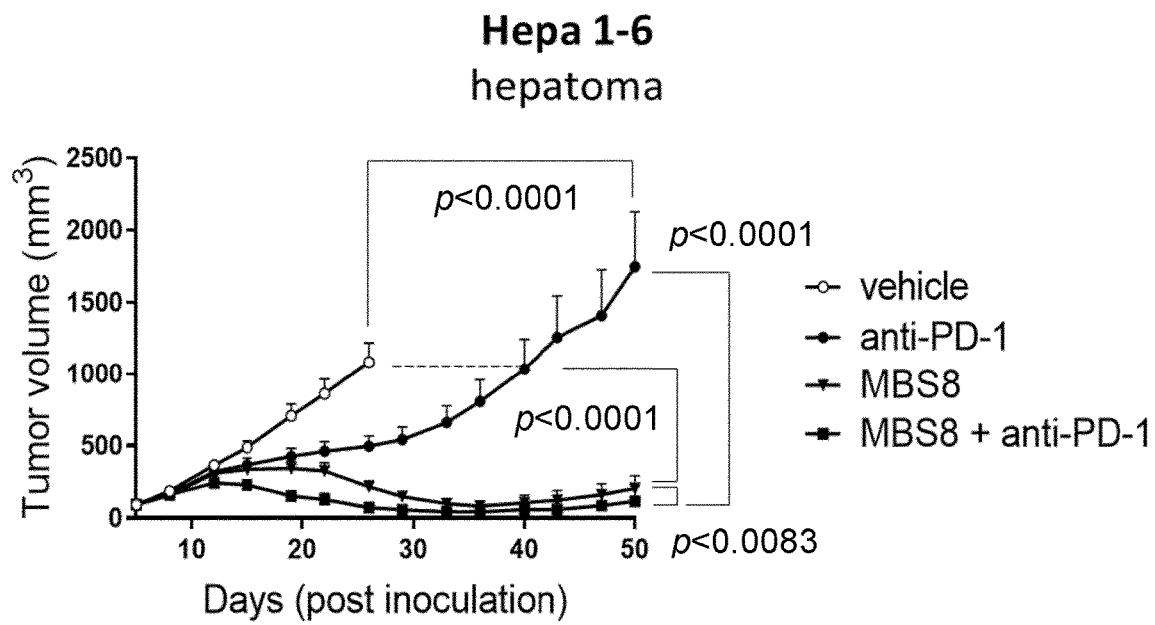
Figure 13C:
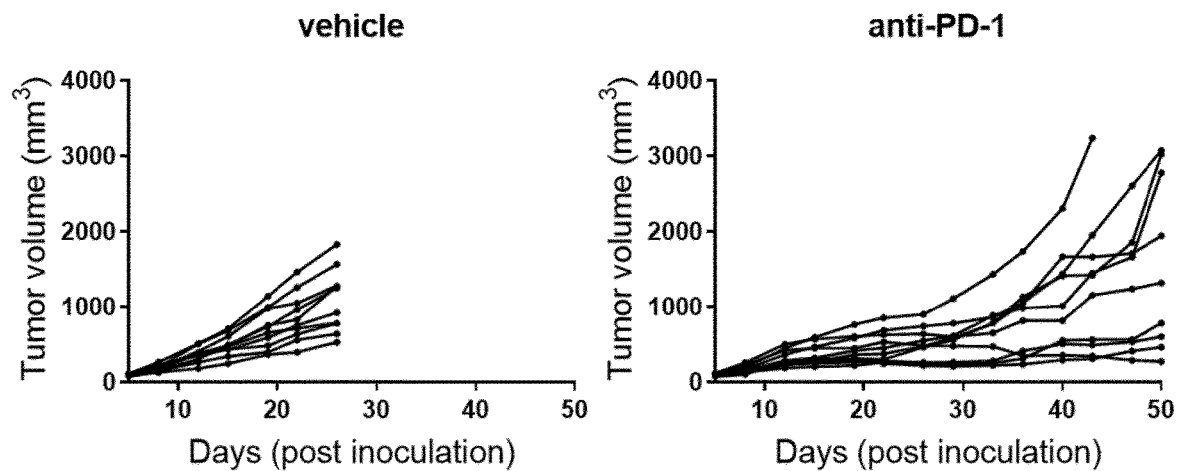
Figure 13C:
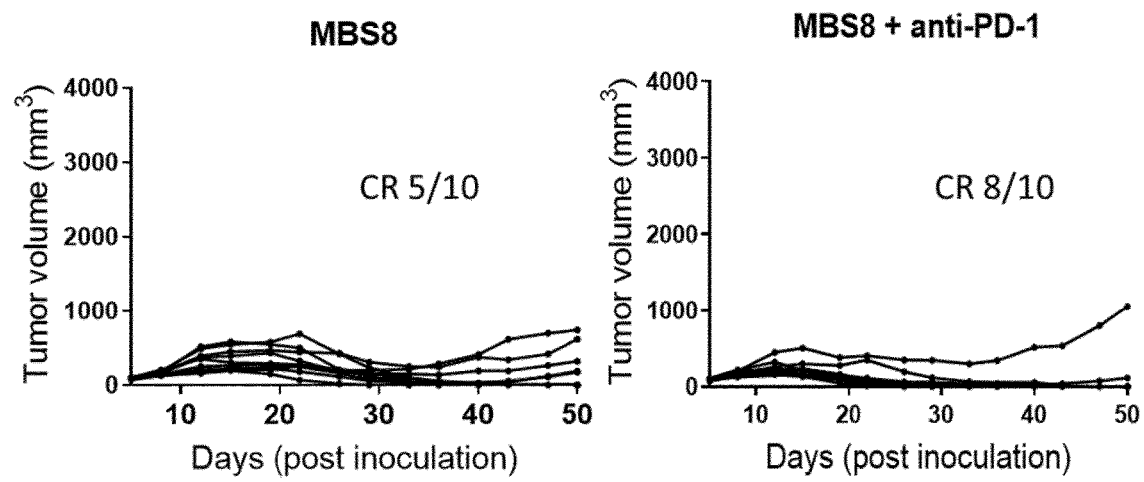
Figure 13D:
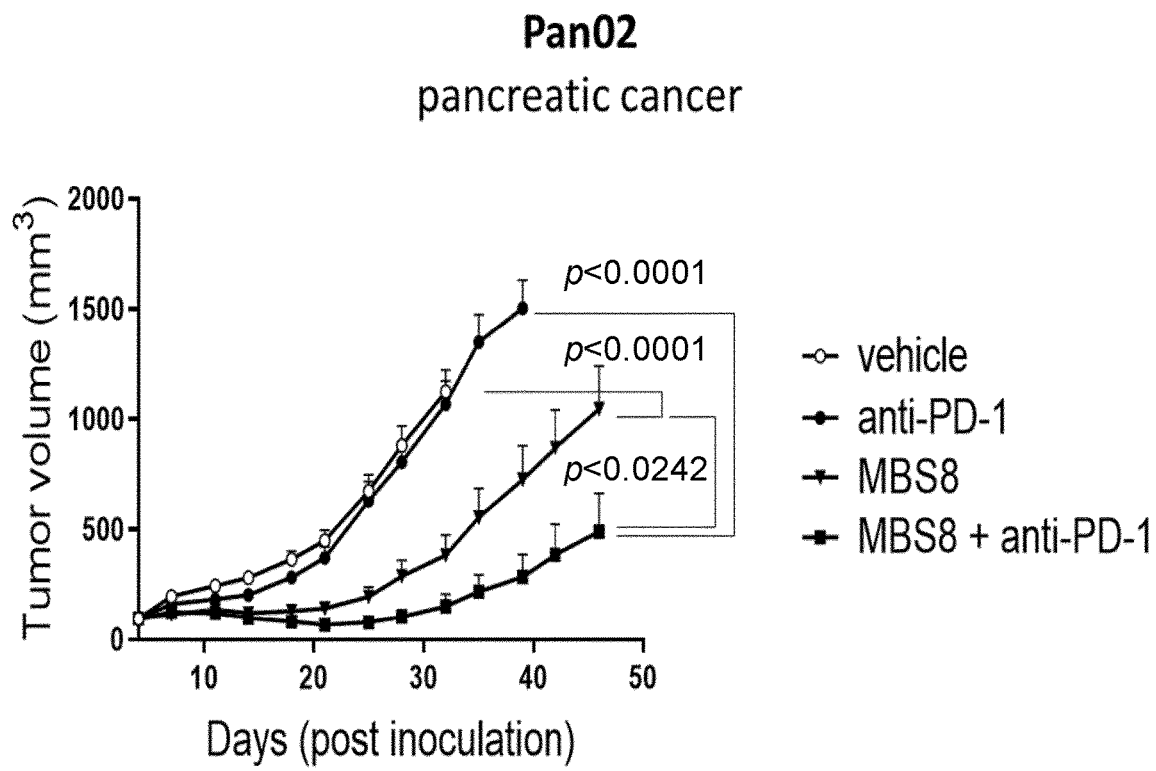
Figure 13D:
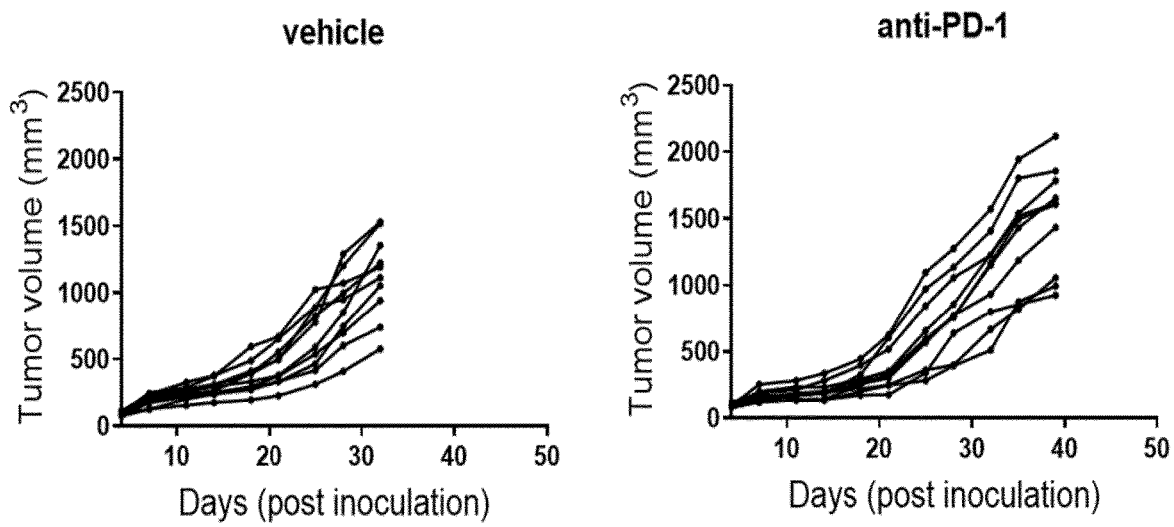
Figure 13D:
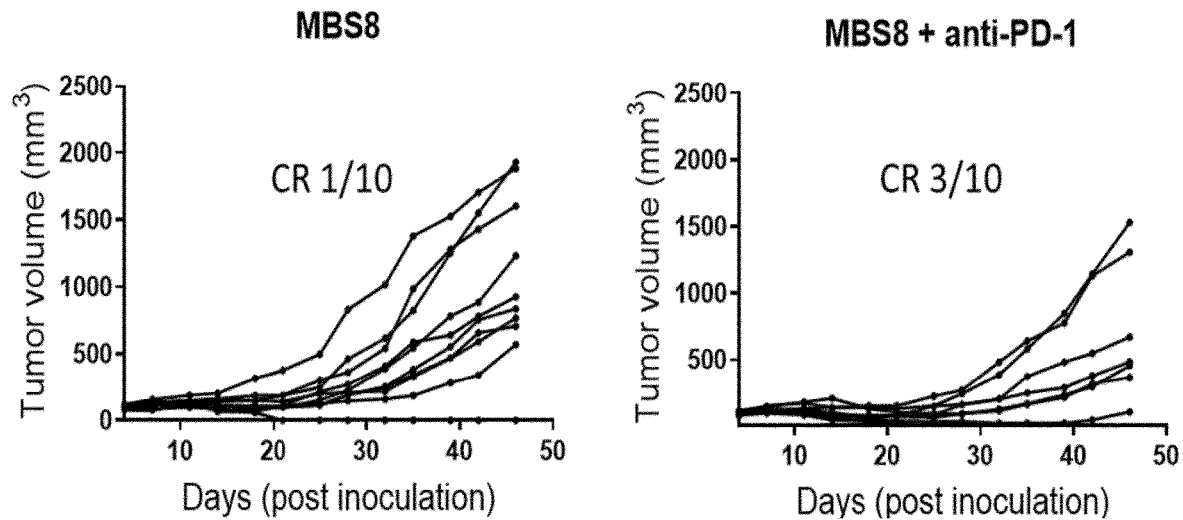

Three different patterns of response were observed:
(1) MBS8 was very potent in monotherapy and hence the benefit of combination with anti-PD-1 cannot be noted due to too strong MBS8 activity (FIG. 13B). The tumors falling into this category were: CT-26 (colon cancer), EMT-6 (breast cancer), A20 (B-cell lymphoma) and H22 (hepatoma).
(2) Both anti-PD-1 and MBS8 showed therapeutic activity in monotherapy. Combo therapy showed an additive benefit (FIG. 13C). This was observed for Hepa1-6 (hepatoma) and M38 (colon cancer).
(3) Anti-PD-1 was inactive in monotherapy while MBS8 monotherapy showed efficacy. Combination of the two drugs resulted in synergistic activity by turning PD-1 non-responsive mice into responsive (FIG. 13D). In this category were RM-1 (prostate cancer), Pan02 (Pancreatic cancer) and Renca (kidney cancer).

Figure 13E:
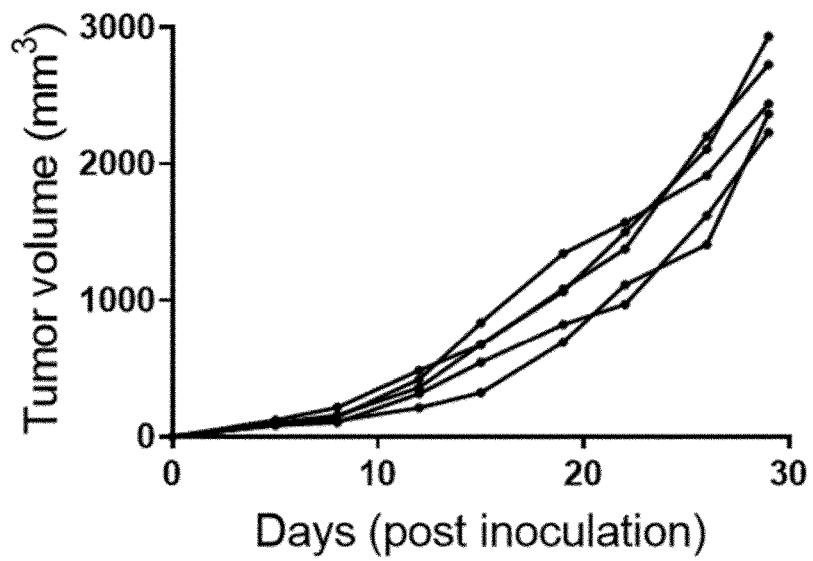
Figure 13E:
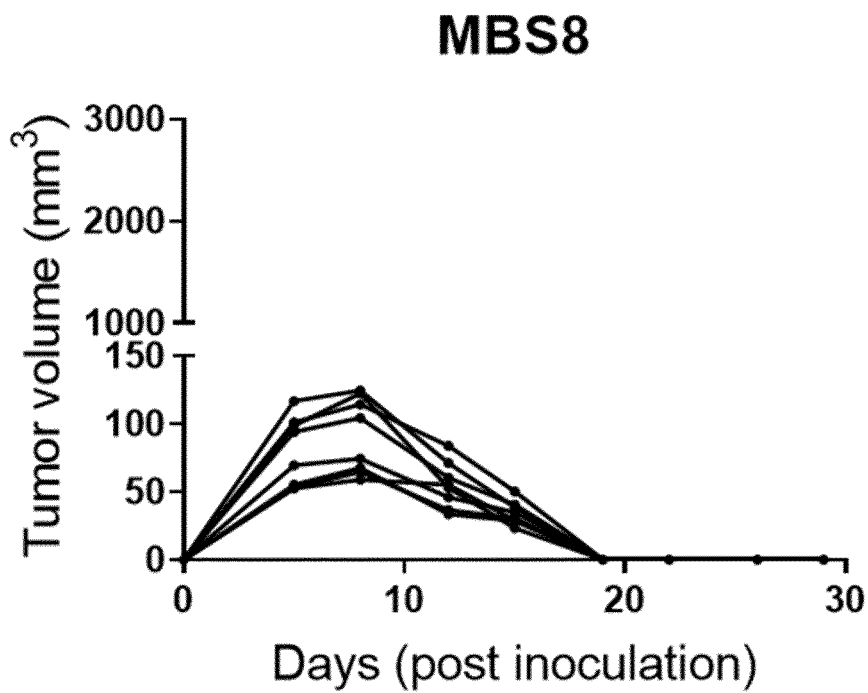
Figure 13E:
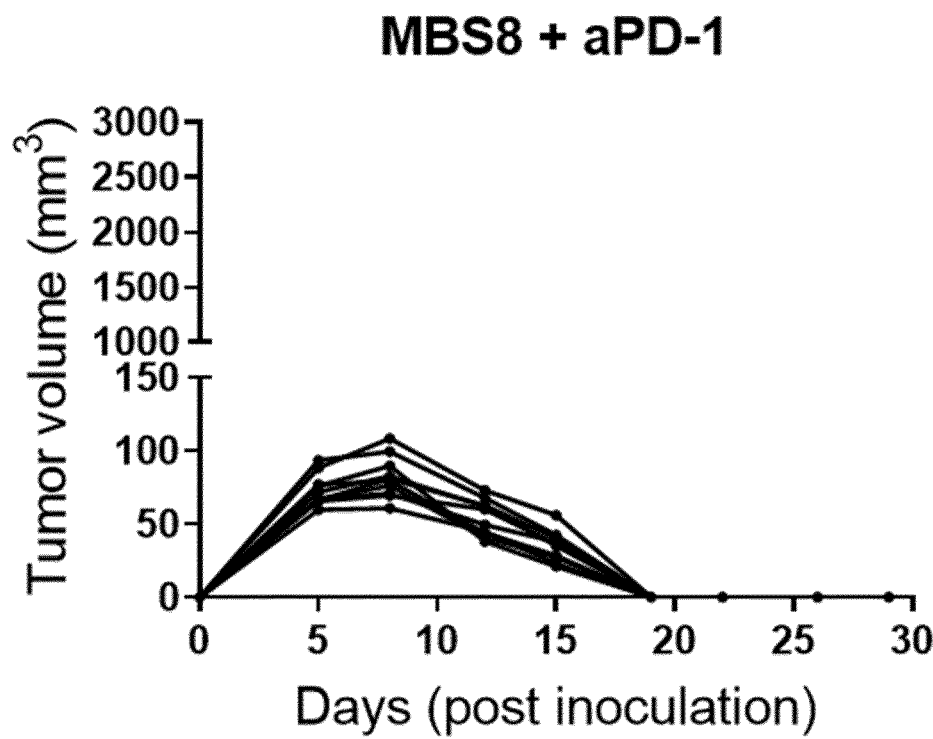
Figure 13F:
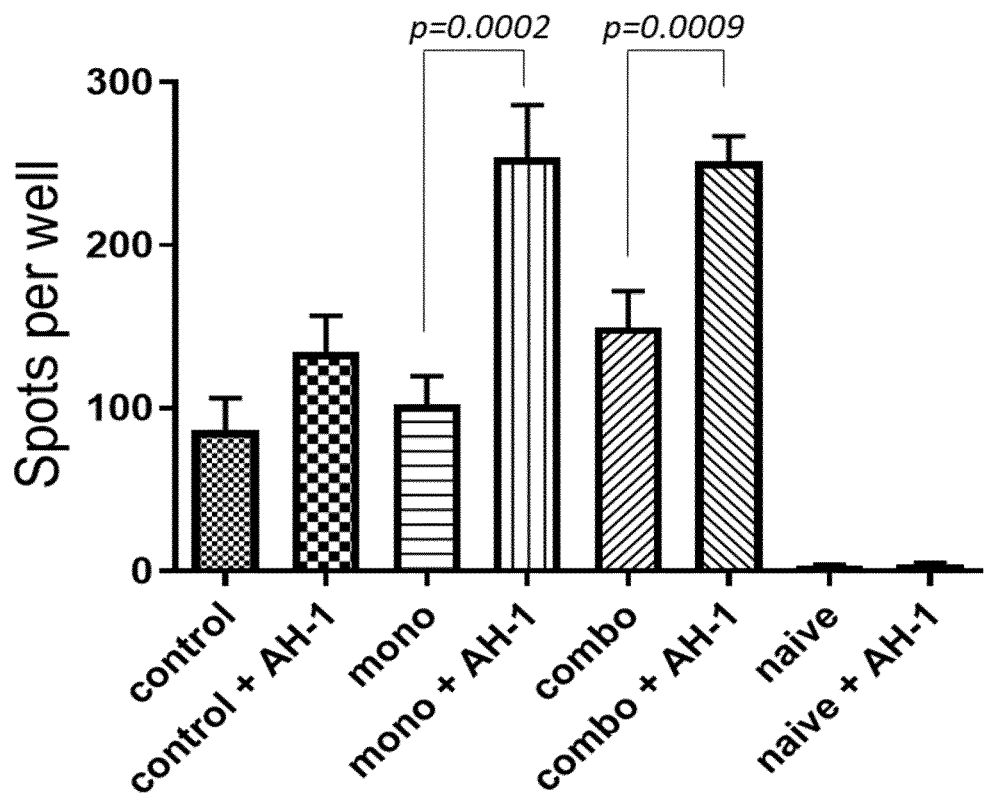
Figure 14A:
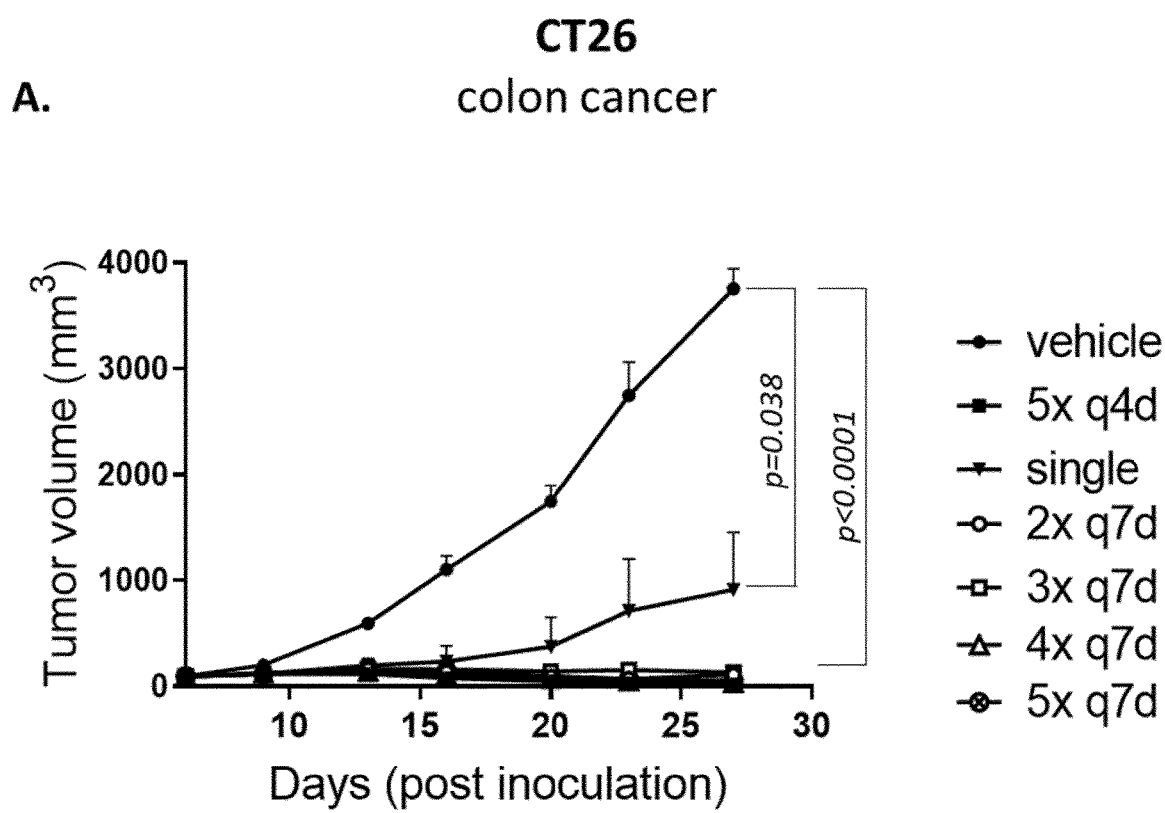
FIG. 14 Comparative efficacy of MBS8 administered at different dose schedules. The CT26 subcutaneous model was used. Mice were randomized when average tumor size reached ~100 mm$^3$ and treated with 200 nmol/mouse i.v. at the indicated dose schedules. (A) Mean tumor volumes+SEM are shown. Significant two-sided p-values are shown (two-tailed Wicoxon rank sum test). (B) Tumor growth curves of individual animals. Animals which tumors at the last measurement were <40 mm$^3$ and showed continuous volume reduction are considered as complete responders (CR).
Figure 14B:
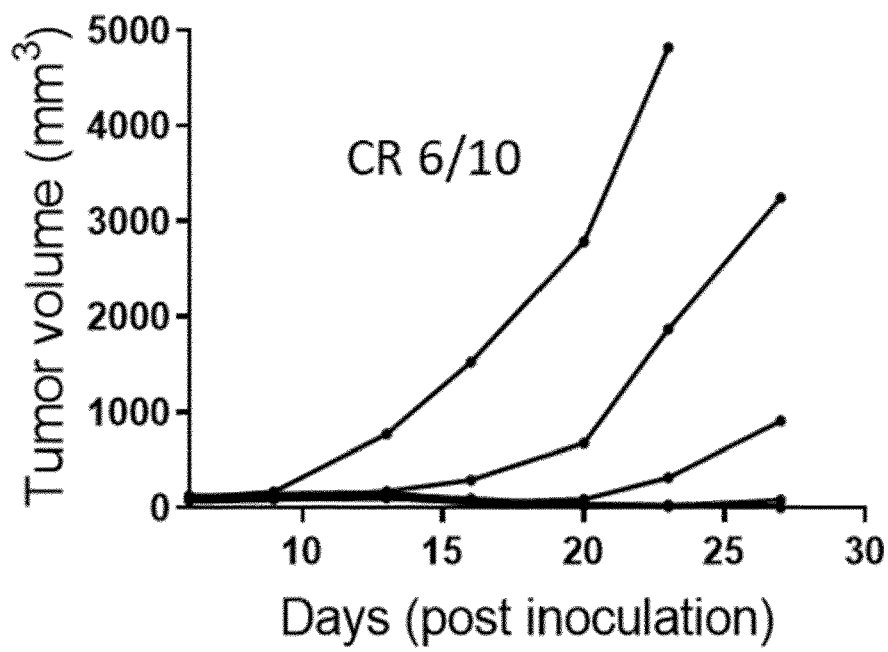
Figure 14B:
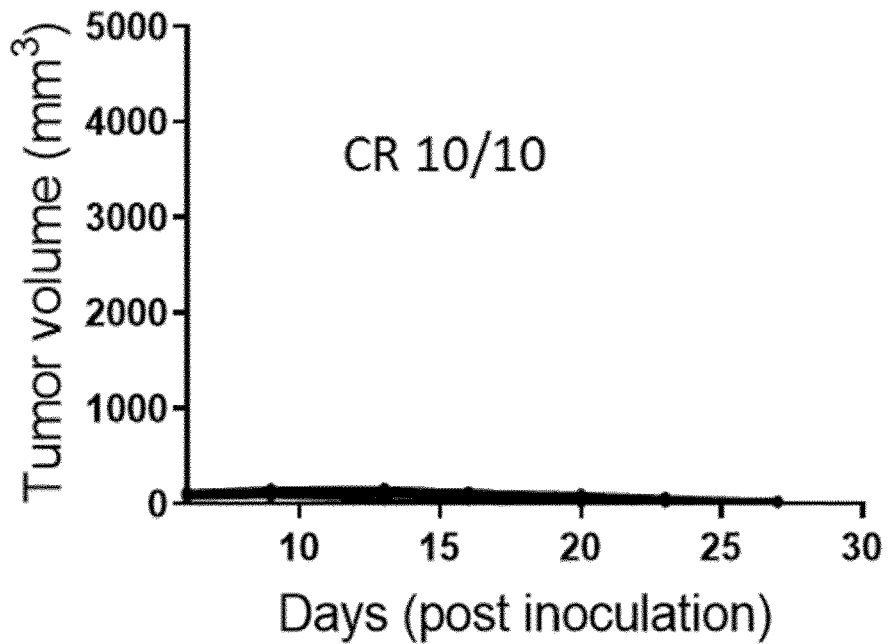
Figure 14B:
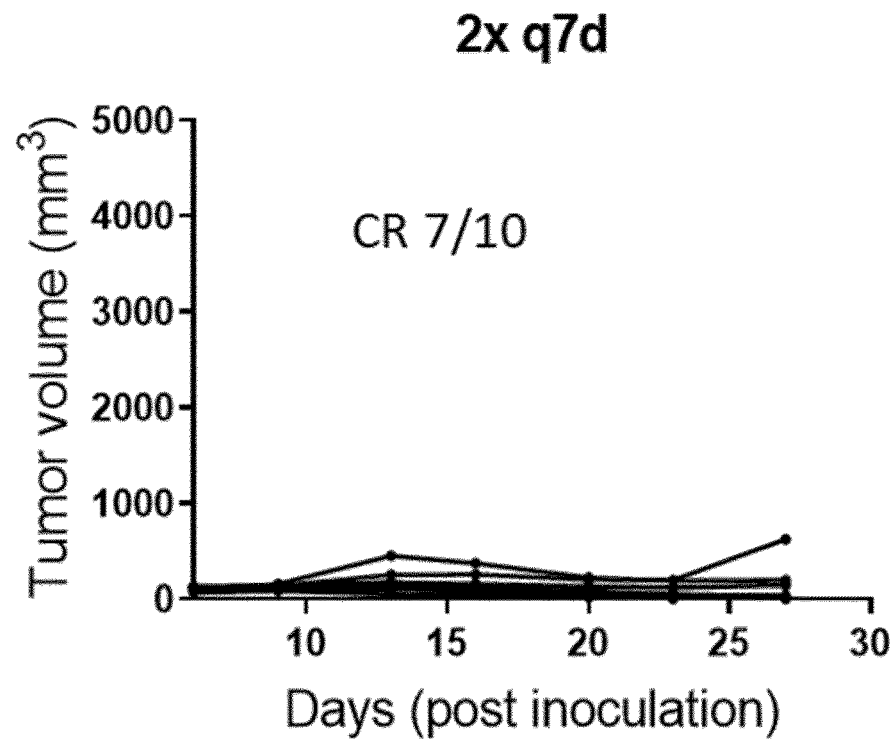
Figure 14B:
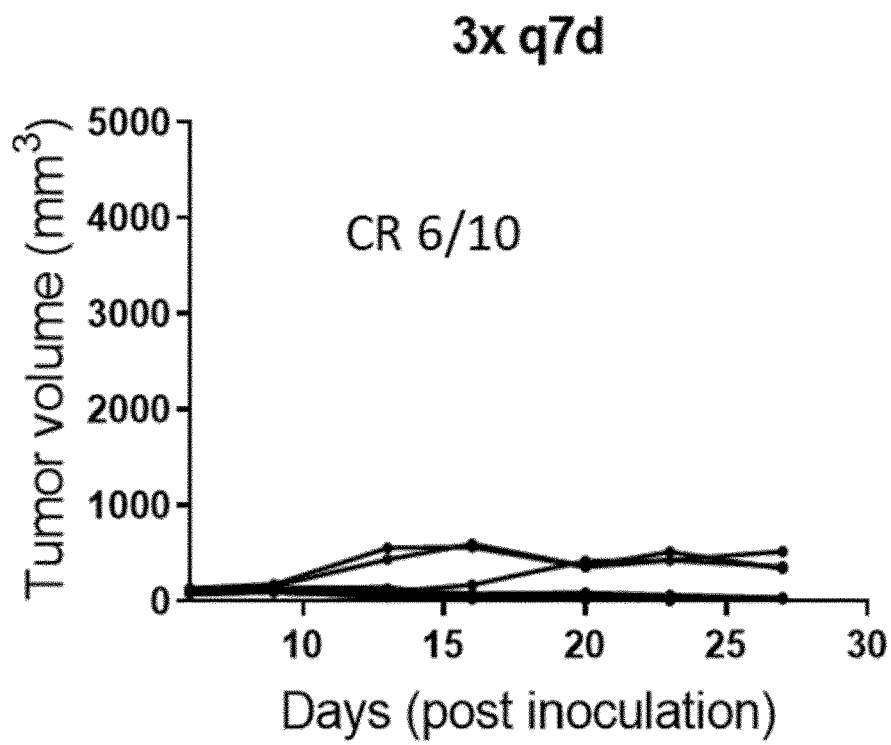
Figure 14B:
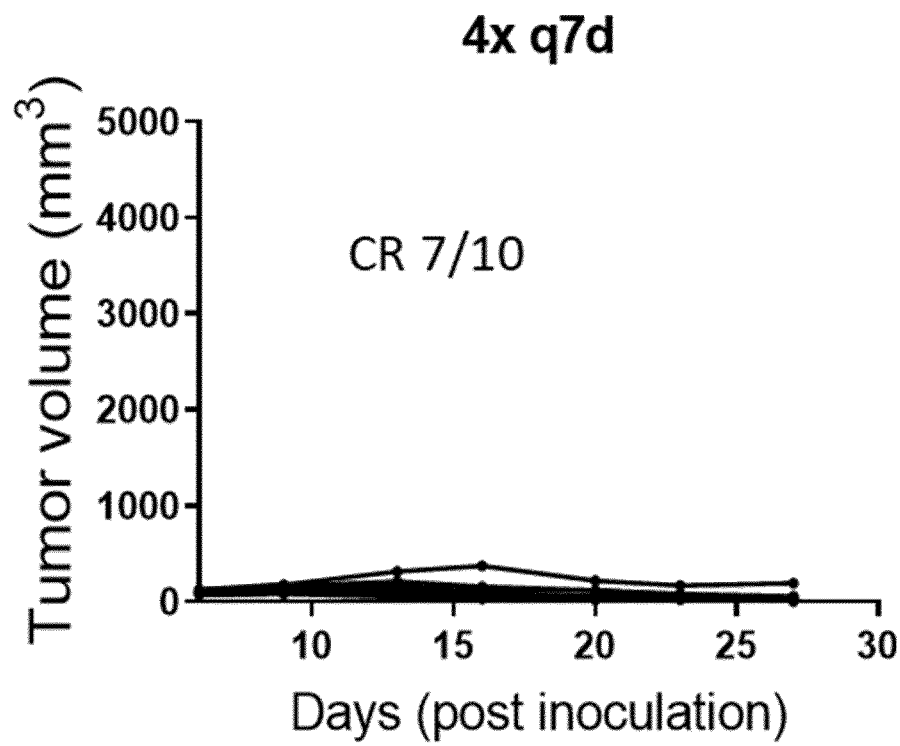
Figure 14B:
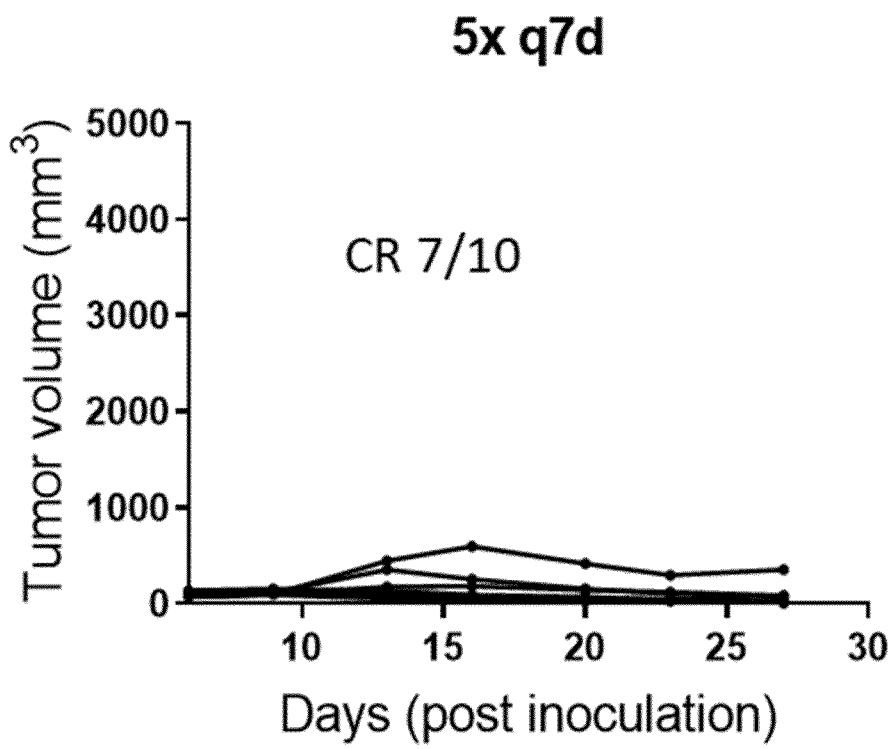

For the EMT-6 model, re-challenge of complete responders from Group 3 and 4, which were tumor-free for at least three weeks, was done with EMT-6 cells injected s.c. on the contralateral flank. The mice were followed for 29 days. All re-challenged animals showed complete rejection of re-challenged tumors (FIG. 13E). In CT26 model, mice which showed complete response to MBS8 or combination of MBS8 with anti-PD-1 therapy and who rejected re-challenged tumors were analysed for the presence of tumor-specific T-cells (FIG. 13F, Elispot graph). Splenocytes from untreated mice bearing CT26 tumors, from mice treated with either MBS8 or MBS8 and anti-PD-1 or naïve tumor-free mice were stimulated in vitro with an AH-1 tumor specific antigen peptide. IFNγ producing cells were quantified using ELISPOT. All mice which rejected re-challenged tumors demonstrated increased numbers of IFNγ positive cells in response to antigen stimulation thus confirming establishment of the immune memory response.

Conclusion:

MBS8 showed therapeutic efficacy in monotherapy. In some tumors, which are weakly responsive to anti-PD-1, combination treatment with MBS8 had an additive effect. In models which were unresponsive to anti-PD-1 treatment, but responsive to MBS8, the latter sensitised tumors to anti-PD-1 and the drugs showed a strong synergistic effect. MBS8 in either monotherapy or combination treatment with anti-PD-1 led to establishment of the immune memory response.

Example 19: Dose Schedule Optimization of MBS8 and Correlation to Anti-Tumor Activity in the CT26 Model That CT26 colon cancer syngeneic mouse model was used to analyze the influence of dose schedule on the efficacy of MBS8 monotherapy. Mice with established tumors were treated with 200 nmol/mouse MBS8 at (1) single injection; (2) two injections at q7d; (3) three injections at q7d; (4) four injections at q7d and (5) five injections at q7d (FIG. 14). As control, vehicle (PBS) treatment was used as well as MBS8 treatment administered in five injections q4d, the schedule which showed good efficacy in previous studies.

Already single injection showed significant inhibition of tumor growth, while multiple weekly administration led to a complete eradication of tumors.

Conclusion:

Only one single injection of MBS8 leads to a significant anti-tumor activity, while additional injections with either 4 or 7 days schedule leads to multiple mice in complete remission

Figure 15A:
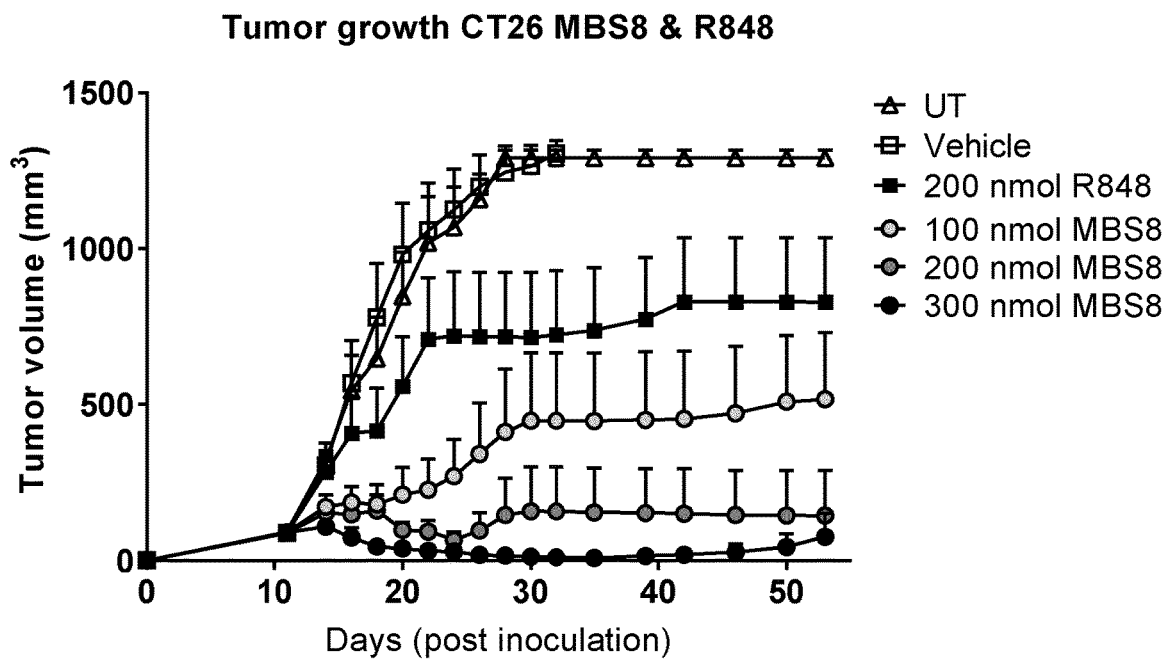
FIG. 15: MBS8 and R848 treatment of mice bearing subcutaneous CT26 tumors. CT26 tumor bearing mice started treatment on day 11 after inoculation and were treated intravenously with MBS8 (100, 200 or 300 nmol) or R848 (200 nmol) in a q4d schedule for a total of 5 treatments. n=9 mice/group. (A) Mean tumor growth curves ±SEM are displayed. (B) Survival of treated CT26 bearing mice. Statistical significance on survival was determined using Mantel-Cox test, ****p<0.0001, *p<0.05 (C) Weight change to baseline, mean weight±SEM is displayed.
Figure 15B:
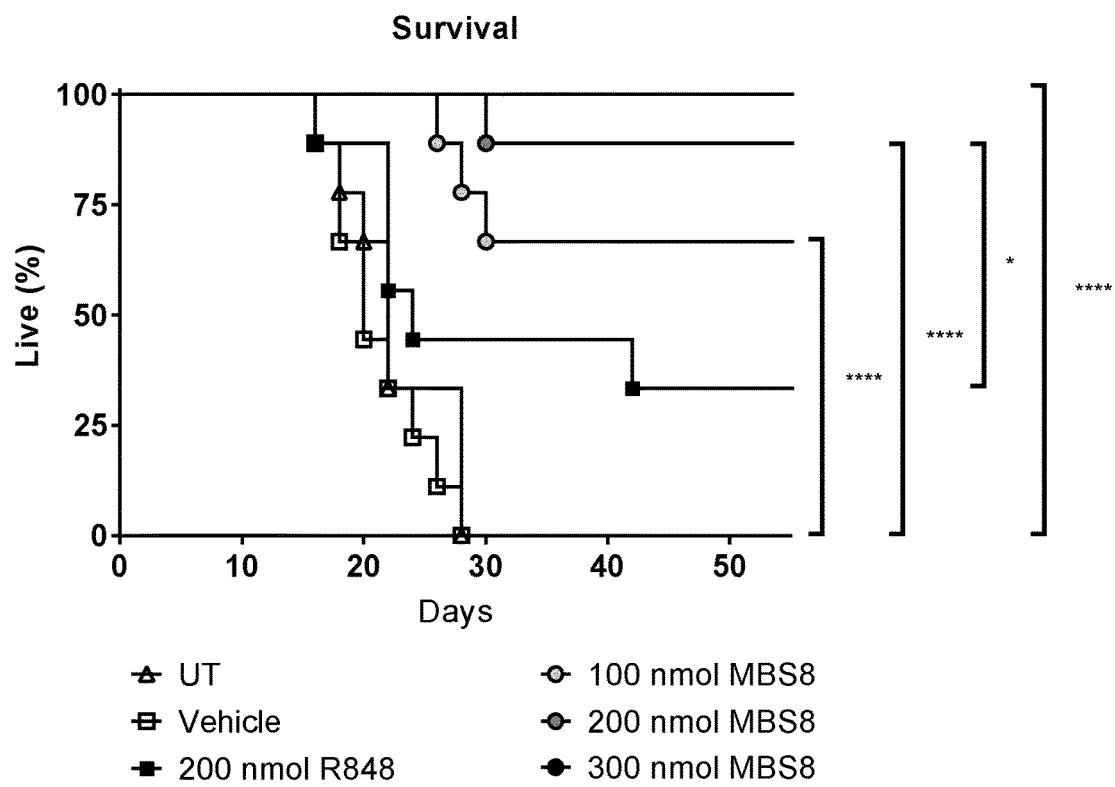
Figure 15C:
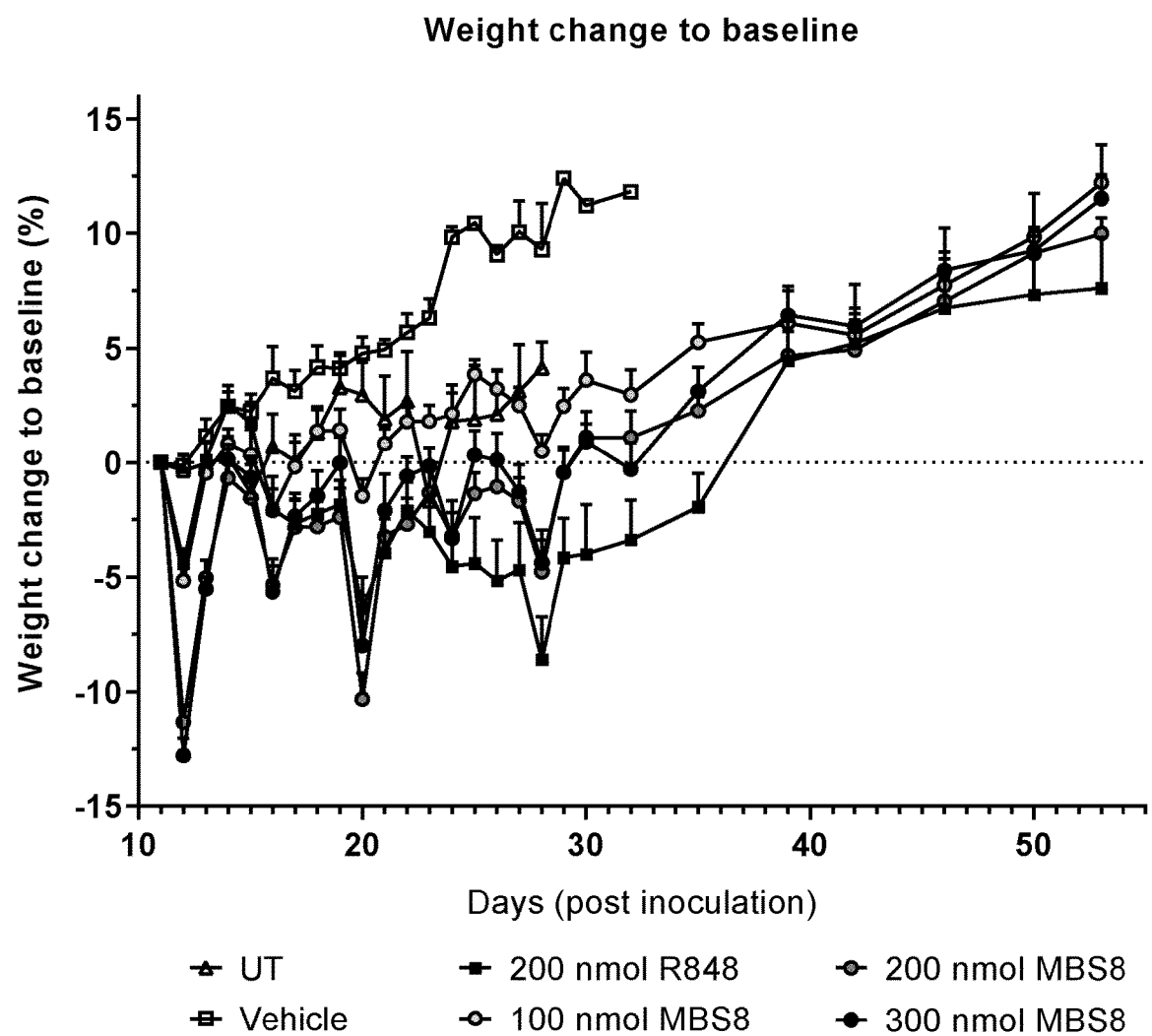

Example 20: Antitumor Activity of MBS8 Micelles in Comparison to R848 Monotherapy Efficacy of MBS8 micelles and R848 was studied as monotherapy in the CT26 syngeneic subcutaneous colon cancer model. Randomisation of mice and treatment started when tumors reached an average volume of 85 mm³ (Day 11). Groups of 9 mice each were treated with vehicle control (MBS0); MBS8 at 100, 200 or 300 nmol/mouse/injection by intravenous bolus or with R848 at 200 nmol/mouse/injection. Treatments were given q4d, total of 5 injections starting on day 11 (day 11, 15, 19, 23 and 27). Growth of tumors was measured twice a week. Mean tumor volumes of treated mice are shown in FIG. 15A, while a survival curve is shown in FIG. 15B. Statistical analysis using a Wilcoxon rank sum test revealed a significant difference between all doses of MBS8 compared to vehicle (p<0.0001). Furthermore, MBS8 at 200 nmol was significantly more efficacious than 200 nmol R848 (p<0.05). Weight change to baseline is shown in FIG. 15C. For the MBS8 micelles weight loss change becomes less severe with more treatments whereas R848 induced the most severe weight loss change from day 25 to day 40.

Conclusion

MBS8 micelles show a better anti-tumor effect than R848 when given in equimolar doses. Due to enhanced therapeutic activity and less severe weight loss, the MBS8 micelles have increased the therapeutic index compared to R848 of a TLR7 agonist.

Example 21: Tumor Gene-Expression Analysis with Nanostring of MBS8 Treated CT26 Tumor Bearing Mice The gene expression profile of CT26 tumors from mice treated with MBS8 as monotherapy was made to determine MBS8 treatment associated gene expression and presence of specific tumor cell types. Gene expression was evaluated with the Pan Cancer Immune Panel (Nanostring) performed on bulk RNA extracted from tumors. Mice were randomized on day 12 into groups of 10 and treated with MBS8 at 200 nmol/mouse/injection by intravenous bolus given in a q4d schedule for a total of 1 or 3 injections. Mice were sacrificed and the tumor snap frozen at days: day 0 (untreated), $1^{st}$ day post $1^{st}$ injection, 2 days post $1^{st}$ injection, 4 days post $1^{st}$ injection, 14 days post $1^{st}$ injection, 2 days post $3^{rd}$ injection, 4 days post $3^{rd}$ injection, n=3-6 for all groups. RNA was extracted and 750 genes were analyzed with the Pan Cancer Immune Panel. A cell type analysis was performed with the advanced analysis module of the Nanostring software. Two-way ANOVA with multiple comparison correction was performed to compare the different time points to untreated. At the early time points (1, 2 and 4 days post $1^{st}$ injection) a significant increase in both neutrophils and dendritic cells is seen demonstrating activation of the innate immune system. At later time points (4 days after 1st injection and later) T cells and especially CD8 T cells are increased in the tumor demonstrating activation of the adaptive immune system. Furthermore, macrophages are also upregulated at the later time points. The time point 14 days post $1^{st}$ injection have a cell type profile resembling UT, indicating that one injection in this setup is not enough to induce lasting immune response.

Conclusion

The gene expression profiling of tumors from mice treated with MBS8 monotherapy show induction of the innate immune response at early time points with presence of high number of neutrophils and dendritic cells. An adaptive immune response is seen at later time points dominated by T-cells, which all-together mediate the anti-tumor effect of the MBS8 treatment.

Figure 17A:
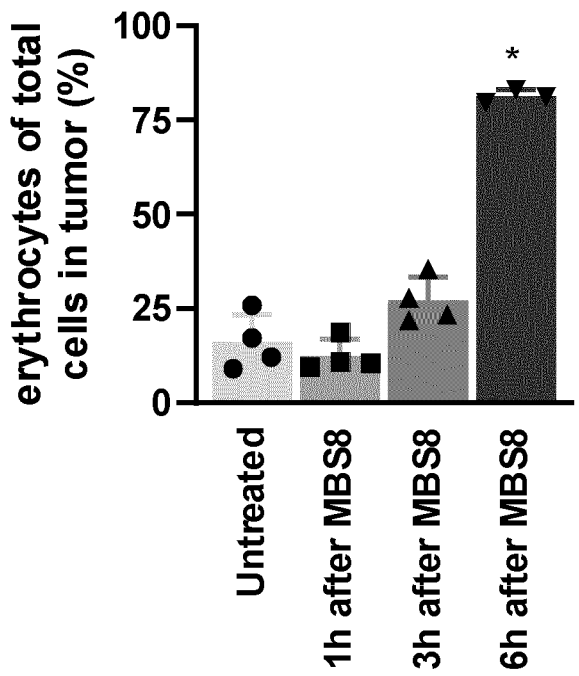
FIG. 17: Effects on the tumor microenvironment shortly after injection of MBS8 based on flow cytometric analysis. CT26-bearing mice were injected with 200 nmol MBS8 and tumors evaluated by flow cytometry. Tumors were collected 1, 3 and 6 hours post injection. All graphs are displayed as mean±SEM. Statistical significance compared to untreated tumors was determined using Kruskal-Wallis test with Dunn's multiple comparisons tests where * indicates p<0.05;  indicates p<0.01; and * indicates p<0.001. n=3-4. MFI=Median fluorescent intensity.
Figure 17B:
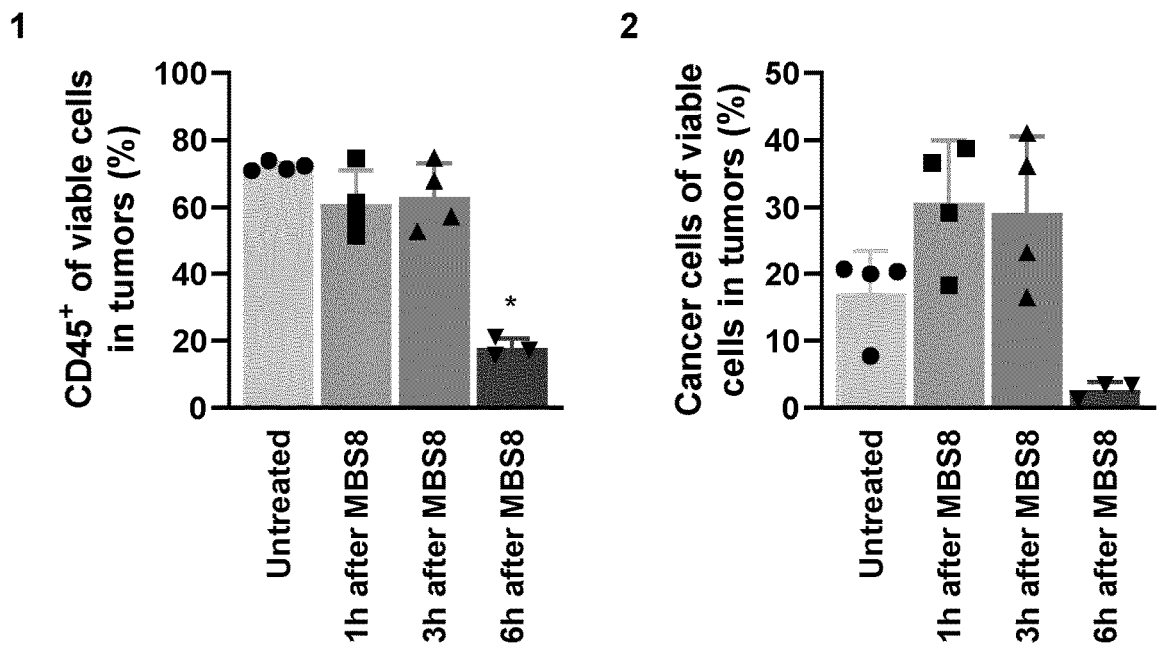
Figure 17C:
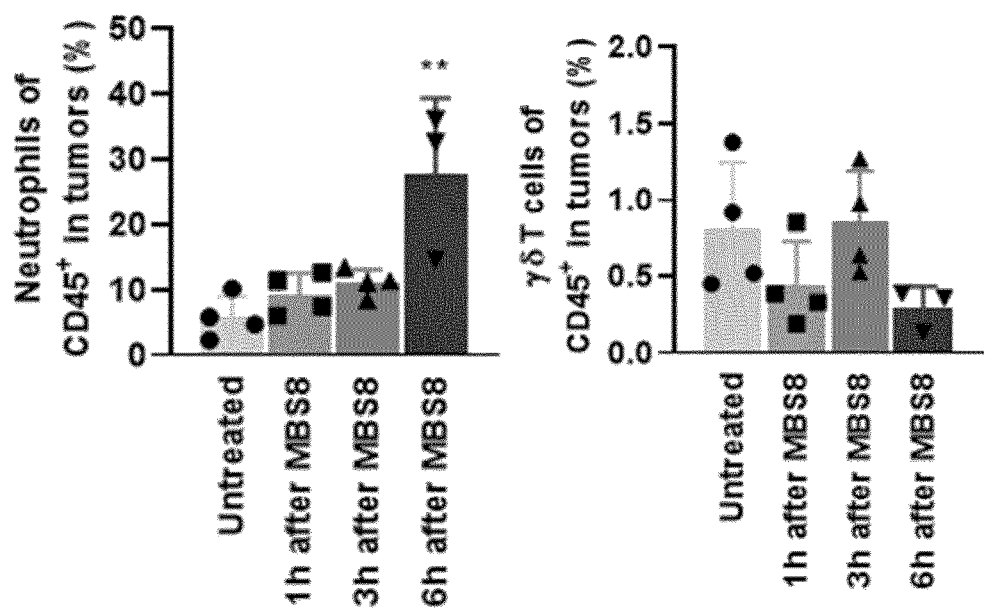
Figure 17C:
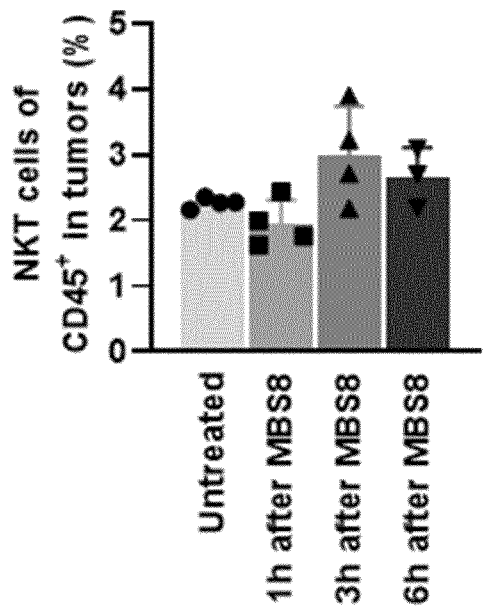
Figure 17C:
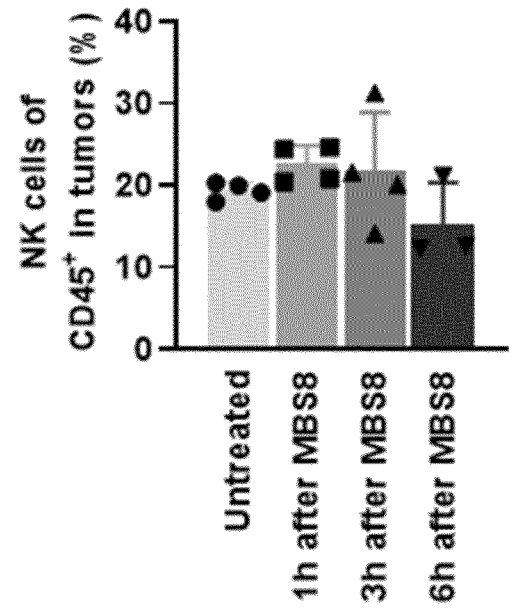
Figure 17C:
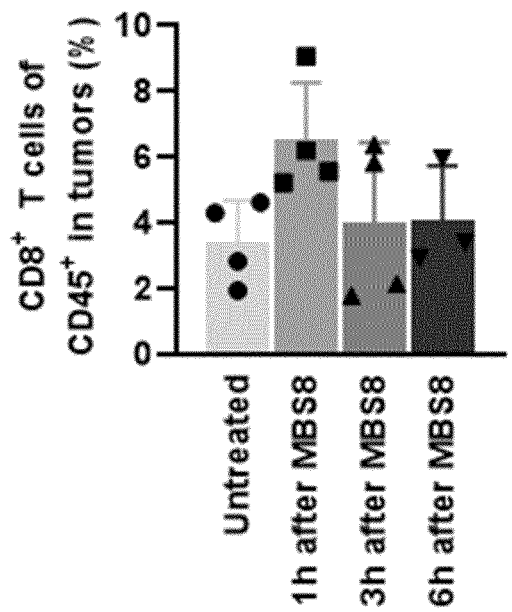
Figure 17D:
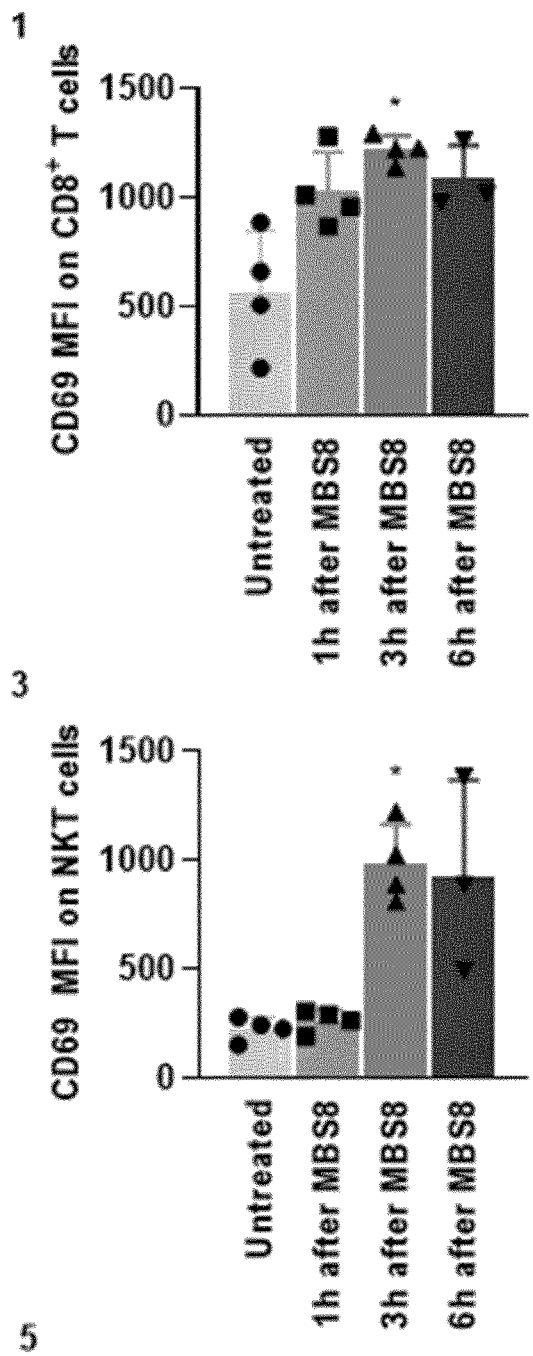
Figure 17D:
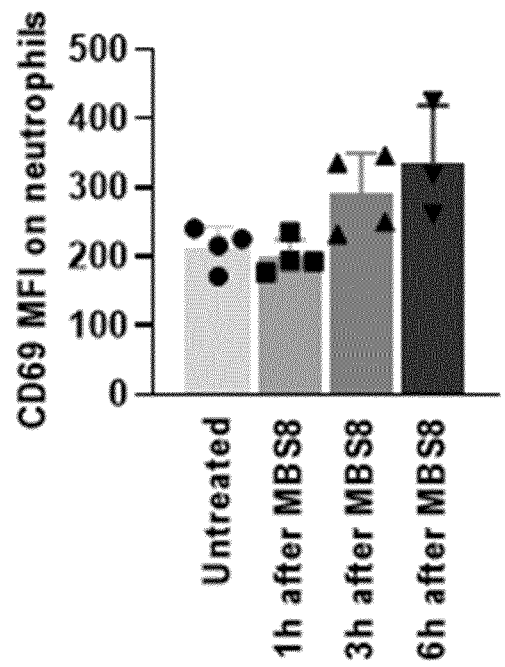

Example 22: Acute Effects on the Tumor Microenvironment Following MBS8 Treatment The acute effects of intravenous injection of 200 nmol MBS8 was evaluated on tumors by multicolor flow cytometry. Mice bearing CT26 tumors were treated with MBS8 and tumors evaluated by flow cytometry 1, 3 and 6 hours after injection. Erythrocytes were determined based on size and Ter-119 expression and excluded from further analyses. All further analyses were determined based on lack of Ter-119 expression and based on size and being stained as alive. CD8+ T cells were defined as CD45+CD3+CD8+. Erythrocytes comprised the majority of cells in the tumors 6 hours after injection of MBS8 (FIG. 17A). Additionally, the tumor microenvironment is characterized by a decrease in immune cells (CD45$^+$) and a remarkable and surprising drop in cancer cells 6 hours after injection of MBS8 (FIG. 17B, graph 1 and 2). Although immune cells were decreased in the tumor, there was a strong increase in neutrophils 6 h after treatment (FIG. 17C, graph 1), whereas T-cells, NKT and NK cells did not significantly change (FIG. 17C, graph 2-5). However, when immune activation was monitored on these cell subsets based on CD69-expression, T-cells, NKT and NK cells showed a significant activation 3 h after treatment (FIG. 17D, graph 1-5).

Conclusion

MBS8 injected intravenously induce enrichment of neutrophils and erythrocytes in the tumors 6 h after treatment and is accompanied by decrease in viable tumor cells and immune cells, whereas significant activation is seen for immune cells; CD8 T-cells, NKT-cells and NK cells.

Figure 18A:
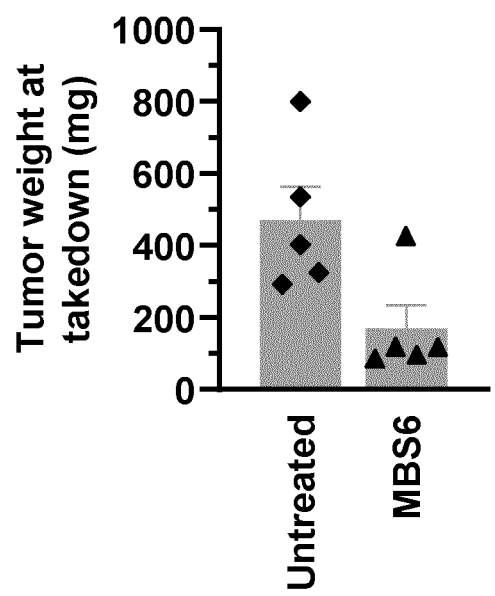
FIG. 18: Effects on the tumor microenvironment during treatment based on flow cytometric analysis. Mice bearing CT26 tumors were treated on day 15 after cancer cell inoculation with 200 nmol MBS6 every fourth day and tumors and spleens analyzed two days after the second injection. All graphs are displayed as mean±SEM. Statistical significance compared to untreated tumors was determined using Mann-Whitney U test where * indicates p<0.05; ** indicates p<0.01; n=5.
Figure 18B:
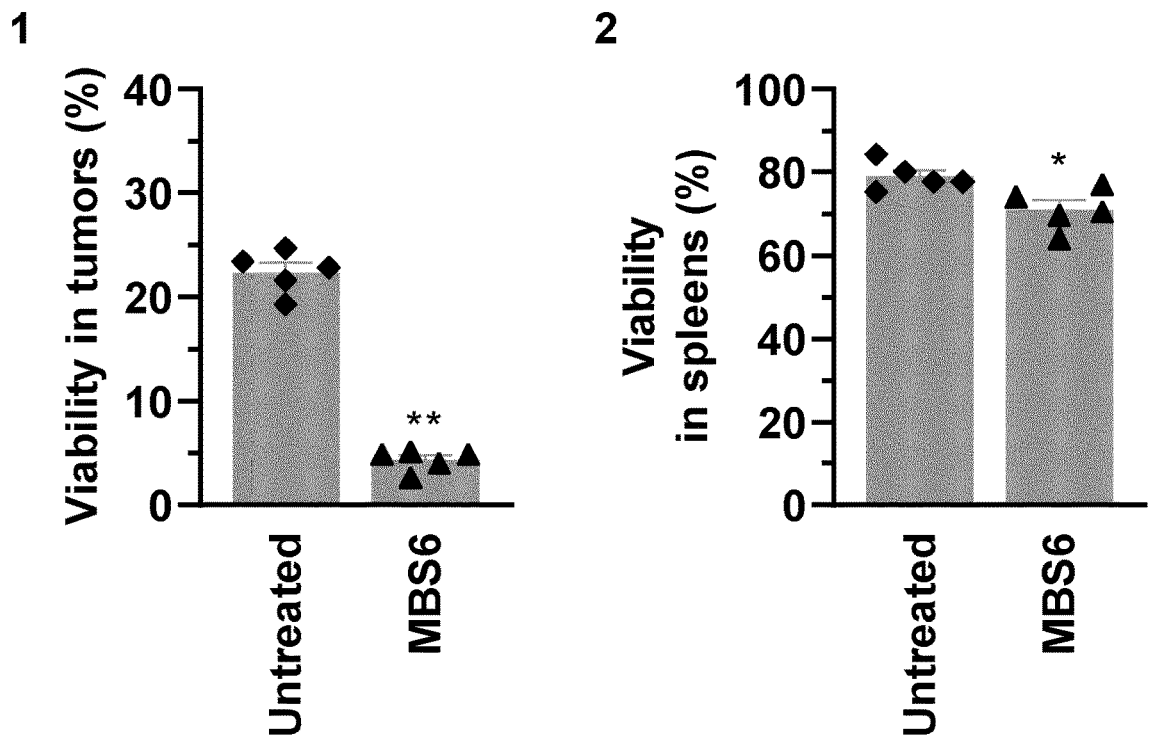
Figure 18C:
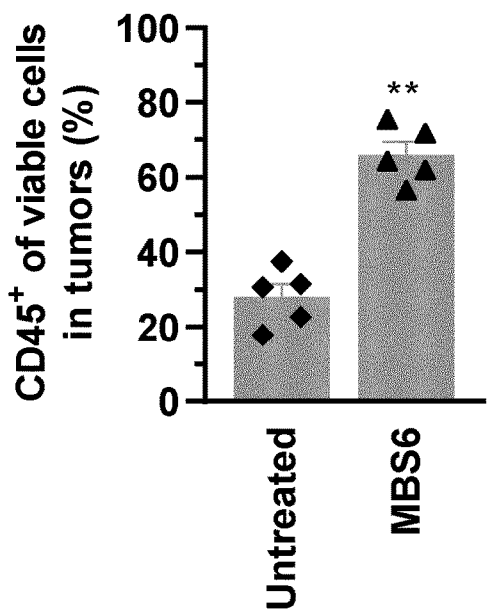
Figure 18D:
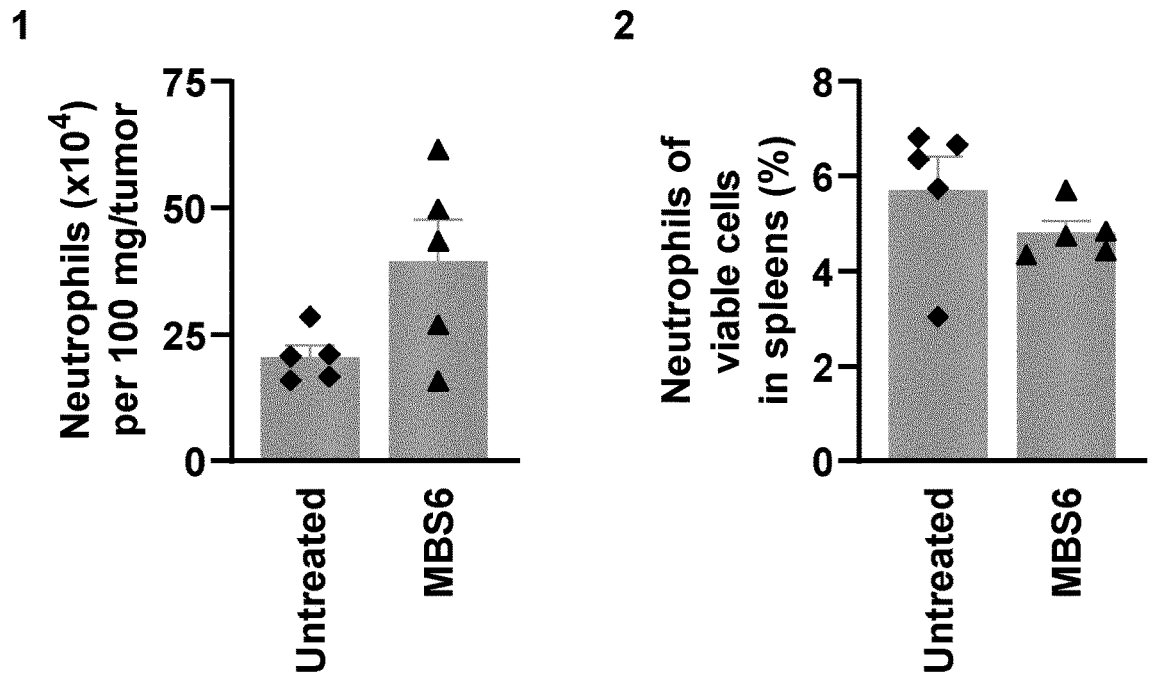
Figure 18E:
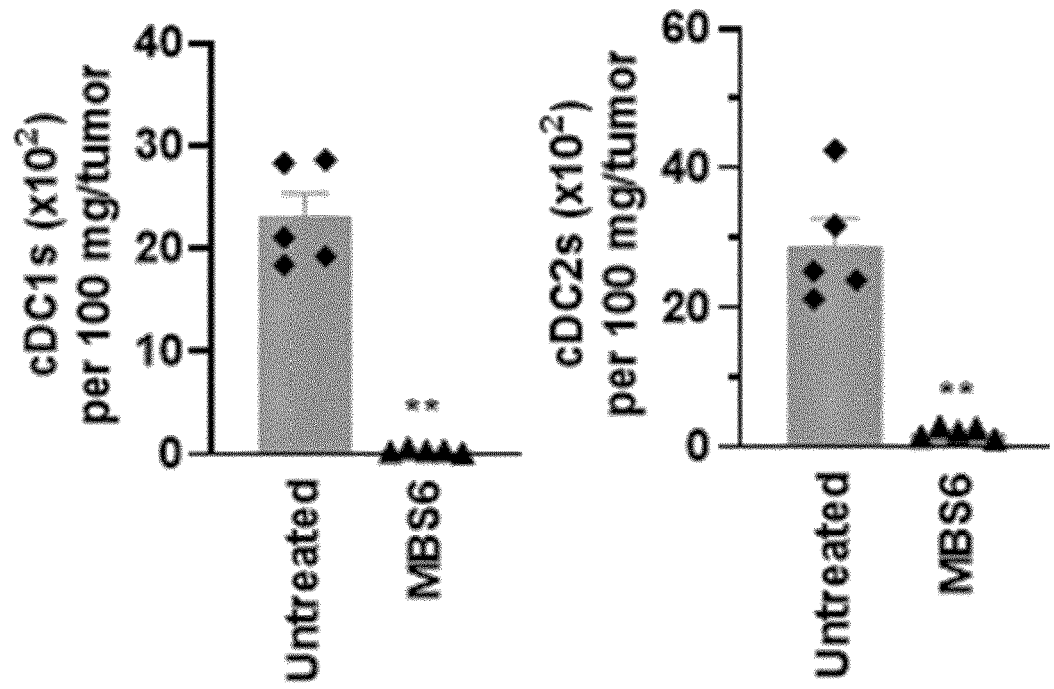
Figure 18E:
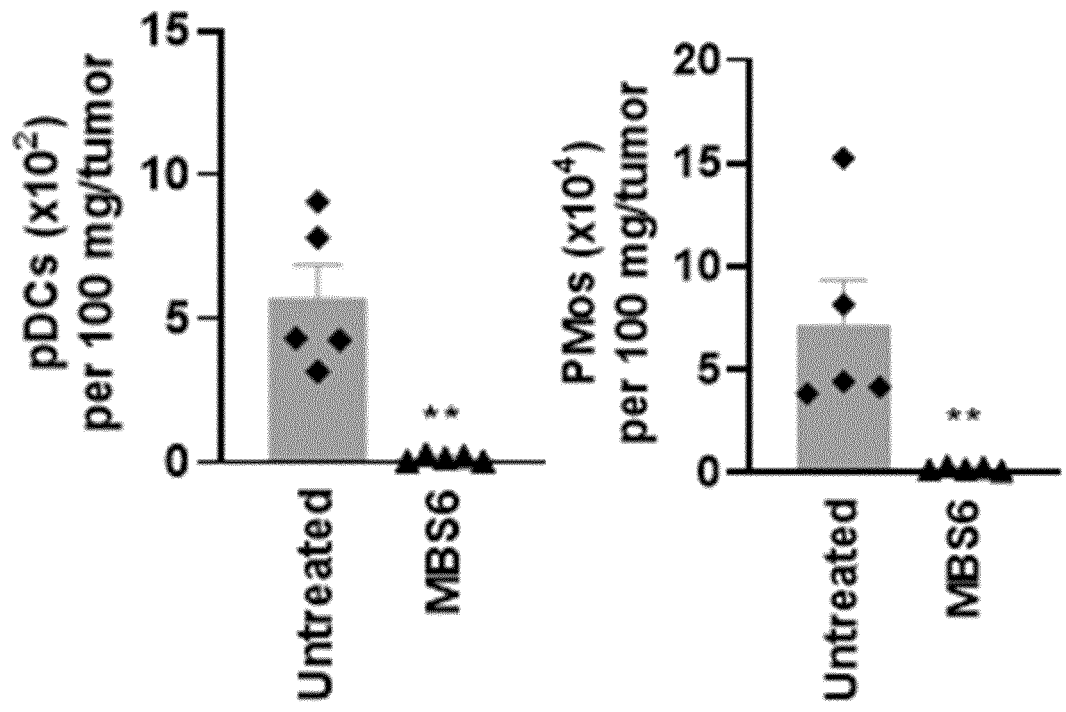
Figure 18E:
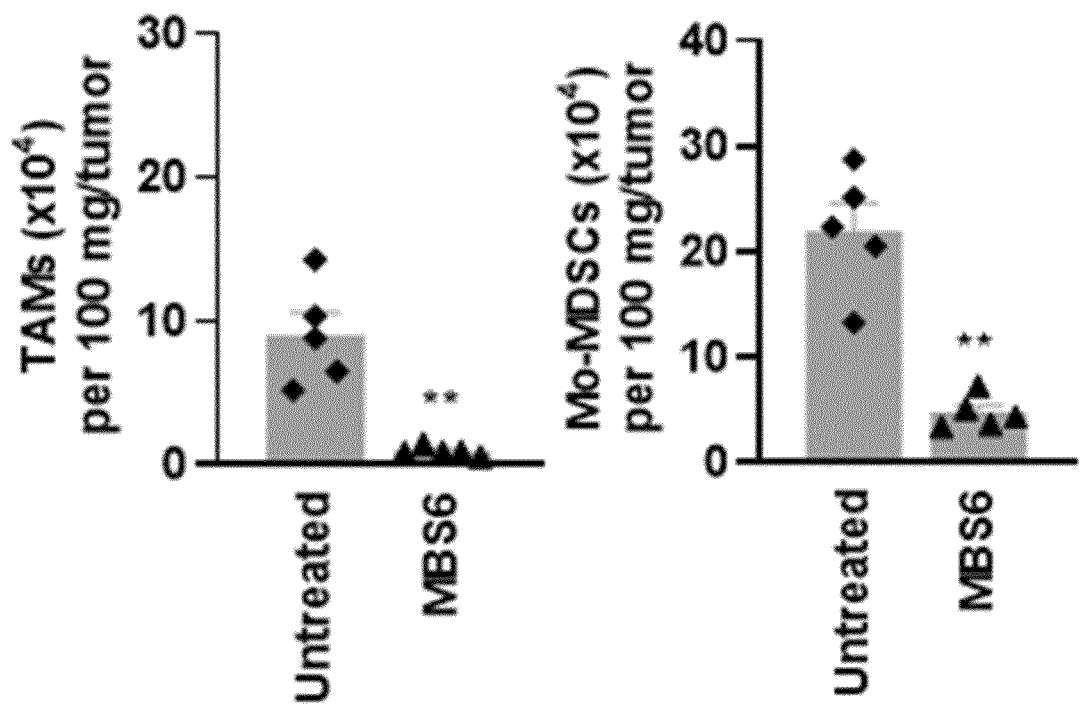
Figure 18E:
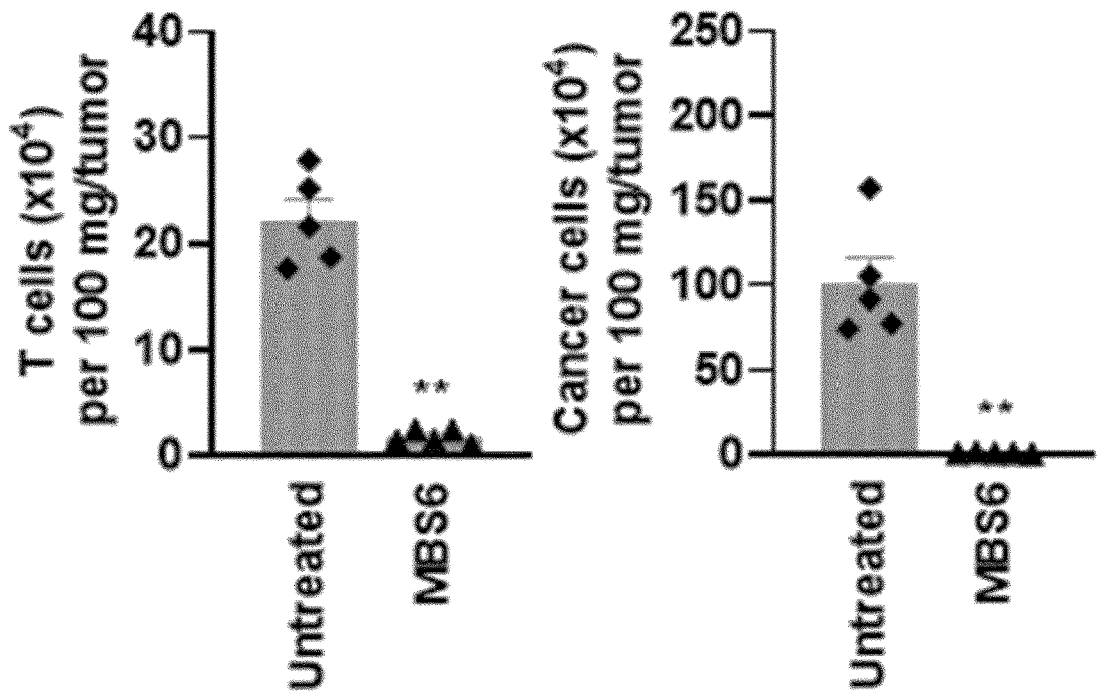

Example 23: Effects on the Tumor Microenvironment and Spleens Following TLR7 Micelles The effects of intravenous injection of MBS6 on the tumor microenvironment was evaluated by multicolor flow cytometry. Mice bearing CT26 tumors were treated on day after cancer cell inoculation with 200 nmol MBS6 every fourth day and tumors and spleens analyzed two days after the second injection and 6 days after the first injection (day 21). Viable cells were identified based on cell size and lack of staining by a viability dye. All further analyses were based on viable cells. Neutrophils were identified as CD45$^+$ CD11b$^+$ Ly6g$^+$. Tumor associated macrophages (TAMs) were identified as CD45$^+$ Ly6g$^-$ CD11c$^+$ CD11b$^+$ CD64$^{high}$. Patrolling monocytes (PMos) were identified as CD45$^+$ Ly6g$^-$ CD11b$^+$ CD11c$^-$ Ly6c$^-$ CD64$^+$. monocytic myeloid-derived suppressor cells (Mo-MDSCs) were identified as CD45$^+$ Ly6g$^-$ CD11b$^+$ CD11c$^-$ Ly6c$^{high}$. Classical DC (cDC)1s were identified as CD45$^+$ Ly6g$^-$ CD11c$^+$ CD64$^{low}$ CD11b$^{low}$ XCR1$^+$. cDC2s were identified as CD45$^+$ Ly6g$^-$ CD11c$^+$ CD64$^{low}$ XCR1$^-$ CD11b$^{high}$. Plasmacytoid DCs (pDCs) were identified as CD45$^+$ Ly6g$^-$ CD11c$^+$ CD64$^{low}$ XCR1$^-$ CD11b$^-$ Ly6c$^{high}$ Siglec-H$^+$. CD8$^+$ T cells were identified as CD45$^+$ side scatter$^{low}$ CD3$^+$ CD4$^-$ CD8$^+$. Cells per 100 mg were calculated based on population of interest, tumor weight and total cells. Tumor weights were lower compared to untreated tumors (FIG. 18A, p=0.056). Additionally, the cellular viability in tumors were significantly reduced after treatment with MBS6, which was barely reflected in spleens (FIG. 18B, graph 1 and 2). Of the viable cells, MBS6 induced a strong increase in immune cells (CD45+) (FIG. 18C). This is in contrast to what was seen in FIG. 17C, but can be explained by the fact that this time point was 6 days after first treatment. Neutrophils were highly enriched within the tumor microenvironment as seen already after 6 h in FIG. 17 (relative to the depletion of other cell types) following MBS6 treatment which was not reflected in spleens (FIG. 18D, graph 1 and 2). All other investigated immune populations and cancer cells were strongly decreased in the tumor microenvironment (FIG. 18E, graph 1-8).

Conclusion

Intravenous injection of MBS6 strongly decreases the cellular viability within the tumor microenvironment while not affecting the viability in spleens. Additionally, MBS6 induced a strong increase in neutrophils in the tumor microenvironment which was not observed in spleens.

Example 24: Optimal Dosing Schedule for MBS8 and Doxil

Figure 19:
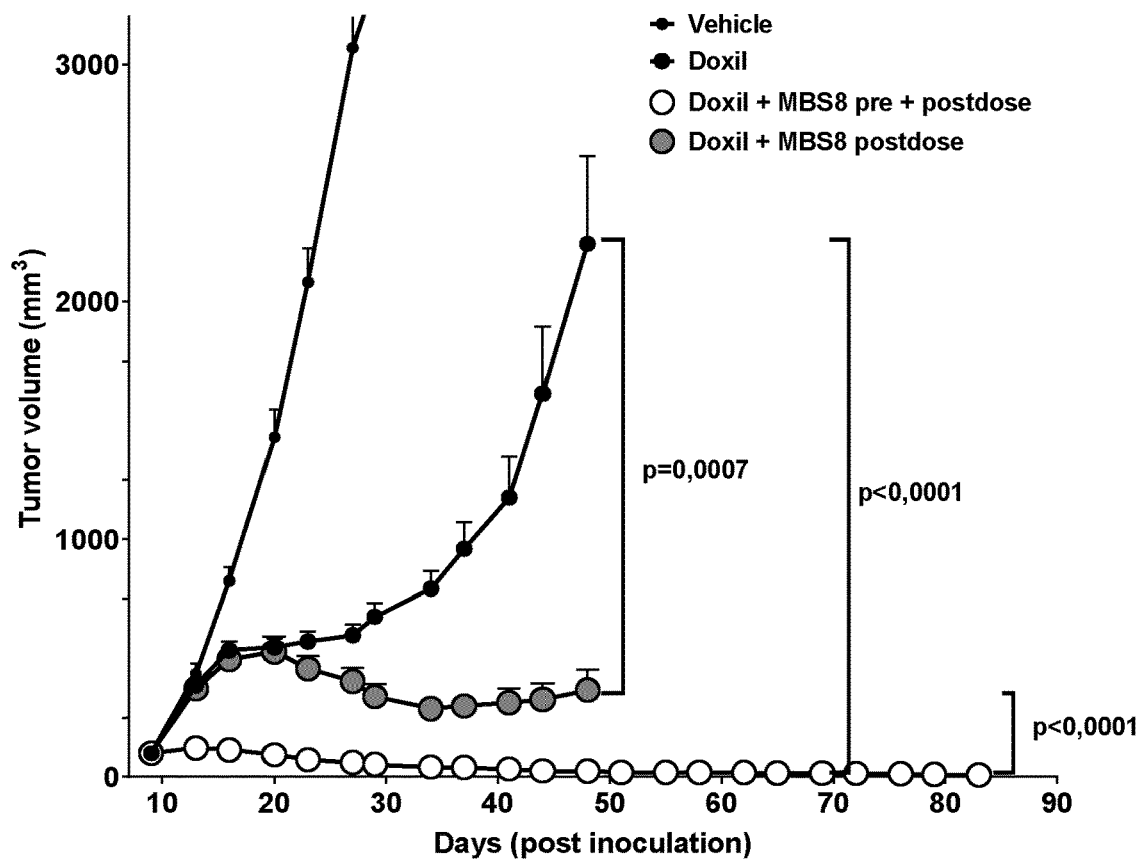
FIG. 19: Dosing schedule study in CT26 tumor bearing mice with Doxil treatment for all groups were done at day 9, 13 and 17 (black circles), the Doxil+MBS8 pre+postdose treatment group was dosed additionally with MBS8 at day 9 and day 19, 23, 27 and 31, and the Doxil+MBS8 postdose treatment group was dosed additionally with MBS8 at day 19, 23, 27 and 31. All graphs are displayed as mean+SEM. Statistical significance compared between indicated groups was determined using Mann-Whitney U test at indicated significance levels, n=10.
Figure 19:
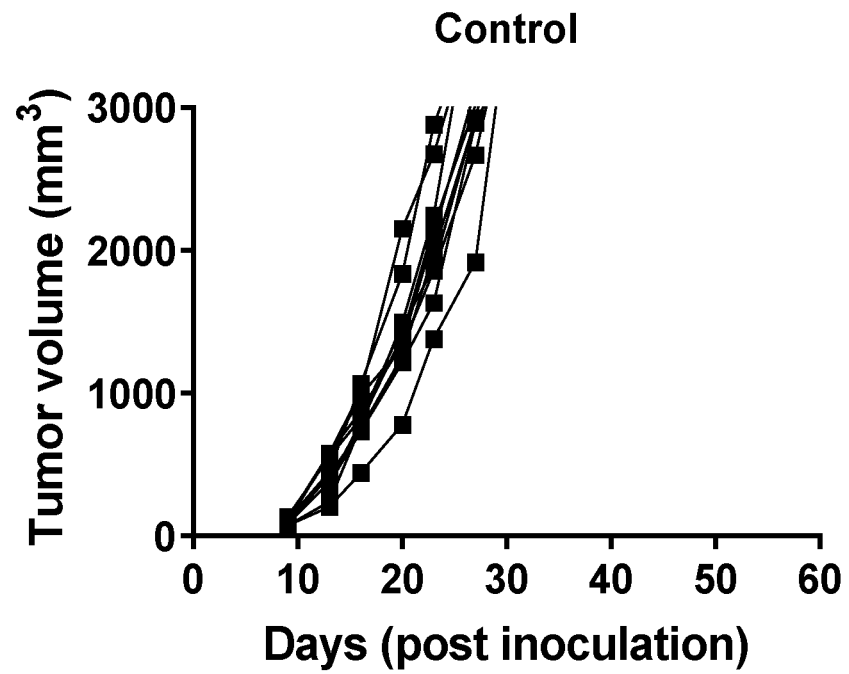
Figure 19:
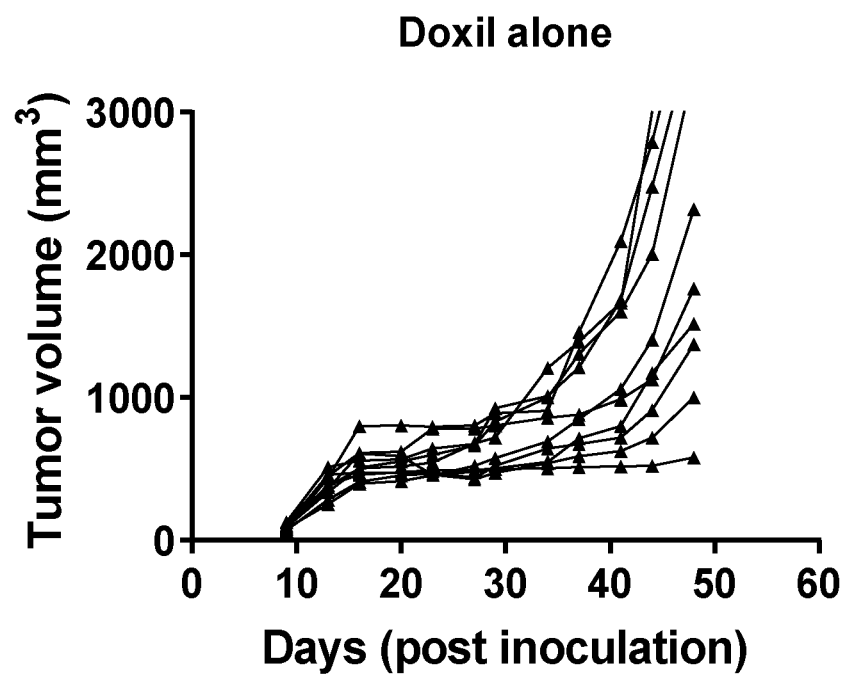
Figure 19:
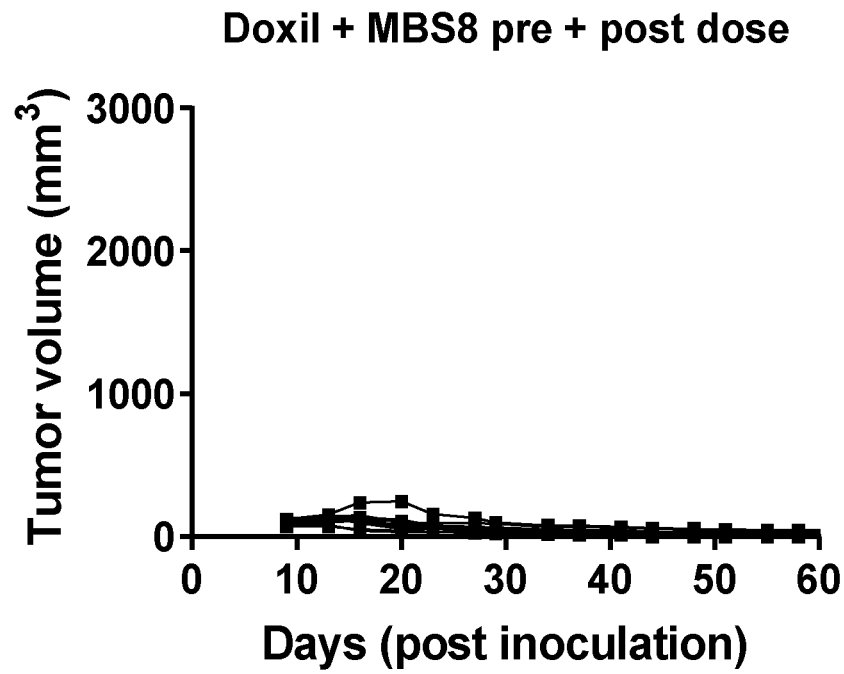
Figure 19:
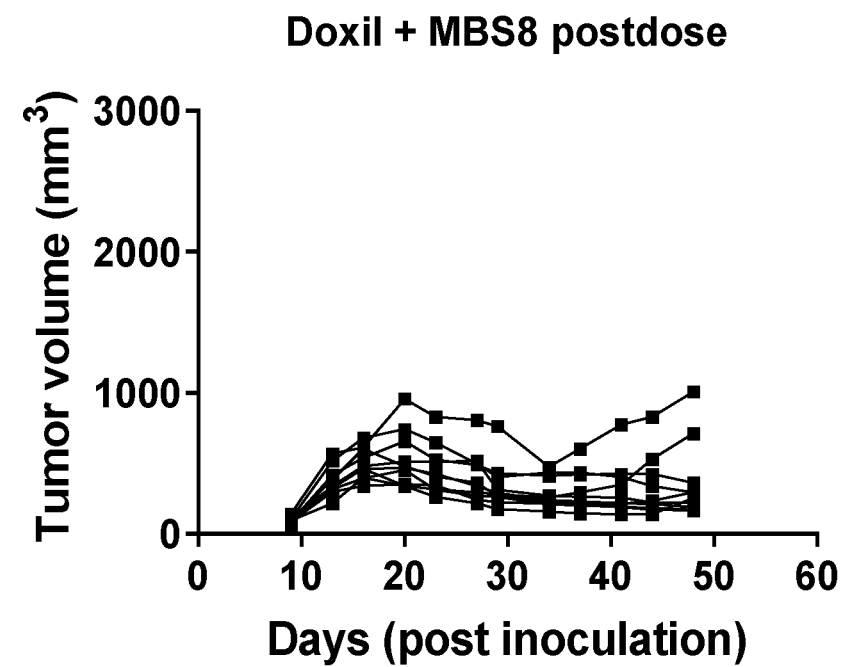

Dosing schedule when using combination treatments with MBS8 and chemotherapy is critical in order to achieve the optimal tumor control. We wanted to test if Doxil treatment was improved in combination with MBS8, and in that case how MBS8 should be dosed to achieve the optimal response (FIG. 19). Doxil treatment alone showed a tumor growth delay but no mice in complete remission, and with a tumor growth inhibition (TGI), compared to Vehicle treated mice at 80% (FIG. 19). When MBS8 was administered starting two days after last Doxil treatment (MBS8 postdose), there was a significant tumor growth inhibition of 90% vs vehicle treated mice, and a significant anti-tumor activity compared to Doxil alone (p=0.0007). However, when MBS8 was dosed initially at the same day as Doxil, (MBS8 pre+ postdose), all mice were in complete remission with a TGI of 98%, and significantly better antitumor activity than for Doxil alone or when MBS8 was only dosed post-Doxil treatment.

Conclusion

These data show that MBS8 immunotherapy is significantly more efficient when a pre-dose is applied the same day as chemotherapy, and then with a follow up treatment after chemotherapy is terminated, compared to the setting where immunotherapy is initiated prior to chemotherapy.

Example 25: Micelles Show No Sign of Accelerated Blood Clearance (ABC)

Figure 20A:
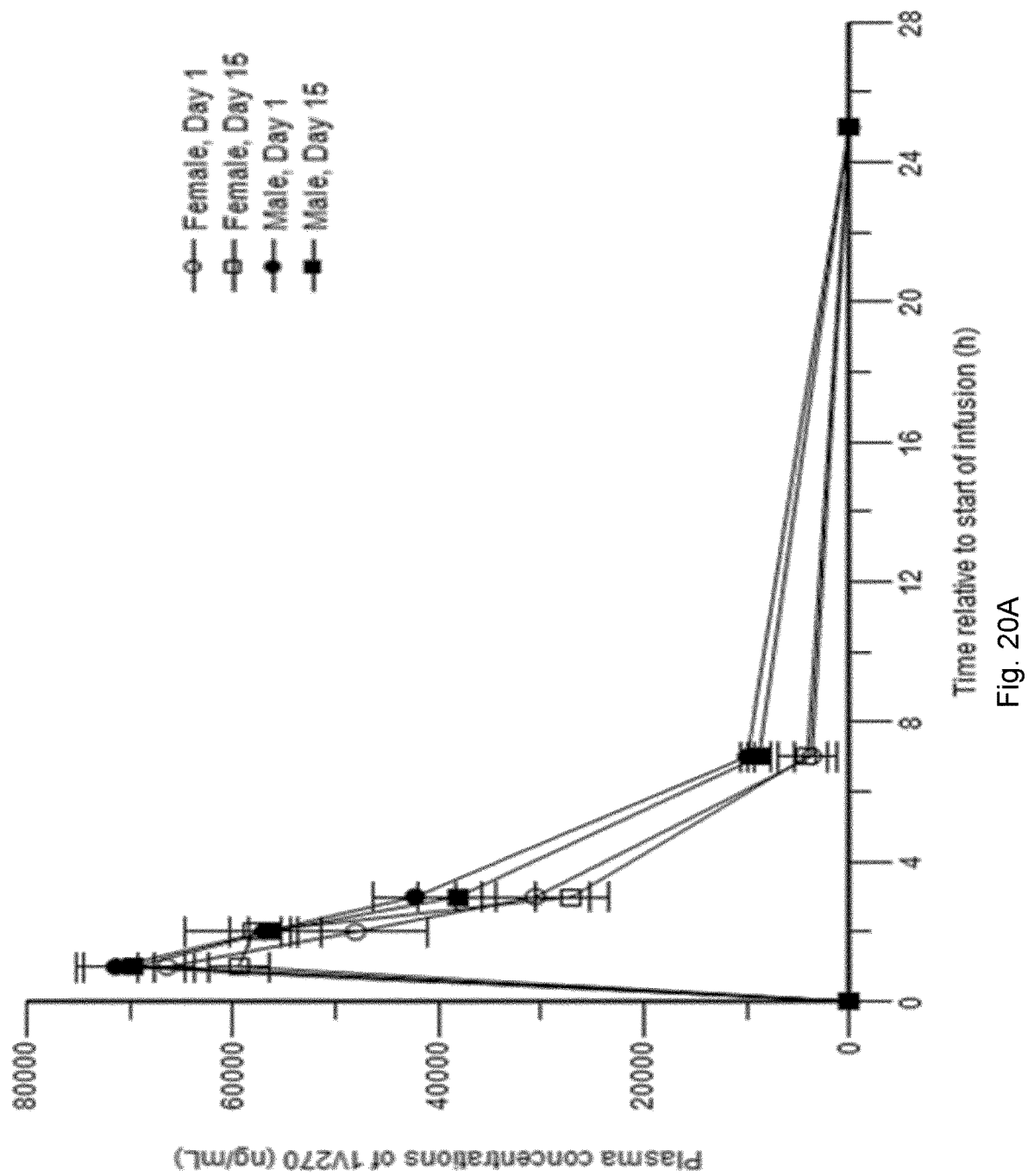
FIG. 20: Mean (+/−SD) plasma concentration-time curves of MBS8 in female and male rats on Day 1 (first dose) and Day 15 (one week after last dose of two doses 1 week apart) after intravenous infusion administration over a period of 1 hour of 3 mg/kg/day MBS8 (1V270) at a linear scale (A) and semi-logarithmic scale (B). This figure demonstrates indifferent kinetics of MBS8 administered after 1 day and 15 days, (third dose) respectively. This observation supports that the micelles of the present invention do not trigger accelerated blood clearance (ABC).
Figure 20B:
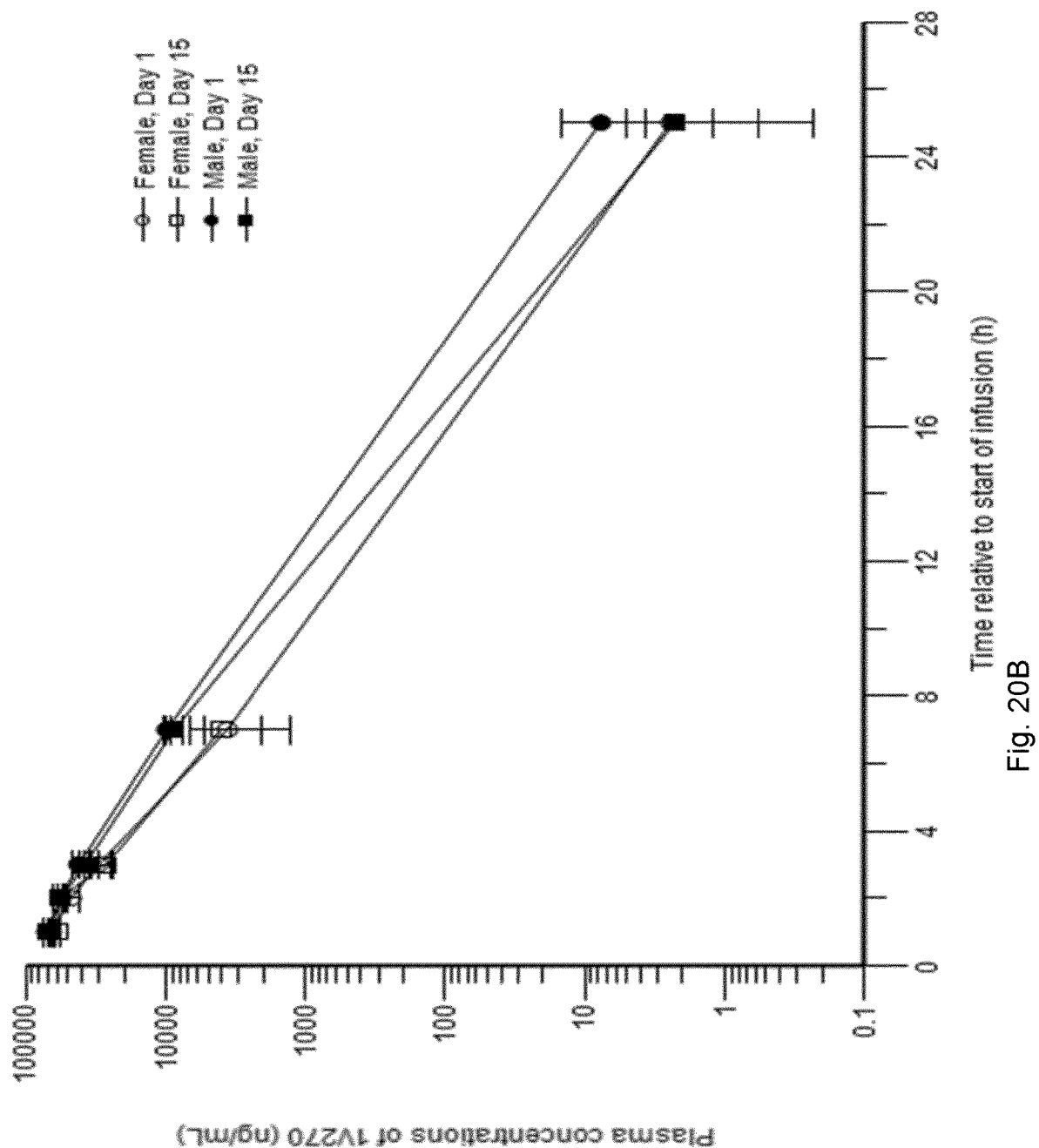

In Mice:

Mean (+/−SD) plasma concentration-time curves of MBS8 in female and male rats on Day 1 (at first dose) and Day 15 (one week after last dose of two doses 1 week apart) after intravenous infusion administration over a period of 1 hour of 3 mg/kg/day MBS8 (1V270) is shown in FIG. 20 at a linear scale (A) and semi-logarithmic scale (B). This example demonstrates indifferent kinetics of MBS8 administered after 1 day and 15 days (third dose), respectively. This observation supports that the micelles of the present invention do not trigger accelerated blood clearance (ABC).

Figure 21A:
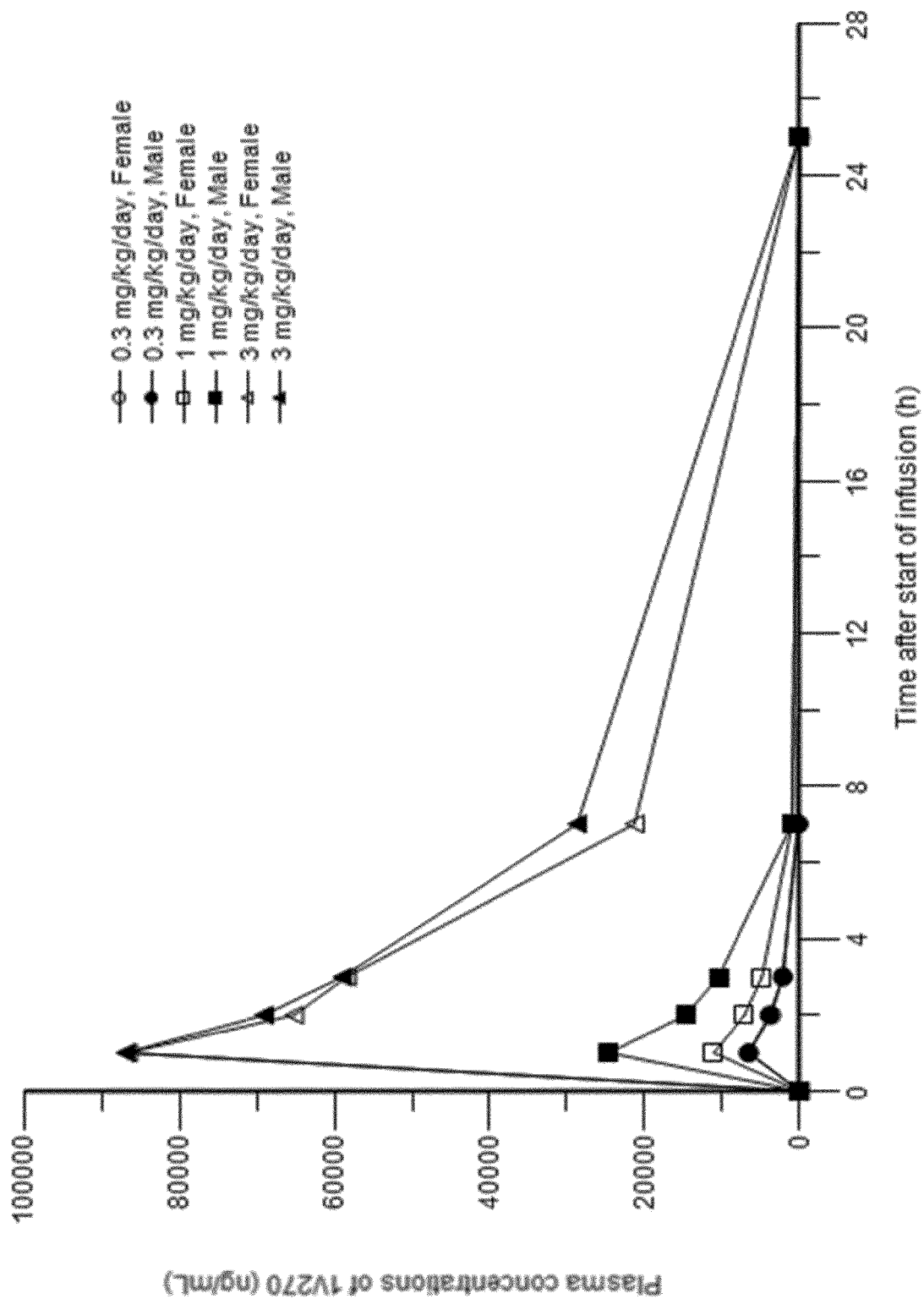
FIG. 21: Overlay of individual plasma concentration-time curves of 1V270 in 1 female and 1 male cynomolgus monkey on Day 1 (A) (first dose) and Day 15 (B) (one week after last dose of two doses 1 week apart) after intravenous infusion administration over a period of 1 hour of 0.3, 1 and 3 mg/kg/day MBS8 (1V270) at a linear scale. This figure demonstrates indifferent kinetics of MBS8 administered after 1 day (one dose) and 15 days (third dose after weekly dosing), respectively. This observation supports that the micelles of the present invention do not trigger accelerated blood clearance (ABC).
Figure 21B:
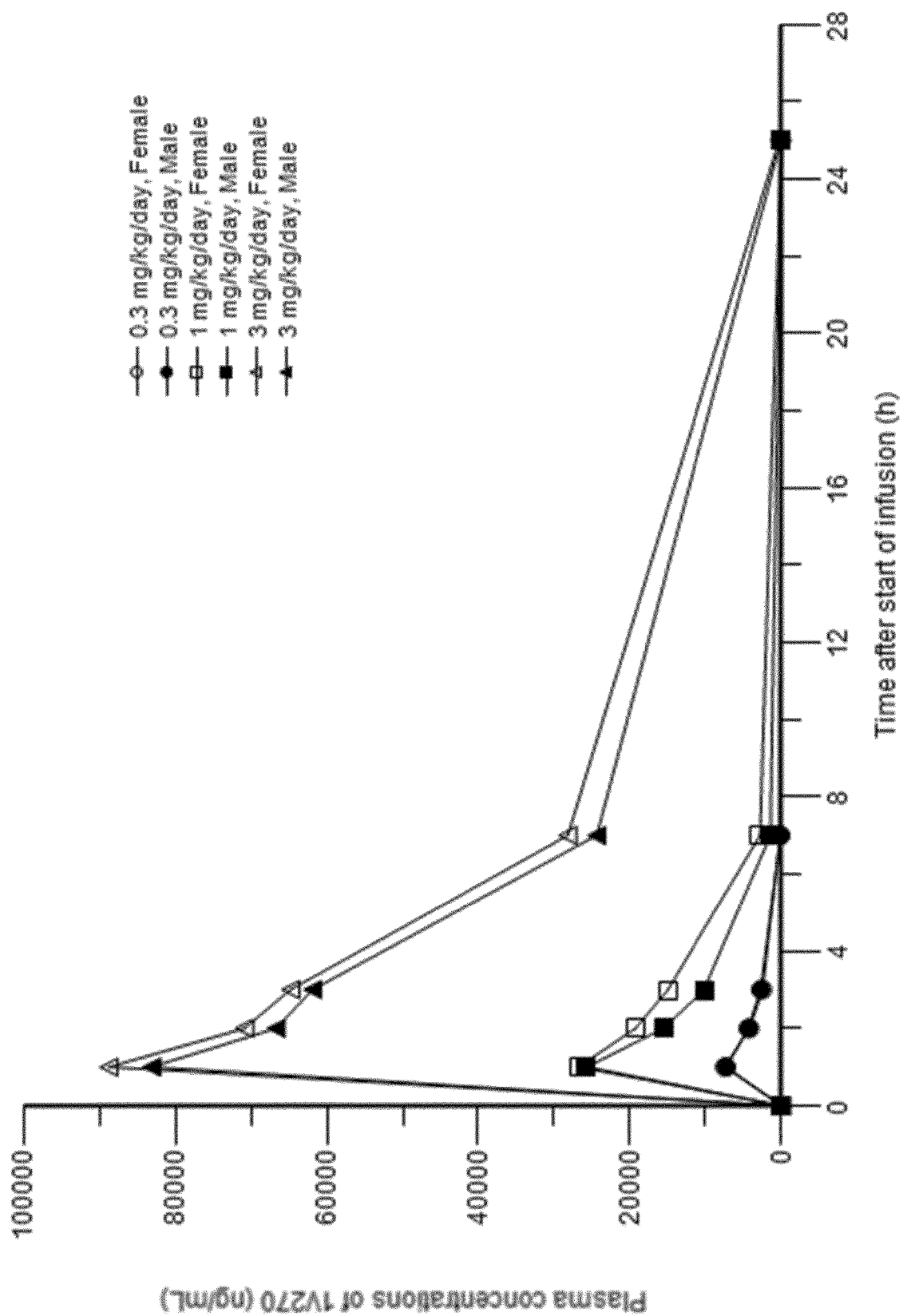

In Cynomolgus Monkeys:

Overlay of individual plasma concentration-time curves of 1V270 in 1 female and 1 male cynomolgus monkey is shown in FIG. 21 on Day 1 (A, first dose) and Day 15 (B, third dose after one weekly dose for two doses) after intravenous infusion administration over a period of 1 hour of 0.3, 1 and 3 mg/kg/day MBS8 (1V270) at a linear scale. This example demonstrates indifferent kinetics of MBS8 administered after 1 day and third dose after 15 days, respectively. This observation supports that the micelles of the present invention do not trigger accelerated blood clearance (ABC).

Conclusion

In both mice and cynomolgus monkeys, the micelles of the present disclosure did not trigger accelerated blood clearance (ABC) when infused at Day 1 (first dose) and Day 15 (third dose). This supports the significantly improved therapeutic utility of micelles at least in comparison with liposomes known to trigger an ABC event.

The invention claimed is:
1. A micelle composition comprising:
(i) a toll-like receptor 7 (TLR7) agonist of formula (I), formula (II), formula (III) or formula (IV);

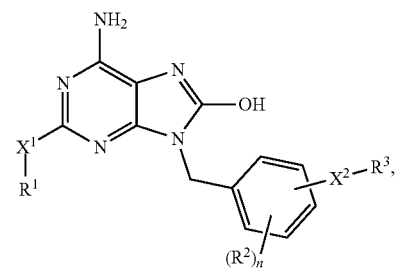
(I)

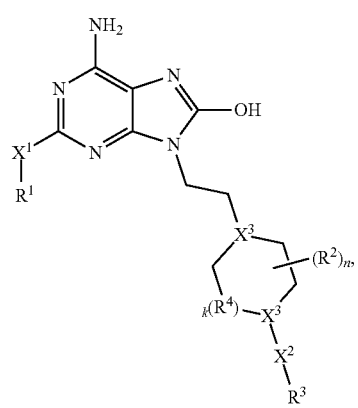
(II)

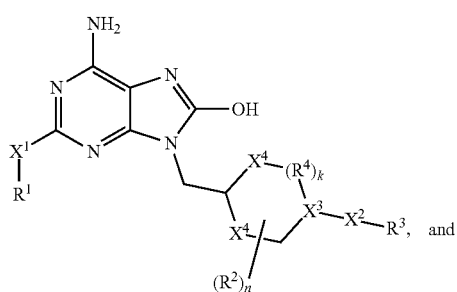
(III)

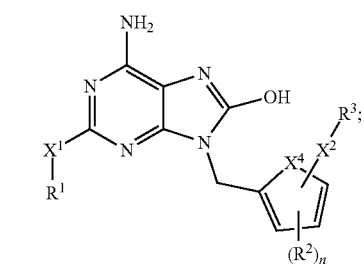
(IV)

or a tautomer thereof;
or a pharmaceutically acceptable salt or solvate thereof, wherein
$X^1$ is —O—, —S—, or —NR$^C$;
$R^1$ is hydrogen, $(C_1-C_{10})$alkyl, substituted $(C_1-C_{10})$alkyl, $(C_6-C_{10})$aryl, substituted $(C_6-C_{10})$aryl, $(C_5-C_9)$heterocyclic, or substituted $(C_5-C_9)$heterocyclic;
$R^C$ is hydrogen, $(C_1-C_{10})$alkyl, or substituted $(C_1-C_{10})$alkyl; or $R^C$ and $R^1$ taken together with the nitrogen atom to which they are attached form a heterocyclic ring or a substituted heterocyclic ring;

each $R^2$ is independently —OH, $(C_1-C_6)$alkyl, substituted $(C_1-C_6)$alkyl, $(C_1-C_6)$alkoxy, substituted $(C_1-C_6)$alkoxy, —C(O)—$(C_1-C_6)$alkyl (alkanoyl), substituted —C(O)—$(C_1-C_6)$alkyl, —C(O)—$(C_6-C_{10})$aryl (aroyl), substituted —C(O)—$(C_6-C_{10})$aryl, —C(O)OH (carboxyl), —C(O)O$(C_1-C_6)$alkyl (alkoxycarbonyl), substituted —C(O)O$(C_1-C_6)$alkyl, —NR$^a$R$^b$, —C(O)NR$^a$R$^b$ (carbamoyl), halo, nitro, or cyano;
each R$^a$ and R$^b$ is independently hydrogen, $(C_1-C_6)$alkyl, substituted $(C_1-C_6)$alkyl, $(C_3-C_5)$cycloalkyl, substituted $(C_3-C_8)$cycloalkyl, $(C_1-C_6)$alkoxy, substituted $(C_1-C_6)$alkoxy, $(C_1-C_6)$alkanoyl, substituted $(C_1-C_6)$alkanoyl, aryl, aryl$(C_1-C_6)$alkyl, Het, Het $(C_1-C_6)$alkyl, or $(C_1-C_6)$alkoxycarbonyl;
wherein the substituents on any substituted alkyl, aryl or heterocyclic groups are hydroxy, $(C_1-C_6)$alkyl, hydroxy $(C_1-C_6)$alkylene, $(C_1-C_6)$alkoxy, $(C_3-C_6)$cycloalkyl, $(C_1-C_6)$alkoxy $(C_1-C_6)$alkylene, amino, cyano, halo, or aryl;
n is 0, 1, 2, 3 or 4;
$X^2$ is a bond or a linking group;
$R^3$ is a lipid;
$X^3$ is —N— or —CH—;
$R^4$ is —CH$_2$— or —CH(R$^2$)—;
k is 0 or 1;
$X^4$ is —O—, —S—, —NH—, —N(R$^4$)—, —CH$_2$—, or —CH(R$^2$)—; and
each R$^d$ is independently —OH, $(C_1-C_6)$alkyl, substituted $(C_1-C_6)$alkyl, $(C_1-C_6)$alkoxy, substituted $(C_1-C_6)$alkoxy, —C(O)—$(C_1-C_6)$alkyl (alkanoyl), substituted —C(O)—$(C_1-C_6)$alkyl, —C(O)—$(C_6-C_{10})$aryl (aroyl), substituted —C(O)—$(C_6-C_{10})$aryl, —C(O)O$(C_1-C_6)$alkyl (alkoxycarbonyl), substituted —C(O)O$(C_1-C_6)$alkyl, or —C(O)NR$^a$R$^b$ (carbamoyl);
wherein the ring system of formula (II) is a piperidine ring with one heteroatom being an N atom and with the N-atom of the piperidine ring adjacent to $X^2$, and
wherein the purine group in any of Formula (I), (II), (III), or (IV) is subject to tautomeric rearrangements;
and (ii) an amphiphilic micelle-forming agent,
wherein the average diameter of the micelles in the micelle composition is from 5 nm to 25 nm.
2. The micelle composition according to claim 1, wherein the TLR7 agonist is of formula (I):

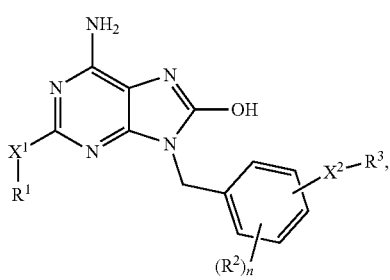
(I)

or a tautomer thereof;
or a pharmaceutically acceptable salt or solvate thereof, wherein
$X^1$ is —O—, —S—, or —NR$^C$;
$R^1$ is hydrogen, $(C_1-C_{10})$alkyl, substituted $(C_1-C_{10})$alkyl, $(C_6-C_{10})$aryl, substituted $(C_6-C_{10})$aryl, $(C_5-C_9)$heterocyclic, or substituted $(C_5-C_9)$heterocyclic;

$R^C$ is hydrogen, $(C_1-C_{10})$alkyl, or substituted $(C_1-C_{10})$alkyl; or $R^C$ and $R^1$ taken together with the nitrogen atom to which they are attached form a heterocyclic ring or a substituted heterocyclic ring;

each $R^2$ is independently —OH, $(C_1-C_6)$alkyl, substituted $(C_1-C_6)$alkyl, $(C_1-C_6)$alkoxy, substituted $(C_1-C_6)$alkoxy, —C(O)—$(C_1-C_6)$alkyl (alkanoyl), substituted —C(O)—$(C_1-C_6)$alkyl, —C(O)—$(C_6-C_{10})$aryl (aroyl), substituted —C(O)—$(C_6-C_{10})$aryl, —C(O)OH (carboxyl), —C(O)O$(C_1-C_6)$alkyl (alkoxycarbonyl), substituted —C(O)O$(C_1-C_6)$alkyl, —NR$^a$R$^b$, —C(O)NR$^a$R$^b$ (carbamoyl), halo, nitro, or cyano;

each $R^a$ and $R^b$ is independently hydrogen, $(C_1-C_6)$alkyl, substituted $(C_1-C_6)$alkyl, $(C_3-C_5)$cycloalkyl, substituted $(C_3-C_8)$cycloalkyl, $(C_1-C_6)$alkoxy, substituted $(C_1-C_6)$alkoxy, $(C_1-C_6)$alkanoyl, substituted $(C_1-C_6)$alkanoyl, aryl, aryl$(C_1-C_6)$alkyl, Het, Het $(C_1-C_6)$alkyl, or $(C_1-C_6)$alkoxycarbonyl;

wherein the substituents on any substituted alkyl, aryl or heterocyclic groups are hydroxy, $(C_1-C_6)$alkyl, hydroxy $(C_1-C_6)$alkylene, $(C_1-C_6)$alkoxy, $(C_3-C_6)$cycloalkyl, $(C_1-C_6)$alkoxy $(C_1-C_6)$alkylene, amino, cyano, halo, or aryl;

n is 0, 1, or 2;

$X^2$ is a bond or a linking group; and $R^3$ is a lipid; and wherein the purine group is subject to tautomeric rearrangements.

3. The micelle composition according to claim 1, wherein the TLR7 agonist is of formula (I):

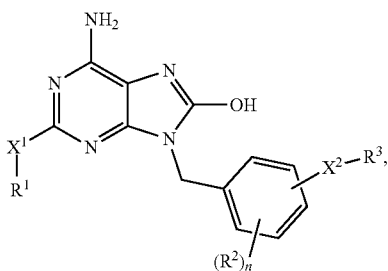

(I)

or a tautomer thereof;

or a pharmaceutically acceptable salt or solvate thereof, wherein $X^1$ is —O—, —S—, or —NR$^C$;

$R^1$ is hydrogen, $(C_1-C_{10})$alkyl, substituted $(C_1-C_{10})$alkyl, $(C_6-C_{10})$aryl, substituted $(C_6-C_{10})$aryl, $(C_5-C_9)$heterocyclic, or substituted $(C_5-C_9)$heterocyclic;

$R^C$ is hydrogen, $(C_1-C_{10})$alkyl, or substituted $(C_1-C_{10})$alkyl; or $R^C$ and $R^1$ taken together with the nitrogen to which they are attached form a heterocyclic ring or a substituted heterocyclic ring;

n is 0;

$X^2$ is a bond or a linking group; and $R^3$ is a lipid;

wherein the purine group is subject to tautomeric rearrangements.

4. The micelle composition according to claim 1, wherein $X^2$ is selected from the group consisting of: a bond, —O—, —C(O)-(carbonyl), $(C_1-C_6)$alkyl, substituted $(C_1-C_6)$alkyl, $(C_1-C_6)$alkoxy, substituted $(C_1-C_6)$alkoxy, —C(O)—$(C_1-C_6)$alkyl (alkanoyl), substituted —C(O)—$(C_1-C_6)$alkyl, —C(O)—$(C_6-C_{10})$aryl (aroyl), substituted —C(O)—$(C_6-C_{10})$aryl, —C(O)OH (carboxyl), —C(O)O$(C_1-C_6)$alkyl (alkoxycarbonyl), substituted —C(O)O$(C_1-C_6)$alkyl, —NR$^a$R$^b$, —C(O)NR$^a$R$^b$ (carbamoyl); and each $R^a$ and $R^b$ is independently hydrogen, $(C_1-C_6)$alkyl, substituted $(C_1-C_6)$alkyl, $(C_3-C_5)$cycloalkyl, substituted $(C_3-C_8)$cycloalkyl, $(C_1-C_6)$alkoxy, substituted $(C_1-C_6)$alkoxy, $(C_1-C_6)$alkanoyl, substituted $(C_1-C_6)$alkanoyl, aryl, aryl$(C_1-C_6)$alkyl, Het, Het $(C_1-C_6)$alkyl, or $(C_1-C_6)$alkoxycarbonyl; and wherein $X^1$ is —O—, —S—, or —NR$^C$;

$R^1$ is hydrogen, $(C_1-C_6)$alkyl, or substituted $(C_1-C_6)$alkyl;

$R^C$ is hydrogen, $(C_1-C_6)$alkyl, or substituted $(C_1-C_6)$alkyl; or $R^C$ and $R^1$ taken together with the nitrogen to which they are attached form a heterocyclic ring or a substituted heterocyclic ring.

5. The micelle composition according to claim 1, wherein $R^3$ is a lipid selected from the group consisting of: a phospholipid comprising one or two carboxylic esters; a gonane; a saccharolipid; and a glyceride.

6. The micelle composition according to claim 1, wherein the amphiphilic micelle-forming agent is selected from the group consisting of: a poloxamer, a poloxamine, a PEG-polyester, a PEG-polyanhydride, a PEG-poly-amino acid, a phospholipid, a polysorbate, and a polyoxyethylene alkyl ether.

7. The micelle composition according to claim 1, wherein the amphiphilic micelle-forming agent is a phospholipid conjugated to polyethylene glycol (PEG).

8. The micelle composition according to claim 7, wherein the average molecular weight (Mn) of the PEG is between 350D and 5000D.

9. The micelle composition according to claim 6, wherein the phospholipid comprises one or more alkyl chains that are each a €8 €24 $C_8-C_{24}$ alkyl.

10. The micelle composition according to claim 7, wherein the phospholipid conjugated to PEG is selected from the group consisting of: 1,2-dioleoyl-sn-glycero-3-phosphoethanolamine (DOPE)-PEG, 1,2-distearoyl-sn-glycero-3-phosphoethanolamine (DSPE)-PEG, 1,2-dimyristoyl-sn-glycero-3-phosphoethanolamine (DMPE)-PEG, and 1,2-dipalmitoyl-sn-glycero-3-phosphoethanolamine (DPPE)-PEG.

11. The micelle composition according to claim 1, wherein the amphiphilic micelle-forming agent is DSPE-PEG2000.

12. The micelle composition according to claim 1, wherein the molar ratio between the amphiphilic micelle-forming agent and the TLR7 agonist is from 60:40 to 99:1.

13. The micelle composition according to claim 1, wherein the molar ratio between the amphiphilic micelle-forming agent and the TLR7 agonist is 90:10.

14. The micelle composition according to claim 1, wherein the TLR7 agonist has a structure according to formula (IA):
(IA)
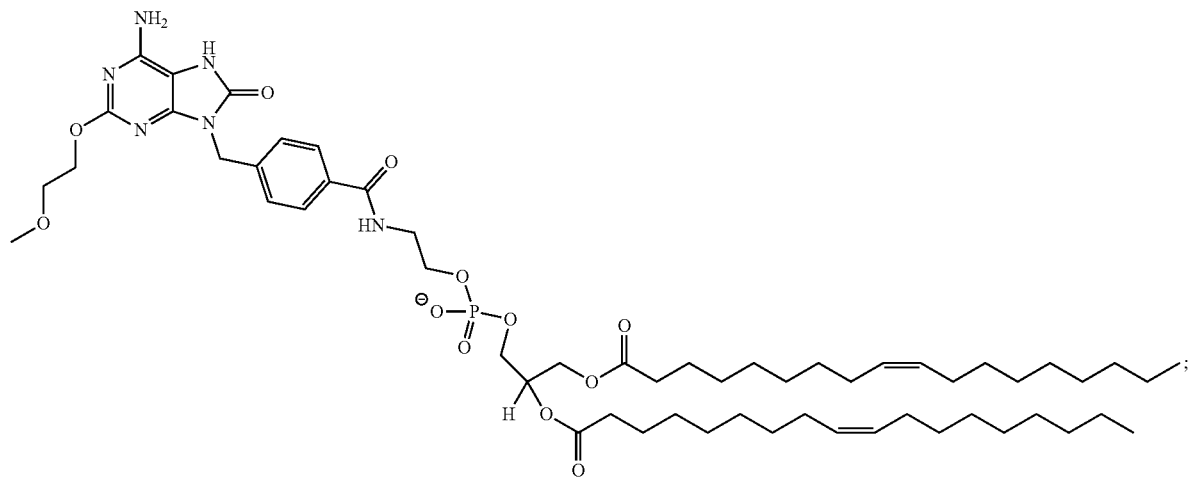
or a tautomer thereof;
or a pharmaceutically acceptable salt or solvate thereof.
15. The micelle composition according to claim 1, wherein the TLR7 agonist is of formula (IA);
(IA)
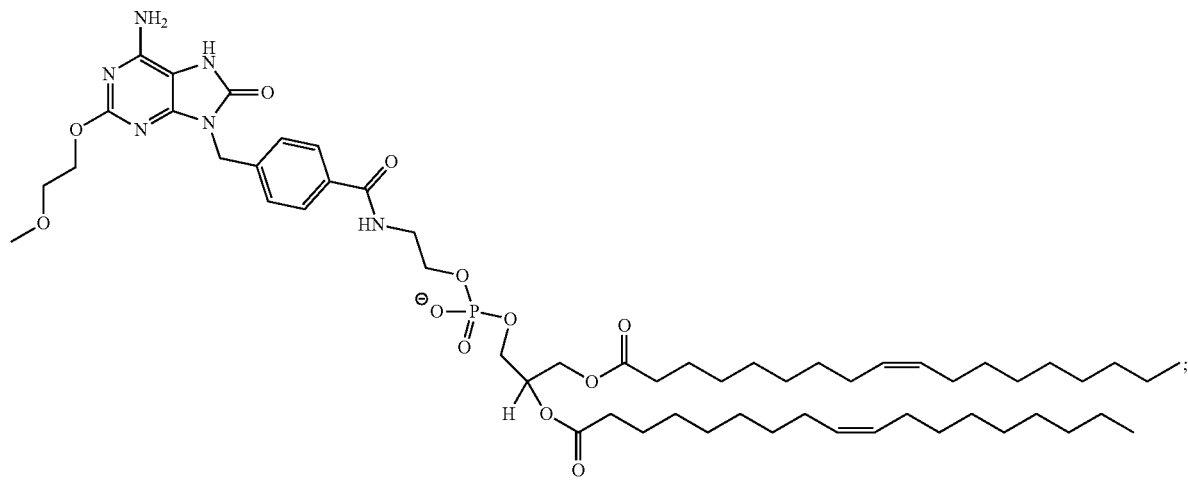

or a tautomer thereof;

or a pharmaceutically acceptable salt or solvate thereof; the amphiphilic micelle-forming agent is DSPE-PEG2000; and the molar ratio between DSPE-PEG2000 and the TLR7 agonist is 95:5, 90:10, or 80:20.

16. The micelle composition according to claim 15, wherein the molar ratio between DSPE-PEG2000 and the TLR7 agonist of formula (IA) is 90:10.

17. A method for the treatment or amelioration of a disease or disorder in a subject, comprising administering a micelle composition to the subject, wherein the micelle composition comprises:

(i) a toll-like receptor 7 (TLR7) agonist of formula (I), formula (II), formula (III) or formula (IV);

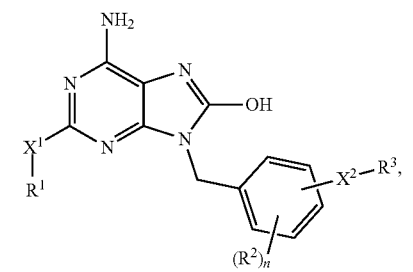

(I)

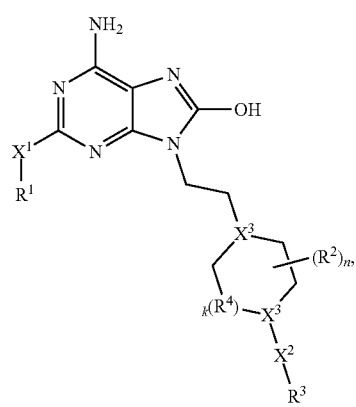

(II)

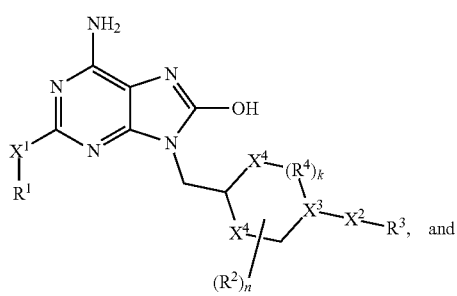

(III)

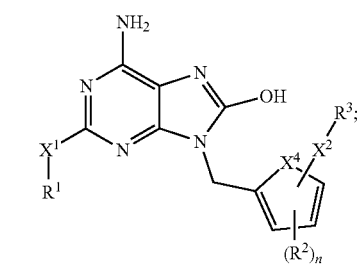

(IV)

or a tautomer thereof;

or a pharmaceutically acceptable salt or solvate thereof, wherein $X^1$ is —O—, —S—, or —$NR^C$;

$R^1$ is hydrogen, $(C_1-C_{10})$alkyl, substituted $(C_1-C_{10})$alkyl, $(C_6-C_{10})$aryl, substituted $(C_6-C_{10})$aryl, $(C_5-C_9)$heterocyclic, or substituted $(C_5-C_9)$heterocyclic;

$R^C$ is hydrogen, $(C_1-C_{10})$alkyl, or substituted $(C_1-C_{10})$alkyl; or $R^C$ and $R^1$ taken together with the nitrogen atom to which they are attached form a heterocyclic ring or a substituted heterocyclic ring;

each $R^2$ is independently —OH, $(C_1-C_6)$alkyl, substituted $(C_1-C_6)$alkyl, $(C_1-C_6)$alkoxy, substituted $(C_1-C_6)$alkoxy, —C(O)—$(C_1-C_6)$alkyl (alkanoyl), substituted —C(O)—$(C_1-C_6)$alkyl, —C(O)—$(C_6-C_{10})$aryl (aroyl), substituted —C(O)—$(C_6-C_{10})$aryl, —C(O)OH (carboxyl), —C(O)O$(C_1-C_6)$alkyl (alkoxycarbonyl), substituted —C(O)O$(C_1-C_6)$alkyl, —$NR^aR^b$, —C(O)$NR^aR^b$ (carbamoyl), halo, nitro, or cyano;

each $R^a$ and $R^b$ is independently hydrogen, $(C_1-C_6)$alkyl, substituted $(C_1-C_6)$alkyl, $(C_3-C_8)$cycloalkyl, substituted $(C_3-C_8)$cycloalkyl, $(C_1-C_6)$alkoxy, substituted $(C_1-C_6)$alkoxy, $(C_1-C_6)$alkanoyl, substituted $(C_1-C_6)$alkanoyl, aryl, aryl$(C_1-C_6)$alkyl, Het, Het $(C_1-C_6)$alkyl, or $(C_1-C_6)$alkoxycarbonyl;

wherein the substituents on any substituted alkyl, aryl or heterocyclic groups are hydroxy, $(C_1-C_6)$alkyl, hydroxy $(C_1-C_6)$alkylene, $(C_1-C_6)$alkoxy, $(C_3-C_6)$cycloalkyl, $(C_1-C_6)$alkoxy $(C_1-C_6)$alkylene, amino, cyano, halo, or aryl;

n is 0, 1, 2, 3 or 4;

$X^2$ is a bond or a linking group;

$R^3$ is a lipid;

$X^3$ is —N— or —CH—;

$R^4$ is —$CH_2$— or —CH($R^2$)—;

k is 0 or 1;

$X^4$ is —O—, —S—, —NH—, —N($R^d$)—, —$CH_2$—, or —CH($R^2$)—; and each $R^d$ is independently —OH, $(C_1-C_6)$alkyl, substituted $(C_1-C_6)$alkyl, $(C_1-C_6)$alkoxy, substituted $(C_1-C_6)$alkoxy, —C(O)—$(C_1-C_6)$alkyl (alkanoyl), substituted —C(O)—$(C_1-C_6)$alkyl, —C(O)—$(C_6-C_{10})$aryl (aroyl), substituted —C(O)—$(C_6-C_{10})$aryl, —C(O)O$(C_1-C_6)$alkyl (alkoxycarbonyl), substituted —C(O)O$(C_1-C_6)$alkyl, —C(O)$NR^aR^b$ (carbamoyl);

wherein the ring system of formula (II) is a piperidine ring with one heteroatom being an N atom and with the N-atom of the piperidine ring adjacent to $X^2$, and wherein the purine group in any of Formula (I), (II), (III), or (IV) is subject to tautomeric rearrangements;

and (ii) an amphiphilic micelle-forming agent, wherein the average diameter of the micelles in the micelle composition is from 5 nm to 25 nm.

18. The method according to claim 17, wherein the disease or disorder is selected from the group consisting of: a cancer, an infectious disease, an inflammatory condition or disease, an autoimmune disease, and an allergy.

19. A method for in vivo activation of immune cells in a subject, comprising administering a micelle composition to said subject in an amount sufficient to activate the immune cells, wherein the micelle composition comprises:

(i) a toll-like receptor 7 (TLR7) agonist of formula (I), formula (II), formula (III) or formula (IV);

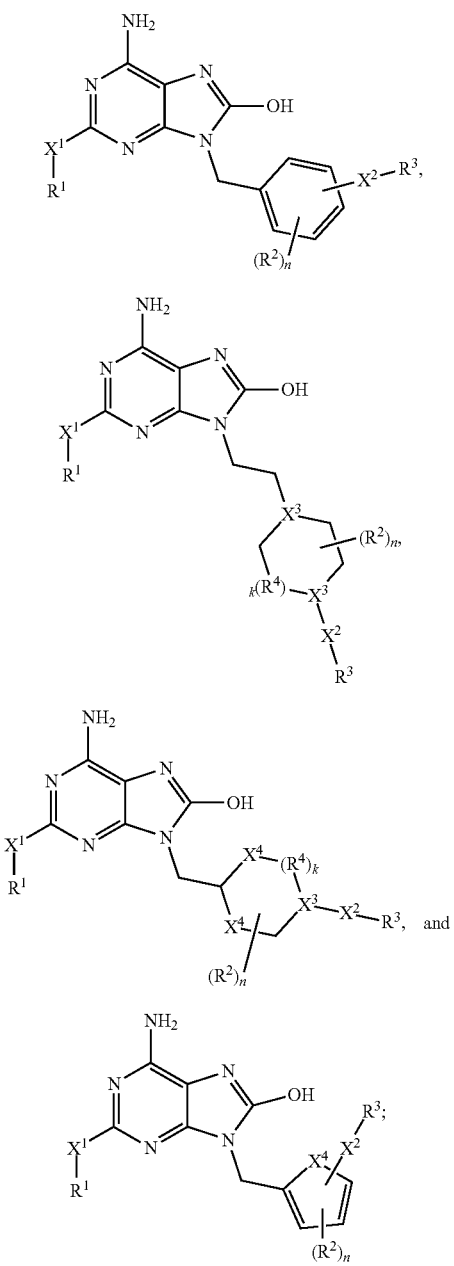

or a tautomer thereof;
or a pharmaceutically acceptable salt or solvate thereof, wherein
$X^1$ is —O—, —S—, or —$NR^C$;
$R^1$ is hydrogen, $(C_1-C_{10})$alkyl, substituted $(C_1-C_{10})$alkyl, $(C_6-C_{10})$aryl, substituted $(C_6-C_{10})$aryl, $(C_5-C_9)$heterocyclic, or substituted $(C_5-C_9)$heterocyclic;

$R^C$ is hydrogen, $(C_1-C_{10})$alkyl, or substituted $(C_1-C_{10})$alkyl; or $R^C$ and $R^1$ taken together with the nitrogen atom to which they are attached form a heterocyclic ring or a substituted heterocyclic ring;

each $R^2$ is independently —OH, $(C_1-C_6)$alkyl, substituted $(C_1-C_6)$alkyl, $(C_1-C_6)$alkoxy, substituted $(C_1-C_6)$alkoxy, —C(O)—$(C_1-C_6)$alkyl (alkanoyl), substituted —C(O)—$(C_1-C_6)$alkyl, —C(O)—$(C_6-C_{10})$aryl (aroyl), substituted —C(O)—$(C_6-C_{10})$aryl, —C(O)OH (carboxyl), —C(O)O$(C_1-C_6)$alkyl (alkoxycarbonyl), substituted —C(O)O$(C_1-C_6)$alkyl, —$NR^aR^b$, —C(O)$NR^aR^b$ (carbamoyl), halo, nitro, or cyano, or $R^2$ is absent;

each $R^a$ and $R^b$ is independently hydrogen, $(C_1-C_6)$alkyl, substituted $(C_1-C_6)$alkyl, $(C_3-C_8)$cycloalkyl, substituted $(C_3-C_8)$cycloalkyl, $(C_1-C_6)$alkoxy, substituted $(C_1-C_6)$alkoxy, $(C_1-C_6)$alkanoyl, substituted $(C_1-C_6)$alkanoyl, aryl, aryl$(C_1-C_6)$alkyl, Het, Het $(C_1-C_6)$alkyl, or $(C_1-C_6)$alkoxycarbonyl;

wherein the substituents on any alkyl, aryl or heterocyclic groups are hydroxy, $(C_1-C_6)$alkyl, hydroxy $(C_1-C_6)$alkylene, $(C_1-C_6)$alkoxy, $(C_3-C_6)$cycloalkyl, $(C_1-C_6)$alkoxy $(C_1-C_6)$alkylene, amino, cyano, halo, or aryl;

n is 0, 1, 2, 3 or 4;
$X^2$ is a bond or a linking group;
$R^3$ is a lipid;
$X^3$ is —N— or —CH—;
$R^4$ is —$CH_2$— or —$CH(R^2)$—;
k is 0 or 1;
$X^4$ is —O—, —S—, —NH—, —$N(R^d)$—, —$CH_2$—, or —$CH(R^2)$—; and each $R^d$ is independently —OH, $(C_1-C_6)$alkyl, substituted $(C_1-C_6)$alkyl, $(C_1-C_6)$alkoxy, substituted $(C_1-C_6)$alkoxy, —C(O)—$(C_1-C_6)$alkyl (alkanoyl), substituted —C(O)—$(C_1-C_6)$alkyl, —C(O)—$(C_6-C_{10})$aryl (aroyl), substituted —C(O)—$(C_6-C_{10})$aryl, —C(O)O$(C_1-C_6)$alkyl (alkoxycarbonyl), substituted —C(O)O$(C_1-C_6)$alkyl, —C(O)$NR^aR^b$ (carbamoyl);

wherein the ring system of formula (II) is a piperidine ring with one heteroatom being an N atom and with the N-atom of the piperidine ring adjacent to $X^2$, and wherein the purine group in any of Formula (I), (II), (III), or (IV) is subject to tautomeric rearrangements;

and (ii) an amphiphilic micelle-forming agent,
wherein the average diameter of the micelles in the micelle composition is from 5 nm to 25 nm.

20. The method of claim 18, wherein the cancer is selected from the group consisting of: colon cancer, hepatoma, pancreatic cancer, lymphoma, breast cancer, prostate cancer, and kidney cancer.

21. The method of claim 18, wherein the cancer is a colon cancer.

22. The method of claim 21, wherein the cancer is characterized by a solid tumor.

* * * * *

UNITED STATES PATENT AND TRADEMARK OFFICE
CERTIFICATE OF CORRECTION

PATENT NO. : 12,318,481 B2
APPLICATION NO. : 17/760885
DATED : June 3, 2025
INVENTOR(S) : Jonas Rosager Henriksen et al.

Page 1 of 1

It is certified that error appears in the above-identified patent and that said Letters Patent is hereby corrected as shown below:

In the Claims

In Claim 1, Column 46, Line 27, delete:
"$X^4$ is —O—, —S—, —NH—, —N($R^4$)—, —$CH_2$—, or"
And insert:
-- $X^4$ is —O—, —S—, —NH—, —N($R^d$)—, —$CH_2$—, or --.

In Claim 9, Column 48, Line 47, delete:
"€8 €24".

Signed and Sealed this
Twenty-ninth Day of July, 2025

Coke Morgan Stewart
*Acting Director of the United States Patent and Trademark Office*